United States Patent
Sakai et al.

(10) Patent No.: US 12,173,295 B2
(45) Date of Patent: *Dec. 24, 2024

(54) ORGANELLE GENOME MODIFICATION USING POLYNUCLEOTIDE GUIDED ENDONUCLEASE

(71) Applicant: Napigen, Inc., Wilmington, DE (US)

(72) Inventors: Hajime Sakai, Newark, DE (US); Byung-Chun Yoo, Newark, DE (US); Emil Meyer Orozco, Jr., Cochranville, PA (US); Ganesh Kishore, St. Louis, MO (US); Narendra Singh Yadav, Wilmington, DE (US)

(73) Assignee: NAPIGEN, INC., Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 18/417,654

(22) Filed: Jan. 19, 2024

(65) Prior Publication Data

US 2024/0294930 A1    Sep. 5, 2024

Related U.S. Application Data

(60) Continuation of application No. 17/867,534, filed on Jul. 18, 2022, now Pat. No. 11,920,140, which is a division of application No. 16/109,523, filed on Aug. 22, 2018, now abandoned.

(60) Provisional application No. 62/548,723, filed on Aug. 22, 2017.

(51) Int. Cl.
| | |
|---|---|
| *C12N 15/82* | (2006.01) |
| *C12N 9/22* | (2006.01) |
| *C12N 15/10* | (2006.01) |
| *C12N 15/113* | (2010.01) |
| *C12N 15/63* | (2006.01) |

(52) U.S. Cl.
CPC .......... *C12N 15/8213* (2013.01); *C12N 9/22* (2013.01); *C12N 15/102* (2013.01); *C12N 15/113* (2013.01); *C12N 15/63* (2013.01); *C12N 15/8289* (2013.01); *C12N 2310/20* (2017.05); *C12N 2310/3513* (2013.01); *C12Y 207/07049* (2013.01)

(58) Field of Classification Search
None
See application file for complete search history.

(56) References Cited

U.S. PATENT DOCUMENTS

| | | |
|---|---|---|
| 4,761,373 A | 8/1988 | Anderson et al. |
| 4,810,648 A | 3/1989 | Stalker |
| 5,013,659 A | 5/1991 | Bedbrook et al. |
| 5,015,580 A | 5/1991 | Christou et al. |
| 5,094,945 A | 3/1992 | Comai |
| 5,106,739 A | 4/1992 | Comai et al. |
| 5,141,870 A | 8/1992 | Bedbrook et al. |
| 5,217,902 A | 6/1993 | Jones et al. |
| 5,273,894 A | 12/1993 | Strauch et al. |
| 5,276,268 A | 1/1994 | Strauch et al. |
| 5,302,523 A | 4/1994 | Coffee et al. |
| 5,322,938 A | 6/1994 | McPherson et al. |
| 5,352,605 A | 10/1994 | Fraley et al. |
| 5,359,142 A | 10/1994 | McPherson et al. |
| 5,378,619 A | 1/1995 | Rogers |
| 5,378,824 A | 1/1995 | Bedbrook et al. |
| 5,384,253 A | 1/1995 | Krzyzek et al. |
| 5,463,175 A | 10/1995 | Barry et al. |
| 5,464,765 A | 11/1995 | Coffee et al. |
| 5,508,184 A | 4/1996 | Negrutiu et al. |
| 5,530,196 A | 6/1996 | Fraley et al. |
| 5,538,880 A | 7/1996 | Lundquist et al. |
| 5,550,318 A | 8/1996 | Adams et al. |
| 5,561,236 A | 10/1996 | Leemans et al. |
| 5,591,616 A | 1/1997 | Hiei et al. |
| 5,605,011 A | 2/1997 | Bedbrook et al. |
| 5,627,061 A | 5/1997 | Barry et al. |
| 5,633,435 A | 5/1997 | Barry et al. |
| 5,633,437 A | 5/1997 | Bernasconi et al. |
| 5,635,055 A | 6/1997 | Sweet et al. |
| 5,637,489 A | 6/1997 | Strauch et al. |
| 5,641,876 A | 6/1997 | McElroy et al. |
| 5,646,024 A | 7/1997 | Leemans et al. |
| 5,767,366 A | 6/1998 | Sathasivan et al. |

(Continued)

FOREIGN PATENT DOCUMENTS

| | | |
|---|---|---|
| CN | 105602935 A | 5/2016 |
| CN | 105602993 A | 5/2016 |

(Continued)

OTHER PUBLICATIONS

Dauville, D. et al., Photosynthesis Research (2004) vol. 79; pp. 219-224. (Year: 2004).*

(Continued)

*Primary Examiner* — Russell Kallis
(74) *Attorney, Agent, or Firm* — Wilson Sonsini Goodrich & Rosati

(57) ABSTRACT

Provided herein are methods and systems for altering the genome of an organelle. In some embodiments, the method comprises introducing into an organelle a recombinant DNA construct comprising a first polynucleotide encoding at least one guide RNA and a second polynucleotide encoding a polynucleotide guided polypeptide; and growing a cell comprising the organelle under conditions in which the first polynucleotide and the second polynucleotide are each expressed.

19 Claims, 2 Drawing Sheets

Specification includes a Sequence Listing.

(56) References Cited

U.S. PATENT DOCUMENTS

| | | |
|---|---|---|
| 5,824,877 A | 10/1998 | Hinchee et al. |
| 5,837,848 A | 11/1998 | Ely et al. |
| 5,850,019 A | 12/1998 | Maiti et al. |
| 5,981,840 A | 11/1999 | Zhao et al. |
| 6,040,497 A | 3/2000 | Spencer et al. |
| 6,051,753 A | 4/2000 | Comai et al. |
| 6,121,513 A | 9/2000 | Zhang et al. |
| 6,140,078 A | 10/2000 | Sanders et al. |
| 6,160,208 A | 12/2000 | Lundquist et al. |
| 6,175,060 B1 | 1/2001 | Lefebvre et al. |
| 6,177,611 B1 | 1/2001 | Rice |
| 6,225,105 B1 | 5/2001 | Sathasivan et al. |
| 6,232,526 B1 | 5/2001 | McElroy et al. |
| 6,252,138 B1 | 6/2001 | Karimi et al. |
| 6,294,714 B1 | 9/2001 | Matsunaga et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,426,446 B1 | 7/2002 | McElroy et al. |
| 6,429,357 B1 | 8/2002 | McElroy et al. |
| 6,429,362 B1 | 8/2002 | Crane |
| 6,433,252 B1 | 8/2002 | Kriz et al. |
| 6,437,217 B1 | 8/2002 | Mcelroy et al. |
| 6,613,963 B1 | 9/2003 | Gingera et al. |
| 6,635,806 B1 | 10/2003 | Kriz et al. |
| 6,849,778 B1 | 2/2005 | Staub et al. |
| 7,151,204 B2 | 12/2006 | Houmard et al. |
| 8,067,671 B2 | 11/2011 | Boukharov et al. |
| 8,278,428 B2 | 10/2012 | Guy et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,697,359 B1 | 4/2014 | Zhang |
| 8,883,755 B2 | 11/2014 | Palladino et al. |
| 9,238,041 B2 | 1/2016 | Teitell et al. |
| 9,441,243 B2 | 9/2016 | Dietrich et al. |
| 9,663,792 B2 | 5/2017 | Malcuit et al. |
| 9,896,696 B2 | 2/2018 | Begemann et al. |
| 9,982,279 B1 | 5/2018 | Gill et al. |
| 10,011,849 B1 | 7/2018 | Gill et al. |
| 10,113,179 B2 | 10/2018 | Begemann et al. |
| 10,316,324 B2 | 6/2019 | Begemann et al. |
| 10,822,611 B2 | 11/2020 | Arimura et al. |
| 11,208,652 B2 * | 12/2021 | Church ............... C12N 15/102 |
| 11,920,140 B2 * | 3/2024 | Sakai ............... C12N 15/8213 |
| 2003/0083480 A1 | 5/2003 | Castle et al. |
| 2003/0087817 A1 | 5/2003 | Cox, III et al. |
| 2003/0115626 A1 | 6/2003 | Weeks et al. |
| 2003/0135879 A1 | 7/2003 | Weeks et al. |
| 2004/0177399 A1 | 9/2004 | Hammer et al. |
| 2006/0142223 A1 | 6/2006 | Schon et al. |
| 2007/0271630 A1 | 11/2007 | Boukharov et al. |
| 2009/0104700 A1 | 4/2009 | Samuel et al. |
| 2009/0178161 A1 | 7/2009 | Arar et al. |
| 2010/0111911 A1 | 5/2010 | Guy et al. |
| 2012/0283317 A1 | 11/2012 | Teitell et al. |
| 2013/0058969 A1 | 3/2013 | Daniell |
| 2015/0166980 A1 | 6/2015 | Liu et al. |
| 2015/0211023 A1 | 7/2015 | Shiboleth et al. |
| 2015/0353885 A1 | 12/2015 | Sourdive |
| 2016/0060637 A1 | 3/2016 | Hommelsheim et al. |
| 2016/0145631 A1 | 5/2016 | Voytas et al. |
| 2016/0304842 A1 | 10/2016 | Donovan et al. |
| 2017/0121693 A1 | 5/2017 | Liu et al. |
| 2017/0175140 A1 | 6/2017 | Hummel et al. |
| 2017/0233756 A1 | 8/2017 | Begemann et al. |
| 2018/0073012 A1 | 3/2018 | Liu et al. |
| 2018/0208941 A1 | 7/2018 | Cai et al. |
| 2018/0230477 A1 | 8/2018 | Arimura et al. |
| 2018/0327785 A1 | 11/2018 | Cigan et al. |
| 2019/0136249 A1 | 5/2019 | Sakai et al. |
| 2019/0290780 A1 | 9/2019 | Burnett et al. |
| 2020/0017865 A1 | 1/2020 | Budin et al. |
| 2021/0002656 A1 | 1/2021 | Voytas et al. |
| 2021/0054404 A1 | 2/2021 | Sakai et al. |
| 2022/0372523 A1 | 11/2022 | Orozco, Jr. et al. |
| 2023/0123175 A1 | 4/2023 | Sakai et al. |

FOREIGN PATENT DOCUMENTS

| | | |
|---|---|---|
| CN | 106520830 A | 3/2017 |
| CN | 108165573 A | 6/2018 |
| CN | 108359691 A | 8/2018 |
| CN | 109456990 A | 3/2019 |
| EP | 3673054 A4 | 6/2021 |
| WO | WO-8704181 A1 | 7/1987 |
| WO | WO-8900193 A1 | 1/1989 |
| WO | WO-9927116 A2 | 6/1999 |
| WO | WO-2004009761 A2 | 1/2004 |
| WO | WO-2004035734 A2 | 4/2004 |
| WO | WO-2004074443 A2 | 9/2004 |
| WO | WO-2005003362 A2 | 1/2005 |
| WO | WO-2007025097 A2 | 3/2007 |
| WO | WO-2007139898 A2 | 12/2007 |
| WO | WO-2013088446 A1 | 6/2013 |
| WO | WO-2014173955 A1 | 10/2014 |
| WO | WO-2014194190 A1 | 12/2014 |
| WO | WO-2014199358 A1 | 12/2014 |
| WO | WO-2015006290 A1 | 1/2015 |
| WO | WO-2015026886 A1 | 2/2015 |
| WO | WO-2015048577 A2 | 4/2015 |
| WO | WO-2015139139 A1 | 9/2015 |
| WO | WO-2016106244 A1 | 6/2016 |
| WO | WO-2016184955 A2 | 11/2016 |
| WO | WO-2016205749 A1 | 12/2016 |
| WO | WO-2017024047 A1 | 2/2017 |
| WO | WO-2017062855 A1 | 4/2017 |
| WO | WO-2017070605 A1 | 4/2017 |
| WO | WO-2017100343 A1 | 6/2017 |
| WO | WO-2017136520 A1 | 8/2017 |
| WO | WO-2017222834 A1 | 12/2017 |
| WO | WO-2018045321 A1 | 3/2018 |
| WO | WO-2018093954 A1 | 5/2018 |
| WO | WO-2018103686 A1 | 6/2018 |
| WO | WO-2019040645 A1 | 2/2019 |

OTHER PUBLICATIONS

An et al.: Development of chloroplast transformation and gene expression regulation technology in land plants. Frontiers in Plant Science. Mini Review. 7 pages (2022).

Areum Jo et al., "Efficient Mitochondrial Genome Editing by CRISPR/Cas9", BioMed Research International, 2015, Article ID 305716, 10 pages, http://dx.doi.org/10.1155/2015/305716.

Barrera et al., "Rapid Screening for the Robust Expression of Recombinant Proteins in Algal Plastids", Methods in Molecular Biology, vol. 1132, 391-399, 2014.

Bevan, Binary Agrobacterium vectors for plant transformation. Nucleic Acids Res 12(22): 8711-8721 (1984).

Bevan et al., T-DNA of the Agrobacterium Ti and Ri plasmids. Annual Review of Genetics, 16 (1982): 357-384.

Bonnefoy et al., "Genetic Transformation of Saccharomyces cerevisiae Mitochondria", Methods in Enzymology, vol. 350, 97-111, 2001.

Bonnefoy N, et al.: Genetic transformation of Saccharomyces cerevisiae and Chlamydomonas reinhardtii mitochondria. Methods Cell Biol. 2007;80:525-48.

Bonnefoy N, Fox TD.: Directed alteration of Saccharomyces cerevisiae mitochondrial DNA by biolistic transformation and homologous recombination. Methods Mol Biol. 2007;372:153-66.

Boynton et al., "Chloroplast Transformation in Chlamydomonas with High Velocity Microprojectiles", Science, vol. 240, 1534-1538, 1988.

Brown GG, et al., Group II intron splicing factors in plant mitochondria. Front Plant Sci. Feb. 18, 2014;5:35 pp. 1-13.

Chen Z, et al.: Plant mitochondrial genome evolution and cytoplasmic male sterility. Critical reviews in plant sciences. Jan. 2, 2017;36(1):55-69.

Choury D, et al.: Different patterns in the recognition of editing sites in plant mitochondria. Nucleic Acids Res. Dec. 7, 2004;32(21):6397-406.

(56) References Cited

OTHER PUBLICATIONS

Christensen et al., Maize Polyubiquitin Genes: Structure, Thermal Perturbation of Expression and Transcript Splicing, and Promoter Activity Following Transfer to Protoplasts by Electroporation. Plant Molecular Biology, 18.4 (Feb. 1992): 675-689.
Chu, et al.: Increasing the efficiency of homology-directed repair for CRISPR-Cas9-induced precise gene editing in mammalian cells. Nat Biotechnol. May 2015;33(5):543-8. doi: 10.1038/nbt.3198. Epub Mar. 24, 2015. with Erratum: Nat Biotechnol. Feb. 6, 2018;36(2):196.
Chuah JA, et al.: Gene introduction into the mitochondria of Arabidopsis thaliana via peptide-based carriers. Sci Rep. Jan. 13, 2015;5:7751.
Chuah JA, et al.: Self-Assembled Peptide-Based System for Mitochondrial-Targeted Gene Delivery: Functional and Structural Insights. Biomacromolecules. Nov. 14, 2016;17(11):3547-3557. Epub Oct. 10, 2016.
Chung SM, et al.: Agrobacterium is not alone: gene transfer to plants by viruses and other bacteria. Trends Plant Sci. Jan. 2006;11(1):1-4. Epub Nov. 15, 2005.
Clark et al., Mitochondrial transformation of mammalian cells, Nature, vol. 295, 605-607, Feb. 18, 2012.
Cong, et al., Multiplex Genome Engineering Using CRISPR/Cas Systems. Science 339(6121):819-823 (2013).
Dauvillee et al., Minimal extent of sequence homology required for homologous recombination at the psbA locus in Chlamydomonas reinhardtii chloroplasts using PCR-generated DNA fragments, Photosynthesis Research, vol. 79, 219-224, 2004.
Feng et al.: Efficient genome editing in plants using a CRISPR/Cas system. Cell Res. 23:1229-1232 (2013).
Fontanesi F.: Mechanisms of mitochondrial translational regulation. IUBMB Life. May 2013;65(5):397-408. Epub Apr. 3, 2013.
Fox et al., Plasmids can stably transform yeast mitochondria lacking endogenous mtDNA, Proc. Natl., Acad. Sci, vol. 85, 7288-7292, Oct. 1988.
Fox, Five TGA "stop codons occur within the translated sequence of the yeast mitochondrial gene for cytochrome c oxidase subunit II", Proc. Natl. Acad. Sci. USA, vol. 76, No. 12, 6534-6538, Dec. 1979.
Fox, T D et al.: "Plasmids can stably transform yeast mitochondria lacking endogenous mtDNA." Proceedings of the National Academy of Sciences of the United States of America vol. 85, 19 (1988): 7288-92. doi:10.1073/pnas.85.19.7288.
Fraley, et al.: Expression of bacterial genes in plant cells. Proc Natl Acad Sci U S A. Aug. 1983;80(15):4803-7.
Franklin et al., "Development of a GFP reporter gene for Chlamydomonas reinhardtii chloroplast", The Plant Journal, vol. 30., No. 6, 733-744, 2002.
Fu, et al.: High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Gammage, Payam A. et al., Mitochondrial Genome Engineering: The Revolution May Not Be CRISPR-Ized, Feb. 2018, Trends in Genetics, vol. 34, No. 2, 101-110, https://doi.org/10.1016/j.tig.2017.11.001.
Gómez G, Pallás V., Noncoding RNA mediated traffic of foreign mRNA into chloroplasts reveals a novel signaling mechanism in plants. PLoS One. Aug. 19, 2010;5(8):e12269.
Green-Willms et al., "Pet111p, an Inner Membrane-bound Translational Activator That Limits Expression of the *Saccharomyces cerevisiae* Mitochondrial Gene COX2", The Journal of Biological Chemistry, vol. 276, No. 9, 6392-6397, 2001.
Guzmán-Zapata D, et al.: Efficient Editing of the Nuclear APT Reporter Gene in Chlamydomonas reinhardtii via Expression of a CRISPR-Cas9 Module. Int J Mol Sci. Mar. 12, 2019;20(5):1247.
Haeussler, "Evaluation of off-target and on-target scoring algorithms and integration into the guide RNA selection tool CRISPOR", Genome Biology, vol. 17, 148-159, 2016.

Hamada H, et al.: An in planta biolistic method for stable wheat transformation. Sci Rep. Sep. 13, 2017;7(1):11443. Erratum in: Sci Rep. Dec. 11, 2017;7(1):17573.
Hernalsteens et al., An Agrobacterium-Transformed Cell Culture From the Monocot Asparagus Officinalis. Journal of Cell Science, 3.13 (Dec. 1984): 3039-3041.
Hirose T, Sugiura M.: Both RNA editing and RNA cleavage are required for translation of tobacco chloroplast ndhD mRNA: a possible regulatory mechanism for the expression of a chloroplast operon consisting of functionally unrelated genes. EMBO J. Nov. 17, 1997;16(22):6804-11.
Horsch et al., A Simple and General Method for Transferring Genes Into Plants. Science, 227.4691 (Mar. 1985): 1229-1231.
Horsch et al.: Inheritance of functional foreign genes in plants. Science 233(4635):496-498 (1984).
International Search Report and Written Opinion for PCT/US2020/040730 issued Oct. 22, 2020.
International Search Report dated Oct. 19, 2018 for International Application Serial No. PCT/US2018/047566, (4 pages).
Jin S et al., "Release of hormones from conjugates: chloroplast expression of β-glucosidase results in elevated phytohormone levels associated with significant increase in biomass and protection from aphids or whiteflies conferred by sucrose esters." Plant Physiol. Jan. 2011;155(1):222-35. Epub Nov. 10, 2010.
Kindle KL.: High-frequency nuclear transformation of Chlamydomonas reinhardtii. Proc Natl Acad Sci U S A. Feb. 1990;87(3):1228-32.
Klein et al.: High-velocity microprojectiles for delivering nucleic acids into living cells. Nature 327:70-73 (1987).
Lakshmanan M, et al.: Rapid and efficient gene delivery into plant cells using designed peptide carriers. Biomacromolecules. Jan. 14, 2013;14(1):10-6. Epub Dec. 14, 2012.
Laughery MF, et al.: New vectors for simple and streamlined CRISPR-Cas9 genome editing in *Saccharomyces cerevisiae*. Yeast. Dec. 2015;32(12):711-20. Epub Sep. 21, 2015.
Leslie, Mitch, Old' genome editors might treat mitochondrial diseases, Sep. 28, 2018, Science 361 (6409), 1302,DOI: 10.1126/science.361.6409.1302.
Makarova et al.: An updated evolutionary classification of CRISPR-Cas systems. Nat Rev Microbiol 13:722-736 (2015).
Matsuoka A, Maliga P.: Prospects for Reengineering Agrobacterium tumefaciens for T-DNA Delivery to Chloroplasts. Plant Physiol. May 27, 2021;186(1):215-220.
McBride et al., "Amplification of a Chimeric Bacillus Gene in Chloroplasts Leads to an Extraordinary Level of an Insectional Protein in Tobacco", BioTechnology, vol. 13, 362-365, Apr. 1995.
McElroy et al.: Isolation of an efficient actin promoter for use in rice transformation. Plant Cell 2 (1990):163-171.
Mireau et al., "Expression of Barstar as a selectable marker in yeast mitochondria", Mol Gen Genomics, 270, 1-8, 2003.
Mogollon CM, et al.: Rapid Generation of Marker-Free *P. falciparum* Fluorescent Reporter Lines Using Modified CRISPR/Cas9 Constructs and Selection Protocol. PLoS One. Dec. 20, 2016;11(12):e0168362.
Nakamura et al.: Codon usage tabulated from international DNA sequence databases: status for the year 2000, Nucleic Acids Research, vol. 28, No. 1, 292, 2000.
NCBI Ref. NC_005353.1. Chlamydomanoas reinherdtii chloroplast, complete genome. Retrieved Jan. 24, 2019 (68 pgs.).
Nicholls SB, et al.: Mechanism of a genetically encoded dark-to-bright reporter for caspase activity. J Biol Chem. Jul. 15, 2011;286(28):24977-86. Epub May 10, 2011.
Nicholls SB, Hardy JA.: Structural basis of fluorescence quenching in caspase activatable-GFP. Protein Sci. Mar. 2013;22(3):247-57. Epub Nov. 8, 2012.
Palmer: Isolation and Structural Analysis of Chloroplast DNA. Plant Mol Biol 118:167-186 (1986).
Quetier, Francis, The CRISPR-Cas9 technology: Closer to the ultimate toolkit for targeted genome editing, Plant Science, 242 (2016) 65-76.
Ramesh et al.: A Simple Method for Chloroplast Transformation in Chlamydomonas reinhardtti, Methods in Molecular Biology, vol. 684, 313-320, 2011.

(56) References Cited

OTHER PUBLICATIONS

Randolph-Anderson et al., "Further characterization of the respiratory deficient dum-1 mutation of Chlamydomonas reinhardtii and its use as a recipient for mitochondrial transformation", Mol Gen Genet, 236, 235-244, 1993.
Redding et al., "Photosystem I Is Indispensable for Photoautotrophic Growth, CO2 Fixation, and H2 Photoproduction in Chlamydomonas reinhardtii*", The Journal of Biological Chemistry, vol. 274, No. 15, 10466-10473, Apr. 1999.
Ricchetti et al, "Mitochondrial DNA repairs double-strand breaks in yeast chromosomes", Nature, vol. 402, 96-100, Nov. 1999.
Rogers SG, et al., Gene transfer in plants: Production of transformed plants using Ti plasmid vectors. Methods in Enzymology 118 (1986): 627-640.
Ruhlman T, et al., The role of heterologous chloroplast sequence elements in transgene integration and expression. Plant Physiol. Apr. 2010; 152(4):2088-104. Epub Feb. 3, 2010.
*Saccharomyces* Genome Database (SGD). (n.d.). COX1 / Q0045 /OXI3. In SGD. Retrieved Oct. 2022, from https://www.yeastgenome.org/locus/S000007260.
Schmiderer et al.: Site-specific CRISPR-based mitochondrial DNA manipulation is limited to gRNA import. Nature Scientific Reports. 12:18687 pp. 1-9 (2022).
Schnable et al., "The molecular basis of cytoplasmic male sterility and fertility restoration", Trends in Plant Science, vol. 3, No. 5, 175-180, May 1998.
Shen BR, et al., An optimized transit peptide for effective targeting of diverse foreign proteins into chloroplasts in rice. Sci Rep. Apr. 11, 2017;7:46231.
Shmakov et al., Discovery and Functional Characterization of Diverse Class 2 CRISPR-Cas Systems. Mol Cell 60(3):385-397 (2015).
Sigma-Aldrich. (n.d.). Yeast Transformation Protocols. online. Retrieved Oct. 2022, from https://www.sigmaaldrich.com/US/en/technical-documents/protocol/protein-biology/protein-expression/yeast-transformation-protocols.
Steele DF, et al., Expression of a recoded nuclear gene inserted into yeast mitochondrial DNA is limited by mRNA-specific translational activation. Proc Natl Acad Sci U S A. May 28, 1996;93(11):5253-7.
Svab et al, "Stable transformation of plastids in higher plants", Proc. Natl. Acad. Sci, vol. 87, 8526-8530, Nov. 1990.
Svitashev et al.: Targeted Mutagenesis, Precise Gene Editing, and Site-Specific Gene Insertion in Maize Using Cas9 and Guide RNA. Plant Physiology. 169:931-945 (2015).
Tang et al.: Improvement of Chloroplast Transformation Using CRISPR/Cas9. Jurnal of biobased Materials and Bioenergy. 14:401-407 (2020).
Tomohiko Kazama et al., "Curing cytoplasmic male sterility via TALEN-mediated mitochondrial genome editing", Nature Plants, vol. 5, Jul. 2019, 722-730.
Tsai, et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Turk EM, et al. The mitochondrial RNA landscape of Saccharomyces cerevisiae. PLoS One. Oct. 15, 2013;8(10):e78105.
U.S. Appl. No. 16/109,523 Final Office Action dated Nov. 25, 2022.
U.S. Appl. No. 16/641,073 Office Action dated Jul. 27, 2023.
U.S. Appl. No. 17/867,534 Notice of Allowance dated Dec. 22, 2023.
U.S. Appl. No. 17/867,534 Office Action dated Mar. 2, 2023.
U.S. Appl. No. 17/867,534 Office Action dated Oct. 5, 2023.
U.S. Appl. No. 16/109,523 Non-Final Office dated Jan. 7, 2021.
U.S. Appl. No. 16/641,073 Office Action dated Mar. 31, 2022.
U.S. Appl. No. 16/641,073 Office Action dated Mar. 15, 2024.
U.S. Appl. No. 16/641,073 Office Action dated Jan. 4, 2023.
Wang et al.: Multiplex Gene Editing in Rice Using the CRISPR-Cpf1 System. Mol Plant 10(7):1011-1013 (2017).
Wan-Ping Bian et al., "Knock-In Strategy for Editing Human and Zebrafish Mitochondrial DNA Using Mito-CRISPR/Cas9 System", ACS Synth. Biol. 2019, 8, 621-632.
Wu, Lanlan et al., "The Rice Pentatricopeptide Repeat Gene TCD10 is Needed for Chloroplast Development under Cold Stress." Rice (New York, N.Y.) vol. 9,1 (2016): 67. doi:10.1186/s12284-016-0134-1.
Xie et al., "Boosting CRISPR/Cas9 multiplex editing capability with the endogenous tRNA-processing system", Proc Natl Acid Sci USA, vol. 112, No. 11, 3570-3575, Mar. 17, 2015.
Yoo BC, et al., Cas9/gRNA-mediated genome editing of yeast mitochondria and Chlamydomonas chloroplasts. PeerJ. Jan. 6, 2020;8:e8362.
Yoshizumi et al., Selective gene delivery for integrating exogenous DNA into plastid and mitochondrial genomes using peptide-DNA complexes. Biomacromolecules 19:1582-1591 (2018).
Zeng X, et al., The Saccharomyces cerevisiae ATP22 gene codes for the mitochondrial ATPase subunit 6-specific translation factor. Genetics. Jan. 2007;175(1):55-63. Epub Nov. 16, 2006.
Zhang Z, et al., Development of an Agrobacterium-delivered CRISPR/Cas9 system for wheat genome editing. Plant Biotechnol J. Aug. 2019;17(8):1623-1635. Epub Mar. 12, 2019.
Zoschke R, Bock R., Chloroplast Translation: Structural and Functional Organization, Operational Control, and Regulation. Plant Cell. Apr. 2018;30(4):745-770. Epub Apr. 2, 2018.

\* cited by examiner

SEQ ID NO: 144 ctattcaggcacattcaggaccTAGTGTAGATTAGCAATTTTTGCATTACATTTAACATCAAT
TTCATCATTATTAGGTGCTATTAATTTCATTGTAACAACATTAAATATGAGAACAAATGGTATG
ACAATGCATAAATTACCATTATTTGTATGATCAATTTTCATTACAGCGTTCTTATTATTATTAT
CATTACCTGTATTATCTGCTGGTATTACAATGTTATTATTAGATAGAAACTTCAATACTTCATT
TTCGGAGTTTCTGGTGGAGGTGGTGGAATGACACATTTAGAAGAAGTAGACAAATGTCAAAA
GGTGAAGAATTATTCACTGGAGTAGTACCTATCTTAGTAGAATTAGATGGTGATGTAAATGGTC
ATAAATTCTCAGTATCAGGTGAAGGTGAAGGTGATGCTACATATGGTAAATTAACATTAAAATT
CATCTGTACAACAGGTAAATTACCTGTACCTTGACCTACATTAGTAACAACATTCGGATATGGA
GTACAATGTTTCGCAAGATATCCTGATCATATGAAACAACATGATTTCTTCAAATCAGCAATGC
CTGAAGGTTACGTACAAGAAGAACAATCTTCTTCAAAGATGATGGTAATTATAAAACAAGAGC
TGAAGTAAAATTCGAAGGTGATACATTAGTAAATAGAATCGAGTTAAAAGGTATCGATTTCAAA
GAAGATGGTAATATCTTAGGTCATAAATTAGAATATAATTATAATTCACATAATGTATATATCA
TGGCTGATAAACAAAAAATGGTATCAAAGTAAATTTCAAAATCAGACATAATATCGAAGACGG
TTCAGTACAATTAGCAGATCATTATCAACAAAATACACCTATCGGTGATGGTCCTGTATTATTA
CCTGATAATCATTACTTAAGTACACAATCAGCTTTATCAAAAGATCCTAATGAAAAAGAGATC
ATATGGTATTATTAGAATTTGTAACAGCTGCTGGTATCACACATGGTATGGATGAATTATATAA
ATAACAACAGGAATTAAAATTTTCTCATGATTAATAAATCCCTTTAGCAAGGATAAAAATAAAA
ATAAAAATAAAAAGTTGATCAGAAATTATCAAAAAATAAATAATAATAATATAATAAAAACATA
TTTAAATAATAATAATATAATTATAATAAATATATATAAAGGTAATTTATATGATATTTATCCA
AGATCAAATAGAAATTATATTCAACCAAATAATATTAATAAAGAATTAGTAGTATATGGTTATA
ATTTAgaatcttgtgttggtatacctct

FIG. 1

SEQ ID NO: 171

GCTGGTTGGTTCCACTACCACAAAGCTGCTCCAAAACTAGAATGGTTCCAAAACG
TTGAATCAATGTTAAACCACCACTTAGGTGGTCTTCTTGGTTTAGGTAGTTTAGC
TTGGGCTGGTCACCAAATTCACGTTTCTTTACCAGTAAACAAATTATTAGATGCT
GGTGTAGATCCAAAAGAAATTCCACTTCCTCATGATTATTATTAAATCGTGCTA
TTATGGCTGACTTATACCCAAGTTTTGCTAAAGGTATT**GCTCCTTTCTTTACTTT
AAACTGGAGTGAATACAGTGATTTCTTAACATTTAAAGGTGGTTTAAACCCTGTT
AC**ATTATCAGGTTCTGCTGGTTCAGCAGCTGGTATGGCTAAAGGTGAAGAATTAT
TCACAGGTGTTGTACCTATTTTAGTAGAATTAGACGGTGATGTAAACGGTCACAA
ATTTCAGTTTCTGGTGAAGGTGAAGGTGACGCAACTTATGGTAAATTAACACTT
AAATTCATTTGTACTACAGGTAAATTACCAGTACCTTGGCCATCATTAGTTACAA
CTTTACATACGGTGTACAATGTTCAGTCGTTACCCTGATCACATGAAACAACA
TGACTTTTCAAATCTGCTATGCCAGAAGGTTATGTTCAAGAACGTACTATTTTT
TTCAAAGATGACGGTAATTATAAACACGTGCTGAAGTAAAATTTGAAGGTGATA
CTTTAGTTAACCGTATTGAATTAAAAGGTATTGACTTCAAAGAAGATGGTAATAT
TTAGGTCACAAACTTGAATATAACTACAATTCACATAACGTATATATTATGGCA
GACAAACAAAAAATGGTATTAAAGTAAACTTTAAAATTCGTCATAATATCGAGG
ATGGTTCTGTACAATTAGCTGACCACTATCAACAAACACACCAATTGGTGATGG
TCCTGTTTTACTTCCAGACAATCATTATTTAAGTACTCAATCTGCTTTATCAAAA
GATCCTAACGAAAAACGTGACCACATGGTATTACTTGAATTTGTTACAGCAGCTG
GTATTACTCACGGTATGGATGAATTATACAAATAA**TCCATTTACAGGTGAAGGTC
ACGTTGGTTTATATGAAATTTTAACAACTTCTTGGCATGCACAATTAGCTATTAA
C**TTAGCTTTATTTGGTTCGTTATCAATTATTGTAGCTCACCACATGTACGCAATG
CCTCCATACCCTTATTTAGCTACTGATTACGGTACACAATTATCATTATTTACAC
ACCACACATGGATTGGTGGTTTCTGTATTGTTGGTGCTGGTGCTCACGCAGCTAT
TTTCATGGTTCGTGACTACGATCCTACTAATAACTACAACAACTTATTAGACCGT
GTAATTCGTCACCGTGATGCTATTATTTCTCAC

FIG. 2

ORGANELLE GENOME MODIFICATION USING POLYNUCLEOTIDE GUIDED ENDONUCLEASE

CROSS-REFERENCE

This application is a continuation of U.S. Ser. No. 17/867,534 (now issued U.S. Pat. No. 11,920,140), filed on Jul. 18, 2022, which is a divisional of U.S. Nonprovisional patent application Ser. No. 16/109,523, filed on Aug. 22, 2018, which claims the benefit of U.S. Provisional Patent Application No. 62/548,723, filed on Aug. 22, 2017, each of which is incorporated herein by reference in its entirety.

SEQUENCE LISTING INCORPORATION BY REFERENCE

The instant application contains a Sequence Listing which has been submitted via EFS-Web and is hereby incorporated by reference in its entirety.

SUMMARY

In an aspect, a method for altering the genome of an organelle may comprise: (a) introducing into an organelle comprising the following: (i) a first polynucleotide encoding at least one guide polynucleic acid, wherein the at least one guide polynucleic acid directs a polynucleotide guided polypeptide to cleave at least one target sequence present in an organelle genome; (ii) a second polynucleotide encoding a polynucleotide guided polypeptide, wherein the polynucleotide guided polypeptide, when associated with the guide polynucleic acid, cleaves the at least one target sequence; (iii) optionally, a third polynucleotide encoding at least one homologous organelle DNA sequence, wherein the at least one homologous organelle DNA is of sufficient size for homologous recombination, wherein integration of the at least one homologous organelle DNA sequence into the organelle genome results in removal of the at least one target sequence; (iv) optionally, a fourth polynucleotide encoding at least one selectable marker or at least one screenable marker, or both; wherein the fourth polynucleotide is operably linked to a promoter that is functional in the organelle; and (v) optionally, a fifth polynucleotide encoding an origin of replication that is functional in the organelle; and (b) growing a cell comprising the organelle of (a) under conditions in which the first polynucleotide of (i) and the second polynucleotide of (ii) are each expressed.

In another aspect, a method for altering the genome of an organelle may comprise: (a) introducing into an organelle a recombinant DNA construct comprising the following: (i) a first polynucleotide encoding at least one guide polynucleic acid, wherein the at least one guide polynucleic acid directs a polynucleotide guided polypeptide to cleave at least one target sequence present in an organelle genome; (ii) a second polynucleotide encoding a polynucleotide guided polypeptide, wherein the polynucleotide guided polypeptide, when associated with the guide polynucleic acid, cleaves the at least one target sequence; (iii) optionally, a third polynucleotide encoding at least one homologous organelle DNA sequence, wherein the at least one homologous organelle DNA is of sufficient size for homologous recombination, wherein integration of the at least one homologous organelle DNA sequence into the organelle genome results in removal of the at least one target sequence; (iv) optionally, a fourth polynucleotide encoding at least one selectable marker or at least one screenable marker, or both; wherein the fourth polynucleotide is operably linked to a promoter that is functional in the organelle; and (v) optionally, a fifth polynucleotide encoding an origin of replication that is functional in the organelle; and (b) growing a cell comprising the organelle of (a) under conditions in which the first polynucleotide of (i) and the second polynucleotide of (ii) are each expressed In some embodiments, the method may further comprise a step (c) of selecting a cell having an organelle that comprises an altered genome. In some embodiments, the method may further comprise a step (d) of selecting a cell that is homoplasmic for the altered genome of the organelle.

In some embodiments, the method may comprise introducing into an organelle the third polynucleotide of (iii), wherein the third polynucleotide of (iii) may comprise a sixth and a seventh polynucleotide, wherein the sixth and the seventh polynucleotides correspond to two adjacent regions of homology in the organelle genome, wherein the sixth and seventh polynucleotides are separated by a sequence that is heterologous to the organelle DNA. In some embodiments, the sequence that is heterologous to the organelle DNA may comprise at least one selected from the group consisting of: the first polynucleotide, the second polynucleotide, the fourth polynucleotide, an eighth polynucleotide, and any combination thereof, wherein the eighth polynucleotide encodes an RNA that is heterologous to the organelle.

In another embodiment, the at least one guide polynucleic acid may be present on a polycistronic transcription unit. In some embodiments, the at least one guide polynucleic acid may be processed from a polycistronic RNA after transcription of the polycistronic transcription unit by use of at least one selected from the group consisting of: an RNA cleavage site, a Csy4 cleavage site, a ribozyme cleavage site, a polynucleotide guided polypeptide cleavage site, the presence of a tRNA sequence, and any combination thereof. In some embodiments, the polycistronic RNA may comprise a first tRNA sequence 5' to the at least one guide RNA and a second tRNA sequence 3' to the at least one guide RNA.

In another embodiment, the method may comprise the eighth polynucleotide, wherein the eighth polynucleotide may encode at least one selected from the group consisting of: a herbicide tolerance protein, a pesticidal protein, an accessory protein that binds to a pesticidal protein, a dsRNA, a siRNA, a miRNA, and any combination thereof, wherein the dsRNA, the siRNA and the miRNA suppress at least one target gene present in a plant pest. In some embodiments, the method may comprise the eighth polynucleotide, wherein the eighth polynucleotide may be operably linked to at least one regulatory element that is active in an organelle. In some embodiments, the at least one regulatory element may be a promoter.

In another embodiment, at least one selected from the group consisting of: the first polynucleotide, the second polynucleotide, the fourth polynucleotide, the fifth polynucleotide, and any combination thereof, may be located outside the region bounded by the sixth and the seventh polynucleotide.

In another embodiment, the method may comprise the fourth and fifth polynucleotides, wherein both the fourth and the fifth polynucleotides may be located outside the region bounded by the sixth and the seventh polynucleotides.

In another embodiment, the method may comprise the fourth polynucleotide, wherein the fourth polynucleotide may comprise a first sequence encoding a positive selectable marker and a second sequence encoding a negative selectable marker, wherein the first and the second sequence may be each operably linked to a promoter that is functional in the organelle.

In another embodiment, the method may comprise the fifth polynucleotide, wherein the fifth polynucleotide may encode an origin of replication that is functional in a plastid (e.g., a chloroplast), wherein the origin of replication functional in a plastid may correspond to DNA sequence from a plastid rRNA intergenic region.

In another embodiment, the method may comprise the fifth polynucleotide, wherein the fifth polynucleotide may encode an origin of replication that is functional in a mitochondrion.

In some embodiments, the polynucleotide-guided polypeptide may be selected from the group consisting of: a Cas9 protein, a MAD2 protein, a MAD7 protein, a CRISPR nuclease, a nuclease domain of a Cas protein, a Cpf1 protein, an Argonaute, modified versions thereof, and any combination thereof.

In some embodiments, the recombinant DNA construct may further comprise a ninth and tenth polynucleotide that have at least 100 nucleotides of 100 percent sequence identity to each other, wherein the ninth and tenth polynucleotides are arranged as direct repeats in the recombinant DNA construct.

In some embodiments, the recombinant DNA construct may be linear and further wherein the ninth and tenth polynucleotides may be present at the 5' and 3' ends of the recombinant DNA construct In another embodiment, the method may comprise a recombinant DNA construct that comprises at least one selected from the group consisting of: the first polynucleotide, the second polynucleotide, the third polynucleotide, the fourth polynucleotide, the fifth polynucleotide, and any combination thereof. In some embodiments, the method may comprise more than one such recombinant DNA construct.

In another embodiment, the recombinant DNA construct may further comprise a ninth and tenth polynucleotide, wherein the ninth and tenth polynucleotide may have 100 percent sequence identity to each other, and further wherein the ninth and tenth polynucleotides may be arranged as direct repeats in the recombinant DNA construct. In some embodiments, the ninth and tenth polynucleotides may have at least 20, 21, 22, 23, 24, 25, 30, 40, 50, 60, 70, 80, 90 or 100 nucleotides of 100 percent sequence identity to each other. Optionally, the recombinant DNA construct may be linear and the ninth and tenth polynucleotides are present at the 5' and 3' ends of the recombinant DNA construct.

In another embodiment, any of the methods herein may further involve introducing into the organelle a polynucleotide encoding at least one selectable marker selected from the group consisting of: a positive selectable marker, a negative selectable marker, and any combination thereof. In some embodiments, the positive selectable marker may be an herbicide tolerance protein. In some embodiments, the herbicide tolerance protein may be at least one selected from the group consisting of: a 4-hydroxphenylpyruvate dioxygenase (HPPD), a sulfonylurea-tolerant acetolactate synthase (ALS), an imidazolinone-tolerant acetolactate synthase (ALS), a glyphosate-tolerant 5-enolpyruvylshikimate-3-phosphate synthase (EPSPS), a glyphosate-tolerant glyphosate oxidoreductase (GOX), a glyphosate N-acetyltransferase (GAT), a phosphinothricin acetyl transferase (PAT), a protoporphyrinogen oxidase (PROTOX), an auxin enzyme or receptor, a P450 polypeptide, an acetyl coenzyme A carboxylase (ACCase), and any combination thereof.

In some embodiments, the method may further involve growing the cell in the presence of a positive selection agent and selecting a cell that is homoplasmic for the altered genome of the organelle. In some embodiments, the method may further involve growing the cell in the absence of the positive selection agent, followed by selecting a cell that lacks a non-integrated recombinant DNA construct. In some embodiments, the method may further involve growing the cell in the absence of the positive selection agent, followed by growing the cell in the presence of a negative selection agent, followed by selecting a cell that lacks a non-integrated recombinant DNA construct. In some embodiments, the cell may be selected from the group consisting of: a yeast cell, an algal cell, a plant cell, an insect cell, a non-human animal cell, an isolated and purified human cell, and a mammalian tissue culture cell. In some embodiments, in the method for a plant cell, the organelle may be a plastid (e.g., a chloroplast) or a mitochondrion. In some embodiments, the method may further involve regenerating or growing a plant from the plant cell comprising an altered organelle genome. In some embodiments, the plant cell may be monocot cell, e.g., a maize cell. The plant cell may be a dicot cell, e.g., a soybean cell.

In some embodiments, the cell maybe a plant cell, wherein the organelle is a plastid or a mitochondrion, and wherein the method further comprises regenerating a plant from the plant cell comprising an altered organelle genome. In some embodiments, the cell may be a yeast cell or an algal cell. In some embodiments, a plant, seed, root, stem, leaf, flower, fruit, or bean produced by the method disclosed herein may comprise an organelle with an altered genome.

In another embodiment, the alteration of the genome of the organelle may comprise an insertion of an expression cassette. In some embodiments, the expression cassette may be a polycistronic expression cassette. In some embodiments, the polycistronic expression cassette may encode a selectable marker or a screenable marker, or both.

In another aspect, a recombinant DNA construct may comprise the following: (i) a first polynucleotide encoding at least one guide polynucleic acid, wherein the at least one guide polynucleic acid directs a polynucleotide guided polypeptide to cleave at least one target sequence present in an organelle genome; (ii) a second polynucleotide encoding a polynucleotide guided polypeptide, wherein the polynucleotide guided polypeptide, when associated with the guide polynucleic acid, cleaves the at least one target sequence; (iii) optionally, a third polynucleotide encoding at least one homologous organelle DNA sequence, wherein the at least one homologous organelle DNA is of sufficient size for homologous recombination, wherein integration of the at least one homologous organelle DNA sequence into the organelle genome results in removal of the at least one target sequence; (iv) optionally, a fourth polynucleotide encoding at least one selectable marker or at least one screenable marker, or both; wherein the fourth polynucleotide is operably linked to a promoter that is functional in the organelle; and (v) optionally, a fifth polynucleotide encoding an origin of replication that is functional in the organelle. In some embodiments, the third polynucleotide of (iii) may comprise a sixth and a seventh polynucleotide, wherein the sixth and the seventh polynucleotides correspond to two adjacent regions of homology in the organelle genome, wherein the sixth and seventh polynucleotides are separated by a sequence that is heterologous to the organelle DNA. In some embodiments, a yeast cell, algal cell, plant cell, plant, seed, root, stem, leaf, flower, fruit, or bean may comprise the recombinant DNA construct.

In another aspect, a recombinant DNA construct may comprise the following: (i) a first polynucleotide encoding at least one guide RNA, wherein the at least one guide RNA directs a polynucleotide guided polypeptide to cleave at least one target sequence present in an organelle genome; (ii) a second polynucleotide encoding a polynucleotide guided polypeptide, wherein the polynucleotide guided polypeptide, when associated with the guide RNA, cleaves the at least one target sequence; (iii) a third polynucleotide comprising a sixth and a seventh polynucleotide, wherein the sixth and the seventh polynucleotides correspond to two adjacent regions of homology in the organelle genome, wherein the sixth and seventh polynucleotides are separated by a sequence that is heterologous to the organelle DNA, wherein the sequence that is heterologous to the organelle DNA comprises at least one selected from the group consisting of: the first polynucleotide, the second polynucleotide, the fourth polynucleotide, an eighth polynucleotide, and any combination thereof, wherein the eighth polynucleotide encodes an RNA that is heterologous to the organelle; (iv) optionally, a fourth polynucleotide encoding at least one selectable marker or at least one screenable marker, or both; wherein the fourth polynucleotide is operably linked to a promoter that is functional in the organelle; and (v) optionally, a fifth polynucleotide encoding an origin of replication that is functional in the organelle.

In another aspect, a method for altering the genome of an organelle may comprise: (a) introducing into a cell: (i) a polynucleotide encoding an RNA sequence comprising an organelle targeting RNA operably linked to a guide polynucleic acid, wherein the guide polynucleic acid directs a polynucleotide guided polypeptide to cleave a target sequence present in an organelle genome, wherein the polynucleotide is operably linked to at least one regulatory element; and (ii) a second polynucleotide encoding a modified polynucleotide guided polypeptide, wherein the second polynucleotide is operably linked to at least one regulatory element, and wherein the modified polynucleotide guided polypeptide comprises a polynucleotide guided polypeptide operably linked to an organelle targeting peptide; wherein the organelle targeting RNA of (i) and the organelle targeting peptide of (ii) each target the same organelle; and (b) growing the cell under conditions in which the polynucleotide of (i) and the second polynucleotide of (ii) are both expressed. In some embodiments, the method may further comprise a step (c) of selecting a cell having an organelle that comprises an altered genome. In some embodiments, the method may further comprise a step (d) of selecting a cell that is homoplasmic for the altered genome of the organelle.

In another aspect, a method for altering the genome of an organelle may comprise: (a) introducing into a cell: (i) a polynucleotide encoding an RNA sequence comprising an organelle targeting RNA operably linked to a guide polynucleic acid, wherein the guide polynucleic acid directs a polynucleotide guided polypeptide to cleave a target sequence present in an organelle genome, wherein the polynucleotide is operably linked to at least one regulatory element; and (ii) a third polynucleotide, wherein the third polynucleotide is operably linked to at least one regulatory element, wherein the third polynucleotide encodes an RNA molecule comprising an organelle targeting RNA operably linked to an RNA sequence encoding a polynucleotide guided polypeptide; wherein the organelle targeting RNA of (i) and the organelle targeting RNA of (ii) each target the same organelle; and (b) growing the cell under conditions in which the polynucleotide of (i) and the third polynucleotide of (ii) are both expressed. In some embodiments, the method may further comprise a step (c) of selecting a cell having an organelle that comprises an altered genome. In some embodiments, the method may further comprise a step (d) of selecting a cell that is homoplasmic for the altered genome of the organelle.

In another embodiment, any of the methods herein may further comprise introducing a polynucleotide comprising at least one donor polynucleotide (e.g. donor DNA) into the organelle, wherein the at least one donor polynucleotide (e.g. donor DNA) is bounded by at least one homologous sequence with respect to the organelle genome, wherein integration of all or part of the at least one donor polynucleotide into the organelle genome results in removal of the target site of the guide polynucleic acid. In some embodiments, the at least one donor polynucleotide (e.g. donor DNA) may comprise a first nucleic acid sequence heterologous to the organelle genome, wherein the first nucleic acid sequence is bounded by a second and a third nucleic acid sequence, wherein the second and the third nucleic acid sequences correspond to two adjacent regions of homology in the organelle genome. In some embodiments, the second or the third nucleic acid sequence, or both, may comprise at least one altered sequence, wherein the at least one altered sequence is altered with respect to at least one additional target site in the organelle genome, wherein the at least one altered sequence is not recognized by at least one additional guide polynucleic acid, wherein the at least one additional guide polynucleic acid may direct a polynucleotide guided polypeptide to cleave the at least one additional target site in the organelle genome. In some embodiments, the at least one additional target site in the organelle genome may be present in at least one essential coding region. In some embodiments, the polynucleotide introduced into the organelle may further comprise a fourth nucleic acid sequence, wherein the fourth nucleic acid sequence encodes the at least one additional guide polynucleic acid. In some embodiments, the at least one additional guide polynucleic acid may be operably linked to a promoter that is active in the organelle.

In some embodiments, the polynucleotide introduced into the organelle further may comprise a fourth nucleic acid sequence, wherein the fourth nucleic acid sequence encodes the at least one additional guide RNA operably linked to a promoter that is active in the organelle. In some embodiments, a cell produced by the method disclosed herein may be selected from the group consisting of: a yeast cell, an algal cell, a plant cell, an insect cell, a non-human animal cell, an isolated and purified human cell, and a mammalian tissue culture cell. In some embodiments, a plant, seed, root, stem, leaf, flower, fruit, or bean produced by the method disclosed herein may comprise an organelle with an altered genome.

In another aspect, a method for altering a genome of an organelle may comprise: (a) introducing into an organelle of a cell the following: (i) at least one guide RNA, wherein the at least one guide RNA directs a polynucleotide guided polypeptide to cleave at least one target sequence present in the genome of the organelle; (ii) a polynucleotide guided polypeptide, wherein the polynucleotide guided polypeptide, when associated with the at least one guide RNA, cleaves the at least one target sequence; and (iii) a replacement DNA; and (b) selecting a cell comprising an organelle comprising the replacement DNA. In some embodiments, the replacement DNA of step (a) part (iii) may comprise fragments of organellar DNA or a complete organellar DNA from a cultivar, line, sub-species and other species and is distinct from the genome of the organelle of step (a). In some embodiments, the replacement DNA may be lacking the at least one target sequence. In some embodiments, after step (a) part (ii) and prior to step (a) part (iii), a cell may be selected in which the genome of the organelle has been eliminated. In some embodiments, the at least one target sequence may not be present in the replacement DNA.

In some embodiments, the guide polynucleic acid in the methods and compositions of matter described herein may comprise the following: i) at least 17 nucleotides that are complementary to at least 17 nucleotides of a target polynucleic acid, wherein said target polynucleic acid is located in the genome of an organelle; and ii) a region that contacts a polynucleotide-guided polypeptide. The guide polynucleic acid may comprise one or more RNA bases. In some embodiments, the guide polynucleic acid may be a guide RNA. The guide polynucleic acid may be a dual guide RNA. In some embodiments, the guide polynucleic acid may be a single guide RNA.

In another embodiment, the polynucleotide-guided polypeptide in the methods and compositions of matter described herein may be selected from the group consisting of: a Cas9 protein, a MAD2 protein, a MAD7 protein, a CRISPR nuclease, a nuclease domain of a Cas protein, a Cpf1 protein, an Argonaute, modified versions thereof, and any combination thereof. In some embodiments, the sequence encoding the polynucleotide-guided polypeptide may be codon-optimized for a human, a yeast, an alga, or a plant species.

In another embodiment, the cell may be a plant cell, the organelle may be a plastid (e.g., a chloroplast) or a mitochondrion, and the method may further comprise regenerating or growing a plant from the plant cell comprising an altered organelle genome.

In another embodiment, a cell produced by any of the methods described herein may be selected from the group consisting of: a yeast cell, an algal cell, a plant cell, an insect cell, a non-human animal cell, an isolated and purified human cell, and a mammalian tissue culture cell.

In another embodiment, a plant, seed, root, stem, leaf, flower, fruit, or bean produced by any of the methods described herein may comprise an organelle with an altered genome.

In another embodiment, a cell comprising any of the recombinant DNA constructs described herein may be selected from the group consisting of: a yeast cell, an algal cell, a plant cell, an insect cell, a non-human animal cell, an isolated and purified human cell, and a mammalian tissue culture cell.

In another embodiment, a plant, seed, root, stem, leaf, flower, fruit, or bean comprising any of the recombinant DNA constructs described herein may comprise an organelle with an altered genome.

In one embodiment, a polynucleotide may comprise a) an organelle targeting sequence; and b) a guide polynucleic acid, wherein the guide polynucleic acid comprises i) at least 17 nucleotides that are complementary to at least 17 nucleotides of a target polynucleic acid, wherein said target polynucleic acid is located in the genome of an organelle; and ii) a region that contacts a polynucleotide-guided polypeptide, wherein said organelle targeting sequence and said guide polynucleic acid sequence are operably linked. In another embodiment, the polynucleotide comprises one or more RNA bases. In another embodiment, the polynucleotide further comprises a sequence encoding the polynucleotide-guided polypeptide. In another embodiment, said polynucleotide-guided polypeptide is a Cas9 protein. In another embodiment, said polynucleotide-guided polypeptide is an Argonaute protein. In another embodiment, said polynucleotide-guided polypeptide is a nuclease in a CRISPR family. In another embodiment, said polynucleotide-guided polypeptide is Cpf1. In another embodiment, the sequence encoding said polynucleotide-guided polypeptide is codon-optimized for a human. In another embodiment, the sequence encoding said polynucleotide-guided polypeptide is codon-optimized for a plant species. In another embodiment, said target polynucleic acid comprises a protospacer adjacent motif (PAM) sequence. In another embodiment, said Cas9 has been engineered to associate with an altered PAM sequence. In another embodiment, said polynucleotide-guided polypeptide selectively cleaves the target polynucleic acid. In another embodiment, said polynucleotide-guided polypeptide selectively induces a double-strand break in the target polynucleic acid. In another embodiment, said polynucleotide-guided polypeptide comprises a nuclease domain that induces a nick in the target polynucleic acid. In another embodiment, the polynucleotide comprises two or more different guide polynucleic acids. In another embodiment, the guide polynucleic acid is comprised of a dual-guide RNA. In another embodiment, the guide polynucleic acid is a single guide RNA. In another embodiment, the guide polynucleic acid is comprised of a crRNA and a trRNA, wherein said crRNA and said trRNA are optionally linked. In another embodiment, said guide polynucleic acid comprises a region that is engineered to be complementary to at least 18 nucleotides of the target polynucleic acid in the organelle of a cell. In another embodiment, said guide polynucleic acid is engineered to be substantially complementary to at least 22 nucleic acids of the target polynucleic acid in the organelle of a cell. In another embodiment, said at least 17 nucleotides are contiguous. In another embodiment, said organelle is a mitochondrion. In another embodiment, said organelle is a plastid. In another embodiment, said guide polynucleic acid is engineered to hybridize to a region of a target gene disclosed herein. In another embodiment, the polynucleotide further comprises a modified RNA donor sequence, wherein the modified RNA donor sequence comprises an organelle targeting RNA operably linked to a donor RNA.

In another embodiment, a DNA sequence that when translated to RNA may result in a polynucleotide of the disclosure.

In another embodiment, a polynucleotide encoding an RNA sequence may comprise an organelle targeting RNA operably linked to a guide RNA, wherein the guide RNA directs a polynucleotide guided polypeptide to cleave a target sequence present in an organelle genome. The RNA sequence may further comprise a sequence encoding a polynucleotide guided polypeptide, and optionally, an RNA cleavage site between the guide RNA and the sequence encoding a polynucleotide guided polypeptide.

In another embodiment, an organelle may comprise the polynucleotide of the disclosure. In some embodiments, the organelle is a mitochondrion. In some embodiments, the organelle is a plastid.

In another embodiment, a cell may comprise any of the polynucleotides of the disclosure. The cell may further comprise a polynucleotide encoding a modified polynucleotide guided polypeptide, wherein the modified polynucleotide guided polypeptide comprises a polynucleotide guided polypeptide operably linked to an organelle targeting peptide.

In another embodiment, a method for introducing a guide polynucleic acid into an organelle of a cell may comprise: (a) introducing into a cell a polynucleotide encoding an RNA sequence comprising an organelle targeting RNA operably linked to a guide polynucleic acid, wherein the guide polynucleic acid directs a polynucleotide guided polypeptide to cleave a target sequence present in an organelle genome, further wherein the polynucleotide is operably linked to at least one regulatory element; and (b) growing the cell under conditions in which the polynucleotide is expressed.

In another embodiment, a method for altering the genome of an organelle may comprise: (a) introducing into a cell: (i) a polynucleotide encoding an RNA sequence comprising an organelle targeting RNA operably linked to a guide polynucleic acid, wherein the guide polynucleic acid directs a polynucleotide guided polypeptide to cleave a target sequence present in an organelle genome, wherein the polynucleotide is operably linked to at least one regulatory element; and (ii) a second polynucleotide encoding a modified polynucleotide guided polypeptide, wherein the second polynucleotide is operably linked to at least one regulatory element, and wherein the modified polynucleotide guided polypeptide comprises a polynucleotide guided polypeptide operably linked to an organelle targeting peptide; wherein the organelle targeting RNA of (i) and the organelle targeting peptide of (ii) each target the same organelle; and (b) growing the cell under conditions in which the polynucleotide of (i) and the second polynucleotide of (ii) are both expressed.

In another embodiment, a method for altering the genome of an organelle may comprise: (a) introducing into a cell: (i) a polynucleotide encoding an RNA sequence comprising an organelle targeting RNA operably linked to a guide polynucleic acid, wherein the guide polynucleic acid directs a polynucleotide guided polypeptide to cleave a target sequence present in an organelle genome, wherein the polynucleotide is operably linked to at least one regulatory element; and (ii) a third polynucleotide, wherein the third polynucleotide is operably linked to at least one regulatory element, wherein the third polynucleotide encodes an RNA molecule comprising an organelle targeting RNA operably linked to an RNA sequence encoding a polynucleotide guided polypeptide; wherein the organelle targeting RNA of (i) and the organelle targeting RNA of (ii) each target the same organelle; and (b) growing the cell under conditions in which the polynucleotide of (i) and the third polynucleotide of (ii) are both expressed.

In another embodiment, a method for altering the genome of an organelle may comprise: (a) introducing into a cell a polynucleotide encoding an RNA sequence comprising: (i) an organelle targeting RNA operably linked to a guide polynucleic acid, wherein the guide polynucleic acid is directs a polynucleotide guided polypeptide to cleave a target sequence present in an organelle genome, (ii) a sequence encoding a polynucleotide guided polypeptide, and (iii) an RNA cleavage site between the guide polynucleic acid and the sequence encoding a polynucleotide guided polypeptide, wherein the polynucleotide is operably linked to at least one regulatory element; and (b) growing the cell under conditions in which the polynucleotide of (a) is expressed.

In another embodiment, any of the methods herein may further comprise introducing a polynucleotide comprising at least one donor polynucleotide (e.g. donor DNA) into the organelle, wherein the at least one donor polynucleotide (e.g. donor DNA) is bounded by at least one homologous sequence with respect to the organelle genome, wherein integration of all or part of the at least one donor polynucleotide into the organelle genome results in removal of the target site of the guide polynucleic acid. The at least one donor polynucleotide (e.g. donor DNA) may comprise a first nucleic acid sequence heterologous to the organelle genome, wherein the first nucleic acid sequence is bounded by a second and a third nucleic acid sequence, wherein the second and the third nucleic acid sequences correspond to two adjacent regions of homology in the organelle genome. Additionally, the second or the third nucleic acid sequence, or both, may comprise at least one altered sequence, wherein the at least one altered sequence is altered with respect to at least one additional target site in the organelle genome, wherein the at least one altered sequence is not recognized by at least one additional guide polynucleic acid, wherein the at least one additional guide polynucleic acid directs a polynucleotide guided polypeptide to cleave the at least one additional target site in the organelle genome. The at least one additional target site in the organelle genome may be present in at least one essential coding region. The polynucleotide introduced into the organelle may further comprise a fourth nucleic acid sequence, wherein the fourth nucleic acid sequence encodes the at least one additional guide polynucleic acid operably linked to a promoter that is active in the organelle.

In another embodiment, a polynucleotide may encode a modified RNA donor sequence, wherein the modified RNA donor sequence may comprise an organelle targeting RNA operably linked to a donor RNA. The modified RNA donor sequence may comprise a reverse transcriptase primer site. Additionally, a cell comprising the polynucleotide, and further comprising a polynucleotide encoding a modified reverse transcriptase, wherein the modified reverse transcriptase comprises a reverse transcriptase operably linked to an organelle targeting peptide.

In another embodiment, a method of altering the genome of an organelle may further comprise introducing a donor polynucleotide into the organelle, wherein the donor polynucleotide is introduced into the organelle by: (a) introducing the polynucleotide encoding a modified RNA donor sequence into the cell, wherein the polynucleotide is operably linked to at least one regulatory element; (b) introducing into the cell a polynucleotide encoding a modified reverse transcriptase, wherein the modified reverse transcriptase comprises a reverse transcriptase operably linked to an organelle targeting peptide, wherein the polynucleotide is operably linked to at least one regulatory element, wherein the organelle targeting RNA of (a) and the organelle targeting peptide of (b) each target the same organelle; and (c) growing the cell under conditions wherein the polynucleotides of (a) and (b) are both expressed.

In another embodiment, a method for altering the genome of an organelle may comprise: (a) introducing into an organelle a recombinant DNA construct comprising the following: (i) a first polynucleotide encoding at least one guide polynucleic acid, wherein the at least one guide polynucleic acid directs a polynucleotide guided polypeptide to cleave at least one target sequence present in an organelle genome; (ii) a second polynucleotide encoding a polynucleotide guided polypeptide, wherein the polynucleotide guided polypeptide, when associated with the guide polynucleic acid, cleaves the at least one target sequence; (iii) a third polynucleotide encoding at least one homologous organelle DNA sequence, wherein the at least one homologous organelle DNA is of sufficient size for homologous recombination, wherein integration of the at least one homologous organelle DNA sequence into the organelle genome results in removal of the at least one target sequence; (iv) optionally, a fourth polynucleotide encoding at least one selectable marker; wherein the fourth polynucleotide is operably linked to a promoter that is functional in the organelle; and (v) optionally, a fifth polynucleotide encoding an origin of replication that is functional in the organelle; and (b) growing a cell comprising the organelle of (a) under conditions in which the first polynucleotide of (i) and the second polynucleotide of (ii) are each expressed. The third polynucleotide of (iii) may comprise a sixth and a seventh polynucleotide, wherein the sixth and the seventh polynucleotides correspond to two adjacent regions of homology in the organelle genome, wherein the sixth and seventh polynucleotides are separated by a sequence that is heterologous to the organelle DNA, wherein the sequence that is heterologous to the organelle DNA comprises at least one selected from the group consisting of: the first polynucleotide, the second polynucleotide, the fourth polynucleotide and an eighth polynucleotide, wherein the eighth polynucleotide encodes an RNA that is heterologous to the organelle.

In another embodiment, a method wherein at least one selected from the group consisting of: the first polynucleotide, the second polynucleotide, the fourth polynucleotide and the fifth polynucleotide, may be located outside the region bounded by the sixth and the seventh polynucleotide.

In another embodiment, a method wherein both the fourth and the fifth polynucleotides may be located outside the region bounded by the sixth and the seventh polynucleotides.

In another embodiment, the fourth polynucleotide comprises a first sequence encoding a positive selectable marker and a second sequence encoding a negative selectable marker, wherein the first and the second sequence are each operably linked to a promoter that is functional in the organelle.

In another embodiment, the fifth polynucleotide encodes a plastid origin of replication, wherein the plastid origin of replication corresponds to DNA sequence from a plastid rRNA intergenic region.

In another embodiment, the fifth polynucleotide encodes a mitochondrial origin of replication.

In another embodiment, the recombinant DNA construct further comprises an eighth and ninth polynucleotide, wherein the eighth and ninth polynucleotide have at least 100 nucleotides of 100 percent sequence identity to each other, wherein the eighth and ninth polynucleotides are arranged as direct repeats in the recombinant DNA construct. Optionally, the recombinant DNA construct is linear and the eighth and ninth polynucleotides are present at the 5' and 3' ends of the recombinant DNA construct.

In another embodiment, the recombinant DNA construct is linear and single-stranded, and the recombinant DNA construct is operably linked to a modified VirD2 protein, wherein the modified VirD2 protein comprises a VirD2 protein operably linked to an organelle targeting peptide, wherein the modified VirD2 protein has also been modified such that each native nuclear localization sequence of the VirD2 protein is no longer functional. Optionally, the recombinant DNA construct is operably linked to at least one modified VirE2 protein, wherein the at least one modified VirE2 protein comprises a VirE2 protein operably linked to an organelle targeting peptide, wherein the at least one modified VirE2 protein has also been modified such that each native nuclear localization sequence of the VirE2 protein is no longer functional. Optionally, the recombinant DNA construct is operably linked to at least one modified RecA protein, wherein the at least one modified RecA protein comprises a RecA protein operably linked to an organelle targeting peptide. Optionally, the recombinant DNA construct is operably linked to at least one chimeric polypeptide, wherein the at least one chimeric polypeptide comprises an organelle targeting peptide and a cell penetrating peptide.

In another embodiment, any of the methods herein may further involve introducing into the organelle a polynucleotide encoding at least one selectable marker selected from the group consisting of: a positive selectable marker, a negative selectable marker, and any combination thereof. The positive selectable marker may be an herbicide tolerance protein. The herbicide tolerance protein may be at least one selected from the group consisting of: a 4-hydroxphenylpyruvate dioxygenase (HPPD), a sulfonylurea-tolerant acetolactate synthase (ALS), an imidazolinone-tolerant acetolactate synthase (ALS), a glyphosate-tolerant 5-enolpyruvylshikimate-3-phosphate synthase (EPSPS), a glyphosate-tolerant glyphosate oxidoreductase (GOX), a glyphosate N-acetyltransferase (GAT), a phosphinothricin acetyl transferase (PAT), a protoporphyrinogen oxidase (PROTOX), an auxin enzyme or receptor, a P450 polypeptide and an acetyl coenzyme A carboxylase (ACCase). The method may further involve growing the cell in the presence of a positive selection agent and selecting a cell that is homoplasmic for the altered genome of the organelle. Optionally, the method may further involve growing the cell in the absence of the positive selection agent, followed by selecting a cell that lacks a non-integrated recombinant DNA construct. Alternatively, the method may further involve growing the cell in the absence of the positive selection agent, followed by growing the cell in the presence of a negative selection agent, followed by selecting a cell that lacks a non-integrated recombinant DNA construct. In the method, the cell may be a plant cell, the organelle may be a plastid. The method may further involve regenerating a plant from the plant cell comprising an altered organelle genome. The plant cell may be monocot cell, e.g., a maize cell. The plant cell may be a dicot cell, e.g., a soybean cell.

In another embodiment, in any of the methods herein for altering the genome of an organelle to contain a heterologous polynucleotide, the heterologous polynucleotide may encode at least one selected from the group consisting of: a herbicide tolerance protein, a pesticidal protein, an accessory protein that binds to a pesticidal protein, a dsRNA, a siRNA and a miRNA, wherein the dsRNA, the siRNA and the miRNA suppress at least one target gene present in a plant pest. The herbicide tolerance protein may be at least one selected from the group consisting of: a 4-hydroxphenylpyruvate dioxygenase (HPPD), a sulfonylurea-tolerant acetolactate synthase (ALS), an imidazolinone-tolerant acetolactate synthase (ALS), a glyphosate-tolerant 5-enolpyruvylshikimate-3-phosphate synthase (EPSPS), a glyphosate-tolerant glyphosate oxidoreductase (GOX), a glyphosate N-acetyltransferase (GAT), a phosphinothricin acetyl transferase (PAT), a protoporphyrinogen oxidase (PROTOX), an auxin enzyme or receptor, a P450 polypeptide and an acetyl coenzyme A carboxylase (ACCase). The pesticidal protein may be at least one selected from the group consisting of: Cry1Ac, Cyt1Aa, Cry1Ab, Cry2Aa, Cry1I, Cry1C, Cry1D, Cry1E, Cry1Be, Cry1Fa and Vip3A. The accessory protein that binds to a pesticidal protein may be at least one selected from the group consisting of: a 20 kDa accessory protein and a 19 kDa accessory protein. The dsRNA, the siRNA and the miRNA can suppress at least one target gene selected from the group consisting of: proteasome A-type subunit peptide (Pas-4), ACT, SHR, EPIC2B and PnPMAI. The heterologous polynucleotide may be operably linked to at least one regulatory element that is active in an organelle. The at least one regulatory element may be selected from the group consisting of: a maize clpP promoter combined with a maize clpP 5'-UTR, a maize clpP promoter combined with a 5'-UTR from gene 10 of bacteriophage T7, a tomato psbA promoter is combined with a 5'-UTR from gene 10 of bacteriophage T7 and a tomato rrn16 promoter combined with a modified accD 5'-UTR. The cell may be a plant cell, wherein the organelle is a plastid, and wherein the method further comprises regenerating a plant from the plant cell comprising an altered organelle genome. The plant cell may be a soybean cell.

In another embodiment, a cell may comprise an organelle with an altered genome, wherein the cell may be produced by any of the above methods. The cell may be selected from the group consisting of: a yeast cell, an algal cell, a plant cell, an insect cell, a non-human animal cell, an isolated and purified human cell, and a mammalian tissue culture cell.

In another embodiment, a method may comprise altering the genome of an organelle in a cell as described above, wherein the cell is a plant cell and further wherein a plant is regenerated from a plant cell, wherein the plant comprises an organelle with an altered genome. Also, a plant (e.g., progeny plant) or seed produced from the regenerated plant, wherein the plant or seed comprises an organelle with an altered genome.

In another embodiment, a plant, seed, root, stem, leaf, flower, fruit, or bean may be produced by a method of the disclosure. In some embodiments, the plant, seed, root, stem, leaf, flower, fruit, or bean comprises an organelle with an altered genome.

In another embodiment, a plant, seed, root, stem, leaf, flower, fruit, or bean may comprise a polynucleotide of the disclosure.

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 1 presents the sequence (SEQ ID NO: 144) obtained from PCR amplification of the replaced DNA locus in transformed yeast mitochondrial DNA modified by the Edit Plasmid approach.

FIG. 2 presents the sequence (SEQ ID NO: 171) obtained from PCR amplification of the replaced DNA locus in transformed Chlamydomonas plastid DNA modified by the Edit Plasmid approach.

BRIEF DESCRIPTION OF THE SEQUENCE LISTING

The disclosure is more fully understood from the following detailed description and Sequence Listing, which form a part of this application.

SEQ ID NO: 1 corresponds to the nucleic acid sequence encoding mCas9-A; i.e., a Cas9 comprising ATPase beta mitochondrial targeting peptide.

SEQ ID NO: 2 corresponds to the nucleic acid sequence encoding mCas9-B; i.e., a Cas9 comprising the 70 kD mitochondrial targeting peptide.

SEQ ID NO: 3 corresponds to the nucleic acid sequence encoding a guide RNA-tRNA$^{Lys}$ (tRK1) fusion ("N" residues indicate the variable targeting domain of the guide RNA).

SEQ ID NO: 4 corresponds to the nucleic acid sequence encoding a guide RNA-tRNA$^{Lys}$ fusion (tRK2-2 version for mitochondrial import; "N" residues indicate the variable targeting domain of the guide RNA).

SEQ ID NO: 5 corresponding to the nucleic acid sequence encoding a guide RNA-tRNA$^{Lys}$ fusion with an altered 5' tRNA end.

SEQ ID NO: 6 corresponds to the nucleic acid sequence encoding a guide RNA-tRNA$^{Lys}$ fusion (modified tRK2 version with altered 5' end; "N" residues at the 5' end indicate the variable targeting domain of the guide RNA).

SEQ ID NO: 7 corresponds to the nucleic acid sequence encoding a gRNA embedded in tRK2 intron in the backbone of tRK2-2 (20-mer of "N" residues indicates the variable targeting domain; 3-mer of "N" residues is complementary to the first three nucleotides of the variable targeting domain to preserve the secondary structure for splicing).

SEQ ID NO: 8 corresponds to the nucleic acid sequence encoding a gRNA embedded in tRK2 type intron in the backbone of tRK1 (20-mer of "N" residues indicates the variable targeting domain; 3-mer of "N" residues is complementary to the first three nucleotides of guide RNA to preserve the secondary structure for splicing).

SEQ ID NO: 9 corresponds to the nucleic acid sequence encoding a gRNA fused with second half of tRK1 (B form).

SEQ ID NO: 10 corresponds to the nucleic acid sequence encoding a form of tRK1 to be co-expressed with guide RNA-B form fusion.

SEQ ID NO: 11 corresponds to the nucleic acid sequence encoding a gRNA constructed between the D arm and F hairpin structures.

SEQ ID NO: 12 corresponds to the nucleic acid sequence encoding a gRNA fused with the D arm.

SEQ ID NO: 13 corresponds to the nucleic acid sequence encoding a gRNA fused with F hairpin structure.

SEQ ID NO: 14 corresponds to the nucleotide sequence for the variable targeting domain of a guide RNA to target the cytochrome b gene in mitochondria.

SEQ ID NO: 15 corresponds to the nucleotide sequence for the variable targeting domain of a guide RNA to target the COX1 gene in mitochondria.

SEQ ID NO: 16 corresponds to the nucleotide sequence for the variable targeting domain of a guide RNA to target the COX1 gene in mitochondria.

SEQ ID NO: 17 corresponds to the nucleotide sequence for the variable targeting domain of a guide RNA to target the COX2 gene in mitochondria.

SEQ ID NO: 18 corresponds to the nucleic acid sequence that is fused with the 3' end of a variable targeting domain to create a functional guide RNA for Cas9.

SEQ ID NO: 19 corresponds to the nucleic acid sequence encoding a SNR52 promoter.

SEQ ID NO: 20 corresponds to the nucleic acid sequence encoding a SUP4 Terminator.

SEQ ID NO: 21 corresponds to the nucleic acid sequence for a oligonucleotide primer for paromomycin-resistance template DNA SEQ ID NO: 22 corresponds to the nucleic acid sequence for a complementary oligonucleotide primer to make template DNA with the primer of SEQ ID NO: 21.

SEQ ID NO: 23 corresponds to the nucleic acid sequence encoding the variable targeting domain for a guide RNA that targets the 15S rRNA gene in mitochondria.

SEQ ID NO: 24 corresponds to a nucleic acid sequence encoding a Cas9 gene optimized for expression in yeast mitochondria.

SEQ ID NO: 25 corresponds to the nucleic acid sequence encoding a COX2 promoter.

SEQ ID NO: 26 corresponds to the nucleic acid sequence encoding a COX2 terminator.

SEQ ID NO: 27 corresponds to the nucleotide sequence of the variable targeting domain for a guide RNA to target the mitochondrial 21S rRNA gene in yeast.

SEQ ID NO: 28 corresponds to the nucleic acid sequence encoding the promoter sequence of the 15S rRNA gene.

SEQ ID NO: 29 corresponds to the nucleic acid sequence encoding the terminator sequence of the 15S rRNA gene.

SEQ ID NO: 30 corresponds to the nucleotide sequence for the variable targeting domain of a guide RNA to target the COB gene in mitochondria.

SEQ ID NO: 31 corresponds to the nucleotide sequence for the variable targeting domain of a guide RNA to target the ATP9 gene in mitochondria.

SEQ ID NO: 32 corresponds to the amino acid sequence for the NDUFV2 mitochondrial targeting peptide.

SEQ ID NO: 33 corresponds to the nucleic acid sequence encoding a Cas9 fused with a mitochondrial targeting peptide derived from NDUFV2.

SEQ ID NO: 34 corresponds to the amino acid sequence of the mitochondrial targeting peptide of citrate synthase.

SEQ ID NO: 35 corresponds to the nucleic acid sequence encoding a Cas9 fused with the mitochondrial signal peptide derived from human citrate synthase.

SEQ ID NO: 36 corresponds to the nucleic acid sequence encoding a human 5S rRNA gene for mitochondrial import (the 4-mer "GTCT can be replaced with guide RNA).

SEQ ID NO: 37 corresponds to the nucleotide sequence of a variable targeting domain for a gRNA sequence targeting the human COX3 gene in mitochondria.

SEQ ID NO: 38 corresponds to the nucleic acid sequence of an expression cassette for a guide RNA utilizing the promoter and terminator of the human 5S rRNA gene.

SEQ ID NO: 39 corresponds to the nucleotide sequence of a variable targeting domain for a guide RNA to target the CAPR locus in mouse mitochondrial DNA (CAP$^R$ allele has an A to G substitution at residue 17).

SEQ ID NO: 40 corresponds to the nucleotide sequence of a polynucleotide modification template with the CAP$^R$ mutation (part of the mouse 16SrRNA).

SEQ ID NO: 41 corresponds to the nucleotide sequence encoding pcoCas9 without NLS & FLAG domains, but with the potato IV intron. The sequence is codon-optimized for *Arabidopsis* (GenBank ID: KF264451).

SEQ ID NO: 42 corresponds to the amino acid sequence of pcoCas9.

SEQ ID NO: 43 corresponds to the amino acid sequence of the transit peptide of AtRbcS (At1g67090). Cleavage occurs after the "N" residue at position 54.

SEQ ID NO: 44 corresponds to the amino acid sequence of the transit peptide of AtCab (NP_001078288.1). Cleavage occurs after the "P" residue at position 55.

SEQ ID NO: 45 corresponds to the amino acid sequence of the transit peptide of At DnaJ8 (NP_178207.1). Cleavage occurs after the "V" residue at position 47.

SEQ ID NO: 46 corresponds to the nucleotide sequence encoding the pcoCas9 with AT-rbcS transit peptide (with potato intron).

SEQ ID NO: 47 corresponds to the amino acid sequence of pcoCas9 with AT-rbcS chloroplast transit peptide.

SEQ ID NO: 48 corresponds to the nucleotide sequence encoding the Vd 5'UTR (gi|301016157|gb|HM136583.11.

SEQ ID NO: 49 corresponds to the nucleotide sequence encoding the AteIF4E1 full-length cDNA.

SEQ ID NO: 50 corresponds to the nucleotide sequence encoding a typical gRNA module (5' terminal 20-mer of "N" residues corresponds to the variable targeting domain).

SEQ ID NO: 51 corresponds to the nucleotide sequence encoding CSY4.

SEQ ID NO: 52 corresponds to the amino acid sequence of the Csy4 polypeptide.

SEQ ID NO: 53 corresponds to the nucleotide sequence of the Csy4 recognition site.

SEQ ID NO: 54 corresponds to the nucleotide sequence encoding a guide RNA flanked by Csy4 recognition sites (multimeric form).

SEQ ID NO: 55 corresponds to the nucleotide sequence encoding a Nt_Chl_rpoB (*Nicotiana tabacum* RNA polymerase beta chain).

SEQ ID NO: 56 corresponds to the nucleotide sequence of variable target region for a guide RNA targeting the plastid rpoB gene from *Nicotiana tabacum*.

SEQ ID NO: 57 corresponds to the nucleotide sequence of variable target region for a guide RNA targeting the plastid rpoB gene from *Nicotiana tabacum*.

SEQ ID NO: 58 corresponds to the nucleotide sequence encoding a Nt_Cp_psbA (*Nicotiana tabacum* photosystem II protein D1).

SEQ ID NO: 59 corresponds to the nucleotide sequence of variable target region for a guide RNA targeting the plastid psbA gene from *Nicotiana tabacum*.

SEQ ID NO: 60 corresponds to the nucleotide sequence of variable target region for a guide RNA targeting the plastid psbA gene from *Nicotiana tabacum*.

SEQ ID NO: 61 corresponds to the nucleotide sequence encoding a Nt_Cp_rps15 (*Nicotiana tabacum* ribosomal protein S15).

SEQ ID NO: 62 corresponds to the nucleotide sequence of variable target region for a guide RNA targeting the plastid rps15 gene from *Nicotiana tabacum*.

SEQ ID NO: 63 corresponds to the nucleotide sequence of variable target region for a guide RNA targeting the plastid rps15 gene from *Nicotiana tabacum*.

SEQ ID NO: 64 corresponds to the nucleotide sequence encoding a Nt_Cp_rpl33 (*Nicotiana tabacum* 50S ribosomal protein L33).

SEQ ID NO: 65 corresponds to the nucleotide sequence of variable target region for a guide RNA targeting the plastid rpl33 gene from *Nicotiana tabacum*.

SEQ ID NO: 66 corresponds to the nucleotide sequence of variable target region for a guide RNA targeting the plastid rpl33 gene from *Nicotiana tabacum*.

SEQ ID NO: 67 corresponds to the nucleotide sequence encoding a GlmaCp rpoB (*Glycine max* RNA polymerase beta chain).

SEQ ID NO: 68 corresponds to the nucleotide sequence of variable target region for a guide RNA targeting the plastid rpoB gene from *Glycine max*.

SEQ ID NO: 69 corresponds to the nucleotide sequence of variable target region for a guide RNA targeting the plastid rpoB gene from *Glycine max*.

SEQ ID NO: 70 corresponds to the nucleotide sequence encoding a GlmaCp psbA (*Glycine max* photosystem II protein D1).

SEQ ID NO: 71 corresponds to the nucleotide sequence of variable target region for a guide RNA targeting the plastid psbA gene from *Glycine max*.

SEQ ID NO: 72 corresponds to the nucleotide sequence of variable target region for a guide RNA targeting the plastid psbA gene from *Glycine max*.

SEQ ID NO: 73 corresponds to the nucleotide sequence encoding a GlmaCp_rps15 (*Glycine max* ribosomal protein S15).

SEQ ID NO: 74 corresponds to the nucleotide sequence of variable target region for a guide RNA targeting the plastid rps15 gene from *Glycine max*.

SEQ ID NO: 75 corresponds to the nucleotide sequence of variable target region for a guide RNA targeting the plastid rps15 gene from *Glycine max*.

SEQ ID NO: 76 corresponds to the nucleotide sequence encoding a GlmaCp_rp133 (*Glycine max* 50S ribosomal protein L33).

SEQ ID NO: 77 corresponds to the nucleotide sequence of variable target region for a guide RNA targeting the plastid rp133 gene from *Glycine max*.

SEQ ID NO: 78 corresponds to the nucleotide sequence of variable target region for a guide RNA targeting the plastid rp133 gene from *Glycine max*.

SEQ ID NO: 79 corresponds to the nucleotide sequence encoding a *Nicotiana benthamiana* rps16 with intron (ribosomal protein S16, GI: KC495035.1).

SEQ ID NO: 80 corresponds to the nucleotide sequence of variable target region for a guide RNA targeting the plastid rps16 gene from *Nicotiana benthamiana*.

SEQ ID NO: 81 corresponds to the nucleotide sequence of variable target region for a guide RNA targeting the plastid rps16 gene from *Nicotiana benthamiana*.

SEQ ID NO: 82 corresponds to the nucleotide sequence encoding a *Nicotiana benthamiana* matK (maturase K, GI: AB040014).

SEQ ID NO: 83 corresponds to the nucleotide sequence of variable target region for a guide RNA targeting the plastid matK gene from *Nicotiana benthamiana*.

SEQ ID NO: 84 corresponds to the nucleotide sequence of variable target region for a guide RNA targeting the plastid matK gene from *Nicotiana benthamiana*.

SEQ ID NO: 85 corresponds to the nucleotide sequence of variable target region for a guide RNA targeting an intergenic region (NtChrC; 57408 . . . 57389) from *Nicotiana tabacum*.

SEQ ID NO: 86 corresponds to the nucleotide sequence of variable target region for a guide RNA targeting an intergenic region (NtChrC; 59412 . . . 59393) from *Nicotiana tabacum*.

SEQ ID NO: 87 corresponds to the nucleotide sequence of variable target region for a guide RNA targeting an intergenic region (NtChrC; 59622 . . . 59603) from *Nicotiana tabacum*.

SEQ ID NO: 88 corresponds to the nucleotide sequence of variable target region for a guide RNA targeting an intergenic region (NtChrC; 65704 . . . 65723) from *Nicotiana tabacum*.

SEQ ID NO: 89 corresponds to the nucleotide sequence of variable target region for a guide RNA targeting an intergenic region (GlmaCp_NC_007942.1_59039-59058) from *Glycine max*.

SEQ ID NO: 90 corresponds to the nucleotide sequence of variable target region for a guide RNA targeting an intergenic region (GlmaCp_NC_007942.1_59100-59119) from *Glycine max*.

SEQ ID NO: 91 corresponds to the nucleotide sequence of variable target region for a guide RNA targeting an intergenic region (GlmaCp_NC_007942.1_62057-62038) from *Glycine max*.

SEQ ID NO: 92 corresponds to the nucleotide sequence of variable target region for a guide RNA targeting an intergenic region (GlmaCp_NC_007942.1_62361-62380) from *Glycine max*.

SEQ ID NO: 93 corresponds to the nucleotide sequence of the target site for the plastid psbA gene.

SEQ ID NO: 94 corresponds to the nucleotide sequence of the region of the polynucleotide modification template that corresponds to the target site of the plastid psbA gene SEQ ID NO: 95 corresponds to the amino acid sequence of the ATPase Beta mitochondrial targeting peptide, which is encoded by SEQ ID NO:1.

SEQ ID NO: 96 corresponds to the amino acid sequence of the Cas9 polypeptide fused to the ATPase Beta mitochondrial targeting peptide, which is encoded by SEQ ID NO:1.

SEQ ID NO: 97 corresponds to the amino acid sequence of the 70 kD mitochondrial targeting peptide, which is encoded by SEQ ID NO:2.

SEQ ID NO: 98 corresponds to the amino acid sequence of the Cas9 polypeptide fused to the 70 kD mitochondrial targeting peptide, which is encoded by SEQ ID NO:2.

SEQ ID NO: 99 corresponds to the nucleotide sequence of the forward primer ZmPclpP-Forward, for PCR amplification of the maize clpP promoter in combination with the clpP 5'-UTR (ZmPclpP:clpP). This forward primer may also be used for PCR amplification of the maize clpP promoter in combination with the 5'-UTR from gene 10 of bacteriophage T7 (ZmPclpP:G10).

SEQ ID NO: 100 corresponds to the nucleotide sequence of the reverse primer ZmPclpP-Reverse, for PCR amplification of the maize clpP promoter in combination with the clpP 5'-UTR (ZmPclpP:clpP).

SEQ ID NO: 101 corresponds to the nucleotide sequence of the reverse primer for PCR amplification of the maize clpP promoter in combination with the 5'-UTR from gene 10 of bacteriophage T7 (ZmPclpP:G10).

SEQ ID NO: 102 corresponds to the nucleotide sequence of the forward primer for PCR amplification of the tomato psbA promoter in combination with the 5'-UTR from gene 10 of bacteriophage T7 (SlPsbA:T7g10).

SEQ ID NO: 103 corresponds to the nucleotide sequence of the reverse primer for PCR amplification of the tomato psbA promoter in combination with the 5'-UTR from gene 10 of bacteriophage T7 (SlPsbA:T7g10).

SEQ ID NO: 104 corresponds to the nucleotide sequence of the forward primer for PCR amplification of the SlPrrn16 promoter portion of the tomato rrn16 promoter in combination with the accD-mod 5'-UTR.

SEQ ID NO: 105 corresponds to the nucleotide sequence of the reverse primer for PCR amplification of the SlPrrn16 promoter portion of the tomato rrn16 promoter in combination with the accD-mod 5'-UTR.

SEQ ID NO: 106 corresponds to the nucleotide sequence of the forward primer for PCR amplification of the accD-mod 5'-UTR portion of the tomato rrn16 promoter in combination with the accD-mod 5'-UTR.

SEQ ID NO: 107 corresponds to the nucleotide sequence of the reverse primer for PCR amplification of the accD-mod 5'-UTR portion of the tomato rrn16 promoter in combination with the accD-mod 5'-UTR.

SEQ ID NO: 108 corresponds to the nucleotide sequence from *Bacillus thuringiensis* serovar *kurstaki* HD73 that encodes a Cry1Ac delta-endotoxin (U89872).

SEQ ID NO: 109 corresponds to the amino acid sequence of the Cry1Ac delta-endotoxin encoded by SEQ ID NO: 108.

SEQ ID NO: 110 corresponds to the nucleotide sequence from *Bacillus thuringiensis* serovar *kurstaki* HD73 that encodes a truncated form of a Cry1Ac delta-endotoxin that has insecticidal activity.

SEQ ID NO: 111 corresponds to the nucleotide sequence from *Bacillus thuringiensis* serovar *israelensis* that encodes a Cyt1Aa protein (Gene ID: 5759908).

SEQ ID NO: 112 corresponds to the nucleotide sequence from *Bacillus thuringiensis* serovar *israelensis* (pBt024) that encodes a 20 kDa accessory protein.

SEQ ID NO: 113 corresponds to the nucleotide sequence from *Bacillus thuringiensis* serovar *israelensis* (pBt022) that encodes a 19 kDa accessory protein.

SEQ ID NO: 114 corresponds to the nucleotide sequence for an open reading frame encoding an *Heterodera glycines* (SCN) specific proteasome A-type subunit peptide referred to herein as Pas-4 (U.S. Pat. No. 8,067,671).

SEQ ID NO: 115 corresponds to nucleotides 552-699 of SEQ ID NO: 114.

SEQ ID NO: 116 corresponds to the nucleotide sequence of a first guide RNA target site in the COX1 gene of *Saccharomyces cerevisiae* mitochondrial DNA. The last three nucleotides are the PAM sequence; these three nucleotides are not present in the variable targeting domain of the corresponding guide RNA.

SEQ ID NO: 117 corresponds to the nucleotide sequence of a second guide RNA target site in the COX1 gene of *Saccharomyces cerevisiae* mitochondrial DNA. The last three nucleotides are the PAM sequence; these three nucleotides are not present in the variable targeting domain of the corresponding guide RNA.

SEQ ID NO: 118 corresponds to the nucleotide sequence of a third guide RNA target site in the COX1 gene of *Saccharomyces cerevisiae* mitochondrial DNA. The last three nucleotides are the PAM sequence; these three nucleotides are not present in the variable targeting domain of the corresponding guide RNA.

SEQ ID NO: 119 corresponds to the nucleotide sequence of a fourth guide RNA target site in the COX1 gene of *Saccharomyces cerevisiae* mitochondrial DNA. The last three nucleotides are the PAM sequence; these three nucleotides are not present in the variable targeting domain of the corresponding guide RNA. This target site sequence is present on the reverse complement of the genic sequence.

SEQ ID NO: 120 corresponds to the nucleotide sequence encoding SpCas9, the Cas9 from *Streptococcus pyogenes*. The coding sequence was optimized for expression in yeast mitochondria.

SEQ ID NO: 121 corresponds to the nucleotide sequence of the minimal promoter and 5' UTR of the COX2 gene of *Saccharomyces cerevisiae* mitochondrial DNA.

SEQ ID NO: 122 corresponds to the nucleotide sequence of the minimal terminator of the COX2 gene of *Saccharomyces cerevisiae* mitochondrial DNA.

SEQ ID NO: 123 corresponds to the nucleotide sequence encoding the tracrRNA, which was used to create guide RNAs targeting the COX2 gene of *Saccharomyces cerevisiae*.

SEQ ID NO: 124 corresponds to the nucleotide sequence of the minimal promoter of the COX3 gene of *Saccharomyces cerevisiae* mitochondrial DNA.

SEQ ID NO: 125 corresponds to the nucleotide sequence encoding the tRNA of the tF(GAA) gene from *Saccharomyces cerevisiae* mitochondrial DNA.

SEQ ID NO: 126 corresponds to the nucleotide sequence encoding the tRNA of the tW(UCA) gene from *Saccharomyces cerevisiae* mitochondrial DNA.

SEQ ID NO: 127 corresponds to the nucleotide sequence of the minimal terminator of the COX3 gene from *Saccharomyces cerevisiae* mitochondrial DNA.

SEQ ID NO: 128 corresponds to the nucleotide sequence encoding the tRNA of the tM(CAU) gene from *Saccharomyces cerevisiae* mitochondrial DNA.

SEQ ID NO: 129 corresponds to the nucleotide sequence encoding GFP. The coding sequence was optimized for expression in yeast mitochondria.

SEQ ID NO: 130 corresponds to the nucleotide sequence encoding the homologous region from *Saccharomyces cerevisiae*, designated HR1, which is adjacent to the first guide RNA target site (SEQ ID NO: 116) in the COX1 gene.

SEQ ID NO: 131 corresponds to the nucleotide sequence encoding the homologous region from *Saccharomyces cerevisiae*, designated HR2, which is adjacent to the second guide RNA target site (SEQ ID NO: 117) in the COX1 gene.

SEQ ID NO: 132 corresponds to the nucleotide sequence encoding the homologous region from *Saccharomyces cerevisiae*, designated HR3, which is adjacent to the third guide RNA target site (SEQ ID NO: 118) in the COX1 gene.

SEQ ID NO: 133 corresponds to the nucleotide sequence encoding the homologous region from *Saccharomyces cerevisiae*, designated HR4, which is adjacent to the fourth guide RNA target site (SEQ ID NO: 119) in the COX1 gene.

SEQ ID NO: 134 corresponds to the nucleotide sequence present in the donor DNA that encodes a variant of the first guide RNA target site (SEQ ID NO: 116) in the COX1 gene. Seven nucleotides have been changed in the variant.

SEQ ID NO: 135 corresponds to the nucleotide sequence present in the donor DNA that encodes a variant of the second guide RNA target site (SEQ ID NO: 117) in the COX1 gene. Sixteen nucleotides at the 5' end have been deleted in the variant.

SEQ ID NO: 136 corresponds to the nucleotide sequence present in the donor DNA that encodes a variant of the third guide RNA target site (SEQ ID NO: 118) in the COX1 gene. Five nucleotides at the 3' end have been deleted in the variant.

SEQ ID NO: 137 corresponds to the nucleotide sequence present in the donor DNA that encodes a variant of the fourth guide RNA target site (SEQ ID NO: 119) in the COX1 gene. Seventeen nucleotides at the 3' end have been deleted in the variant.

SEQ ID NO: 138 corresponds to the nucleotide sequence of PCR primer C, present in the COX1 gene of *Saccharomyces cerevisiae*.

SEQ ID NO: 139 corresponds to the nucleotide sequence of PCR primer D, present in the COX1 gene of *Saccharomyces cerevisiae*.

SEQ ID NO: 140 corresponds to the nucleotide sequence of PCR primer E, present in the COX1 gene of *Saccharomyces cerevisiae*.

SEQ ID NO: 141 corresponds to the nucleotide sequence of PCR primer F, present in the COX1 gene of *Saccharomyces cerevisiae*.

SEQ ID NO: 142 corresponds to the nucleotide sequence of PCR primer 11, present in the GFP coding region of the donor DNA.

SEQ ID NO: 143 corresponds to the nucleotide sequence of PCR primer 12, present in the GFP coding region of the donor DNA.

SEQ ID NO: 144 corresponds to the nucleotide sequence derived from the PCR amplification products of the GFP integration region in transformed yeast mitochondrial DNA.

SEQ ID NO: 145 corresponds to the nucleotide sequence of a first guide RNA target site in the psaA gene of *Chlamydomonas reinhardtii* plastid DNA. The last three nucleotides are the PAM sequence; these three nucleotides are not present in the variable targeting domain of the corresponding guide RNA.

SEQ ID NO: 146 corresponds to the nucleotide sequence of a second guide RNA target site in the psaA gene of *Chlamydomonas reinhardtii* plastid DNA. The last three nucleotides are the PAM sequence; these three nucleotides are not present in the variable targeting domain of the corresponding guide RNA. This target site sequence is present on the reverse complement of the genic sequence.

SEQ ID NO: 147 corresponds to the nucleotide sequence of a third guide RNA target site in the psaA gene of *Chlamydomonas reinhardtii* plastid DNA. The last three nucleotides are the PAM sequence; these three nucleotides are not present in the variable targeting domain of the corresponding guide RNA.

SEQ ID NO: 148 corresponds to the nucleotide sequence of a fourth guide RNA target site in the psaA gene of *Chlamydomonas reinhardtii* plastid DNA. The last three nucleotides are the PAM sequence; these three nucleotides are not present in the variable targeting domain of the corresponding guide RNA. This target site sequence is present on the reverse complement of the genic sequence.

SEQ ID NO: 149 corresponds to the nucleotide sequence encoding SpCas9, the Cas9 from *Streptococcus pyogenes*. The coding sequence was codon-optimized for expression in *Chlamydomonas* chloroplasts.

SEQ ID NO: 150 corresponds to the amino acid sequence of SpCas9, the Cas9 from *Streptococcus pyogenes*, which is encoded by the nucleotide sequences of SEQ ID NO: 150 and SEQ ID NO: 120.

SEQ ID NO: 151 corresponds to the nucleotide sequence of the promoter and 5' UTR of the psaA-exon 1 gene of *Chlamydomonas reinhardtii* plastid DNA.

SEQ ID NO: 152 corresponds to the nucleotide sequence of the promoter and 5' UTR of the psbD gene of *Chlamydomonas reinhardtii* plastid DNA.

SEQ ID NO: 153 corresponds to the nucleotide sequence of the terminator of the rbcL gene of *Chlamydomonas reinhardtii* plastid DNA.

SEQ ID NO: 154 corresponds to the nucleotide sequence of the promoter of the trnW gene of *Chlamydomonas reinhardtii* plastid DNA.

SEQ ID NO: 155 corresponds to the nucleotide sequence of the 3' UTR of the trnW gene of *Chlamydomonas reinhardtii* plastid DNA.

SEQ ID NO: 156 corresponds to the nucleotide sequence encoding the tRNA of the trnW gene of *Chlamydomonas reinhardtii* plastid DNA.

SEQ ID NO: 157 corresponds to the nucleotide sequence encoding the tRNA of the trnK gene of *Chlamydomonas reinhardtii* plastid DNA.

SEQ ID NO: 158 corresponds to the nucleotide sequence encoding the tRNA of the trnL gene of *Chlamydomonas reinhardtii* plastid DNA.

SEQ ID NO: 159 corresponds to the nucleotide sequence encoding the aadA selectable marker.

SEQ ID NO: 160 corresponds to the nucleotide sequence of the promoter and 5' UTR of the rbcL gene of *Chlamydomonas reinhardtii* plastid DNA.

SEQ ID NO: 161 corresponds to the nucleotide sequence of the 3' UTR of the psbA gene of *Chlamydomonas reinhardtii* plastid DNA.

SEQ ID NO: 162 corresponds to the nucleotide sequence encoding GFP. The coding sequence was codon-optimized for expression in *Chlamydomonas* chloroplasts.

SEQ ID NO: 163 corresponds to the nucleotide sequence encoding HR1, a homologous region from *Chlamydomonas reinhardtii* plastid DNA, that is present in a donor DNA.

SEQ ID NO: 164 corresponds to the nucleotide sequence encoding HR2, a homologous region from *Chlamydomonas reinhardtii* plastid DNA, that is present in a donor DNA.

SEQ ID NO: 165 corresponds to the nucleotide sequence encoding HR3, a homologous region from *Chlamydomonas reinhardtii* plastid DNA, that is present in a donor DNA.

SEQ ID NO: 166 corresponds to the nucleotide sequence encoding HR4, a homologous region from *Chlamydomonas reinhardtii* plastid DNA, that is present in a donor DNA.

SEQ ID NO: 167 corresponds to the nucleotide sequence of the forward primer of Primer Set 1 (PS1 FWD Primer), designed to amplify 852 bp of the GFP integration region in the transformed *Chlamydomonas reinhardtii* plastid DNA. PS1 FWD Primer is a chloroplast genomic region-specific primer.

SEQ ID NO: 168 corresponds to the nucleotide sequence of the reverse primer of Primer Set 1 (PS1 REV Primer), designed to amplify 852 bp of the GFP integration region in the transformed *Chlamydomonas reinhardtii* plastid DNA. PS1 REV Primer is a GFP gene-specific primer.

SEQ ID NO: 169 corresponds to the nucleotide sequence of the forward primer of Primer Set 2 (PS2 FWD Primer), designed to amplify 712 bp of the GFP integration region in the transformed *Chlamydomonas reinhardtii* plastid DNA. PS2 FWD Primer is a GFP gene-specific primer.

SEQ ID NO: 170 corresponds to the nucleotide sequence of the reverse primer of Primer Set 2 (PS2 REV Primer), designed to amplify 712 bp of the GFP integration region in the transformed *Chlamydomonas reinhardtii* plastid DNA. PS2 REV Primer is a chloroplast genomic region-specific primer.

SEQ ID NO: 171 corresponds to the nucleotide sequence derived from the PCR amplification products of the GFP integration region in transformed *Chlamydomonas reinhardtii* plastid DNA.

SEQ ID NO: 172 corresponds to the amino acid sequence of a permeant peptide derived from the third alpha helix of *Drosophila melanogaster* transcription factor *Antennapedia*.

DETAILED DESCRIPTION

The present disclosure now will be described more fully hereinafter but should not be construed as limited to the embodiments set forth herein.

The meaning of abbreviations can be as follows: "sec" can mean second(s), "min" can mean minute(s), "h" can mean hour(s), "d" can mean day(s), "µL" can mean microliter(s), "ml" can mean milliliter(s), "L" can mean liter(s), "µM" can mean micromolar, "mM" can mean millimolar, "M" can mean molar, "mmol" can mean millimole(s), "µmole" can mean micromole(s), "g" can mean gram(s), "µg" can mean microgram(s), "ng" can mean nanogram(s), "U" can mean unit(s), "nt" can mean nucleotide(s); "bp" can mean base pair(s), "kb" can mean kilobase(s) and "kbp" can mean kilobase pair(s).

"Transgenic" can refer to any cell, cell line, callus, tissue, organism part or whole organism (e.g., plant), the genome of which has been altered by the presence of a heterologous nucleic acid, such as a recombinant DNA construct. Transgenic events can include those created by sexual crosses or asexual propagation. In some embodiments, the term "transgenic" may not encompass the alteration of the genome (e.g., chromosomal or extra-chromosomal) by breeding methods or by naturally occurring events such as random cross-fertilization, non-recombinant viral infection, non-recombinant bacterial transformation, non-recombinant transposition, or spontaneous mutation. In some embodiments, the term "transgenic" may encompass the alteration of the genome (e.g., chromosomal or extra-chromosomal) by breeding methods or by naturally occurring events such as random cross-fertilization, non-recombinant viral infection, non-recombinant bacterial transformation, non-recombinant transposition, or spontaneous mutation.

"Genome", for example, of a cell or whole organism can encompass chromosomal DNA found within the nucleus (nuclear DNA), and organellar DNA (e.g., mitochondrial DNA, plastid DNA) found within subcellular components of the cell. Methods and compositions of the disclosure can be used for editing of the nuclear genome, organellar genome (e.g., mitochondria, chloroplasts), or both.

The terms "full complement" and "full-length complement" can be used interchangeably herein, and can refer to a complement of a given nucleotide sequence. In some aspects, the complement and the nucleotide sequence comprise of the same number of nucleotides. In some aspects, the complement and the nucleotide sequence can comprise 100% complementary. The complement and the nucleotide sequence can differ in the number of nucleotides. Complementarity (e.g., between the complement and the nucleotide sequence) can be at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. Complementarity (e.g., between the complement and the nucleotide sequence) can be at most about 10%, at most about 20%, at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%.

"Polynucleotide", "nucleic acid", "nucleic acid sequence", "nucleotide sequence", or "nucleic acid fragment", which can be used interchangeably, can refer to a polymer of a nucleic acid (e.g., RNA, DNA, or both, and analogs thereof) that can be single-stranded or double-stranded, optionally containing synthetic, non-natural or altered nucleotide bases. Nucleotides (e.g., in their 5'-monophosphate form) can be referred to by their single letter designation as follows (for RNA or DNA, respectively): "A" for adenylate or deoxyadenylate, "C" for cytidylate or deoxycytidylate, "G" for guanylate or deoxyguanylate, "U" for uridylate, "T" for deoxythymidylate, "R" for purine-based nucleotides (A or G), "Y" for pyrimidine-based nucleotides (C or T), "K" for G or T, "H" for A or C or T, "I" for inosine, and "N" for any nucleotide.

"Polypeptide", "peptide", "amino acid sequence" and "protein", which can be used interchangeably herein, can refer to a polymer of amino acid residues. The terms can apply to amino acid polymers in which one or more amino acid residue can be, for example, an artificial chemical analogue of a corresponding naturally occurring amino acid and/or to naturally occurring amino acid polymers. The terms "polypeptide", "peptide", "amino acid sequence", and "protein" can be inclusive of modifications including, but not limited to, glycosylation, lipid attachment, sulfation, gamma-carboxylation of glutamic acid residues, hydroxylation and ADP-ribosylation.

A "functional fragment" of a polynucleotide or polypeptide can refer to any subset of contiguous nucleotides or contiguous amino acids, respectively, in which the original (e.g., wild type) activity (or substantially similar activity) of the polynucleotide or polypeptide can be retained. The terms "functional fragment", "functional subfragment", "fragment that is functionally equivalent", "subfragment that is functionally equivalent", "functionally equivalent fragment" and "functionally equivalent subfragment" can be used interchangeably herein.

The terms "functional variant", "variant that is functionally equivalent" and "functionally equivalent variant" can be used interchangeably herein. In the context of a polynucleotide or a polypeptide, these terms can refer to a variant of the nucleic acid sequence or the amino acid sequence, respectively, in which the original activity (or substantially similar activity) of the polynucleotide or polypeptide can be retained. Fragments and variants can be obtained via methods such as site-directed mutagenesis and synthetic construction.

The activity of the functional fragment or function variant can be, for example, about: 100%, 95%, 90%, 85%, 80%, 75%, 70%, 65%, 60%, 55%, 50%, 40%, 30%, 20%, 10%, or less than 10% of that of the original (e.g., wild type) activity.

"RNA transcript" can refer to the product resulting from RNA polymerase-catalyzed transcription of a DNA sequence. When the RNA transcript is a perfect complimentary copy of the DNA sequence, it can be referred to as the primary transcript. A RNA transcript can be referred to as the mature RNA, for example, when it is a RNA sequence derived from post-transcriptional processing of the primary transcript.

"Messenger RNA" or "mRNA" can refer to the RNA that is without introns and that can be translated into protein by the cell.

"Sense" RNA can refer to the RNA transcript that includes the mRNA. Sense RNA can be translated into protein within a cell or in vitro.

"Antisense RNA" can refer to an RNA transcript that can be complementary to all or part of a target RNA (e.g., a primary transcript or mRNA). Antisense RNA can be used to block expression of a target gene. The complementarity of an antisense RNA may be with any part of the specific gene transcript, i.e., at the 5' non-coding sequence, 3' non-coding sequence, introns, or the coding sequence. "Functional RNA" can refer to antisense RNA, ribozyme RNA, or other RNA that may not be translated but yet can have an effect on cellular processes. The terms "complement" and "reverse complement" can be used interchangeably herein, for example, with respect to mRNA transcripts and may be used to define the antisense RNA of the message.

"cDNA" can refer to a DNA that can be complementary to and synthesized from a mRNA template using the enzyme reverse transcriptase. The cDNA can be single-stranded or converted into the double-stranded form using the Klenow fragment of DNA polymerase I.

"Coding region" can refer to the portion of a messenger RNA (or the corresponding portion of another nucleic acid molecule such as a DNA molecule) which can encode a protein or polypeptide. "Non-coding region" can refer to a portion of a messenger RNA or other nucleic acid molecule that are not a coding region, including but not limited to, for example, the promoter region, 5' untranslated region ("UTR"), 3' UTR, intron and terminator. The terms "coding region" and "coding sequence" can be used interchangeably herein. The terms "non-coding region" and "non-coding sequence" can be used interchangeably herein.

"Coding sequence" can be abbreviated "CDS". "Open reading frame" can be abbreviated "ORF".

An "Expressed Sequence Tag" ("EST") can be a DNA sequence derived from a cDNA library. An EST can be a sequence which has been transcribed. An EST can be obtained by a single sequencing pass of a cDNA insert. The sequence of an entire cDNA insert can be termed the "Full-Insert Sequence" ("FIS"). A "Contig" sequence can be a sequence assembled from two or more sequences that can be selected from, but not limited to, the group consisting of an EST, FIS and PCR sequence. A sequence encoding an entire or functional protein can be termed a "Complete Gene Sequence" ("CGS"). A CGS can be derived from an FIS or a contig.

"Gene" can refer to a nucleic acid fragment that can express a functional molecule such as, but not limited to, a specific protein, including: introns, exons, regulatory sequences preceding (5' non-coding sequences) and following (3' non-coding sequences) the coding sequence. "Native gene" can refer to a gene as found in nature, for example, with its own regulatory sequences.

A "mutated gene" can be a gene that has been altered relative to the corresponding naturally occurring gene; e.g., through human intervention. Such a "mutated gene" can have a sequence that differs from the sequence of the corresponding non-mutated gene by at least one nucleotide addition, deletion, or substitution. In certain embodiments of the disclosure, the mutated gene can comprise an alteration that results from a polynucleotide guided polypeptide system as disclosed herein. A mutated organism can be an organism comprising a mutated gene; e.g., a mutated plant with an organellar genome comprising a mutated gene. The terms "mutated gene" and "mutant gene" can be used interchangeably herein.

A "silent mutation" can refer to a mutated sequence that has the same functionality as the wild-type sequence; e.g., replacement of a codon in a protein-coding region with a synonymous codon that can encode the same amino acid.

As used herein, a "targeted mutation" can be a DNA modification made at or near a specific target site in the genome. The targeted mutation may be as small as a single nucleotide change in a native gene. The targeted mutation may involve a larger DNA modification such as the insertion of one or more heterologous DNAs; e.g., a heterologous regulatory element, a heterologous protein-coding sequence, or an expression cassette coding for a heterologous protein or functional RNA. The targeted mutation may also involve a change in the sequence of a target site.

The term "SDN" can refer to "site-directed nuclease". The following are non-limiting examples of SDN-induced mutations: (1) induction of site-specific random mutations; (2) the induction of mutations in a predefined sequence of a particular gene; and (3) the replacement or the insertion of an entire gene. These SDN-induced mutations can be referred to as SDN-1, SDN-2 and SDN-3, respectively.

A "codon-modified gene" or "codon-preferred gene" or "codon-optimized gene" can be a gene having its frequency of codon usage designed to mimic the frequency of preferred codon usage of the host cell in the compartment of interest, e.g., the nucleus, the mitochondria or the chloroplast.

"Mature" protein can refer to a post-translationally processed polypeptide; for example, one from which any pre- or pro-peptides present in the primary translation product have been removed.

"Precursor" protein can refer to the primary product of translation of an mRNA; for example, with pre- and pro-peptides still present. Pre- and pro-peptides may, for example, comprise intracellular localization signals.

"Isolated" can refer to materials, such as nucleic acid molecules, proteins, and cells that may be substantially free or otherwise removed from components that normally accompany or interact with the materials in a naturally occurring environment. Isolated polynucleotides may be purified from a host cell in which they naturally occur. Nucleic acid purification methods can be used to obtain isolated polynucleotides. Isolated polynucleotides can include, for example, recombinant polynucleotides and chemically synthesized polynucleotides.

"Heterologous", for example, with respect to sequence, can mean a sequence that originates from a foreign species, or, if from the same species, is substantially modified from its native form in composition and/or genomic locus by deliberate human intervention. The terms "heterologous nucleotide sequence", "heterologous sequence", "heterologous nucleic acid fragment", and "heterologous nucleic acid sequence" can be used interchangeably herein.

"Recombinant" can refer to an artificial combination of two or more otherwise separated segments of sequence, e.g., by chemical synthesis or by the manipulation of isolated segments of nucleic acids by genetic engineering techniques. "Recombinant" can also include reference to a cell or vector, for example, that has been modified by the introduction of a heterologous nucleic acid or a cell derived from a cell so modified.

"Recombinant DNA construct" can refer to a combination of nucleic acid fragments that may not normally be found together in nature. A recombinant DNA construct may comprise, for example, regulatory sequences and coding sequences that are derived from different sources, or regulatory sequences and coding sequences derived from the same source. The sequences in a recombinant DNA construct can be arranged in a manner different than that normally found in nature. The terms "recombinant DNA construct", "recombinant DNA molecule", "recombinant construct", "DNA construct" and "construct" can be used interchangeably herein.

"Expression" can refer to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Expression cassette" can refer to a construct containing, for example, a polynucleotide, a regulatory element(s), and a polynucleotide that allow for expression of the polynucleotide in a host. The terms "expression cassette" and "expression construct" can be used interchangeably herein.

The terms "entry clone" and "entry vector" can be used interchangeably herein.

"Regulatory sequences" can refer to nucleotide sequences, for example, located upstream (e.g., 5' noncoding sequences), within (e.g., in introns), or downstream (e.g., 3' non-coding sequences) of a coding sequence. Regulatory sequences can influence, for example, the transcription, RNA processing or stability, or translation of the associated coding sequence. Regulatory sequences may include, but are not limited to, promoters, translation leader sequences, 5' untranslated sequences, 3' untranslated sequences, introns, polyadenylation target sequences, RNA processing sites, effector binding sites, and stem-loop structures. A regulatory sequence may act in "cis" or "trans". The nucleic acid molecule regulated by a regulatory sequence may not necessarily have to encode a functional peptide or polypeptide, e.g., the regulatory sequence can modulate the expression of a short interfering RNA or an anti-sense RNA. The terms "regulatory sequence" and "regulatory element" can be used interchangeably herein.

"Promoter" can refer to a nucleic acid fragment that can control transcription of another nucleic acid fragment. A promoter can include a core promoter (also known as minimal promoter) sequence. A core promoter can be a minimal sequence for direct transcription initiation. A core promoter can optionally include enhancers or other regulatory elements. Promoters may be derived in their entirety from a native gene, or be composed of different elements derived from different promoters found in nature, or even comprise synthetic DNA segments. Different promoters may direct the expression of a gene in different tissues or cell types, or at different stages of development, or in response to different environmental conditions.

"Promoter functional in a plant" can be a promoter that can control transcription in plant cells. The promoter can be from any suitable origin, which can include plant cells and non-plant cells.

"Tissue-specific promoter" and "tissue-preferred promoter" can be used interchangeably, and can refer to a promoter that can be expressed predominantly in one tissue, one organ or one cell type. A tissue-specific promoter may not be necessarily exclusive in one tissue, one organ or one cell type. Root-preferred promoters include, for example, the following: soybean root-specific glutamine synthase gene; cytosolic glutamine synthase (GS); root-specific control element in the GRP 1.8 gene of French bean; root-specific promoter of *A. tumefaciens* mannopine synthase (MAS); root-specific promoters isolated from *Parasponia andersonii* and *Trema tomentosa*; *A. rhizogenes* rolC and rolD root-inducing genes; *Agrobacterium* wound-induced TR1' and TR2' genes; VfENOD-GRP3 gene promoter; and rolB promoter. Seed-preferred promoters include both seed-specific promoters active during seed development, as well as seed-germinating promoters active during seed germination. Seed-preferred promoters include, but are not limited to, the following: Cim1 (cytokinin-induced message); cZ19B1 (maize 19 kDa zein); milps (myo-inositol-1-phosphate synthase); END1; and END2. For dicots, seed-preferred promoters include, but are not limited to, the following: bean 0-phaseolin; napin; β-conglycinin; soybean lectin; cruciferin; and the like. For monocots, seed-preferred promoters include, but are not limited to, the following: maize 15 kDa zein; 22 kDa zein; 27 kDa gamma zein; waxy; shrunken 1; shrunken 2; globulin 1; oleosin; nud; and *Zea mays*-Rootmet2 promoter. Leaf-preferred promoters include, but are not limited to, the following: plant rbcS promoters, such as the soybean rbcS promoter and the maize rbcS promoter; *Zea mays* PEPC1 promoter.

"Developmentally regulated promoter" can refer to a promoter whose activity can be determined by developmental events.

"Inducible promoter" can refer to a promoter that selectively expresses an operably linked DNA sequence in response to the presence of an endogenous or exogenous stimulus, for example by chemical compounds (e.g., chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners. Pathogen-inducible promoters induced following infection by a pathogen include, but are not limited to those regulating expression of PR proteins, SAR proteins, beta-1,3-glucanase, chitinase, etc. Stress-inducible promoters include plant RAB17 promoters, such as the maize RAB17 promoter. Chemical-inducible promoters include, but are not limited to, the following: the maize ln2-2 promoter, activated by benzene sulfonamide herbicide safeners; the maize GST promoter, activated by hydrophobic electrophilic compounds used as pre-emergent herbicides; and the tobacco PR-1a promoter, activated by salicylic acid. Other chemical-regulated promoters include steroid-responsive promoters, for example, the glucocorticoid-inducible promoter, and tetracycline-inducible and tetracycline-repressible promoters.

"Constitutive promoter" can refer to promoters active in all or most tissues or cell types of an organism at all or most developing stages. As with other promoters classified as "constitutive" (e.g. ubiquitin), some variation in absolute levels of expression can exist among different tissues or stages. The term "constitutive promoter" or "tissue-independent promoter" can be used interchangeably herein. Constitutive promoters include the following: the core promoter of the Rsyn7 promoter; the core CaMV 35S promoter; plant actin promoter, such as a rice actin promoter and a maize actin promoter; plant ubiquitin promoter, such as a maize ubiquitin promoter and a soybean ubiquitin promoter; pEMU; MAS promoter; ALS promoter; plant GOS2 promoter, such as a maize GOS2 promoter; soybean GM-EF1 A2 promoter; plant U6 polymerase III promoter, such as a maize U6 polymerase III promoter and a soybean U6 polymerase III promoter (GM-U6-9.1 and GM-U6-13.1).

An enhancer element can be any nucleic acid molecule that increases transcription of a nucleic acid molecule when functionally linked to a promoter regardless of its relative position. An enhancer may be an innate element of the promoter or a heterologous element inserted to enhance the level or tissue-specificity of a promoter.

A repressor (also sometimes called herein silencer) can be defined as any nucleic acid molecule which inhibits the transcription when functionally linked to a promoter regardless of relative position.

"Translation leader sequence" can refer to a polynucleotide sequence located between the promoter sequence of a gene and the coding sequence. The translation leader sequence can be present in the fully processed mRNA upstream of the translation start sequence. The translation leader sequence may affect processing of the primary transcript to mRNA, mRNA stability or translation efficiency.

"Transcription terminator", "termination sequence", or "terminator" can refer to DNA sequences that, when operably linked to the 3' end of a polynucleotide sequence that is to be expressed, can terminate transcription from the polynucleotide sequence. Transcription termination can refer to the process by which RNA synthesis by RNA polymerase can be stopped and both the RNA and the enzyme are released from the DNA template.

"Operably linked" can refer to the association of fragments in a single fragment (e.g., a polynucleotide or polypeptide), or in a single complex, so that the function of one can be regulated by the other. The linkage may be covalent or non-covalent. For example, with respect to nucleic acid fragments, a promoter can be operably linked with a nucleic acid fragment if the promoter can regulate the transcription of that nucleic acid fragment. For example, with respect to a polypeptide, an organelle targeting peptide can be operably linked with a polypeptide if the organelle targeting peptide can transport that polypeptide into the relevant organelle. For example, with respect to a complex, a guide RNA can be operably linked to a Cas polypeptide if the guide RNA/Cas polypeptide complex can cleave a target sequence as directed by the guide RNA.

"Phenotype" can refer to the detectable characteristics of a cell or organism.

The term "introduced" can mean providing a polynucleic acid (e.g., expression construct) or protein into a cell. Introduced can include reference to the incorporation of a nucleic acid into a eukaryotic or prokaryotic cell, for example, where the nucleic acid may be incorporated into the genome of the cell. Introduced can include reference to the transient provision of a nucleic acid or protein to the cell. Introduced can include reference to stable or transient transformation methods. Introduced can include sexually crossing. Introduced, for example, in the context of inserting a nucleic acid fragment (e.g., a recombinant DNA construct) into a cell, can include "transfection" or "transformation" or "transduction". Introduced can include reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" can be any cell into which a nucleic acid fragment (e.g., a recombinant DNA construct) has been introduced.

"Transformation" as used herein can refer to stable transformation. Transformation can refer to transient transformation.

"Stable transformation" can refer to the introduction of a nucleic acid fragment into a genome of a host organism resulting in genetically stable inheritance. Once stably transformed, the nucleic acid fragment can be stably integrated in the genome of the host organism and any subsequent generation.

"Transient transformation" can refer to the introduction of a nucleic acid fragment into the nucleus, or DNA-containing organelle, of a host organism resulting in gene expression without genetically stable inheritance.

Host organisms containing the transformed nucleic acid fragments can be referred to as "transgenic" organisms.

"Transformation cassette" can refer to a construct having elements that facilitates transformation of a particular host cell. The terms "transformation cassette" and "transformation construct" can be used interchangeably herein.

"Allele" can be one of several alternative forms of a gene occupying a given locus on a chromosome. When the alleles present at a given locus on a pair of homologous chromosomes in a diploid plant are the same that plant can be homozygous at that locus. If the alleles present at a given locus on a pair of homologous chromosomes in a diploid plant differ, that plant can be heterozygous at that locus. If a transgene is present on one of a pair of homologous chromosomes in a diploid plant that plant can be hemizygous at that locus.

A "chloroplast transit peptide" can be an amino acid sequence that can direct a protein to the chloroplast or other plastid types present in the cell. The chloroplast transit peptide can be translated in conjunction with the protein in the cell in which the protein can be made. The terms "chloroplast transit peptide", "plastid transit peptide", "chloroplast targeting peptide" and "plastid targeting peptide" can be used interchangeably herein. "Chloroplast transit sequence" can refer to a nucleotide sequence that can encode a chloroplast transit peptide.

A "signal peptide" can be an amino acid sequence that can direct a protein to the secretory system. The signal peptide can be translated in conjunction with a protein. For example, if the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present may be removed and a nuclear localization signal can be included.

A "mitochondrial signal peptide" can be an amino acid sequence which can direct a precursor protein into the mitochondria. The terms "mitochondrial signal peptide", "mitochondrial transit peptide" and "mitochondrial targeting peptide" can be used interchangeably herein.

An "organelle targeting polynucleotide" can be a nucleotide sequence which can direct import of the polynucleotide into an organelle. The terms "organelle targeting polynucleotide", "organelle targeting nucleic acid" and "organelle targeting nucleic acid sequence" can be used interchangeably herein. An organelle targeting polynucleotide may be directed to, for example, the plastid ("plastid targeting polynucleotide") or the mitochondria ("mitochondria targeting polynucleotide"). The polynucleotide may be RNA ("organelle targeting RNA"), DNA ("organelle targeting DNA) or a combination of RNA and DNA. An organelle targeting RNA directed to the plastid can be termed a "plastid targeting RNA". The terms "plastid targeting RNA", "chloroplast targeting RNA" and "transit RNA" are used interchangeably herein. An organelle targeting RNA directed to the mitochondria can be termed a "mitochondria targeting RNA".

RNAs can be imported into mitochondria. One such mitochondrial targeting RNA can be the yeast tRNA$^{Lys}$. The yeast tRNA$^{Lys}$ and its variants can be imported into human mitochondria. Another RNA that can be imported into mitochondria can be 5S rRNA. 5S rRNA can function as a vector for delivering heterologous RNA sequences into, for example, mitochondria (e.g., human). Such RNAs can be used with the compositions and methods of the disclosure for example, for targeting to an organelle (e.g., the mitochondria).

RNAs can be imported into plastids. Plastid targeting RNAs that can mediate import of attached heterologous RNA can include vd-5'UTR (e.g., viroid-derived ncRNA sequence acting as 5'UTR and eIF4E1 mRNA. Such RNAs can be used with the compositions and methods of the disclosure for targeting to an organelle (e.g., the plastid).

As used herein, "fusion" can refer to a protein and/or nucleic acid comprising one or more non-native sequences (e.g., moieties). Any of the molecules described herein (e.g., nucleic acids, proteins, polypeptides, polynucleic acid, Cas protein, guide polynucleotide) can be engineered as fusions. A fusion can comprise one or more of the same non-native sequences. A fusion can comprise one or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the site-directed polypeptide. A fusion can provide a non-native sequence (e.g., affinity tag) that can be used to track or purify. A fusion can be a small molecule such as biotin or a dye such as alexa fluor dyes, Cyanine3 dye, and Cyanine5 dye.

A fusion can refer to any protein with a functional effect. For example, a fusion protein can comprise deaminase activity, cytidine deaminase activity (US Patent Publication No. US20150166980, herein incorporated by reference), adenine deaminase activity (US Patent Publication No. US20180073012, herein incorporated by reference), uracil glycosylase inhibitor activity (US Patent Publication No. US20170121693, herein incorporated by reference), methyltransferase activity, demethylase activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodeling activity, protease activity, oxidoreductase activity, transferase activity, hydrolase activity, lyase activity, isomerase activity, synthase activity, synthetase activity, or demyristoylation activity. An effector protein can modify a genomic locus. A fusion protein can be a fusion in a Cas protein. The Cas protein may be a modified form that has nickase activity or that has no substantial nucleic acid-cleaving activity. A fusion protein can be a non-native sequence in a Cas protein.

As used herein, a "nucleic acid" can refer to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backgone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine.

Suppression of Gene Expression

"Suppression DNA construct" can be a recombinant DNA construct which when transformed or stably integrated into the genome of the plant, can result in "silencing" of a target gene (e.g., in a plant). The target gene may be endogenous or transgenic to a target cell (e.g., plant).

"Silencing," as used herein with respect to the target gene, can refer to the suppression of levels of mRNA or protein/enzyme expressed by the target gene, and/or the level of the enzyme activity or protein functionality. The terms "suppression", "suppressing" and "silencing", which can be used interchangeably herein, can include lowering, reducing, declining, decreasing, inhibiting, eliminating or preventing. "Silencing" or "gene silencing" can occur by any suitable mechanism. Non-limiting examples of silencing can include anti-sense, cosuppression, viral-suppression, hairpin suppression, stem-loop suppression, RNAi-based approaches, and small RNA-based approaches A suppression DNA construct may comprise a region derived from a target gene of interest. A suppression DNA construct may comprise all or part of the nucleic acid sequence of the sense strand (or antisense strand, or both) of the target gene of interest. The region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand, or both) of the gene of interest. A suppression DNA construct may comprise 20, 30, 40, 50, 60, 70, 80, 90, 100, 200, 300, 400, 500, 600, 700, 800, 900 or 1000 contiguous nucleotides of the sense strand (or antisense strand, or both) of the gene of interest, and combinations thereof.

Suppression DNA constructs can be readily constructed, for example, once the target gene of interest is selected. A suppression DNA construct can include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

Suppression of gene expression may also be achieved by, for example, use of artificial miRNA precursors, ribozyme constructs and gene disruption. A modified plant miRNA precursor may be used, wherein the precursor has been modified, for example, to replace the miRNA encoding region with a sequence designed to produce a miRNA directed to the nucleotide sequence of interest. Gene disruption may be achieved by use of transposable elements or by use of chemical agents that cause site-specific mutations.

"Antisense inhibition" can refer to the production of antisense RNA transcripts that can suppress the expression of the target gene or gene product. "Antisense RNA" can refer to an RNA transcript that is complementary to all or part of a target primary transcript or mRNA. Antisense RNA can block the expression of a target isolated nucleic acid fragment. The complementarity of an antisense RNA may be with any part of the specific gene transcript, i.e., at the 5' non-coding sequence, 3' non-coding sequence, introns, or the coding sequence.

"Cosuppression" can refer to the production of sense RNA transcripts that can suppress the expression of the target gene or gene product. "Sense" RNA can refer to RNA transcript that can include the mRNA. Sense RNA can be translated into protein within a cell or in vitro. Cosuppression constructs in plants can be designed, for example, by focusing on overexpression of a nucleic acid sequence having homology to a native mRNA, in the sense orientation, which can result in the reduction of RNA having homology to the overexpressed sequence.

Plant viral sequences can be used to direct the suppression of proximal mRNA encoding sequences.

RNA interference can refer to the process of sequence-specific post-transcriptional gene silencing (e.g., in animals) mediated by, for example, short interfering RNAs (siRNAs). The corresponding process in plants can be referred to as post-transcriptional gene silencing (PTGS) or RNA silencing and can also referred to as quelling in fungi. The process of post-transcriptional gene silencing can be an evolutionarily-conserved cellular defense mechanism used to prevent the expression of foreign genes. Post-transcriptional gene silencing can be shared by diverse flora and phyla.

Small RNAs can play an important role in controlling gene expression. Small RNAs can function by base-pairing to complementary RNA or DNA target sequences. When bound to RNA, small RNAs can trigger either RNA cleavage or translational inhibition of the target sequence. When bound to DNA target sequences, small RNAs can mediate DNA methylation of the target sequence. Small RNAs can lead to inhibition of gene expression.

MicroRNAs (miRNAs) can be noncoding RNAs with a length of, for example, about 19 to about 24 nucleotides (nt). MicroRNAs can occur in animals and plants. miRNAs can be processed from longer precursor transcripts that can range in size, for example, from approximately 70 to 200 nt. The precursor transcripts can form stable hairpin structures.

MicroRNAs (miRNAs) can regulate target genes, for example, by binding to complementary sequences located in the transcripts produced by these genes. miRNAs can enter, for example, at least two pathways of target gene regulation: (1) translational inhibition; and/or (2) RNA cleavage. MicroRNAs entering the RNA cleavage pathway can be analogous to the 21-25 nt short interfering RNAs (siRNAs) generated during RNA interference (RNAi) in animals and posttranscriptional gene silencing (PTGS) in plants. These microRNAs entering the RNA cleavage pathway can be incorporated into an RNA-induced silencing complex (RISC) that can be similar or identical to that seen for RNAi.

The terms "miRNA-star sequence" and "miRNA* sequence" can be used interchangeably herein and can refer to a sequence in the miRNA precursor that can be highly complementary to the miRNA sequence. The miRNA and miRNA* sequences can form part of the stem region of the miRNA precursor hairpin structure.

Sequence Identity, Similarity and Variation

Sequence alignments and percent identity or similarity calculations may be determined using a variety of comparison methods designed to detect homologous sequences including, but not limited to, the MEGALIGN™ program of the LASERGENE™ bioinformatics computing suite (DNASTAR™ Inc., Madison, WI). In some embodiments, where sequence analysis software is used for analysis, the results of the analysis can be based on the "default values" of the program referenced. As used herein "default values" can mean any set of values or parameters that originally load with the software when first initialized.

The "Clustal V method of alignment" can correspond to the alignment method labeled Clustal V and, for example, found in the MEGALIGN™ program of the LASERGENE™ bioinformatics computing suite (DNASTAR™ Inc., Madison, WI). For multiple alignments, the default values can correspond to GAP PENALTY=10 and GAP LENGTH PENALTY=10. Default parameters for pairwise alignments and calculation of percent identity of protein sequences using the Clustal method can be, for example, KTUPLE=1, GAP PENALTY=3, WINDOW=5 and DIAGONALS SAVED=5. For nucleic acids these parameters can be for example KTUPLE=2, GAP PENALTY=5, WINDOW=4 and DIAGONALS SAVED=4. After alignment of the sequences using the Clustal V program, "percent identity" and "divergence" values can be obtained by viewing the "sequence distances" table in the same program.

The "Clustal W method of alignment" can correspond to the alignment method labeled Clustal W and, for example, found in the MEGALIGN™ v6.1 program of the LASERGENE™ bioinformatics computing suite (DNASTAR™ Inc., Madison, WI). Default parameters for multiple alignment can correspond to for example: GAP PENALTY=10, GAP LENGTH PENALTY=0.2, Delay Divergence Sequences=30%, DNA Transition Weight=0.5, Protein Weight Matrix=Gonnet Series, DNA Weight Matrix=IUB. After alignment of the sequences using the Clustal W program, "percent identity" values can be obtained by viewing the "sequence distances" table in the same program.

Sequence identity/similarity values can also be obtained using GAP Version 10 (GCG, Accelrys, San Diego, CA) using for example the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix. GAP can use an algorithm to find an alignment of two complete sequences that can maximize the number of matches and minimizes the number of gaps. GAP can consider all possible alignments and gap positions. GAP can create the alignment with the largest number of matched bases and the fewest gaps, using, for example, a gap creation penalty and a gap extension penalty in units of matched bases.

"BLAST" can be a searching algorithm provided by the National Center for Biotechnology Information (NCBI) that can be used to find regions of similarity between biological sequences. The program can compare nucleotide or protein sequences to sequence databases. The program can calculate the statistical significance of matches to identify sequences having sufficient similarity to a query sequence such that the similarity may not be predicted to have occurred randomly. BLAST can report the identified sequences and their local alignment to the query sequence.

The term "conserved domain" or "motif" can mean a set of amino acids conserved at specific positions along an aligned sequence of evolutionarily related proteins. While amino acids at other positions can vary between homologous proteins, amino acids that are highly conserved at specific positions can indicate, for example, amino acids that are essential to the structure, the stability, or the activity of a protein.

Conserved domains or motifs can be identified by their high degree of conservation in aligned sequences of a family of protein homologues. Conserved domains can be used as identifiers, or "signatures", for example, to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These can refer to polypeptide or nucleic acid fragments wherein changes in one or more amino acids or nucleotide bases may not affect the function of the molecule, such as the ability to mediate gene expression or to produce a certain phenotype. These terms can also refer to modification(s) of nucleic acid fragments that may not substantially alter the functional properties of the resulting nucleic acid fragment relative to the initial, unmodified fragment. These modifications can include deletion, substitution, and/or insertion of one or more nucleotides in the nucleic acid fragment.

Substantially similar nucleic acid sequences encompassed may be defined by their ability to hybridize (for example, under moderately stringent conditions, e.g., 0.5×SSC, 0.1% SDS, 60° C.) with the sequences exemplified herein, or to any portion of the nucleotide sequences disclosed herein. Substantially similar nucleic acid sequences can be functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes can determine stringency conditions.

The term "selectively hybridizes" can include reference to hybridization, for example under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences can have, for example, about at least 80% sequence identity, or 90% sequence identity, up to and including 100% sequence identity (i.e., fully complementary) with each other.

The term "stringent conditions" or "stringent hybridization conditions" can include reference to conditions under which a probe can selectively hybridize to its target sequence in an in vitro hybridization assay. Stringent conditions can be sequence-dependent. Stringent conditions can be different in different circumstances. By controlling the stringency of the hybridization and/or washing conditions, target sequences can be identified which are 100% complementary to the probe (homologous probing).

Alternatively, stringency conditions can be adjusted to allow some mismatching in sequences so that lower degrees of similarity are detected (heterologous probing). In some embodiments, a probe can be less than about 1000 nucleotides in length, optionally less than 500 nucleotides in length.

In some embodiments, stringent conditions can be those in which the salt concentration is less than about 1.5 M Na ion, for example, about 0.01 to 1.0 M Na ion concentration (or other salt(s)) at pH 7.0 to 8.3, and, for example, at least about 30° C. for short probes (e.g., 10 to 50 nucleotides) and, for example, at least about 60° C. for long probes (e.g., greater than 50 nucleotides). Stringent conditions may also be achieved with the addition of destabilizing agents such as formamide. Exemplary low stringency conditions can include hybridization with a buffer solution of, for example, 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions can include hybridization in 40 to 45% formamide, 1 M NaCl, 1% SDS at 37° C., and a wash in 0.5× to 1×SSC at 55 to 60° C. Exemplary high stringency conditions can include hybridization in, for example, 50% formamide, 1 M NaCl, 1% SDS at 37° C., and a wash in 0.1×SSC at 60 to 65° C.

"Sequence identity" or "identity" in the context of nucleic acid or polypeptide sequences can refer to the nucleic acid bases or amino acid residues in two sequences that are the same when aligned for maximum correspondence over a specified comparison window.

The term "percentage of sequence identity" can refer to the value determined by comparing two optimally aligned sequences over a comparison window. The portion of the polynucleotide or polypeptide sequence in the comparison window may comprise additions or deletions (i.e., gaps) as compared to the reference sequence (which may or may not comprise additions or deletions) for optimal alignment of the two sequences. The percentage can be calculated by, for example, determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Percent sequence identities can include, but are not limited to, 50%, 55%, 60%, 65%, 70%, 75%, 80%, 85%, 90% or 95%, or any percentage from 50% to 100%. Sequence identity can include an integer percentage from 50% to 100%. These identities can be determined using any of the programs described herein.

Sequence identity can be useful in identifying polypeptides from other species or modified naturally or synthetically wherein such polypeptides have the same or similar function or activity. Percent identities can include, but are not limited to, 50%, 55%, 60%, 65%, 70%, 75%, 80%, 85%, 90% or 95%. Sequence identity (e.g, amino acid sequence identity) can include an integer percentage from 50% to 100%. Sequence (e.g., amino acid) identity can include, for example, about: 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

Definitions, Traits and Processes Relevant to Plants

"Plant" can include reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Propagule" can include products of meiosis and/or mitosis able to propagate a new plant. Propagule can include seeds, spores and parts of a plant that can serve as a means of vegetative reproduction, such as corms, tubers, offsets, or runners. Propagule can include grafts where one portion of a plant can be grafted to another portion of a different plant (even one of a different species) to create a living organism. Propagule can include plants and seeds produced by cloning or by bringing together meiotic products, or allowing meiotic products to come together to form an embryo or fertilized egg (naturally or with human intervention).

"Progeny" can comprise any subsequent generation of a plant.

The terms "monocot" and "monocotyledonous plant" can be used interchangeably herein. A monocot can include the Gramineae.

The terms "dicot" and "dicotyledonous plant" can be used interchangeably herein. A dicot can include, for example, the following families: Brassicaceae, Leguminosae, and Solanaceae.

"Transgenic plant" can include reference to a plant which comprises within its genome a heterologous polynucleotide. For example, the heterologous polynucleotide may be stably integrated within the genome (e.g., nuclear, plastid, mitochondrial) such that the polynucleotide can be passed on to successive generations. The heterologous polynucleotide may be integrated into the genome alone or as part of a recombinant DNA construct.

"Transgenic plant" can include reference to plants which can comprise more than one heterologous polynucleotide within their genome. Each heterologous polynucleotide may confer a different trait to the transgenic plant.

Multiple traits can be introduced into crop plants, and can be referred to as a gene stacking approach. Gene stacking can be used, for example, for development of genetically improved germplasm. In this approach, multiple genes conferring different characteristics of interest can be introduced into a plant. Gene stacking can be accomplished by many means including but not limited to co-transformation, retransformation, and crossing lines with different transgenes. As used herein, the term "stacked" can include having multiple traits present in the same plant (e.g., both traits are incorporated into the nuclear genome, one trait is incorporated into the nuclear genome and one trait is incorporated into the genome of an organelle, or both traits are incorporated into the genome of an organelle).

The term "crossed" or "cross" or "crossing" in the context of the disclosure can mean the fusion of gametes (e.g., via pollination) to produce progeny (e.g., cells, seeds, or plants). The term can encompass both sexual crosses (e.g., the pollination of one plant by another) and selfing (e.g., self-pollination; when the pollen and ovule are from the same plant or genetically identical plants).

The term "maternal inheritance" can refer to the transmission of traits that can be solely dependent on properties of the genome of the female gamete.

The term "paternal inheritance" can refer to the transmission of traits that are solely dependent on properties of the genome of the male gamete.

The term "introgression" can refer to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a selected allele of a marker or QTL.

"A plant-optimized nucleotide sequence" can be a nucleotide sequence that has been optimized for increased expression in plants, particularly for increased expression in plants or in one or more plants of interest. For example, a plant-optimized nucleotide sequence can be synthesized by modifying a nucleotide sequence encoding a protein such as, for example, a double-strand-break-inducing agent (e.g., an endonuclease) as disclosed herein, using one or more plant-preferred codons for improved expression. A host-preferred codon usage can be utilized for codon optimization.

Plant-preferred genes can be synthesized. Additional sequence modifications can enhance gene expression in a plant host. These can include, for example, elimination of: one or more sequences encoding spurious polyadenylation signals, one or more exon-intron splice site signals, one or more transposon-like repeats, and sequences that may be deleterious to gene expression. The G-C content of the sequence may be adjusted, for example, to levels average for a given plant host, as calculated by reference to genes expressed in the host plant cell. When possible, the sequence can be modified to avoid one or more predicted hairpin secondary mRNA structures. Thus, "a plant-optimized nucleotide sequence" of the present disclosure can comprise one or more of such sequence modifications.

A "trait" can refer to, for example, a physiological, morphological, biochemical, or physical characteristic of a plant or particular plant material or cell. In some instances, this characteristic can be visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield.

"Agronomic characteristic" can be a measurable parameter including but not limited to, abiotic stress tolerance, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress.

Particular phenotypes may include, but are not limited to kernel number, kernel area, grain weight, and predicted weight of the grain on the ear (based on the calibration of kernel area to grain weight).

Abiotic stress may be at least one condition selected from the group consisting of: drought, water deprivation, flood, high light intensity, high temperature, low temperature, salinity, etiolation, defoliation, heavy metal toxicity, anaerobiosis, nutrient deficiency, nutrient excess, UV irradiation, atmospheric pollution (e.g., ozone) and exposure to chemicals (e.g., paraquat) that induce production of reactive oxygen species (ROS).

"Increased stress tolerance" of a plant can be measured relative to a reference or control plant, and can be a trait of the plant to survive under stress conditions over prolonged periods of time, without exhibiting the same degree of physiological or physical deterioration relative to the reference or control plant grown under similar stress conditions.

A plant with "increased stress tolerance" can exhibit increased tolerance to one or more different stress conditions.

"Stress tolerance activity" of a polypeptide can indicate that over-expression of the polypeptide in a transgenic plant can confer increased stress tolerance to the transgenic plant relative to a reference or control plant.

Increased biomass can be measured, for example, as an increase in plant height, plant total leaf area, plant fresh weight, plant dry weight or plant seed yield, as compared with control plants.

The ability to increase the biomass or size of a plant can have several important commercial applications. Crop species may be generated that can produce larger cultivars, generating higher yield in, for example, plants in which the vegetative portion of the plant can be useful as food, biofuel or both.

Increased leaf size can be produced by the methods and composition of the disclosure. Increasing leaf biomass can be used to increase production of plant-derived pharmaceutical or industrial products. An increase in total plant photosynthesis can be achieved by, for example, increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of a tissue, such as root tissue, may be useful to improve a plant's ability to grow under harsh environmental conditions, including drought or nutrient deprivation. Larger roots may better reach water or nutrients or take up water or nutrients.

The ability to provide larger varieties can be highly desirable, for example, for some ornamental plants. For many plants, including fruit-bearing trees, trees that are used for lumber production, or trees and shrubs that serve as view or wind screens, increased stature can provide improved benefits in the forms of greater yield or improved screening.

Herbicide Resistance in Plants

An "herbicide resistance protein" or a protein resulting from expression of an "herbicide resistance-encoding nucleic acid molecule" can include proteins that can confer upon a cell the ability to tolerate a higher concentration of an herbicide, for example, compared with cells that do not express the protein. An herbicide resistance protein or a protein resulting from expression of a herbicide resistance-encoding nucleic acid molecule can include proteins that can confer upon a cell the ability to tolerate a concentration of a herbicide for a longer period of time than cells that do not express the protein. Herbicide resistance traits may be introduced into plants by, for example, genes coding for resistance to herbicides. Genes coding for resistance to herbicides include, for example, genes that act to inhibit the action of acetolactate synthase (ALS), such as the sulfonylurea-type herbicides, genes that act to inhibit the action of glutamine synthase, such as phosphinothricin or basta (e.g., the bar gene), glyphosate (e.g., the EPSP synthase gene), HPPD inhibitors (e.g, the HPPD gene).

Herbicide resistance proteins can include the following: a 4-hydroxphenylpyruvate dioxygenase (HPPD), a sulfonylurea-tolerant acetolactate synthase (ALS), an imidazolinone-tolerant acetolactate synthase (ALS), a glyphosate-tolerant 5-enolpyruvylshikimate-3-phosphate synthase (EPSPS), a glyphosate-tolerant glyphosate oxidoreductase (GOX), a glyphosate N-acetyltransferase (GAT), a phosphinothricin acetyl transferase (PAT), a protoporphyrinogen oxidase (PROTOX), an auxin enzyme or receptor, a P450 polypeptide and an acetyl coenzyme A carboxylase (AC-Case). Non-limiting examples of genes useful for conferring herbicide resistance in plants can include genes that encode the above proteins.

As used herein, "Hydroxyphenylpyruvate dioxygenase" and "HPPD", "4-hydroxy phenyl pyruvate (or pyruvic acid) dioxygenase (4-HPPD)" and "p-hydroxy phenyl pyruvate (or pyruvic acid) dioxygenase (p-OHPP)" can be synonymous and can refer to a non-heme iron-dependent oxygenase that catalyzes the conversion of 4-hydroxyphenylpyruvate to homogentisate. In organisms that degrade tyrosine, the reaction catalyzed by HPPD can be the second step in the pathway. In plants, formation of homogentisate can be necessary for the synthesis of plastoquinone, which can serve as a redox cofactor, and tocopherol. A polynucleotide molecule encoding hydroxyphenylpyruvate dioxygenase (HPPD) can provide tolerance to HPPD inhibitors.

As used herein, an "HPPD inhibitor" can comprise any compound or combinations of compounds which can decrease the ability of HPPD to catalyze the conversion of 4-hydroxyphenylpyruvate to homogentisate. In specific embodiments, the HPPD inhibitor can comprise an herbicidal inhibitor of HPPD. Non-limiting examples of HPPD inhibitors include, triketones (such as, mesotrione, sulcotrione, topramezone, and tembotrione); isoxazoles (such as, pyrasulfotole and isoxaflutole); pyrazoles (such as, benzofenap, pyrazoxyfen, and pyrazolynate); and benzobicyclon. Agriculturally acceptable salts of the various inhibitors can include salts (e.g., the cations or anions) for the formation of salts for agricultural or horticultural use.

An "ALS inhibitor-tolerant polypeptide" can comprise any polypeptide which when expressed in a plant can confer tolerance to at least one ALS inhibitor. ALS inhibitors include, for example, sulfonylurea, imidazolinone, triazolopyrimidines, pryimidinyoxy(thio)benzoates, and/or sulfonylaminocarbonyltriazolinone herbicides. ALS mutations can fall into different classes with regard to tolerance to, for example, sulfonylureas, imidazolinones, triazolopyrimidines, and pyrimidinyl(thio)benzoates. ALS mutations can include mutations having one or more of the following characteristics: (1) broad tolerance to all four of these groups (e.g., sulfonylureas, imidazolinones, triazolopyrimidines, and pyrimidinyl(thio)benzoates); (2) tolerance to imidazolinones and pyrimidinyl(thio)benzoates; (3) tolerance to sulfonylureas and triazolopyrimidines; and (4) tolerance to sulfonylureas and imidazolinones.

Polynucleotide molecules encoding proteins involved in herbicide resistance can include a polynucleotide molecule encoding 5-enolpymvylshikimate-3-phosphate synthase (EPSPS) for example, for imparting glyphosate tolerance.

Glyphosate tolerance can also be obtained by expression of polynucleotide molecules encoding a glyphosate oxidoreductase (GOX) or a glyphosate-N-acetyl transferase (GAT).

Polynucleotides encoding an exogenous phosphinothricin acetyltransferase can be used for herbicide resistance. Plants containing an exogenous phosphinothricin acetyltransferase can exhibit improved tolerance to glufosinate herbicides, which can inhibit, for example, the enzyme glutamine synthase.

Polynucleotides conferring altered protoporphyrinogen oxidase (protox) activity can be used for herbicide resistance. Plants containing such polynucleotides can exhibit improved tolerance to any of a variety of herbicides which can target, for example, the protox enzyme (also referred to as "protox inhibitors").

Dicamba monooxygenase can be used for providing dicamba tolerance.

A polynucleotide molecule encoding AAD12 or encoding AAD1 can be used for providing resistance to, for example, auxin herbicides.

A P450 sequence can be used for conferring herbicide resistance. A P450 sequence can provide tolerance to HPPD inhibitors by, for example, metabolism of the herbicide. Such sequences include, but are not limited to, the NSF1 gene.

Pest Resistance in Plants by Gene Silencing

A "plant pest" can mean any living stage of an entity that can directly or indirectly injure, cause damage to, or cause disease in any plant or plant product. A plant pest can include a protozoan, a nonhuman animal, a parasitic plant, a bacterium, a fungus, a virus, a viroid, an infectious agent, a pathogen, or any article similar to or allied thereof.

Double-stranded RNA (dsRNA) can be used to provide resistance to plant pests.

Plant pest invertebrates can include, but are not limited to, pest nematodes, pest mollusks (slugs and snails), and pest insects. Plant pathogens can include fungi and nematodes.

The plant pathogen can be a eukaryotic plant pathogen. This includes for example, a fungal pathogen, such as a phytopathogenic fungus.

Non-limiting examples of fungal plant pathogens include, e. g., the fungi that cause powdery mildew, rust, leaf spot and blight, damping-off, root rot, crown rot, cotton boll rot, stem canker, twig canker, vascular wilt, smut, or mold, including, but not limited to, *Fusarium* spp., *Phakospora* spp., *Rhizoctonia* spp., *Aspergillus* spp., *Gibberella* spp., *Pyricularia* spp., *Alternaria* spp., and *Phytophthora* spp. Specific examples of fungal plant pathogens include *Phakospora pachirhizi* (Asian soy rust), *Puccinia sorghi* (corn common rust), *Puccinia polysora* (corn Southern rust), *Fusarium oxysporum* and other *Fusarium* spp., *Alternaria* spp., *Penicillium* spp., *Pythium aphanidermatum* and other *Pythium* spp., *Rhizoctonia solani*, *Exserohilum turcicum* (Northern corn leaf blight), *Bipolaris maydis* (Southern corn leaf blight), *Ustilago maydis* (corn smut), *Fusarium graminearum* (*Gibberella zeae*), *Fusarium verticilliodes* {*Gibberella moniliformis*}, *F. proliferatum* (*G. fujikuroi* var. *intermedia*), *F. sub glutinous* (*G. subglutinans*), *Diplodia maydis*, *Sporisorium holci-sorghi*, *Colletotrichum graminicola*, *Setosphaeria turcica*, *Aureobasidium zeae*, *Phytophthora infestans*, *Phytophthora sojae*, *Sclerotinia sclerotiorum*, and fungal species.

Non-limiting examples of invertebrate pests can include cyst nematodes *Heterodera* spp. such as soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., foliar nematodes *Aphelenchus* spp. or *Aphelenchoides* spp., corn rootworms, *Lygus* spp., aphids and similar sap-sucking insects such as *phylloxera* (*Daktulosphaira vitifoliae*), corn borers, cutworms, armyworms, leafhoppers, Japanese beetles, grasshoppers, and other pest coleopterans, dipterans, and lepidopterans. Additional examples of invertebrate pests can include pests that can infest the root systems of crop plants, e. g., northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), claybacked cutworm (*Agrotis gladiaria*), wireworm (*Melanotus* spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape colaspis (*Colaspis brunnea*), seedcorn beetle (*Stenolophus lecontei*), and slender seedcorn beetle (*Clivinia impressifrons*), and parasitic nematodes.

A target gene of interest (e.g., for gene silencing) may include any coding or non-coding sequence from any species (including, but not limited to, eukaryotes such as fungi; plants, including monocots and dicots, such as crop plants, ornamental plants, and non-domesticated or wild plants; invertebrates such as arthropods, annelids, nematodes, and mollusks; and vertebrates such as amphibians, fish, birds, and mammals). Non-limiting examples of a non-coding sequence (e.g., that can be expressed by a gene expression element such as a regulatory sequence) include, but not limited to, 5' untranslated regions, promoters, enhancers, or other non-coding transcriptional regions, 3' untranslated regions, terminators, introns, microRNAs, microRNA precursor DNA sequences, small interfering RNAs, RNA components of ribosomes or ribozymes, small nucleolar RNAs, and other non-coding RNAs. Non-limiting examples of a gene of interest further include, but are not limited to, translatable (coding) sequence, such as genes encoding transcription factors and genes encoding enzymes involved in the biosynthesis or catabolism of molecules of interest (such as amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

The target gene (e.g., for gene silencing) may be an essential gene of the plant pest or plant pathogen. Essential genes can include genes that may be required for development of the pest or pathogen to a fertile reproductive adult. Essential genes can include genes that, when silenced or suppressed, can result in the death of the organism (e.g., as an adult or at any developmental stage, including gametes) or in the organism's inability to successfully reproduce (e. g., sterility in a male or female parent or lethality to the zygote, embryo, or larva). Non-limiting examples of nematode essential genes include major sperm protein, RNA polymerase II, and chitin synthase. Additional soybean cyst nematode essential genes are provided in U. S. Patent Publication US20070271630, incorporated by reference herein. The gene can be a *Drosophila* essential gene. The gene can be a fungal essential gene.

Target genes (e.g., from pests) can include invertebrate genes for major sperm protein, alpha tubulin, beta tubulin, vacuolar ATPase, glyceraldehyde-3-phosphate dehydrogenase, PvNA polymerase ττ, chitin synthase, cytochromes, miRNAs, miRNA precursor molecules and miRNA promoters. Target genes (e.g., from pathogens) can include genes for miRNAs, miRNA precursor molecules, fungal tubulin, fungal vacuolar ATPase, fungal chitin synthase, fungal MAP kinases, fungal Pad Tyr/Thr phosphatase, enzymes involved in nutrient transport (e. g., amino acid transporters or sugar transporters), enzymes involved in fungal cell wall biosynthesis, cutinases, melanin biosynthetic enzymes, polygalacturonases, pectinases, pectin lyases, cellulases, proteases, genes that interact with plant avirulence genes, and genes involved in invasion and replication of the pathogen in the infected plant.

Plants may be transformed (e.g., in the nucleus, an organelle, or both) with an expression cassette encoding, for example, a dsRNA, a siRNA or a miRNA. The dsRNA, siRNA, or miRNA can suppress (e.g., expression of) at least one (e.g., at least 1, at least 2, at least 3, at least 4, at least 5, at least 6, at least 7, at least 8, at least 9, or at least 10) target gene present in a plant pest. The dsRNA, siRNA, or miRNA can suppress, for example, 1, 2, 3, 4, 5, 6, 7, 8, 9, 10, 15, 20 or more target genes of a plant pest. Suppression of a target gene present in the plant pest can provide complete or nearly complete protection from the plant pest. "Complete protection" can mean that no (e.g., substantial) damage can be caused to the plant by the plant pest.

The dsRNA, the siRNA or the miRNA may be designed for suppression of a gene selected from the group consisting of: proteasome A-type subunit peptide (Pas-4), ACT, SHR, EPIC2B and PnPMAI.

SEQ ID NO:114 corresponds to an open reading frame encoding an *Heterodera glycines* (SCN) specific proteasome A-type subunit peptide that can be referred to herein as Pas-4. SEQ ID NO: 115 corresponds to nucleotides 552-699 of SEQ ID NO: 114. SEQ ID NO: 115 or SEQ ID NO: 114 can be useful for dsRNA-mediated suppression of Pas-4.

ACT can encode β-actin, which can be an essential cytoskeletal protein. SHR can encode Shrub (also known as Vps32 or Snf7), which can be an essential subunit of a protein complex involved in membrane remodeling for vesicle transport. EPIC2B can encode a *Phytophthora infestans* protein that can interact with and/or inhibit a novel papain-like extracellular Cys protease, for b. Cas Protein A Cas protein can be a protein of a CRISPR/Cas system. A Cas protein can be a Class 1 or a Class 2 Cas protein. A Cas protein can be a Type I, Type II, Type III, Type IV, Type V, or Type VI Cas protein.

"Cas gene" can refer to a gene that encodes a Cas protein. The terms Cas protein and Cas polypeptide can be used interchangeably herein. Cas gene can be coupled, associated or close to or in the vicinity of flanking CRISPR loci. The terms "Cas gene", "CRISPR-associated (Cas) gene" can be used interchangeably herein.

A Cas protein can bind to a target nucleic acid. A Cas protein can be a Cas nuclease. A Cas protein can be a Cas endonuclease. A Cas protein can complex with a guide polynucleotide. A Cas protein can be directed to a target nucleic acid by a guide polynucleotide. A Cas protein can complex with a guide polynucleotide to recognize a target nucleic acid. A Cas protein can introduce a single strand or double strand break at a target nucleic acid sequence (e.g., DNA or RNA). A Cas protein can be enabled by the guide polynucleotide to recognize and introduce a single strand or double strand break at a specific target site into the genome of a cell.

A Cas protein can comprise one or more domains. Non-limiting examples of domains include, guide nucleic acid recognition and/or binding domain, nuclease domains (e.g., DNase or RNase domains, RuvC, HNH), DNA binding domain, RNA binding domain, helicase domains, protein-protein interaction domains, and dimerization domains. A guide nucleic acid recognition and/or binding domain can interact with a guide nucleic acid. A nuclease domain can comprise catalytic activity for nucleic acid cleavage. A nuclease domain can lack catalytic activity to prevent nucleic acid cleavage. A Cas protein can be a chimeric Cas protein that is fused to other proteins or polypeptides. A Cas protein can be a chimera of various Cas proteins, for example, comprising domains from different Cas proteins (e.g., homologues).

Non-limiting examples of Cas proteins include c2c1, C2c2, c2c3, Cas1, Cas1B, Cas2, Cas3, Cas4, Cas5, Cas5e (CasD), Cas6, Cas6e, Cas6f, Cas7, Cas8a, Cas8a1, Cas8a2, Cas8b, Cas8c, Cas9 (Csn1 or Csx12), Cas10, Cas10d, Cas1O, Cas1Od, CasF, CasG, CasH, Cpf1, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx1O, Csx16, CsaX, Csx3, Csx1, Csx15, Csf1, Csf2, Csf3, Csf4, and Cul966, and homologs or modified versions thereof.

A Cas protein may be from any suitable organism. Non-limiting examples include *Streptococcus pyogenes, Streptococcus thermophilus, Streptococcus* sp., *Staphylococcus aureus, Nocardiopsis dassonvillei, Streptomyces pristinae spiralis, Streptomyces viridochromo* genes, *Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Pseudomonas aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Leptotrichia shahii,* and *Francisella novicida*. In some aspects, the organism can be *Streptococcus pyogenes (S. pyogenes)*.

A Cas protein as used herein can be a wildtype or a modified form of a Cas protein. A Cas protein can be an active variant, inactive variant, or fragment of a wild type or modified Cas protein. A Cas protein can comprise an amino acid change such as a deletion, insertion, substitution, variant, mutation, fusion, chimera, or any combination thereof relative to a wild-type version of the Cas protein. A Cas protein can be a polypeptide with at least about 5%, 10%, 20%, 30%, 40%, 50%, 60%, 70%, 80%, 90%, 91%, 92%, 93%, 94%, 95%, 96%, 97%, 98%, 99%, or 100% sequence identity or sequence similarity to a wild type exemplary Cas protein (e.g., Cas9 from *S. pyogenes*). A Cas protein can be a polypeptide with at most about 5%, 10%, 20%, 30%, 40%, 50%, 60%, 70%, 80%, 90%, 100% sequence identity and/or sequence similarity to a wild type exemplary Cas protein. Variants or fragments can comprise at least about 5%, 10%, 20%, 30%, 40%, 50%, 60%, 70%, 80%0, 90%, 91%, 92%, 93%, 94%, 95%, 96%, 97%, 98%, 99%, or 100% sequence identity or sequence similarity to a wild type or modified Cas protein or a portion thereof. Variants or fragments can be targeted to a nucleic acid locus in complex with a guide nucleic acid while lacking nucleic acid cleavage activity.

A Cas protein can comprise one or more nuclease domains, such as DNase domains. For example, a Cas9 protein can comprise a RuvC-like nuclease domain and/or an HNH-like nuclease domain. The RuvC and HNH domains can each cut a different strand of double-stranded DNA to make a double-stranded break in the DNA. A Cas protein can comprise only one nuclease domain (e.g., Cpf1 comprises RuvC domain but lacks HNH domain)

A Cas protein can comprise an amino acid sequence having at least about 5%, 10%, 20%, 30%, 40%, 50%, 60%, 70%, 80%, 90%, 91%, 92%, 93%, 94%, 95%, 96%, 97%, 98%, 99%, or 100% sequence identity or sequence similarity to a nuclease domain (e.g., RuvC domain, HNH domain) of a wild-type Cas protein.

A Cas protein can be modified to optimize activity e.g., cleavage, regulation of gene expression. A Cas protein can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

A Cas protein can be a fusion protein. For example, a Cas protein can be fused to a cleavage domain, an epigenetic modification domain, a transcriptional activation domain, or a transcriptional repressor domain. A Cas protein can also be fused to a heterologous polypeptide providing increased or decreased stability. The fused domain or heterologous polypeptide can be located at the N-terminus, the C-terminus, or internally within the Cas protein.

A Cas protein can comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalama1, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, SI, T7, V5, VSV-G, histidine (His), biotin carboxyl carrier protein (BCCP), and calmodulin.

A Cas protein can be provided in any form. For example, a Cas protein can be provided in the form of a protein, such as a Cas protein alone or complexed with a guide nucleic acid. A Cas protein can be provided in the form of a nucleic acid encoding the Cas protein, such as an RNA (e.g., messenger RNA (mRNA)) or DNA.

The nucleic acid encoding the Cas protein can be codon optimized for efficient translation into protein in a particular cell, organelles, or organism.

Nucleic acids encoding Cas proteins can be stably integrated in the genome of an organelle or a cell. Nucleic acids encoding Cas proteins can be operably linked to a promoter active in the cell. Nucleic acids encoding Cas proteins can be operably linked to a promoter in an expression construct. Expression constructs can include any nucleic acid constructs that can direct expression of a gene or other nucleic acid sequence of interest (e.g., a Cas gene). Expression constructs can include any nucleic acid constructs that can transfer such a nucleic acid sequence of interest to a target cell (e.g., into an organelle).

In some aspects, a Cas protein can be a Class 2 Cas protein. In some aspects, a Cas protein can be a type II Cas protein. In some aspects, the Cas protein can be a Cas9 protein, a modified version of a Cas9 protein, or derived from a Cas9 protein.

Cas9 can refer to a polypeptide with at least about 5%, 10%, 20%, 30%, 40%, 50%, 60%, 70%, 80%, 90%, 100% sequence identity and/or sequence similarity to a wild type exemplary Cas9 polypeptide (e.g., Cas9 from *S. pyogenes*). Cas9 can refer to a polypeptide with at most about 5%, 10%, 20%, 30%, 40%, 50%, 60%, 70%, 80%, 90%, 100% sequence identity and/or sequence similarity to a wild type exemplary Cas9 polypeptide (e.g., from *S. pyogenes*). Cas9 can refer to the wildtype or a modified form of the Cas9 protein that can comprise an amino acid change such as a deletion, insertion, substitution, variant, mutation, fusion, chimera, or any combination thereof.

In one embodiment, the polynucleotide guided polypeptide gene can be a Cas9 protein, such as but not limited to, Cas9 sequences listed in SEQ ID NOs: 462, 474, 489, 494, 499, 505, and 518 of WO2007/025097 and incorporated herein by reference. The Cas9 protein can unwind the DNA duplex in close proximity of the genomic target site. The Cas9 protein can cleave for example both DNA strands upon recognition of a target sequence by a guide polynucleic acid. In some aspects, the Cas9 endonuclease can cleave only if the correct protospacer-adjacent motif (PAM) is approximately oriented at the 3' end of the target sequence. Mutagenesis of *Streptococcus pyogenes* Cas9 catalytic domains can produce "nicking" enzymes (Cas9n) that can induce single-strand nicks rather than double-strand breaks.

In another embodiment, the polynucleotide guided polypeptide coding sequence can be modified to use codons preferred by the target organism, e.g., a plant, maize or soybean codon-optimized sequence encoding a Cas (e.g., Cas9) protein. In another embodiment, the sequence that encodes a polynucleotide guided polypeptide can be operably linked to one or more sequences encoding nuclear localization signals; e.g., to a SV40 nuclear targeting signal upstream of the Cas protein coding region and a bipartite VirD2 nuclear localization signal downstream of the Cas protein coding region.

In another embodiment, the polynucleotide guided polypeptide may be an Argonaute protein such as *Natronobacterium gregoryi* Argonaute ("NgAgo"). The Argonaute protein can be a DNA-guided endonuclease. Argonaute proteins can bind a guide DNA such as a 5'-phosphorylated single-stranded guide DNA (gDNA) of for example, 24 nucleotides. Argonaute proteins can create site-specific target nucleic acid (e.g., DNA) breaks (e.g., double-stranded breaks) when loaded with the gDNA. The Argonaute protein—gDNA system may not require a protospacer-adjacent motif (PAM) for recognition of a target nucleic acid.

In some aspects, the polynucleotide guided polypeptide can be a dead Cas protein. A Cas protein can be a dead Cas protein. A dead Cas protein can be a protein that lacks nucleic acid cleavage activity.

A Cas protein can comprise a modified form of a wild type Cas protein. The modified form of the wild type Cas protein can comprise an amino acid change (e.g., deletion, insertion, or substitution) that reduces the nucleic acid-cleaving activity of the Cas protein. For example, the modified form of the Cas protein can have less than less than 90%, less than 80%, less than 70%, less than 60%, less than 50%, less than 40%, less than 30%, less than 20%, less than 10%, less than 5%, or less than 1% of the nucleic acid-cleaving activity of the wild-type Cas protein (e.g., Cas9 from *S. pyogenes*). The modified form of Cas protein can have no substantial nucleic acid-cleaving activity. When a Cas protein is a modified form that has no substantial nucleic acid-cleaving activity, it can be referred to as enzymatically inactive and/or "dead" (abbreviated by "d"). A dead Cas protein (e.g., dCas, dCas9) can bind to a target polynucleotide but may not cleave the target polynucleotide. In some aspects, a dead Cas protein can be a dead Cas9 protein.

Enzymatically inactive can refer to a polypeptide that can bind to a nucleic acid sequence in a polynucleotide in a sequence-specific manner, but may not cleave a target polynucleotide. An enzymatically inactive site-directed polypeptide can comprise an enzymatically inactive domain (e.g. nuclease domain). Enzymatically inactive can refer to no activity. Enzymatically inactive can refer to substantially no activity. Enzymatically inactive can refer to essentially no activity. Enzymatically inactive can refer to an activity less than 1%, less than 2%, less than 3%, less than 4%, less than 5%, less than 6%, less than 7%, less than 8%, less than 9%, or less than 10% activity compared to a wild-type exemplary activity (e.g., nucleic acid cleaving activity, wild-type Cas9 activity).

One or a plurality of the nuclease domains (e.g., RuvC, HNH) of a Cas protein can be deleted or mutated so that they are no longer functional or comprise reduced nuclease activity. For example, in a Cas protein comprising at least two nuclease domains (e.g., Cas9), if one of the nuclease domains is deleted or mutated, the resulting Cas protein, known as a nickase, can generate a single-strand break at a CRISPR RNA (crRNA) recognition sequence within a double-stranded DNA but not a double-strand break. Such a nickase can cleave the complementary strand or the non-complementary strand, but may not cleave both. If all of the nuclease domains of a Cas protein (e.g., both RuvC and HNH nuclease domains in a Cas9 protein; RuvC nuclease domain in a Cpf1 protein) are deleted or mutated, the resulting Cas protein can have a reduced or no ability to cleave both strands of a double-stranded DNA. An example of a mutation that can convert a Cas9 protein into a nickase can be a D10A (aspartate to alanine at position 10 of Cas9) mutation in the RuvC domain of Cas9 from S. pyogenes. H939A (histidine to alanine at amino acid position 839) or H840A (histidine to alanine at amino acid position 840) in the HNH domain of Cas9 from S. pyogenes can convert the Cas9 into a nickase. An example of a mutation that can convert a Cas9 protein into a dead Cas9 is a D10A (aspartate to alanine at position 10 of Cas9) mutation in the RuvC domain and H939A (histidine to alanine at amino acid position 839) or H840A (histidine to alanine at amino acid position 840) in the HNH domain of Cas9 from S. pyogenes.

A dead Cas protein can comprise one or more mutations relative to a wild-type version of the protein. The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type Cas protein. The mutation can result in one or more of the plurality of nucleic acid-cleaving domains retaining the ability to cleave the complementary strand of the target nucleic acid but reducing its ability to cleave the non-complementary strand of the target nucleic acid. The mutation can result in one or more of the plurality of nucleic acid-cleaving domains retaining the ability to cleave the non-complementary strand of the target nucleic acid but reducing its ability to cleave the complementary strand of the target nucleic acid. The mutation can result in one or more of the plurality of nucleic acid-cleaving domains to lack the ability to cleave the complementary strand and the non-complementary strand of the target nucleic acid. The residues to be mutated in a nuclease domain can correspond to one or more catalytic residues of the nuclease. For example, residues in the wild type exemplary S. pyogenes Cas9 polypeptide such as Asp10, His840, Asn854 and Asn856 can be mutated to inactivate one or more of the plurality of nucleic acid-cleaving domains (e.g., nuclease domains). The residues to be mutated in a nuclease domain of a Cas protein can correspond to residues Asp10, His840, Asn854 and Asn856 in the wild type S. pyogenes Cas9 polypeptide, for example, as determined by sequence and/or structural alignment.

As non-limiting examples, residues D10, G12, G17, E762, H840, N854, N863, H982, H983, A984, D986, and/or A987 (or the corresponding mutations of any of the Cas proteins) can be mutated. For example, e.g., D10A, G12A, G17A, E762A, H840A, N854A, N863A, H982A, H983A, A984A, and/or D986A. Mutations other than alanine substitutions can be suitable.

A D10A mutation can be combined with one or more of H840A, N854A, or N856A mutations to produce a polynucleotide guided polypeptide (e.g., Cas9 protein) substantially lacking DNA cleavage activity (e.g., a dead Cas9 protein).

In another embodiment, the polynucleotide guided polypeptide can be a polypeptide moiety (e.g., a chimeric polypeptide) that can form a programmable nucleoprotein molecular complex with a specificity conferring nucleic acid (SCNA). The programmable nucleoprotein molecular complex can assemble in-vivo, in a target cell, or in an organelle. The programmable nucleoprotein molecular complex can interact with a predetermined target nucleic acid sequence. The programmable nucleoprotein molecular complex may comprise a polynucleotide molecule encoding a chimeric polypeptide. The chimeric polypeptide can comprise a functional domain that can modify a target nucleic acid site. The functional domain can be devoid of a specific nucleic acid binding site. The chimeric polypeptide can comprise a linking domain that can interact with a SCNA. The linking domain can be devoid of a specific target nucleic acid binding site. A SCNA can comprise a nucleotide sequence complementary to a region of a target nucleic acid flanking the target site. A SCNA can comprise a recognition region that can specifically attach to the linking domain of a chimeric polypeptide. Assembly of the chimeric polypeptide and the SCNA within the target cell can form a functional nucleoprotein complex. The nucleoprotein complex can specifically modify a target nucleic acid at the target site.

In another embodiment, the polynucleotide guided endonuclease gene can be a full-length polynucleotide guided endonuclease (e.g., Cas endonuclease, Cas9 endonuclease), or any functional fragment or functional variant thereof.

The terms "functional fragment", "fragment that is functionally equivalent" and "functionally equivalent fragment" can be used interchangeably herein. In the context of a sequence encoding a polynucleotide guided polypeptide, these terms can refer to a portion or subsequence of the polynucleotide guided polypeptide sequence. The portion or subsequence of the polynucleotide guided polypeptide sequence can comprise the ability to create a single-strand or double-strand break.

The terms "functional variant", "variant that is functionally equivalent" and "functionally equivalent variant" can be used interchangeably herein. In the context of a polynucleotide guided polypeptide, these terms can refer to a variant of the polynucleotide guided polypeptide. The variant can comprise the ability to create a single-strand or double-strand break. Fragments and variants can be obtained via methods such as site-directed mutagenesis and synthetic construction.

In one embodiment, the polynucleotide guided polypeptide coding sequence can be a plant codon-optimized *Streptococcus pyogenes* Cas9 coding sequence. The codon optimized Cas9 sequence can recognize any genomic sequence, for example, of the form N(12-30)NGG.

In one embodiment, the polynucleotide guided polypeptide can be introduced directly into a cell by any suitable method, for example, but not limited to transient introduction methods, transfection and/or topical application.

Compositions and methods of the disclosure can use endonucleases. Endonucleases can be enzymes that cleave the phosphodiester bond within a polynucleotide chain. Endonucleases can include restriction endonucleases that cleave DNA at specific sites without damaging the bases. Restriction endonucleases can include Type I, Type II, Type III, and Type IV endonucleases, which can further include subtypes. In the Type I and Type III systems, both the methylase and restriction activities can be contained in a single complex. Endonucleases can also include meganucleases, also known as homing endonucleases (HEases). Meganucleases can bind and cut at a specific recognition site, which can be about 18 bp or more. Meganucleases can be classified into four families based on conserved sequence motifs. The meganuclease families can be LAGLIDADG, GIY-YIG, H—N—H, and His-Cys box families. These motifs can participate in the coordination of metal ions and hydrolysis of phosphodiester bonds. HEases can have long recognition sites, and can tolerate sequence polymorphisms in their DNA substrates. The naming convention for meganuclease can be similar to the convention for other restriction endonuclease.

Meganucleases can also be characterized by prefix F-, I-, or PI- for enzymes encoded by free-standing ORFs, introns, and inteins, respectively. One step in the recombination process can involve polynucleotide cleavage at or near the recognition site. This cleaving activity can be used to produce a double-strand break. In some examples the recombinase can be from the Integrase or Resolvase families.

Compositions and methods of the disclosure can use Transcription activator-like effector nucleases (TALENs; TAL effector nucleases) can be a class of sequence-specific nucleases. TALENs can be used to cleave (e.g., double-strand breaks) at specific target sequences (e.g., in the genome of a plant or other organism). TAL effector nucleases can be created by fusing a native or engineered transcription activator-like (TAL) effector, or functional part thereof, to the catalytic domain of an endonuclease, such as, for example, FokI. The unique, modular TAL effector DNA binding domain can allow for the design of proteins with potentially any given DNA recognition specificity.

Compositions and methods of the disclosure can use zinc finger nucleases (ZFNs). ZFNs can be engineered cleavage (e.g., double-strand break) inducing agents comprised of a zinc finger DNA binding domain and a double-strand-break-inducing agent domain. Recognition site specificity can be conferred by the zinc finger domain, which can comprise two, three, or four zinc fingers, for example having a C2H2 structure. Zinc finger domains can be amenable for designing polypeptides which specifically bind a selected polynucleotide recognition sequence. ZFNs can consist of an engineered DNA-binding zinc finger domain linked to a non-specific endonuclease domain, for example, a nuclease domain from a Type IIS endonuclease such as FokI. Additional functionalities can be fused to the zinc-finger binding domain, including transcriptional activator domains, transcription repressor domains, and methylases. In some examples, dimerization of nuclease domain may be required for cleavage activity. Each zinc finger can recognize, for example, three consecutive base pairs in the target DNA. For example, a 3 finger domain recognized a sequence of 9 contiguous nucleotides, with a dimerization requirement of the nuclease, two sets of zinc finger triplets can be used to bind an 18 nucleotide recognition sequence.

c. Guide Polynucleic Acid

Bacteria and archaea can have evolved adaptive immune defenses termed clustered regularly interspaced short palindromic repeats (CRISPR)/CRISPR-associated (Cas) systems that can use short RNA to direct degradation of foreign nucleic acids. The type II CRISPR/Cas system from bacteria can employ a crRNA and tracrRNA to guide the Cas polypeptide to a nucleic acid target. The crRNA (CRISPR RNA) can contain the region complementary to one strand of the double strand DNA target. The crRNA can base pair with the tracrRNA (trans-activating CRISPR RNA) to form a RNA duplex that can direct the Cas polypeptide to recognize and optionally cleave the DNA target.

As used herein, the term "guide polynucleotide", can refer to a polynucleotide sequence that can form a complex with a polynucleotide guided polypeptide (e.g., a Cas protein). The guide polynucleotide can direct the polynucleotide guided polypeptide to recognize and optionally cleave (or nick) a DNA target site. The terms "guide polynucleotide" and "guide polynucleic acid" can be used interchangeably herein. The guide polynucleotide can be comprised of a single molecule (unimolecular) or two molecules (bimolecular). The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids can also be referred to as a "guide RNA" (gRNA). In some embodiments, the guide polynucleic acid can be a guide RNA.

As used herein, the term "single guide RNA" (sgRNA) can refer to a synthetic fusion of two RNA molecules, for example, a crRNA (CRISPR RNA) comprising a variable targeting domain, and a tracrRNA. In one embodiment, the guide RNA can comprise a variable targeting domain of 12 to 30 nucleotide sequences and a RNA fragment that can interact with a Cas protein.

As used herein, "crRNA" can refer to a nucleic acid with at least about 5%, 10%, 20%, 30%, 40%, 50%, 60%, 70%, 80%, 90%, 100% sequence identity and/or sequence similarity to a wild type exemplary crRNA (e.g., a crRNA from S. pyogenes). crRNA can refer to a nucleic acid with at most about 5%, 10%, 20%, 30%, 40%, 50%, 60%, 70%, 80%, 90%, 100% sequence identity and/or sequence similarity to a wild type exemplary crRNA (e.g., a crRNA from S. pyogenes). crRNA can refer to a modified form of a crRNA that can comprise a nucleotide change such as a deletion, insertion, or substitution, variant, mutation, or chimera. A crRNA can be a nucleic acid having at least about 60% identical to a wild type exemplary crRNA (e.g., a crRNA from S. pyogenes) sequence over a stretch of at least 6 contiguous nucleotides. For example, a crRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical, to a wild type exemplary crRNA sequence (e.g., a crRNA from S. pyogenes) over a stretch of at least 6 contiguous nucleotides As used herein, "tracrRNA" can refer to a nucleic acid with at least about 5%, 10%, 20%, 30%, 40%, 50%, 60%, 70%, 80%, 90%, 100% sequence identity and/or sequence similarity to a wild type exemplary tracrRNA sequence (e.g., a tracrRNA from S. pyogenes). tracrRNA can refer to a nucleic acid with at most about 5%, 10%, 20%, 30%, 40%, 50%, 60%, 70%, 80%, 90%, 100% sequence identity and/or sequence similarity to a wild type exemplary tracrRNA sequence (e.g., a tracrRNA from S. pyogenes). tracrRNA can refer to a modified form of a tracrRNA that can comprise a nucleotide change such as a deletion, insertion, or substitution, variant, mutation, or chimera. A tracrRNA can refer to a nucleic acid that can be at least about 60% identical to a wild type exemplary tracrRNA (e.g., a tracrRNA from *S. pyogenes*) sequence over a stretch of at least 6 contiguous nucleotides. For example, a tracrRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical, to a wild type exemplary tracrRNA (e.g., a tracrRNA from *S. pyogenes*) sequence over a stretch of at least 6 contiguous nucleotides.

A guide polynucleotide can be bimolecular (i.e., two molecules; also referred to as "double molecule", "dual" or "duplex" guide polynucleotide) comprising, for example, a first nucleotide sequence domain (referred to as Variable Targeting domain or VT domain) that is complementary to a nucleotide sequence in a target polynucleic acid (e.g., target DNA) and a second nucleotide sequence domain (referred to as Cas endonuclease recognition domain or CER domain) that interacts with a Cas polypeptide. The VT domain can refer to the spacer region of a guide polynucleic acid. The VT domain can comprise a spacer region of a guide polynucleic acid. The spacer region can interact with a protospacer region of a target nucleic acid in a sequence-specific manner via hybridization (e.g., base pairing). The CER domain of the bimolecular guide polynucleotide can comprise two separate molecules that can be hybridized along a region of complementarity to form, for example, a duplex or a partial duplex. The two separate molecules can be RNA, DNA, and/or RNA-DNA-combination sequences. In some embodiments, the first molecule of the duplex guide polynucleotide comprising a VT domain linked to a CER domain can be referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the crRNA naturally occurring in bacteria and archaea. In one embodiment, the size of the fragment of the crRNA naturally occurring in bacteria and archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments, the second molecule of the duplex guide polynucleotide comprising a CER domain can be referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one embodiment, the RNA that guides the RNA/Cas9 polypeptide complex, can be a duplexed RNA comprising a duplex crRNA-tracrRNA.

Complementarity between a guide polynucleic acid (e.g., the VT domain, spacer region) and a target polynucleic acid (e.g., protospacer) can be perfect, substantial, or sufficient. Perfect complementarity between two nucleic acids can mean that the two nucleic acids can form a duplex in which every base in the duplex can be bonded to a complementary base by Watson-Crick pairing. Substantial or sufficient complementary can mean that a sequence in one strand may not be completely and/or perfectly complementary to a sequence in an opposing strand, but that sufficient bonding occurs between bases on the two strands to form a stable hybrid complex in a set of hybridization conditions (e.g., salt concentration and temperature).

A guide polynucleotide can also be a single molecule (i.e., unimolecular), comprising a first nucleotide sequence domain (referred to as Variable Targeting domain or VT domain) that can be complementary to a nucleotide sequence in a target polynucleic acid (e.g., target DNA) and a second nucleotide domain (referred to as Cas endonuclease recognition domain or CER domain) that interacts with a Cas polypeptide.

For a single molecule guide polynucleotide, the CER domain can be formed from a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments, the single guide polynucleotide comprises a crNucleotide (comprising a VT domain linked to a CER domain) linked to a tracrNucleotide (comprising a CER domain), wherein the linkage can be a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (sgRNA; when composed of a contiguous stretch of RNA nucleotides) or "single guide DNA" (sgDNA; when composed of a contiguous stretch of DNA nucleotides) or "single guide RNA-DNA" (sgDNA-RNA; when composed of a combination of DNA and RNA nucleotides). In one embodiment of the disclosure, the single guide RNA (sgRNA) comprises a crRNA or crRNA fragment and a tracrRNA or tracrRNA fragment of the type II CRISPR/Cas system that can form a complex with a type II Cas polypeptide, wherein said guide RNA/Cas polypeptide complex can direct the Cas polypeptide to a plant genomic target site, enabling the Cas polypeptide to introduce a double strand break into the genomic target site.

The term "variable targeting domain" or "VT domain" can be used interchangeably herein and can refer to a nucleotide sequence that can be present in the guide polynucleotide. VT domain can be complementary to one strand of a double stranded DNA target site. The percent complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable target domain can comprise at least 17 nucleotides that are complementary to at least 17 nucleotides of a target polynucleic acid. In some embodiments, the variable targeting domain can comprise a contiguous stretch of nucleotides that are complementary to the target polynucleic acid. In some embodiments, the nucleotides of the guide polynucleic acid that are complementary to the target polynucleic acid can be non-contiguous. In some embodiments, the variable targeting domain can comprise a contiguous stretch of 12 to 30 nucleotides. The variable targeting domain can be composed of a DNA sequence, a RNA sequence, a modified DNA sequence, a modified RNA sequence, or any combination thereof.

A target polynucleotide can be identified by identifying a protospacer adjacent motif (PAM) within a region of interest and selecting a region of a desired size upstream or downstream of the PAM as the protospacer. A corresponding spacer sequence can be designed by determining the complementary sequence of the protospacer region.

The term "Cas endonuclease recognition domain" or "CER domain" of a guide polynucleotide can be used interchangeably herein and can refer to a nucleotide sequence (such as a second nucleotide sequence domain of a guide polynucleotide), that interacts with a Cas polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetranucleotide loop sequence, such as, but not limiting to a GAAA tetranucleotide loop sequence. Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide polynucleotide to a subcellular location, a modification or sequence that provides for tracking, a modification or sequence that provides a binding site for proteins, a Locked Nucleic Acid (LNA), a 5-methyl-2'-deoxycytodine (5mdC), a 2,6-Diaminopurine nucleotide, a 2'-Fluoroadenosine nucleotide, a 2'-Fluorouridine nucleotide; a 2'-O-Methyl RNA nucleotide, a phosphorothioate (PS) bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature can be selected from the group consisting of: modified or regulated stability, subcellular targeting, tracking, a fluorescent label, a binding site for a protein or protein complex, modified binding affinity to complementary target sequence, modified resistance to cellular degradation, and increased cellular permeability.

In one embodiment, the guide RNA and Cas polypeptide can form a complex that can enable the Cas polypeptide to introduce a single strand or double strand break at a DNA target site.

In one embodiment, the variable target domain can be 12, 13, 14, 15, 16, 17, 18, 19, 20, 21, 22, 23, 24, 25, 26, 27, 28, 29 or 30 nucleotides in length.

In one embodiment, the guide RNA can comprise a crRNA (or crRNA fragment) and a tracrRNA (or tracrRNA fragment) of the type II CRISPR/Cas system that can form a complex with a type II Cas polypeptide. The guide RNA/Cas polypeptide complex can direct the Cas polypeptide to a target nucleic acid site (e.g., DNA target). The Cas polypeptide can introduce a double strand break into the DNA target site.

In one embodiment the guide polynucleic acid can be introduced into a cell directly using any suitable method such as, but not limited to, particle bombardment or topical applications.

In another embodiment the guide polynucleic acid can be introduced indirectly by introducing a recombinant DNA molecule comprising a polynucleotide encoding the guide polynucleic acid operably linked to a nuclear or organellar promoter that can transcribe the polynucleotide in said nucleus or organelle, respectively.

In some embodiments, the guide polynucleic acid can be introduced into a plant cell via particle bombardment or *Agrobacterium* transformation of a recombinant DNA construct comprising a polynucleotide encoding the guide polynucleic acid operably linked to a promoter functional in a plant; e.g., a plant U6 polymerase III promoter, a CaMV 35S polymerase II promoter.

In one embodiment, the guide polynucleic acid can be a duplexed RNA comprising a duplex crRNA-tracrRNA. A single guide polynucleic acid (e.g., single guide RNA) can require one expression cassette to express the single guide RNA. A duplexed crRNA-tracrRNA can require one or more expression cassette needs to express the duplexed crRNA-tracrRNA.

A plurality of polynucleic acids can be multiplexed to target multiple target nucleic acids. For example, 2, 3, 4, 5, 6, 7, 9, 10, or more than 10 target nucleic acids can be targeted simultaneously or iteratively. Multiplexing can be used, as non-limiting examples, to generate large genomic deletions, modify multiple different sequences at once, and/or in conjunction with dual-nickases to target a gene. In some examples, more than one CRISPR/Cas system can be delivered to target two or more nucleic acid sequence targets. Homologous Cas proteins can be used for multiplexing applications.

Target Sites for Genome Modification

The terms "target site", "target sequence", "target polynucleotide", "target polynucleic acid", "target locus", "genomic target site", "genomic target sequence", and "genomic target locus" can be used interchangeably herein. Target polynucleic acid can refer to a polynucleotide sequence in the genome (e.g., plastid or mitochondrial genome) of, for example, a plant cell. Target polynucleic acid can refer to the site (e.g., in a genome) recognized by a guide polynucleic acid. Target polynucleic acid can refer to the site (e.g., in a genome) at which a single-strand or double-strand break can be induced (e.g., by a Cas polypeptide). The target site can be an endogenous site in the genome. The target site can be heterologous to the organism and thereby not be naturally occurring in the genome. Target site can be found in a heterologous genomic location compared to where it occurs in nature. As used herein, terms "endogenous target sequence" and "native target sequence" can be used interchangeably herein and can refer to a target sequence that can be endogenous or native to the genome of the organism. Endogenous target sequence can occur at the endogenous or native position of that target sequence in the genome of the organism.

A target polynucleic acid can be DNA, RNA, or both. In some embodiments, the target polynucleic acid can be DNA (e.g., target DNA). In some embodiments, the target polynucleic acid can be genomic DNA. In some embodiments, the target polynucleic acid can be nuclear genomic DNA. In some embodiments, the target polynucleic acid can be organelle genomic DNA. In some embodiments, the target polynucleic acid can be nuclear genomic DNA and organelle genomic DNA.

The terms "artificial target site" and "artificial target sequence" can be used interchangeably herein and can refer to a target sequence that has been introduced into the genome of a plant. Such an artificial target sequence can be identical in sequence to an endogenous or native target sequence in the genome of an organism but may be located in a different position (i.e., a non-endogenous or non-native position) in the genome of the organism.

An "altered target site", "altered target sequence", "modified target site", "modified target sequence" can be used interchangeably herein and can refer to a target sequence as disclosed herein that can comprise at least one alteration when compared to the non-altered target sequence. Such "alterations" can include, for example: (i) replacement of at least one nucleotide, (ii) a deletion of at least one nucleotide, (iii) an insertion of at least one nucleotide, or (iv) any combination of (i)-(iii).

Methods for modifying an organellar genomic target site are disclosed herein.

In one embodiment, a method for modifying a target site in the genome of an organelle can comprise introducing a guide polynucleic acid (e.g, guide RNA, single guide RNA) into a plant cell. The plant cell can comprise a polynucleotide guided polypeptide (e.g., a Cas polypeptide). The guide polynucleic acid and polynucleotide guided polypeptide can form a complex that can direct the polynucleotide guided polypeptide to introduce a single strand or double strand break at the target site.

Also provided is a method for modifying a target site in the genome of an organelle. The method can comprise introducing a guide polynucleic acid and a polynucleotide guided polypeptide (e.g., a Cas polypeptide) into the organelle. The guide polynucleic acid and polynucleotide guided polypeptide can form a complex. The complex can direct the polynucleotide guided polypeptide to introduce a single strand or double strand break at the target site in the genome of the organelle.

Further provided is a method for modifying a target site in the genome of an organelle. The method can comprise introducing a guide polynucleic acid and a donor polynucleotide (e.g. donor DNA) into an organelle. The organelle can comprise a polynucleotide guided polypeptide (e.g., a Cas polypeptide). The guide polynucleic acid and polynucleotide guided polypeptide can form a complex that can direct the polynucleotide guided polypeptide to introduce a single strand or double strand break at the target site. The donor polynucleotide can be inserted into the site of cleavage in the genome.

Further provided is a method for modifying a target site in the genome of an organelle. The method can comprise: a) introducing into an organelle a guide polynucleic acid comprising a variable targeting domain and a polynucleotide guided polypeptide (e.g., a Cas polypeptide), wherein said guide polynucleic acid and said polynucleotide guided polypeptide can form a complex that can enable the polynucleotide guided polypeptide to introduce a single strand or double strand break at said target site; and, b) identifying at least one organelle that has a modification at said target site, wherein the modification includes at least one deletion or substitution of one or more nucleotides in said target site.

Further provided, a method for modifying a target polynucleic acid (e.g., target DNA) sequence in the genome of an organelle, the method comprising: a) introducing into an organelle a first recombinant DNA construct that can express a guide polynucleic acid and a second recombinant DNA construct that can express a polynucleotide guided polypeptide (e.g., a Cas polypeptide), wherein said guide polynucleic acid and said polynucleotide guided polypeptide can form a complex that can enable the polynucleotide guided polypeptide to introduce a single strand or double strand break at said target site; and, b) identifying at least one organelle that has a modification at said target site, wherein the modification includes at least one deletion or substitution of one or more nucleotides in said target site.

The length of the target site can vary and includes, for example, target sites that are at least 12, 13, 14, 15, 16, 17, 18, 19, 20, 21, 22, 23, 24, 25, 26, 27, 28, 29, 30 or more nucleotides in length. The target site can be palindromic, that is, the sequence on one strand reads the same in the opposite direction on the complementary strand. The nick/cleavage site can be within the target sequence. The nick/cleavage site can be outside of the target sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

The target nucleic acid sequence can be 5' or 3' of the PAM. The target nucleic acid sequence can be, for example, 16, 17, 18, 19, 20, 21, 22, or 23 bases immediately 5' of the first nucleotide of the PAM. The target nucleic acid sequence can be, for example, 16, 17, 18, 19, 20, 21, 22, or 23 bases immediately 3' of the last nucleotide of the PAM.

The target nucleic acid sequence can be 20 bases immediately 5' of the first nucleotide of the PAM. The target nucleic acid sequence can be 20 bases immediately 3' of the last nucleotide of the PAM.

Site-specific cleavage of a target nucleic acid by a polynucleotide guided polypeptide (e.g., Cas protein) can occur at locations determined by base-pairing complementarity between the guide nucleic acid and the target nucleic acid. Site-specific cleavage of a target nucleic acid by a polynucleotide guided polypeptide (e.g., Cas protein) can occur at locations determined by the protospacer adjacent motif (PAM). For example, the cleavage site of Cas (e.g., Cas9) can be about 1 to about 25, or about 2 to about 5, or about 19 to about 23 base pairs (e.g., 3 base pairs) upstream or downstream of the PAM sequence. In some embodiments, the cleavage site of Cas (e.g., Cas9) can be 3 base pairs upstream of the PAM sequence. In some embodiments, the cleavage site of Cas (e.g., Cpf1) can be 19 bases on the (+) strand and 23 base on the (−) strand, producing a 5' overhang 5 nt in length. In some cases, the cleavage can produce blunt ends. In some cases, the cleavage can produce staggered or sticky ends with 5' overhangs. In some cases, the cleavage can produce staggered or sticky ends with 3' overhangs.

Different organisms can comprise different PAM sequences. Different Cas proteins can recognize different PAM sequences. For example, in *S. pyogenes*, the PAM can be a sequence in the target nucleic acid that comprises the sequence 5'-XRR-3', where R can be either A or G, where X can be any nucleotide and X can be immediately 3' of the target nucleic acid sequence targeted by the spacer sequence. The PAM sequence of *S. pyogenes* Cas9 (SpyCas9) can be 5'-XGG-3', where X can be any DNA nucleotide and can be immediately 3' of the CRISPR recognition sequence of the non-complementary strand of the target DNA. The PAM of Cpf1 can be 5'-TTX-3', where X can be any DNA nucleotide and can be immediately 5' of the CRISPR recognition sequence.

Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site.

The active variants can retain biological activity. The active variants can be recognized by a polynucleotide guided polypeptide (e.g., Cas protein). The active variants can be cleaved by a polynucleotide guided polypeptide (e.g., Cas protein). Assays can be used to measure the double-strand break of a target site by an endonuclease. Assays can measure the overall activity and/or specificity of an endonuclease on DNA substrates containing recognition sites (e.g., target sites, active variants).

Methods for Integrating a Donor Polynucleotide

The disclosure provides methods to obtain an organelle comprising a donor polynucleotide. Such methods can employ homologous recombination to provide integration of the polynucleotide at the target site. A polynucleotide of interest can be provided to the organelle in a donor DNA molecule.

A donor polynucleotide can be a nucleic acid sequence (e.g., DNA, RNA, or both) that can be integrated into a target nucleic acid, for example, the genome of an organelle. The donor polynucleotide can be inserted into a genome e.g., at a cleavage site of a polynucleotide guided polypeptide. The donor polynucleotide can be inserted into a genome by homologous recombination. In some embodiments, the donor polynucleotide can comprise DNA and can be referred to as donor DNA.

A donor polynucleotide of any suitable size can be integrated into a genome. In some embodiments, the donor polynucleotide integrated into a genome can be less than 3, about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 kilobases (kb) in length. In some embodiments, the donor polynucleotide integrated into a genome can be at least about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 (kb) in length. In some embodiments, the donor polynucleotide integrated into a genome can be up to about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 (kb) in length.

A donor polynucleotide can comprise a polynucleotide of interest, a polynucleotide modification template, a heterologous expression cassette, or both. A donor polynucleotide (e.g. donor DNA) can be flanked by a first and a second region of homology. The polynucleotide modification template can be, for example, a single nucleotide change to create a different allele in the organelle genome. The first and second regions of homology of the donor polynucleotide (e.g. donor DNA) can share homology to a first and a second genomic region, respectively, present in or flanking the target site (e.g., of the organellar genome).

"Homology" can mean DNA sequences that are similar. Homology can mean, for example, nucleic acid sequences with about: 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% homology or identity. For example, a "region of homology to a genomic region" can be a region of DNA that has a similar sequence to a given "genomic region" in the organellar genome. A region of homology can be of any length that can be sufficient to promote homologous recombination at the cleaved target site. For example, the region of homology can comprise at least 5, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100 or more bases in length such that the region of homology has sufficient homology to undergo homologous recombination with the corresponding genomic region. "Sufficient homology" can indicate that two polynucleotide sequences can have sufficient structural similarity to act as substrates for a homologous recombination reaction.

The donor polynucleotide (e.g., donor DNA) may comprise an expression cassette (e.g., encoding a heterologous polynucleotide of interest). The donor polynucleotide may comprise multiple expression cassettes. The expression cassette may be a polycistronic expression cassette; e.g., where multiple protein-coding regions, functional RNAs, or a combination of both, are expressed under control of a single promoter.

A "donor RNA" can be a corresponding RNA molecule that comprises, for example, the same nucleic acid sequence as a donor DNA; i.e., with uridylate ("U") in place of deoxythymidylate ("T"). A "donor polynucleotide" may be either a donor DNA or a donor RNA, or a combination of DNA and RNA. The donor polynucleotide may be either single-stranded or double-stranded.

An alternative method for modification of an organellar genome can be the replacement of part or all of the organelle DNA with a "replacement DNA". Endogenous organellar DNA can be reduced or eliminated by use of site-specific endonucleases such as polynucleotide guided polypeptides (e.g., Cas polypeptide, Cas9 polypeptide). At the same time or subsequently, a replacement DNA may be introduced. The term "replacement DNA" can refer to fragments of organellar DNA or complete organellar DNA that can convey a new genotype and corresponding trait(s) when transformed into the organelle. The terms "replacement DNA" and "replacement organellar DNA" can be used interchangeably herein. In the case of organellar DNA fragments, they can be integrated into the remaining endogenous organellar DNA by homologous recombination. In the case of complete organellar DNA replacement, the replacement DNA can be isolated from cultivars, lines, sub species and other species which possess DNA compositions distinct from the endogenous organellar DNA of recipient cells. In some embodiments, the replacement DNA can comprise a DNA element functioning as a DNA replication origin in the recipient organelles.

A sequence functional as an origin of replication can be included with the compositions (e.g., polynucleotides, constructs, cassettes) of the disclosure. Such sequences can include origin of replication for an organelle. The origin of replication sequence can be a plastid origin of replication (e.g., plastid rRNA intergenic region) sequence. The origin of replication sequence can be a mitochondrial origin of replication sequence.

As used herein, a "genomic region" can refer to a segment of a chromosome in the genome of, for example, an organelle. Genomic region can be present on either side of the target site. Genomic region can comprise a portion of the target site. The genomic region can comprise at least 5, 10, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100 or more bases. The genomic region can comprise sufficient homology to undergo homologous recombination with the corresponding region of homology.

Donor polynucleotides, polynucleotides of interest and/or traits can be stacked together in a complex trait locus. The guide polynucleotide/polypeptide system can be used to generate double strand breaks and for stacking traits in a complex trait locus.

Two or more polynucleotides encoding RNA and/or proteins can be included in a cassette as a polycistronic unit. Polynucleotides encoding RNA can be expressed from separate cassettes.

In one embodiment, the guide polynucleotide/polypeptide system can be used for introducing one or more donor polynucleotides or one or more traits of interest into one or more target sites by providing one or more guide polynucleotides, one or more polynucleotide guided polypeptides (e.g., Cas polypeptides), and optionally one or more donor polynucleotides (e.g. donor DNA) to a plant cell. An organism can be produced from that cell that comprises an alteration at said one or more target sites of the organellar DNA, wherein the alteration can be selected from the group consisting of (i) replacement of at least one nucleotide, (ii) a deletion of at least one nucleotide, (iii) an insertion of at least one nucleotide, and (iv) any combination of (i)-(iii).

The structural similarity between a given genomic region and the corresponding region of homology flanking the donor polynucleotide (e.g. donor DNA) can be any degree of sequence identity that allows for homologous recombination to occur. For example, the amount of homology or sequence identity shared by the "region of homology" flanking the donor polynucleotide (e.g. donor DNA) and the "genomic region" of the plant genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology flanking the donor polynucleotide (e.g. donor DNA) can have homology to any sequence flanking the target site. While in some embodiments, the regions of homology share significant sequence homology to the genomic sequence immediately flanking the target site, the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" can refer to the exchange of DNA fragments between two DNA molecules at the sites of homology. The frequency of homologous recombination can be influenced by a number of factors. The length of the region of homology can affect the frequency of homologous recombination events, for example, the longer the region of homology, the greater the frequency. The length of the homology region needed to observe homologous recombination may vary among species.

Intermolecular recombination can occur in plastids, for example, transplastomic plants can arise through site-specific integration of foreign sequences by homologous recombination with the flanking sequence on the transformation vector.

The generation of novel plastome genotypes by transformation can rely on integration of foreign sequence by intermolecular homologous recombination (HR). Mechanistically similar to gene conversion, HR and repair pathways can participate in the subsequent events that yield homoplasmic transplastomic cells and eventually stable transplastomic plants. Intra- or intermolecular recombination between repeated sequences, both in wild-type plastomes, can generate, for example, inversions when repeats are palindromic or deletions when direct. The role of HR proteins in damage repair may be compromised, for example, when foreign DNA is introduced, and through associated tissue culture and selective pressure, as these manipulations can place additional stress on recombination machinery leading to unintended events.

Among the DNA repair and recombination genes identified in the nuclear genomes of Oryza and Arabidopsis, about 19 and 17%, respectively, can be targeted to plastids.

Plastid-localized RecA (e.g., from P. sativum) can comprise DNA strand transfer activity. RecA can be implicated in recombination-mediated repair of damaged ptDNA. Reduced RecA1 (AT1G79050) activity can lead to a destabilization and reduction in ptDNA. The reduction in plastome copy number in mutant lines relative to wild type can suggest that RecA1 may participate in recombination-mediated replication.

Methods of the disclosure can use any suitable plastid enzymes for homologous DNA recombination pathway. The predominance of homologous recombination in plastids can result from suppression of illegitimate recombination by plastid-localized members of the whirly family of single-stranded DNA binding proteins. HR activity in a cell can be optimized by increasing HR pathway members.

To achieve efficient foreign sequence integration by homologous recombination endogenous plastome sequences can be used to target insertions. A positive correlation can be present between the rate of recombination and the length and/or degree of sequence homology.

The minimum flanking sequence length for plastid transformation can be as little as 400 bp on either side of the expression cassette and can be sufficient to obtain transformation at a reasonable frequency. Targeting sequences can extend from 1 to 1.5 kb on either size of the expression cassette.

Non-homologous end-joining (NHEJ) can be a major DNA repair pathway in the eukaryotic nucleus. NHEJ can also be active in bacteria and in plant mitochondria. In some cases, NHEJ may not occur in angiosperm plastids. NHEJ products can be produced in Arabidopsis. In some cases, repair of DSBs by NHEJ following I-CreII activity can be detected at low frequency. NHEJ repair events can represent 17% of the rearranged products in Whirly knockout lines. NHEJ can occur in plastids. NHEJ can be a quantitatively minor pathway.

The methods of the disclosure can use homology-directed repair (HDR) or NHEJ. In some embodiments, HDR can be used. In some embodiments, the efficiency of HDR can be increased by, for example, increasing expression of proteins and enzymes involved in HDR. In some embodiments, the efficiency of NHEJ can be reduced, by for example, targeting genes and/or proteins (e.g., DNA ligase) involved in NHEJ.

In some embodiments, the efficiency of the disclosed methods for genome engineering or modification can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100%.

In one embodiment provided herein, the method can comprise contacting an organelle of a plant cell with the donor polynucleotide (e.g. donor DNA), the guide polynucleic acid and the polynucleotide guided polypeptide. At least one single-strand or double-strand break can be introduced in the target site by the polynucleotide guided polypeptide, the first and second regions of homology flanking the donor polynucleotide (e.g. donor DNA) can undergo homologous recombination with their corresponding genomic regions of homology resulting in exchange of DNA between the donor and the genome. As such, the provided methods can result in the integration of the donor polynucleotide (e.g. donor DNA) into the single-strand or double-strand break(s) in the target site in the organellar genome, thereby altering the original target site and producing an altered genomic target site.

The donor polynucleotide (e.g. donor DNA) may be introduced by any suitable means. For example, a plant having a target site can be provided. The donor polynucleotide (e.g. donor DNA) may be provided by any suitable transformation method including, for example, *Agrobacterium*-mediated transformation or biolistic particle bombardment. The donor polynucleotide (e.g. donor DNA) may be present transiently in the cell or it could be introduced via a viral replicon. In the presence of the guide polynucleotide (e.g., guide RNA), the polynucleotide guided polypeptide (e.g., Cas polypeptide) and the target site, the donor polynucleotide (e.g. donor DNA) can be inserted into the organellar genome.

Donor polynucleotides can be reflective of the commercial markets. Donor polynucleotides can be reflective of traits for the development of the crop. Crops and markets of interest can change, and as developing nations open up world markets, new crops and technologies can emerge also. In addition, as the understanding of agronomic traits and characteristics such as yield and heterosis increase, the choice of genes for transformation can change accordingly.

Methods for Modulating Gene Expression

In some aspects are provided methods for modulating expression (e.g., transcription) of a target nucleic acid (e.g., a gene) in a host cell or organelle. The methods can involve contacting the target nucleic acid with an enzymatically inactive Cas protein (e.g., dead Cas) and a guide polynucleic acid.

In some aspects, the present disclosure provides a method of selectively modulating transcription of a target nucleic acid in a host cell. The method can involve introducing into the host cell an enzymatically inactive Cas protein (e.g., dead Cas) and a guide polynucleic acid. The guide nucleic acid and the dead Cas protein can form a complex in the host cell. The complex can selectively modulate transcription of a target polynucleic acid (e.g., target DNA) in the host cell or organelle.

In some aspects, the present disclosure provides for selective transcription modulation (e.g., reduction or increase) of a target nucleic acid in a host cell. Selective modulation of transcription of a target nucleic acid can reduce or increase transcription of the target nucleic acid, but may not substantially modulate transcription of a non-target nucleic acid or off-target nucleic acid, e.g., transcription of a non-target nucleic acid may be modulated by less than 1%, less than 5%, less than 10%, less than 20%, less than 30%, less than 40%, or less than 50% compared to the level of transcription of the non-target nucleic acid in the absence of the guide nucleic acid/enzymatically inactive or enzymatically reduced Cas protein complex. For example, selective modulation (e.g., reduction or increase) of transcription of a target nucleic acid can reduce or increase transcription of the target nucleic acid by at least about 10%, at least about 20%, at least about 30%, at least about 40%, at least about 50%, at least about 60%, at least about 70%, at least about 80%, at least about 90%, or greater than 90%, compared to the level of transcription of the target nucleic acid in the absence of a guide nucleic acid/enzymatically inactive or enzymatically reduced Cas protein complex.

In some aspects, the disclosure provides methods for increasing transcription of a target nucleic acid. The transcription of a target nucleic acid can increase by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 12 fold, at least about 15 fold, at least about 20-fold, at least about 50-fold, at least about 70-fold, or at least about 100-fold compared to the level of transcription of the target polynucleic acid (e.g., target DNA) in the absence of a guide nucleic acid/enzymatically inactive or enzymatically reduced Cas protein complex. Selective increase of transcription of a target nucleic acid increases transcription of the target nucleic acid, but may not substantially increase transcription of a non-target polynucleic acid, e.g., transcription of a non-target nucleic acid can be increased, if at all, by less than about 5-fold, less than about 4-fold, less than about 3-fold, less than about 2-fold, less than about 1.8-fold, less than about 1.6-fold, less than about 1.4-fold, less than about 1.2-fold, or less than about 1.1-fold compared to the level of transcription of the non-targeted DNA in the absence of the guide nucleic acid/enzymatically inactive or enzymatically reduced Cas protein complex.

In some aspects, the disclosure provides methods for decreasing transcription of a target nucleic acid. The transcription of a target nucleic acid can decrease by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 12 fold, at least about 15 fold, at least about 20-fold, at least about 50-fold, at least about 70-fold, or at least about 100-fold compared to the level of transcription of the target polynucleic acid (e.g., target DNA) in the absence of a guide nucleic acid/enzymatically inactive or enzymatically reduced Cas protein complex. Selective decrease of transcription of a target nucleic acid decreases transcription of the target nucleic acid, but may not substantially decrease transcription of a non-target DNA, e.g., transcription of a non-target nucleic acid can be decreased, if at all, by less than about 5-fold, less than about 4-fold, less than about 3-fold, less than about 2-fold, less than about 1.8-fold, less than about 1.6-fold, less than about 1.4-fold, less than about 1.2-fold, or less than about 1.1-fold compared to the level of transcription of the non-targeted DNA in the absence of the guide nucleic acid/enzymatically inactive or enzymatically reduced Cas protein complex.

Transcription modulation can be achieved by fusing the enzymatically inactive Cas protein to a heterologous sequence. The heterologous sequence can be a suitable fusion partner, e.g., a polypeptide that provides an activity that indirectly increases, decreases, or otherwise modulates transcription by acting directly on the target nucleic acid or on a polypeptide (e.g., a histone or other DNA-binding protein) associated with the target nucleic acid. Non-limiting examples of suitable fusion partners include a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

A suitable fusion partner can include a polypeptide that directly provides for increased transcription of the target nucleic acid. For example, a transcription activator or a fragment thereof, a protein or fragment thereof that recruits a transcription activator, or a small molecule/drug-responsive transcription regulator. A suitable fusion partner can include a polypeptide that directly provides for decreased transcription of the target nucleic acid. For example, a transcription repressor or a fragment thereof, a protein or fragment thereof that recruits a transcription repressor, or a small molecule/drug-responsive transcription regulator.

The heterologous sequence or fusion partner can be fused to the C-terminus, N-terminus, or an internal portion (i.e., a portion other than the N- or C-terminus) of the dead Cas protein.

Methods for Delivery

Any suitable delivery method can be used for introducing the compositions and molecules of the disclosure into a host cell or organelle. The compositions (e.g., Cas protein, polynucleotide-guided polypeptide, guide polynucleic acid, donor polynucleotide) can be delivered simultaneously or temporally separated. The choice of method of genetic modification can be dependent on the type of cell being transformed and/or the circumstances under which the transformation is taking place (e.g., in vitro, ex vivo, or in vivo).

A method of delivery can involve contacting a target polynucleotide or introducing into a cell (or a population of cells) one or more nucleic acids comprising nucleotide sequences encoding the compositions of the disclosure. Suitable nucleic acids comprising nucleotide sequences encoding the compositions of the disclosure can include expression vectors, where an expression vector comprising a nucleotide sequence encoding one or more compositions of the disclosure can be a recombinant expression vector.

Non-limiting examples of delivery methods or transformation include, for example, viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, and nanoparticle-mediated nucleic acid delivery.

In some aspects, the present disclosure provides methods comprising delivering one or more polynucleotides, or one or more vectors as described herein, or one or more transcripts thereof, and/or one or proteins transcribed therefrom, to a host cell or organelle. In some aspects, the disclosure further provides cells produced by such methods, and organisms (such as animals, plants, or fungi) and organelles comprising or produced from such cells. In some embodiments, a Cas protein in combination with, and optionally complexed with, a guide sequence can be delivered to a cell or organelle.

Viral and non-viral based gene transfer methods can be used to introduce nucleic acids. Such methods can be used to administer nucleic acids encoding compositions of the disclosure to cells in culture, or in a host organism. Non-viral vector delivery systems can include DNA plasmids, RNA (e.g. a transcript of a vector described herein), naked nucleic acid, and nucleic acid complexed with a delivery vehicle, such as a liposome. Viral vector delivery systems can include DNA and RNA viruses, which can have either episomal or integrated genomes after delivery to the cell.

Methods of non-viral delivery of nucleic acids can include lipofection, nucleofection, microinjection, biolistics, virosomes, liposomes, immunoliposomes, polycation or lipid: nucleic acid conjugates, naked DNA, artificial virions, and agent-enhanced uptake of DNA. Cationic and neutral lipids that are suitable for efficient receptor-recognition lipofection of polynucleotides can be used. Delivery can be to cells (e.g. in vitro or ex vivo administration) or target tissues (e.g. in vivo administration). The preparation of lipid:nucleic acid complexes, including targeted liposomes such as immunolipid complexes, can be used.

RNA or DNA viral based systems can be used to target specific cells and trafficking the viral payload to an organelle of the cell. Viral vectors can be administered directly (in vivo) or they can be used to treat cells in vitro, and the modified cells can optionally be administered (ex vivo). Viral based systems can include retroviral, lentivirus, adenoviral, adeno-associated and herpes simplex virus vectors for gene transfer. Integration in the host genome can occur with the retrovirus, lentivirus, and adeno-associated virus gene transfer methods, which can result in long term expression of the inserted transgene. High transduction efficiencies can be observed in many different cell types and target tissues.

The tropism of a retrovirus can be altered by incorporating foreign envelope proteins, expanding the potential target population of target cells. Lentiviral vectors are retroviral vectors that can transduce or infect non-dividing cells and produce high viral titers. Selection of a retroviral gene transfer system can depend on the target tissue. Retroviral vectors can comprise cis-acting long terminal repeats with packaging capacity for up to 6-10 kb of foreign sequence. The minimum cis-acting LTRs can be sufficient for replication and packaging of the vectors, which can be used to integrate the therapeutic gene into the target cell to provide permanent transgene expression. Retroviral vectors can include those based upon murine leukemia virus (MuLV), gibbon ape leukemia virus (GaLV), Simian Immuno deficiency virus (SIV), human immuno deficiency virus (HIV), and combinations thereof.

An adenoviral-based systems can be used. Adenoviral-based systems can lead to transient expression of the transgene. Adenoviral based vectors can have high transduction efficiency in cells and may not require cell division. High titer and levels of expression can be obtained with adenoviral based vectors. Adeno-associated virus ("AAV") vectors can be used to transduce cells with target nucleic acids, e.g., in the in vitro production of nucleic acids and peptides, and for in vivo and ex vivo gene therapy procedures.

Packaging cells can be used to form virus particles that can infect a host cell. Such cells can include 293 cells, (e.g., for packaging adenovirus), and .psi.2 cells or PA317 cells (e.g., for packaging retrovirus). Viral vectors can be generated by producing a cell line that packages a nucleic acid vector into a viral particle. The vectors can contain the minimal viral sequences required for packaging and subsequent integration into a host. The vectors can contain other viral sequences being replaced by an expression cassette for the polynucleotide(s) to be expressed. The missing viral functions can be supplied in trans by the packaging cell line. For example, AAV vectors can comprise ITR sequences from the AAV genome which are required for packaging and integration into the host genome. Viral DNA can be packaged in a cell line, which can contain a helper plasmid encoding the other AAV genes, namely rep and cap, while lacking ITR sequences. The cell line can also be infected with adenovirus as a helper. The helper virus can promote replication of the AAV vector and expression of AAV genes from the helper plasmid. Contamination with adenovirus can be reduced by, e.g., heat treatment to which adenovirus can be more sensitive than AAV. Additional methods for the delivery of nucleic acids to cells can be used, for example, as described in US20030087817, incorporated herein by reference.

A host cell can be transiently or non-transiently transfected with one or more vectors described herein. A cell can be transfected as it naturally occurs in a subject. A cell can be taken or derived from a subject and transfected. A cell can be derived from cells taken from a subject, such as a cell line. In some embodiments, a cell transfected with one or more vectors described herein can be used to establish a new cell line comprising one or more vector-derived sequences. In some embodiments, a cell transiently transfected with the compositions of the disclosure (such as by transient transfection of one or more vectors, or transfection with RNA), and modified through the activity of a CRISPR complex, can be used to establish a new cell line comprising cells containing the modification but lacking any other exogenous sequence.

Any suitable vector compatible with the host cell can be used with the methods of the disclosure. Non-limiting examples of vectors include pXT1, pSG5 (Stratagene™) pSVK3, pBPV, pMSG, and pSVLSV40 (Pharmacia™).

In some embodiments, a nucleotide sequence encoding a guide nucleic acid and/or Cas protein can be operably linked to a control element, e.g., a transcriptional control element, such as a promoter. In some embodiments, a nucleotide sequence encoding a guide nucleic acid and/or a Cas protein can be operably linked to multiple control elements that allow expression of the nucleotide sequence encoding a guide nucleic acid and/or a Cas protein or chimera.

Depending on the host/vector system utilized, any of a number of suitable transcription and translation control elements, including constitutive and inducible promoters, transcription enhancer elements, transcription terminators, etc. may be used in the expression vector (e.g., U6 promoter, H1 promoter, etc.; see above).

In some embodiments, compositions of the disclosure can be provided as RNA. In such cases, the compositions of the disclosure can be produced by direct chemical synthesis or may be transcribed in vitro from a DNA. The compositions of the disclosure can be synthesized in vitro using an RNA polymerase enzyme (e.g., T7 polymerase, T3 polymerase, SP6 polymerase, etc.). Once synthesized, the RNA can directly contact a target polynucleic acid (e.g., target DNA) or can be introduced into a cell using any suitable technique for introducing nucleic acids into cells (e.g., microinjection, electroporation, transfection, etc).

Nucleotides encoding a guide nucleic acid (introduced either as DNA or RNA) and/or a Cas protein (introduced as DNA or RNA) can be provided to the cells using a suitable transfection technique. Nucleic acids encoding the compositions of the disclosure may be provided on vectors or cassettes (e.g., DNA vectors). Many vectors, e.g. plasmids, cosmids, minicircles, phage, viruses, etc., useful for transferring nucleic acids into target cells are available. The vectors comprising the nucleic acid(s) can be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, and ALV.

A Cas protein can be provided to cells as a polypeptide. Such a protein may optionally be fused to a polypeptide domain that increases solubility of the product. The domain may be linked to the polypeptide through a defined protease cleavage site, e.g. a TEV sequence, which can be cleaved by TEV protease. The linker may also include one or more flexible sequences, e.g. from 1 to 10 glycine residues. In some embodiments, the cleavage of the fusion protein can be performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

The compositions of the disclosure may be fused to a polypeptide permeant domain to promote uptake by the cell. A number of permeant domains can be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK. As another example, the permeant peptide can comprise the HIV-1 tat basic region amino acid sequence, which may include, for example, amino acids 49-57 of naturally-occurring tat protein. Other permeant domains can include poly-arginine motifs, for example, the region of amino acids 34-56 of HIV-1 rev protein, nona-arginine, and octa-arginine. The nona-arginine (R9) sequence can be used. The site at which the fusion can be made may be selected in order to optimize the biological activity, secretion or binding characteristics of the polypeptide.

The compositions of the disclosure may be produced in vitro or by host cells, and it may be further processed by unfolding, e.g. heat denaturation, DTT reduction, etc. and may be further refolded.

The compositions of the disclosure may be prepared by in vitro synthesis. Various commercial synthetic apparatuses can be used. By using synthesizers, naturally occurring amino acids can be substituted with unnatural amino acids. The particular sequence and the manner of preparation can be determined by convenience, economics, and purity required.

The compositions of the disclosure may also be isolated and purified in accordance with recombinant synthesis methods. A lysate may be prepared of the expression host and the lysate purified using HPLC, exclusion chromatography, gel electrophoresis, affinity chromatography, or other purification technique. The compositions can comprise, for example, at least 20% by weight of the desired product, at least about 75% by weight, at least about 95% by weight, and for therapeutic purposes, for example, at least about 99.5% by weight, in relation to contaminants related to the method of preparation of the product and its purification. The percentages can be based upon total protein.

The compositions of the disclosure, whether introduced as nucleic acids or polypeptides, can be provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which can be repeated with a frequency of about every day to about every 4 days, e.g., every 1.5 days, every 2 days, every 3 days, or any other frequency from about every day to about every four days. The compositions may be provided to the subject cells one or more times, e.g. one time, twice, three times, or more than three times, and the cells allowed to incubate with the agent(s) for some amount of time following each contacting event e.g. 16-24 hours, after which time the media can be replaced with fresh media and the cells can be cultured further.

In cases in which two or more different targeting complexes are provided to the cell (e.g., two different guide nucleic acids that are complementary to different sequences within the same or different target polynucleic acid (e.g., target DNA)), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

An effective amount of the compositions of the disclosure can be provided to the target polynucleic acid (e.g., target DNA) or cells. An effective amount can be the amount to induce, for example, at least about a 2-fold change (increase or decrease) or more in the amount of target nucleic acid modulation (e.g., expression) observed between two homologous sequences relative to a negative control, e.g. a cell contacted with an empty vector or irrelevant polypeptide. An effective amount or dose can induce, for example, about 2-fold change, about 3-fold change, about 4-fold change, about a 7-fold, about 8-fold increase, about 10-fold, about 50-fold, about 100-fold, about 200-fold, about 500-fold, about 700-fold, about 1000-fold, about 5000-fold, or about 10.000-fold change in target gene modulation (e.g., expression). The amount of target gene modulation may be measured by any suitable method.

Contacting the cells with a composition of the disclosure can occur in any culture media and under any culture conditions that promote the survival of the cells. For example, cells may be suspended in any appropriate nutrient medium. The culture may contain growth factors to which the cells are responsive. Growth factors can be molecules that can promote survival, growth and/or differentiation of cells (e.g., in culture, in the intact tissue), for example, through specific effects on a transmembrane receptor. Growth factors can include polypeptides and non-polypeptide factors.

In numerous embodiments, the chosen delivery system can be targeted to specific cell types. In some cases, tissue- or cell-targeting of the delivery system can be achieved by binding the delivery system to tissue- or cell-specific markers, such as cell surface proteins. Viral and non-viral delivery systems can be customized to target tissue or cell-types of interest.

Genome Editing Using a Polynucleotide Guided Polypeptide System

As described herein, the polynucleotide guided polypeptide system can be used in combination with a co-delivered polynucleotide modification template to allow for editing of an organellar nucleotide sequence of interest. Also, as described herein, for each embodiment that uses an RNA guided polypeptide system, a similar polynucleotide guided polypeptide system can be deployed where the guide polynucleotide may not solely comprise ribonucleic acids but wherein the guide polynucleotide comprises a combination of RNA-DNA molecules or solely comprises DNA molecules.

Genome modification methods can rely on the homologous recombination system. Homologous recombination (HR) can provide molecular means for finding genomic DNA sequences of interest and modifying them according to the experimental specifications. Homologous recombination can be enhanced by introducing double-strand breaks (DSBs) at selected endonuclease target sites. Described herein is the use of a polynucleotide guided polypeptide system which can provide flexible genome cleavage specificity and can result in a high frequency of double-strand breaks at an organellar DNA target site. This specific cleavage can enable efficient gene editing of a nucleotide sequence of interest. The nucleotide sequence of interest to be edited can be located within or outside the target site recognized and/or cleaved by a polynucleotide guided polypeptide (e.g., a Cas polypeptide).

The term "polynucleotide modification template" can refer to a polynucleotide that can comprise at least one nucleotide modification when compared to the nucleotide sequence to be edited. A nucleotide modification can be at least one nucleotide substitution, addition or deletion. Examples of minor genome modifications created by use of a polynucleotide modification template include creation of a mutant allele (e.g., antibiotic resistant rRNA gene) and removal of a target site for a polynucleotide guided polypeptide. Optionally, the polynucleotide modification template can be flanked by homologous nucleotide sequences, wherein the flanking homologous nucleotide sequences can provide sufficient homology to the desired nucleotide sequence to be edited. The polynucleotide modification template can be a donor polynucleotide.

In one embodiment, the disclosure provides a method for editing a nucleotide sequence in the organellar genome of a cell. The method can comprise providing a guide polynucleotide (e.g., guide RNA), a polynucleotide modification template, and at least one polynucleotide guided polypeptide (e.g., Cas polypeptide) to an organelle. The polynucleotide guided polypeptide can introduce a single-strand or double-strand break at a target sequence in the organellar genome of the cell. The polynucleotide modification template can include at least one nucleotide modification of said nucleotide sequence. Cells include, but are not limited to, human, animal, bacterial, fungal, insect, and plant cells as well as organisms and tissues, e.g., plants and seeds, produced by the methods described herein. Cell can be an isolated and purified human cell. The nucleotide to be edited can be located within or outside a target site recognized and cleaved by a polynucleotide guided polypeptide. In one embodiment, the at least one nucleotide modification may not be a modification at a target site recognized and cleaved by a polynucleotide guided polypeptide. In another embodiment, there can be at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the organellar DNA target site.

In another embodiment, the disclosure provides a method for editing a nucleotide sequence in the organellar genome of a cell. The method can comprise providing a guide polynucleotide (e.g., guide RNA), a polynucleotide modification template and at least one polynucleotide guided polypeptide (e.g., Cas polypeptide) to an organelle, wherein said guide polynucleotide and said polynucleotide guided polypeptide can form a complex that can enable the polynucleotide guided polypeptide to introduce a single-strand or double-strand break at an organellar target site, wherein said polynucleotide modification template comprises at least one nucleotide modification of said nucleotide sequence.

In another embodiment, the disclosure provides a method for editing a nucleotide sequence in the organellar genome of a plant cell. The method can comprise introducing a guide polynucleotide (e.g., guide RNA), a polynucleotide modification template, and at least one organelle codon-optimized polynucleotide guided polypeptide (e.g., Cas9 polypeptide) into an organelle, wherein the organelle optimized polynucleotide guided polypeptide can introduce a single-strand or double-strand break at an organellar target sequence, wherein said polynucleotide modification template includes at least one nucleotide modification of said nucleotide sequence.

The nucleotide sequence to be edited can be a sequence that can be endogenous, artificial, pre-existing, or transgenic to the cell that is being edited. For example, the nucleotide sequence in the organellar genome of a cell can be a transgene that is stably incorporated into the organellar genome of a cell. Editing of such transgene may result in a further desired phenotype or genotype. The nucleotide sequence in the genome of a cell can also be a mutated or pre-existing sequence that was either endogenous or artificial from origin such as an endogenous gene or a mutated gene of interest.

In one embodiment, the region of interest can be flanked by two independent guide polynucleotide/polypeptide target sequences. Cutting can be done concurrently. The deletion event can be the repair of the two chromosomal ends without the region of interest. Alternative results can include inversions of the region of interest, mutations at the cut sites and duplication of the region of interest.

Methods for Identifying at Least One Plant Cell Comprising in its Organellar Genome a Polynucleotide of Interest Integrated at the Target Site.

Further provided are methods for identifying at least one plant cell comprising in its organellar genome a polynucleotide of interest integrated at the target site. A donor polynucleotide can comprise a polynucleotide of interest. A polynucleotide of interest can be integrated at a target site in a cell (e.g., genome). A variety of methods can be used for identifying those plant cells with insertion into the genome at or near to the target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

The method can also comprise recovering a plant from the plant cell comprising a polynucleotide of interest integrated into its organellar genome. The plant may be sterile or fertile. Any polynucleotide of interest can be provided, integrated into the plant organellar genome at the target site, and expressed in a plant.

Polynucleotides of interest can be reflective of the commercial markets and interests of those involved in the development of the crop. Crops and markets of interest change, and as developing nations open up world markets, new crops and technologies can emerge also. In addition, as our understanding of agronomic traits and characteristics such as yield, stress tolerance and heterosis increase, the choice of genes for transformation can change accordingly.

Polynucleotides/polypeptides of interest include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. polynucleotides of interest can include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. Genes of interest can include, for example, those genes involved in information, such as zinc fingers, those involved in communication, such as kinases, and those involved in housekeeping, such as heat shock proteins. Polynucleotides of interest can include genes encoding important traits for agronomics, insect resistance, disease resistance, herbicide resistance, fertility or sterility, grain characteristics, and commercial products. Genes of interest can include, generally, those involved in oil, starch, carbohydrate, or nutrient metabolism as well as those affecting photosynthesis, photorespiration and ATP metabolism.

Commercial traits can also be obtained by expression of proteins encoded on a polynucleotide. A commercial use of transformed plants can be the production of polymers and bioplastics. Polynucleotides of interest can include genes such as β-ketothiolase, PHBase (polyhydroxybutyrate synthase), and acetoacetyl-CoA reductase can facilitate expression of polyhydroxyalkanoates (PHAs).

Polynucleotides/polypeptides that can influence amino acid biosynthesis include, for example, anthranilate synthase (AS; EC 4.1.3.27) which can catalyze the first reaction branching from the aromatic amino acid pathway to the biosynthesis of tryptophan in plants, fungi, and bacteria. In plants, the chemical processes for the biosynthesis of tryptophan can be compartmentalized in the chloroplast. Additional donor sequences of interest can include Chorismate Pyruvate Lyase (CPL) which can refer to a gene encoding an enzyme can which catalyze the conversion of chorismate to pyruvate and pHBA. Once example of CPL gene is from *E. coli* and bears the GenBank accession number M96268.

Polynucleotide sequences of interest may encode proteins involved in providing disease or pest resistance. By "disease resistance" or "pest resistance" can be intended that the plants can avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin; avirulence (avr) and disease resistance (R) genes; and the like. Insect resistance genes may encode resistance to pests that have great yield drag such as rootworm, cutworm, European Corn Borer, and the like. Such genes include, for example, *Bacillus thuringiensis* toxic protein genes; and the like.

An "herbicide resistance protein" or a protein resulting from expression of an "herbicide resistance-encoding nucleic acid molecule" can include proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), for example, the sulfonylurea-type herbicides, genes coding for resistance to herbicides that can act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes. The bar gene can encodes resistance to the herbicide basta, the aadA can encode resistance to spectinomycin and streptomycin, the nptII gene can encode resistance to the antibiotics kanamycin and geneticin, and certain ALS-gene mutants can encode resistance to the herbicide chlorsulfuron.

Sterility genes can also be encoded in an expression cassette or integrated into the genome. Sterility genes can provide an alternative to physical detasseling. Examples of genes used in such ways include male fertility genes such as MS26, MS45, or MSCA1. Maize plants (*Zea mays* L.) can be bred by both self-pollination and cross-pollination techniques. Maize can have male flowers, located on the tassel, and female flowers, located on the ear, on the same plant. It can self-pollinate ("selfing") or cross pollinate. Natural pollination can occur in maize when wind blows pollen from the tassels to the silks that protrude from the tops of the incipient ears. Pollination may be readily controlled by suitable methods. The development of maize hybrids can require the development of homozygous inbred lines, the crossing of these lines, and the evaluation of the crosses. Pedigree breeding and recurrent selections are two of the breeding methods that can be used to develop inbred lines from populations. Breeding programs can combine desirable traits from two or more inbred lines or various broad-based sources into breeding pools from which new inbred lines are developed by selfing and selection of desired phenotypes. A hybrid maize variety can be a cross of two such inbred lines, each of which may have one or more desirable characteristics lacked by the other or which complement the other. The new inbreds can be crossed with other inbred lines and the hybrids from these crosses can be evaluated to determine which have commercial potential. The hybrid progeny of the first generation can be designated F1. The F1 hybrid can be more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel can be removed from the growing female inbred parent, which can be planted in various alternating row patterns with the male inbred parent. Consequently, providing that there is sufficient isolation from sources of foreign maize pollen, the ears of the female inbred can be fertilized only with pollen from the male inbred. The resulting seed can therefore be hybrid (F1) and can form hybrid plants.

Field variation impacting plant development can result in plants tasseling after manual detasseling of the female parent is completed. Or, a female inbred plant tassel may not be completely removed during the detasseling process. In any event, the result can be that the female plant can successfully shed pollen and some female plants can be self-pollinated. This can result in seed of the female inbred being harvested along with the hybrid seed which can be normally produced. Female inbred seed may not exhibit heterosis and therefore may not be as productive as F1 seed. In addition, the presence of female inbred seed can represent a germplasm security risk for the company producing the hybrid.

Alternatively, the female inbred can be mechanically detasseled by machine. Mechanical detasseling can be approximately as reliable as hand detasseling, but may be faster and less costly. However, most detasseling machines can produce more damage to the plants than hand detasseling. Thus, no form of detasseling may be presently entirely satisfactory, and a need continues to exist for alternatives which further reduce production costs and to eliminate self-pollination of the female parent in the production of hybrid seed.

One method to convey male sterility without mechanical detasseling can be the use of cytoplasmic male sterility (CMS) genes. Chimeric mitochondrial ORFs can be found to lead to male sterility, producing unisex-female plants. The methods described herein could be used to introduce custom-designed, CMS ORFs into mitochondria of maize elite inbred lines. Additionally, these methods can provide a means to introduce the CMS system into other crops; e.g., rice, wheat and soybean.

The donor polynucleotide may also encode an RNA or double-stranded RNA that can be complementary to a target gene from a plant pest or plant pathogen. A method of alleviating pest infestation of plants can comprise, for example, a) identifying a DNA sequence from said pest which can be critical either for its survival, growth, proliferation or reproduction, b) cloning said sequence or a fragment thereof in a suitable vector relative to one or more promoters that can transcribe said sequence to RNA or dsRNA upon binding of an appropriate transcription factor to said promoters, and/or c) introducing said vector into the plant. The plant pest can be a nematode. Another method for alleviating pest infestation can include, for example, providing: a) DNA sequences which when transcribed yield a double-stranded RNA molecule that can reduce the expression of an essential gene of a plant sap-sucking insect; b) methods of using such DNA sequences and plants or plant cells transformed with such DNA sequences; and c) the use of cationic oligopeptides that facilitate the entry of dsRNA or siRNA molecules in insect cells, such as plant sap-sucking insect cells.

The donor polynucleotide may comprise and/or lead to expression of antisense sequences complementary to at least a portion of the messenger RNA (mRNA) for a targeted gene sequence of interest; e.g., a target gene from a plant pest or plant pathogen. Antisense nucleotides can be constructed to hybridize with the corresponding mRNA. Antisense nucleotides can be targeted to bind a splicing site on a pre-mRNA and modify the exon content of an mRNA, thereby modulating (e.g., disrupting) expression of a target gene.

Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The donor polynucleotide can also be a phenotypic marker. A phenotypic marker can be screenable or a selectable marker that includes visual markers and selectable markers whether it is a positive or negative selectable marker. Any phenotypic marker can be used. Specifically, a selectable or screenable marker can comprise a DNA segment that can allow one to identify, or select for or against a molecule or a cell that contains it, e.g., under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that can confer resistance to herbicidal compounds, such as glyphosate, sulfonylureas, glufosinate ammonium, bromoxynil, imidazolinones, and 2,4-dichlorophenoxyacetate (2,4-D).

Commercial traits can also be encoded on a gene or genes that could increase for example, starch for ethanol production, or provide expression of proteins. Another important use of transformed plants can be the production of polymers and bioplastics. Genes such as β-Ketothiolase, PHBase (polyhydroxyburyrate synthase), and acetoacetyl-CoA reductase can facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This can be achieved by the expression of such proteins having enhanced amino acid content.

The transgenes, recombinant DNA molecules, DNA sequences of interest, and donor polynucleotides can comprise one or more DNA sequences for gene silencing of a target gene; e.g., a target gene in a plant pest or plant pathogen. Methods for gene silencing involving the expression of DNA sequences in plant can include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and microRNA (miRNA) interference.

In one embodiment, the targeted mutation can involve use of a double-strand-break-inducing agent that can induce a double-strand break in the DNA of the target sequence.

In one embodiment, the targeted mutation can be the result of a guide polynucleotide/polypeptide induced gene editing as described herein. The guide polynucleotide/polypeptide induced targeted mutation can occur in a nucleotide sequence that can be located within or outside a genomic target site that can be recognized and cleaved by a polynucleotide guided polypeptide.

In certain embodiments, a fertile plant can be a plant that can produce viable male and female gametes and can be self-fertile. Such a self-fertile plant can produce a progeny plant without the contribution from any other plant of a gamete and the genetic material contained therein. Other embodiments may involve the use of a plant that may not be self-fertile, for example, because the plant may not produce male gametes, or female gametes, or both, that are viable or otherwise capable of fertilization. As used herein, a "male sterile plant" can be a plant that does not produce male gametes that are viable or otherwise capable of fertilization. As used herein, a "female sterile plant" can be a plant that does not produce female gametes that are viable or otherwise capable of fertilization. Male-sterile and female-sterile plants can be female-fertile and male-fertile, respectively. A male fertile (but female sterile) plant can produce viable progeny when crossed with a female fertile plant and that a female fertile (but male sterile) plant can produce viable progeny when crossed with a male fertile plant.

Breeding Methods and Methods for Selecting Plants Utilizing a Two Component RNA Guide and Cas Polypeptide System The present disclosure can find use in the breeding of plants comprising one or more transgenic traits. Transgenic traits can be randomly inserted throughout the plant genome as a consequence of transformation systems based on *Agrobacterium*, biolistics, or other suitable procedures. Directed transgene insertion can be used. Site-specific integration (SSI) can enable the targeting of a transgene to the same chromosomal location as a previously inserted transgene. Custom-designed meganucleases and custom-designed zinc finger meganucleases can be used to design nucleases to target specific chromosomal locations, and these reagents can allow the targeting of transgenes at the chromosomal site cleaved by these nucleases.

Genetic engineering of eukaryotic genomes, e.g. plant genomes, using homing endonucleases, meganucleases, zinc finger nucleases, and transcription activator-like effector nucleases (TALENs) can require de novo protein engineering for every new target locus. The highly specific, polynucleotide guided polypeptide system (e.g., guide RNA/Cas polypeptide system) described herein, can be more easily customizable and can be more useful when modification of many different target sequences is the goal. The polynucleotide guided polypeptide system can be a two component system, for example, with its constant protein component, the polynucleotide guided polypeptide (e.g., Cas polypeptide), and its variable and easily reprogrammable targeting component, the guide polynucleotide (e.g., guide RNA or crRNA).

The polynucleotide guided polypeptide system described herein can be especially useful for genome engineering in circumstances where endonuclease off-target cutting can be toxic to the targeted cells. In one embodiment of the polynucleotide guided polypeptide system described herein, the constant component, a polynucleotide encoding an organelle targeted polynucleotide guided polypeptide, can be stably integrated into the nuclear genome of the cell. The polynucleotide can encode a modified polynucleotide guided polypeptide comprising an enzymatically active polynucleotide guided polypeptide (e.g., Cas polypeptide) fused to an organellar transport sequence (e.g., a mitochondrial targeting peptide or a chloroplast targeting peptide). Expression of the polynucleotide encoding the modified polynucleotide guided polypeptide can be under control of a promoter. The promoter can be a constitutive promoter, a tissue-specific promoter or an inducible promoter, e.g. a temperature-inducible, stress-inducible, developmental stage inducible, or chemically inducible promoter. In the absence of the variable component (e.g., the guide RNA or crRNA), the polynucleotide guided polypeptide may not cut the target nucleic acid. In the absence of the variable component (e.g., the guide RNA or crRNA) the presence of the polynucleotide guided polypeptide in the plant cell may have little or no consequence. A polynucleotide guided polypeptide system can be used to create and/or maintain a cell line or transgenic organism capable of efficient expression of the polynucleotide guided polypeptide. Expression of the polynucleotide guided polypeptide in the cell line or transgenic organism may have little or no consequence to cell viability. In order to induce cutting at desired genomic sites to achieve targeted genetic modifications, guide polynucleotides (e.g., guide RNAs or crRNAs) can be introduced by a variety of methods into cells containing the stably-integrated and expressed expression cassette for the polynucleotide guided polypeptide. For example, guide polynucleotide (e.g., guide RNAs or crRNAs) can be chemically or enzymatically synthesized, and introduced into the polynucleotide guided polypeptide expressing cells via direct delivery methods such a particle bombardment or electroporation. A guide polynucleic acid may be fused to an RNA molecule that allows for transport into an organelle. Alternatively, a guide polynucleic acid may be fused to an RNA molecule that allows for binding to a protein that facilitates transport into the organelle.

Alternatively, genes that can efficiently express guide polynucleotides (e.g., guide RNAs or crRNAs) in the target cells can be synthesized chemically, enzymatically or in a biological system. These genes can be introduced into the polynucleotide guided polypeptide expressing cells, for example, via direct delivery methods such a particle bombardment, electroporation or biological delivery methods such as *Agrobacterium*-mediated DNA delivery.

One embodiment of the disclosure can be a method for selecting a plant comprising an altered target site in its organellar genome. The method can comprise a) obtaining a first plant that can comprise at least one polynucleotide guided polypeptide (e.g., Cas polypeptide) that can be transported into an organelle and can introduce a single-strand or double strand break at a target site in the organellar genome. In some cases, the polynucleotide guided polypeptide (e.g., dead Cas) may not cleave a target site. The method can further comprise b) obtaining a second plant comprising a guide polynucleotide (e.g., guide RNA) that can be transported into an organelle and can form a complex with the polynucleotide guided polypeptide of (a). The method can further comprise c) crossing the first plant of (a) with the second plant of (b). The method can further comprise d) evaluating the progeny of (c) for an alteration in the target site. The method can further comprise e) selecting a progeny plant that possesses the desired alteration of said target site. When an enzymatically inactive polynucleotide guided polypeptide is used, the method can comprise evaluating and selecting a progeny with altered target gene regulation or expression.

Another embodiment of the disclosure can be a method for selecting a plant comprising an altered target site in its organellar genome. The method can comprise: a) obtaining a first plant comprising at least one polynucleotide guided polypeptide (e.g., Cas polypeptide) that can be transported into an organelle and can introduce a single-strand or double strand break at a target site in the organellar genome. The method can further comprise b) obtaining a second plant comprising a guide polynucleotide (e.g., guide RNA) and a donor polynucleotide (e.g. donor DNA). The guide polynucleotide and donor polynucleotide (e.g. donor DNA) can be transported into the organelle. The guide polynucleotide can form a complex with the polynucleotide guided polypeptide of (a). The method can further comprise c) crossing the first plant of (a) with the second plant of (b). The method can further comprise d) evaluating the progeny of (c) for an alteration in the target site. The method can further comprise e) selecting a progeny plant that comprises the donor polynucleotide inserted at said target site.

Another embodiment of the disclosure can be a method for selecting a plant comprising an altered target site in its organellar genome. The method can comprise selecting at least one progeny plant that comprises an alteration at a target site in its organellar genome. The progeny plant can be a plant, for example, obtained by crossing a first plant expressing at least one polynucleotide guided polypeptide (e.g., Cas polypeptide) that can be transported into an organelle to a second plant comprising a guide polynucleotide (e.g., guide RNA) and optionally a donor polynucleotide (e.g. donor DNA), wherein said guide polynucleotide and said donor polynucleotide (e.g. donor DNA) can be transported into an organelle, wherein said polynucleotide guided polypeptide can introduce a single-strand or double strand break at said target site.

A suitable method can be used to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

Proteins may be altered in various ways including amino acid substitutions, deletions, truncations, and insertions. For example, amino acid sequence variants of the protein(s) can be prepared by mutations in the DNA. Methods for mutagenesis and nucleotide sequence alterations can be used.

Guidance regarding amino acid substitutions not likely to affect biological activity of the protein can be determined.

Conservative substitutions, such as exchanging one amino acid with another having similar properties, can be carried out. Conservative deletions, insertions, and amino acid substitutions may not produce radical changes in the characteristics of the protein. The effect of any substitution, deletion, insertion, or combination thereof can be evaluated by screening assays. Assays for double-strand-break-inducing activity can measure, for example, the overall activity and specificity of the agent on DNA substrates containing target sites.

Sufficient homology or sequence identity can indicate that two polynucleotide sequences have sufficient structural similarity to act as substrates for a homologous recombination reaction. The structural similarity can include overall length of each polynucleotide fragment, and the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary. For example, the length of sequence homology may be at least one of the following: 20 bp, 50 bp, 100 bp, 150 bp, 250 bp, 300 bp, 400 bp, 500 bp, 600 bp, 700 bp, 800 bp, 900 bp, 1000 bp, 1250 bp, 1500 bp, 1750 bp, 2000 bp, 2.5 kb, 3 kb, 4 kb, 5 kb, 6 kb, 7 kb, 8 kb, 9 kb or 10 kb. The amount of homology can also be described by percent sequence identity over the full aligned length of the two polynucleotides which includes percent sequence identity of at least any of the following: 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology can include any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions.

A variety of methods can be used for the introduction of nucleotide sequences and polypeptides into an organism, including, for example, transformation, sexual crossing, and the introduction of the polypeptide, DNA, or mRNA into the cell. Methods for contacting, providing, and/or introducing a composition into various organisms can include but are not limited to, stable transformation methods, transient transformation methods, virus-mediated methods, and sexual breeding. Stable transformation can indicate that the introduced polynucleotide can integrate into the genome of the organism and can be inherited by progeny thereof. Transient transformation can indicate that the introduced composition can only temporarily be expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection, meristem transformation, electroporation, *Agrobacterium*-mediated transformation, direct gene transfer, and ballistic particle acceleration.

Alternatively, polynucleotides may be introduced into plants by contacting plants with a virus or viral nucleic acids. Such methods can involve incorporating a polynucleotide within a viral DNA or RNA molecule. In some examples a polypeptide of interest may be initially synthesized as part of a viral polyprotein, which can be later processed by proteolysis in vivo or in vitro to produce the desired recombinant protein. Methods for introducing polynucleotides into plants and expressing a protein encoded therein, can involve viral DNA or RNA molecules. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment.

DNA transformation of organellar genomes can be performed in, for example, plastids and mitochondria (e.g., yeast). Selectable marker genes can include, for example, photosynthesis (atpB, tscA, psaA B, petB, petA, ycf3, rpoA, rbcL), antibiotic resistance (rrnS, rrnL, aadA, nptII, aphA-6), herbicide resistance (psbA, bar, AHAS (ALS), EPSPS, HPPD) and metabolism (BADH, codA, ARG9, ASA2) genes.

DNA transformation of, for example, the yeast nuclear genome can be facilitated by the development of shuttle vectors that can replicate in *E. coli* and yeast as autonomous plasmids. Vector systems can include low-copy-number plasmids and integrative DNA through homologous recombination.

Methods of the invention can provide transformation efficiency into an organelle (e.g., mitochondria, plastids) of, for example, at least about: 1%, 2%, 5%, 10%, 20%, 30%, 40%, 50%, 60%, 70%, 80%, 90%, or 100% transformation efficiency.

In one embodiment, an expression construct of the current disclosure may comprise a promoter operably linked to a nucleotide sequence encoding a Cas gene and a promoter operably linked to a guide RNA. The promoter can drive expression of an operably linked nucleotide sequence in a cell.

The cells having the introduced sequence may be grown or regenerated into plants. These plants may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide can be stably maintained and inherited, and seeds harvested.

Any plant can be used, including monocot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), maize, wheat (*Triticum aestivum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), Arabidopsis (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

The transgenes, recombinant DNA molecules, DNA sequences of interest, and donor polynucleotides can comprise one or more genes of interest. Such genes of interest can encode, for example, a protein that can provide an agronomic advantage to the plant.

Also, as described herein, for each example or embodiment that cites a guide RNA, a similar guide polynucleotide can be designed wherein the guide polynucleotide does not solely comprise ribonucleic acids but wherein the guide polynucleotide comprises a combination of RNA-DNA molecules or solely comprises DNA molecules.

In order to edit organellar genomes with polynucleotide guided (e.g., RNA guided) methodologies, two molecular components, a polynucleotide guided polypeptide (e.g., Cas protein, Cas9) and a guide polynucleotide (e.g., guide RNA), can be introduced into organelles. The introduction of these components may be accomplished by a combination of a suitable approach. One approach can be to create a modified polynucleotide guided polypeptide by a translational fusion of the polynucleotide guided polypeptide with an organelle targeting peptide that can allow protein import into an organelle. Another approach can be to create a transcriptional fusion of a guide polynucleic acid with an RNA molecule that can be imported into an organelle. For the latter, the configuration of imported guide polynucleic acid (e.g., guide RNA) can be designed to enable appropriate function, i.e., the 5'end of guide RNA can be accessible to bind with the target site on the organellar DNA. The combination of these two components can be sufficient to edit organellar genomes to create small deletions (e.g., SDN1 modifications) and additions of a few nucleotides at the cleavage sites (e.g., SDN2 modifications). To achieve organellar genome editing with more extensive SDN2 and SDN3 modifications, a polynucleotide modification template can be introduced into the corresponding organelle.

After creating a designed change in organellar DNA, the next step can be to maintain the edited organellar DNA in the pool of unmodified organellar DNA and to shift the balance among organellar DNA to favor the maintenance of genome edited organellar DNA. This can be achieved by reducing the amplification of unmodified organellar DNA. In one approach, guide polynucleic acids can be designed for multiple target sites in the unmodified organelle genome. The donor polynucleotide (e.g. donor DNA) can be designed such that these target sites have been altered to no longer be recognized by the relevant polynucleotide guided polypeptide system(s). Expression of the polynucleotide guided polypeptides can result in the introduction of single-strand or double-strand breaks into the unmodified organellar DNA and can thereby increase the proportion of modified genomes. In one variation, cells may be pretreated with relevant polynucleotide guided polypeptide systems to introduce cleavages in organellar DNA. The pretreatment can reduce the number of organelle DNA molecules available for homologous recombination.

Embodiments can involve a single guide RNA (sgRNA), i.e., where the variable targeting domain can be fused to a polynucleotide that contains a tracrRNA sequence. Alternatively, embodiments may involve a duplex guide RNA, i.e., where the variable targeting domain and the tracrRNA sequence are present on separate RNA molecules. The terms "duplex guide RNA" and "dual guide RNA" are used interchangeably herein.

In some cases, protein and/or RNA expression levels can be higher when transformed into an organelle (e.g., plastid, mitochondria) compared with that in nucleus. For example, protein expression level can be at least about: 1%, 5%, 10%, 20%, 30%, 40%, 50%, 60%, 70%, 80%, or 90% higher with organelle transformation when compared with nuclear transformation. The expression stability of a transcript can be higher with organelle transformation compared with nuclear transformation.

Embodiments

In one embodiment, a polynucleotide encoding an RNA sequence may comprise an organelle targeting RNA operably linked to a guide polynucleic acid (e.g., single guide RNA), wherein the guide polynucleic acid can direct a polynucleotide guided polypeptide (e.g., Cas polypeptide; Cas9 polypeptide) to cleave a target sequence present in an organelle genome. The guide polynucleic acid may be single guide RNA or a duplex guide RNA; for a duplex RNA, each component RNA is operably linked to an organelle targeting RNA. The RNA sequence may further comprise a sequence encoding a polynucleotide guided polypeptide (e.g., Cas polypeptide; Cas9 polypeptide). The RNA sequence may further comprise an RNA cleavage site between the guide polynucleic acid and the sequence encoding a polynucleotide guided polypeptide. The RNA cleavage site may be at least one selected from the group consisting of: a Csy4 cleavage site, a C2c2 cleavage site, a ribozyme cleavage site, an RNAse III cleavage site, and any combination thereof.

In another embodiment, a cell may comprise any of the polynucleotides of the disclosure.

In another embodiment, a cell may comprise any of the above polynucleotide, wherein the cell further comprising a polynucleotide encoding a modified polynucleotide guided polypeptide, wherein the modified polynucleotide guided polypeptide comprises a polynucleotide guided polypeptide (e.g., Cas polypeptide; Cas9 polypeptide) operably linked to an organelle targeting peptide.

In another embodiment, a method for introducing a guide polynucleic acid into an organelle of a cell may comprise: (a) introducing into a cell any of the above polynucleotides, wherein the polynucleotide is operably linked to at least one regulatory element; and (b) growing the cell under conditions in which the polynucleotide is expressed. The method may further comprise (c) selecting a cell having an organelle that comprises a guide polynucleic acid.

In another embodiment, a method for altering the genome of an organelle may comprise: (a) introducing into a cell: (i) a first polynucleotide encoding an RNA sequence comprising an organelle targeting RNA operably linked to a guide polynucleic acid, wherein the guide polynucleic acid can direct a polynucleotide guided polypeptide (e.g., Cas polypeptide; Cas9 polypeptide) to cleave a target sequence present in an organelle genome, wherein the polynucleotide is operably linked to at least one regulatory element; and (ii) a second polynucleotide encoding a modified polynucleotide guided polypeptide, wherein the second polynucleotide is operably linked to at least one regulatory element, and wherein the modified polynucleotide guided polypeptide comprises a polynucleotide guided polypeptide (e.g., Cas polypeptide; Cas9 polypeptide) operably linked to an organelle targeting peptide; wherein the organelle targeting RNA of (i) and the organelle targeting peptide of (ii) each target the same organelle; and (b) growing the cell under conditions in which the first polynucleotide of (i) and the second polynucleotide of (ii) are both expressed. The method may further comprise (c) selecting a cell having an organelle that comprises an altered genome.

In another embodiment, a method for altering the genome of an organelle may comprise: (a) introducing into a cell: (i) a first polynucleotide encoding an RNA sequence comprising an organelle targeting RNA operably linked to a guide polynucleic acid, wherein the guide polynucleic acid can direct a polynucleotide guided polypeptide (e.g., Cas polypeptide; Cas9 polypeptide) to cleave a target sequence present in an organelle genome, wherein the polynucleotide is operably linked to at least one regulatory element; and (ii) a third polynucleotide, wherein the third polynucleotide is operably linked to at least one regulatory element, wherein the third polynucleotide encodes an RNA molecule comprising an organelle targeting RNA operably linked to an RNA sequence encoding a polynucleotide guided polypeptide (e.g., Cas polypeptide; Cas9 polypeptide); wherein the organelle targeting RNA of (i) and the organelle targeting RNA of (ii) each target the same organelle; and (b) growing the cell under conditions in which the polynucleotide of (i) and the third polynucleotide of (ii) are both expressed. The method may further comprise (c) selecting a cell having an organelle that comprises an altered genome.

In another embodiment, a method for altering the genome of an organelle may comprise: (a) introducing into a cell a polynucleotide encoding an RNA sequence comprising an organelle targeting RNA operably linked to a guide polynucleic acid, wherein the guide polynucleic acid can direct a polynucleotide guided polypeptide (e.g., Cas polypeptide; Cas9 polypeptide) to cleave a target sequence present in an organelle genome, wherein the RNA sequence further comprises a second RNA sequence encoding a polynucleotide guided polypeptide (e.g., Cas polypeptide; Cas9 polypeptide), wherein the polynucleotide is operably linked to at least one regulatory element; and (b) growing the cell under conditions in which the polynucleotide of (a) is expressed. The method may further comprise (c) selecting a cell having an organelle that comprises an altered genome.

In any of the above methods for altering the genome of an organelle, the method may further comprise introducing a polynucleotide comprising at least one donor polynucleotide (e.g., donor DNA) into the organelle, wherein the at least one donor polynucleotide is bounded by at least one homologous sequence with respect to the organelle genome, wherein integration of all or part of the at least one donor polynucleotide into the organelle genome results in removal of the target site of the guide polynucleic acid. The at least one donor polynucleotide may comprise a first nucleic acid sequence that is heterologous to the organelle genome, wherein the first nucleic acid sequence is bounded by a second and a third nucleic acid sequence, wherein the second and the third nucleic acid sequences correspond to two adjacent regions of homology in the organelle genome. The first nucleic acid sequence that is heterologous to the organelle genome may encode a selectable marker. The selectable marker may be aadA and the selection agent may be spectinomycin or streptomycin. The first nucleic acid sequence that is heterologous to the organelle genome may be operably linked to at least one regulatory element that is active in the organelle. The second or the third nucleic acid sequence, or both, may comprise at least one altered sequence, wherein the at least one altered sequence is altered with respect to at least one additional target site in the organelle genome, wherein the at least one altered sequence is not cleavable by at least one additional guide polynucleic acid, wherein the at least one additional guide polynucleic acid can direct a polynucleotide guided polypeptide (e.g., Cas polypeptide; Cas9 polypeptide) to cleave the at least one additional target site in the organelle genome. The at least one additional target site in the organelle genome may be present in at least one essential coding region. The polynucleotide introduced into the organelle may further comprise a fourth nucleic acid sequence, wherein the fourth nucleic acid sequence encodes the at least one additional guide polynucleic acid operably linked to a promoter that is active in the organelle.

In another embodiment, a polynucleotide may encode a modified RNA donor sequence, wherein the modified RNA donor sequence may comprise an organelle targeting RNA operably linked to a donor RNA. The modified RNA donor sequence may comprise a reverse transcriptase primer site.

In another embodiment, the cell may comprise the polynucleotide encoding the modified RNA donor sequence, and further comprise a polynucleotide encoding a modified reverse transcriptase, wherein the modified reverse transcriptase comprises a reverse transcriptase operably linked to an organelle targeting peptide.

In any of the above methods for altering the genome of an organelle, the method may further comprise introducing a polynucleotide comprising at least one donor polynucleotide (e.g., donor DNA) into the organelle, wherein the donor polynucleotide is introduced into the organelle by: (a) introducing into a cell a polynucleotide encoding a modified RNA donor sequence, wherein the modified RNA donor sequence comprises an organelle targeting RNA operably linked to a donor RNA, wherein the modified RNA donor sequence comprises a reverse transcriptase primer site, and wherein the polynucleotide is operably linked to at least one regulatory element; (b) introducing into the cell a polynucleotide encoding a modified reverse transcriptase, wherein the modified reverse transcriptase comprises a reverse transcriptase operably linked to an organelle targeting peptide, wherein the polynucleotide is operably linked to at least one regulatory element, wherein the organelle targeting RNA of (a) and the organelle targeting peptide of (b) each target the same organelle; and (c) growing the cell under conditions wherein the polynucleotides of (a) and (b) are both expressed. The method may further comprise (d) selecting a cell having an organelle that comprises an altered genome.

In another embodiment, a method for altering the genome of an organelle may comprise: (a) introducing into an organelle the following: (i) a first polynucleotide encoding at least one guide polynucleic acid, wherein the at least one guide polynucleic acid can direct a polynucleotide guided polypeptide (e.g., Cas polypeptide; Cas9 polypeptide) to cleave at least one target sequence present in an organelle genome; (ii) a second polynucleotide encoding a polynucleotide guided polypeptide (e.g., Cas polypeptide; Cas9 polypeptide), wherein the polynucleotide guided polypeptide, when associated with the guide polynucleic acid (e.g., guide RNA), can cleave the at least one target sequence; (iii) optionally, a third polynucleotide encoding at least one homologous organelle DNA sequence, wherein the at least one homologous organelle DNA is of sufficient size for homologous recombination, wherein integration of the at least one homologous organelle DNA sequence into the organelle genome results in removal of the at least one target sequence; (iv) optionally, a fourth polynucleotide encoding at least one selectable marker or at least one screenable marker, or both, wherein the sequence encoding the at least one selectable marker, or at least one screenable marker, or both, is operably linked to a promoter that is functional in the organelle; and (v) optionally, a fifth polynucleotide encoding an origin of replication that is functional in the organelle; and (b) growing a cell comprising the organelle of (a) under conditions in which the first polynucleotide of (i) and the second polynucleotide of (ii) are each expressed. The method may further comprise a step (c) of selecting a cell having an organelle that comprises an altered genome. The method may further comprise a step (d) of selecting a cell that is homoplasmic for the altered genome of the organelle. The third polynucleotide of (iii) may comprise a sixth and a seventh polynucleotide, wherein the sixth and the seventh polynucleotides correspond to two adjacent regions of homology in the organelle genome, wherein the sixth and seventh polynucleotides are separated by a sequence that is heterologous to the organelle DNA. The sequence that is heterologous to the organelle DNA may comprise at least one selected from the group consisting of: the first polynucleotide of (i), the second polynucleotide of (ii), the fourth polynucleotide of (iv), an eighth polynucleotide, and any combination thereof, wherein the eighth polynucleotide encodes an RNA that is heterologous to the organelle or comprises a non-coding sequence (e.g., a regulatory sequence, such as a promoter) that is heterologous to the organelle, or both. The RNA that is heterologous to the organelle may be at least one selected from the group consisting of: an mRNA, a functional RNA, and any combination thereof. The functional RNA may be at least one selected from the group consisting of: guide RNA, siRNA, miRNA, dsRNA, tRNA, rRNA, and any combination thereof. At least one selected from the group consisting of: the first polynucleotide of (i), the second polynucleotide of (ii), the fourth polynucleotide of (iv), the fifth polynucleotide of (v), and any combination thereof, may be located outside the region bounded by the sixth and the seventh polynucleotide. The fifth polynucleotide of (v) may encode a plastid origin of replication, a mitochondrial origin of replication, or both. The plastid origin of replication may correspond to DNA sequence from a plastid rRNA intergenic region.

In any of the methods described herein, one or more of the polynucleotides described herein may be present on a recombinant DNA construct.

In any of the methods described herein, the method may comprise more than one such recombinant DNA construct.

In any of the methods described herein, the recombinant DNA construct may further comprise a ninth and tenth polynucleotide, wherein the ninth and tenth polynucleotides have 100 percent sequence identity to each other, and further wherein the ninth and tenth polynucleotides are arranged as direct repeats in the recombinant DNA construct. The ninth and tenth polynucleotides may have at least 20, 21, 22, 23, 24, 25, 30, 40, 50, 60, 70, 80, 90 or 100 nucleotides of 100 percent sequence identity to each other. The recombinant DNA construct may be linear, and the ninth and tenth polynucleotides may be present at the 5' and 3' ends of the recombinant DNA construct, respectively.

In any of the methods described herein for altering the genome of an organelle, the recombinant DNA construct may be linear, single-stranded and operably linked to a modified VirD2 protein. The modified VirD2 protein may comprise a VirD2 protein operably linked to an organelle targeting peptide, wherein the modified VirD2 protein has also been modified such that at least one native nuclear localization sequence of the VirD2 protein is no longer functional.

In the above methods for altering the genome of an organelle, the recombinant DNA construct may be operably linked to at least one modified VirE2 protein. The at least one modified VirE2 protein may comprise a VirE2 protein operably linked to an organelle targeting peptide, wherein the at least one modified VirE2 protein has also been modified such that at least one native nuclear localization sequence of the VirE2 protein is no longer functional.

In any of the methods described herein for altering the genome of an organelle, the recombinant DNA construct may be operably linked to at least one modified RecA protein. The at least one modified RecA protein may comprise a RecA protein operably linked to an organelle targeting peptide.

In any of the methods described herein for altering the genome of an organelle, the recombinant DNA construct may be operably linked to at least one chimeric polypeptide. The at least one chimeric polypeptide may comprise an organelle targeting peptide and a cell penetrating peptide and optionally, a DNA-binding polypeptide.

In another embodiment, a method for altering the genome of an organelle may comprise using of both a site-directed nuclease (e.g., TALENS, Zinc-Finger Nuclease or Meganuclease) and a polynucleotide guided polypeptide. The initial cleavage of the organelle genome may be done by a site-directed nuclease (e.g., TALENS, Zinc-Finger Nuclease, Meganuclease), to facilitate homologous recombination with a donor polynucleotide. The donor polynucleotide may contain modified target sites that are not recognized by a polynucleotide guided polypeptide. A homoplasmic state may be facilitated by cleavage of the unmodified organelle genomes at the target sites by treatment with a polynucleotide guided polypeptide. In another embodiment, any of the above methods may further comprise introducing into the organelle a polynucleotide encoding at least one marker selected from the group consisting of: a positive selectable marker, a negative selectable marker, a screenable marker, and any combination thereof.

The positive selectable marker may be an herbicide tolerance protein. The herbicide tolerance protein may be at least one selected from the group consisting of: a 4-hydroxphenylpyruvate dioxygenase (HPPD), a sulfonylurea-tolerant acetolactate synthase (ALS), an imidazolinone-tolerant acetolactate synthase (ALS), a glyphosate-tolerant 5-enolpyruvylshikimate-3-phosphate synthase (EPSPS), a glyphosate-tolerant glyphosate oxidoreductase (GOX), a glyphosate N-acetyltransferase (GAT), a phosphinothricin acetyl transferase (PAT), a protoporphyrinogen oxidase (PROTOX), an auxin enzyme or receptor, a P450 polypeptide, an acetyl coenzyme A carboxylase (ACCase), and any combination thereof. The method may further involve growing the cell in the presence of a positive selection agent and selecting a cell that is homoplasmic for the altered genome of the organelle. Optionally, the method may further involve growing the cell in the absence of the positive selection agent, followed by selecting a cell that lacks a non-integrated recombinant DNA construct. Alternatively, the method may further involve growing the cell in the absence of the positive selection agent, followed by growing the cell in the presence of a negative selection agent, followed by selecting a cell that lacks a non-integrated recombinant DNA construct. In the method, the cell may be a plant cell, the organelle may be a plastid, and the method may further involve regenerating a plant from the plant cell comprising an altered organelle genome. The plant cell may be monocot cell, e.g., a maize cell. The plant cell may be a dicot cell, e.g., a soybean cell.

In another embodiment, a method for altering a genome of an organelle may comprise: (a) introducing into an organelle of a cell the following: (i) at least one guide RNA, wherein the at least one guide RNA directs a polynucleotide guided polypeptide to cleave at least one target sequence present in the genome of the organelle; (ii) a polynucleotide guided polypeptide, wherein the polynucleotide guided polypeptide, when associated with the at least one guide RNA, cleaves the at least one target sequence; and (iii) a replacement DNA; and (b) selecting a cell comprising an organelle comprising the replacement DNA. The replacement DNA of step (a) part (iii) may comprise fragments of organellar DNA or a complete organellar DNA from a cultivar, line, sub-species and other species and is distinct from the genome of the organelle of step (a). The replacement DNA may be lacking the at least one target sequence. Additionally, after step (a) part (ii) and prior to step (a) part (iii), a cell may be selected in which the genome of the organelle has been eliminated.

In another embodiment, the guide polynucleic acid in the methods and compositions of matter described herein may comprise the following: i) at least 17 nucleotides that are complementary to at least 17 nucleotides of a target polynucleic acid, wherein said target polynucleic acid is located in the genome of an organelle; and ii) a region that contacts a polynucleotide-guided polypeptide. The guide polynucleic acid may comprise one or more RNA bases. The guide polynucleic acid may be a guide RNA. The guide polynucleic acid may be a dual guide RNA. The guide polynucleic acid may be a single guide RNA.

In another embodiment, the polynucleotide-guided polypeptide in the methods and compositions of matter described herein may be selected from the group consisting of: a Cas9 protein, a MAD2 protein (U.S. Pat. No. 10,011,849; herein incorporated by reference), a MAD7 protein (U.S. Pat. No. 9,982,279; herein incorporated by reference), a CRISPR nuclease, a nuclease domain of a Cas protein, a Cpf1 protein, an Argonaute, modified versions thereof, and any combination thereof. The sequence encoding the polynucleotide-guided polypeptide may be codon-optimized for a human, a yeast, an alga, or a plant species.

In any of the methods described herein for altering the genome of an organelle, the method may further involve growing the cell in the presence of a positive selection agent and selecting a cell that is homoplasmic for the altered genome of the organelle. The method may further involve: (i) growing the cell in the absence of the positive selection agent, followed by selecting a cell that lacks a non-integrated recombinant DNA construct; or (ii) growing the cell in the absence of the positive selection agent, followed by growing the cell in the presence of a negative selection agent, followed by selecting a cell that lacks a non-integrated recombinant DNA construct.

In any of the methods described herein that involve a guide polynucleic acid and a polynucleotide guided polypeptide, the method may comprise an increase in transformation efficiency of at least 10%, 20%, 30%, 40%, 50%, 60%, 70%, 80%, 90%, 100%, 200%, 300%, 400%, or 500%, as compared to the corresponding method lacking the guide polynucleic acid, the polynucleotide guided polypeptide, or lacking both.

In any of the methods described herein that involve a guide polynucleic acid and a polynucleotide guided polypeptide, the method may comprise a decrease in the amount of time required to achieve a homoplasmic state, wherein the decrease is at least 10%, 20%, 30%, 40%, 50%, 60%, 70%, 80% or 90%, as compared to the amount of time required for the corresponding method lacking the guide polynucleic acid, the polynucleotide guided polypeptide, or lacking both.

In another embodiment, a recombinant DNA construct (e.g., for use in any of the methods described herein) may comprise any one or more of the polynucleotides described herein.

In another embodiment, a cell may comprise an organelle, wherein the organelle may comprise at least one of the above recombinant DNA constructs. The cell may be selected from the group consisting of: a yeast cell, an algal cell, a plant cell, an insect cell, a non-human animal cell and a mammalian tissue culture cell.

In another embodiment, a plant or seed may comprise any of the above organelles, cells or recombinant DNA constructs.

In another embodiment, a cell comprising an organelle with an altered genome may be produced by any of the above methods. The cell may be selected from the group consisting of: a yeast cell, an algal cell, a plant cell, an insect cell, a non-human animal cell and a mammalian tissue culture cell.

In another embodiment, a method may alter the genome of an organelle in a cell, wherein the cell is a plant cell. Furthermore, a plant may be regenerated from the plant cell comprising an organelle with an altered genome, wherein the regenerated plant comprises an organelle with an altered genome. Also, a plant (e.g., progeny plant) or seed may be produced from the regenerated plant, wherein the plant or seed comprises an organelle with an altered genome.

In any of the above embodiments involving guide polynucleic acid (e.g., guide RNA), the guide polynucleic acid may be a single guide RNA (unimolecular) or a duplex guide RNA (bimolecular). In any embodiment involving multiple guide RNAs, the multiple guide RNAs may be single guide RNAs, duplex guide RNAs, or both.

In any of the above embodiments, multiple guide RNAs (and/or other heterologous RNAs) may be encoded on separate transcription units or may be encoded on a polycistronic transcription unit. A guide RNA may be processed from a polycistronic RNA after transcription; e.g., by use of an RNA cleavage site (e.g., Csy4; C2c2), a ribozyme cleavage site, a polynucleotide guided polypeptide cleavage site or the presence of a tRNA sequence. A guide RNA may be processed from a polycistronic RNA by having a first tRNA sequence 5' to the guide RNA and a second tRNA sequence 3' to the guide RNA. Multiple guide RNAs may be arrayed with multiple tRNA sequences (at each guide RNA 5' and 3' end) for processing from a polycistronic RNA.

In any of the above embodiments, the polynucleotide (e.g., donor DNA, donor RNA) that can be introduced into the organelle may comprise at least one selected from the group consisting of: an expression cassette encoding a polynucleotide of interest and an expression cassette encoding a polycistronic transcript that comprises multiple polynucleotides of interest; e.g., a polycistronic transcript comprising multiple protein-coding regions, multiple functional RNAs, or a combination of both. The polynucleotide of interest may be heterologous with respect to the genome of the organelle.

In any of the above methods for altering the genome of an organelle to contain a heterologous polynucleotide, the heterologous polynucleotide may encode at least one selected from the group consisting of: an herbicide tolerance protein, a pesticidal protein, an accessory protein that binds to a pesticidal protein, a dsRNA, a siRNA, a miRNA, and any combination thereof, wherein the dsRNA, the siRNA and the miRNA can suppress at least one target gene present in a plant pest. The herbicide tolerance protein may be at least one selected from the group consisting of: a 4-hydroxphenylpyruvate dioxygenase (HPPD), a sulfonylurea-tolerant acetolactate synthase (ALS), an imidazolinone-tolerant acetolactate synthase (ALS), a glyphosate-tolerant 5-enolpyruvylshikimate-3-phosphate synthase (EPSPS), a glyphosate-tolerant glyphosate oxidoreductase (GOX), a glyphosate N-acetyltransferase (GAT), a phosphinothricin acetyl transferase (PAT), a protoporphyrinogen oxidase (PROTOX), an auxin enzyme or receptor, a P450 polypeptide, an acetyl coenzyme A carboxylase (ACCase), and any combination thereof. The pesticidal protein may be at least one selected from the group consisting of: Cry1Ac, Cyt1Aa, Cry1Ab, Cry2Aa, Cry1I, Cry1C, Cry1D, Cry1E, Cry1Be, Cry1Fa and Vip3A. The accessory protein that binds to a pesticidal protein may be at least one selected from the group consisting of: a 20 kDa accessory protein and a 19 kDa accessory protein. The dsRNA, the siRNA and the miRNA can suppress at least one target gene selected from the group consisting of: proteasome A-type subunit peptide (Pas-4), ACT, SHR, EPIC2B, PnPMAI, and any combination thereof. The heterologous polynucleotide may be operably linked to at least one regulatory element that is active in an organelle. The at least one regulatory element may be selected from the group consisting of: a maize clpP promoter combined with a maize clpP 5'-UTR, a maize clpP promoter combined with a 5'-UTR from gene 10 of bacteriophage T7, a tomato psbA promoter is combined with a 5'-UTR from gene 10 of bacteriophage T7, a tomato rrn16 promoter combined with a modified accD 5'-UTR, and any combination thereof. The cell may be a plant cell, wherein the organelle is a plastid (e.g., a chloroplast), and wherein the method further comprises regenerating a plant from the plant cell comprising an altered organelle genome. The plant cell may be a soybean cell.

In any of the above methods for altering the genome of an organelle to contain a heterologous polynucleotide, the heterologous polynucleotide may be flanked by direct repeat sequences. The direct repeat sequences may have at least 20, 21, 22, 23, 24, 25, 30, 40, 50, 60, 70, 80, 90, 100, 200, 300, 400, 500 or 600 nucleotides of 100 percent sequence identity to each other. The direct repeat sequences may comprise a site-specific recombinase site (e.g., loxP, attP, attB). The heterologous polynucleotide may encode at least one marker selected from the group consisting of: a positive selectable marker, a negative selectable marker, a screenable marker, and any combination thereof. Optionally, the method may further involve growing the cell in the absence of the positive selection agent, followed by selecting a cell that is homoplasmic for organelles that lack the heterologous polynucleotide. Alternatively, the method may further involve growing the cell in the presence of a negative selection agent, followed by selecting a cell that is homoplasmic for organelles that lack the heterologous polynucleotide. Optionally, the method may involve growing the cell under conditions in which a heterologous site-specific recombinase (e.g., Cre, phiC31, Bxb1) is expressed in the organelle.

In the above embodiments, the target organelle may be a plastid (e.g., chloroplast) or a mitochondrion. The organelle targeting polynucleotide may be tRNA, viroid RNA or eIF4E RNA.

In the above embodiments, expression of an antibiotic marker gene may be used in conjunction with antibiotic selection for obtaining (and selecting) a plastid or mitochondrial transformation event (e.g., a homoplasmic event). The polynucleotide comprising the donor polynucleotide (e.g., donor DNA) may also comprise an expression cassette for the antibiotic marker gene; the expression cassette may be within the donor polynucleotide region (i.e., for integration into the organelle genome) or outside the donor polynucleotide region.

EXAMPLES

The present disclosure is further defined in the following Examples, in which parts and percentages are by weight and degrees are Celsius, unless otherwise stated. It should be understood that these Examples, while indicating embodiments, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Such modifications are also intended to fall within the scope of the appended claims.

Experiments typically involve a single guide RNA (sgRNA), i.e., where the variable targeting domain is fused to a polynucleotide that contains a tracrRNA sequence. Alternatively, experiments may involve a duplex guide RNA, i.e., where the variable targeting domain and the tracrRNA sequence are present on separate RNA molecules.

Example 1

Targeting Cas9 and Guide RNA into Yeast Mitochondria

To create the Cas9 protein for mitochondrial genome editing, a protein functional in nuclear genome editing is modified by fusing a mitochondrial targeting peptide at the amino terminal end and by deleting any NLS (nuclear localization signal) elements. The organelle targeting peptides of the ATPase beta subunit and the 70 KD protein are used for the modification, creating mCas9-A (encoded by SEQ ID NO: 1) and mCas9-B (encoded by SEQ ID NO: 2), respectively. Each polynucleotide encoding a modified Cas9 is cloned into a yeast shuttle vector with expression of the polynucleotide under control of the Gal1 promoter, whose activity is induced by galactose as a carbon source in the media.

To create guide RNA for mitochondrial genome editing, the tRNA$^{Lys}$ (tRK1 and modified tRK2 forms) that can be imported into mitochondria is used. Several versions of fusion RNA between tRNA and guide RNA are made. One approach is to fuse guide RNA to the 5'end of the tRNA (SEQ ID NO: 3 and 4). To suppress 5'end cleavage by RNAse P, the first base of tRNA is modified in an alternative construct to prevent the pairing with the corresponding base on the acceptor stem of the tRNA (SEQ ID NO: 5 and 6). The second approach is to replace the intron of tRK2 with efficient mitochondrial import in the backbone of tRK2-2 and tRK1 (SEQ ID NO: 7 and 8, respectively). The third approach is to use the fact that tRK1 (tRNA$^{Lys}$) can be split into two molecules that together retain the property of mitochondrial import. In this case, guide RNA is fused to the 5'end of second half of the tRK1 in the region called variable loop in tRNA structure in a manner that retain the secondary structure of the tRNA splicing site (SEQ ID NO: 9). The guide RNA fused with B form (SEQ ID NO: 10) is co-expressed with A form to facilitate co-import into mitochondria.

A variation of creating synthetic guide RNA with RNA that serves as the efficient vehicle for mitochondrial import is to use the combination of F-hairpin and D-arm structures of tRK1. These structures are shown to facilitate import into mitochondria. In this approach, guide RNA is placed between two structures (SEQ ID NO: 11) or fused with one of them at the 5' or 3' ends (e.g. SEQ ID NO: 12 and 13).

For the site-specific cleavage sites, the following mitochondrial sequences were identified as target sites for guide RNA; the guide RNA variable targeting domain is shown below:

```
                                       (SEQ ID NO: 14)
1. ACTGATAGAAGTGTAGTAAG_(cytochrome b gene)

(SEQ ID NO: 15)
2. ATGATTATTGCAATTCCAAC (COX1 gene)

(SEQ ID NO: 16)
3. ATTCCACGATACTTACTACG (COX1 gene)

(SEQ ID NO: 17)
4. TCAGCAACACCAAATCAAGA (COX2 gene)
```

Each of the above variable targeting domains precedes a PAM sequence. SEQ ID NO: 14-17 precede the following PAM sequences: AGG, AGG, TGG and AGG, respectively.

Eleven nucleotides from the 3' end of each underlined sequence (adjacent to the PAM sequence), which are considered critical for Cas9 target site recognition, are unique to the yeast mitochondrial genome based on blast analyses. Each of the above variable targeting domains is fused at the 3' end with a tracrRNA sequence for Cas9 recognition (SEQ ID NO: 18). Polynucleotides encoding each engineered guide RNA are expressed in the nucleus under control of the SNR52 promoter and the SUP4 termination element (SEQ ID NO: 19 and 20, respectively). In this experiment, a yeast shuttle vector for transformation is used. For example, SNR52 expression cassettes are cloned into a yeast expression vector such as p416-Gal1 (URA3+, multicopy plasmid purchased from ATCC). Expression cassettes encoding mitochondrial targeted Cas9 ("mCas9") are cloned into the SalI-XhoI sites of centromeric p415-galL vector (LEU+) with expression under control of the GalL promoter whose activity is induced by galactose in the media as sole carbon source. Vectors are transformed into a yeast strain allowing auxotropy selection such as BY4733 (mat a) line, and selected for Leu and Ura independent growth.

The transformants of each and/or the combination of mCas9 and guide RNA constructs are selected on media selective for corresponding auxotropy as single colony lines. The expression of mCas9 endonuclease is induced by shifting media to the one containing galactose as sole carbon source. Cells derived from single colonies are grown in the inducing media for several generations. These lines are analyzed for genome editing efficacies at the molecular level. Cells from multiple lines of each construct and each construct combination are combined together and their DNA are isolated by using standard DNA isolation protocols such as by using Yeast DNA Extraction Kit from TheromoFisher (cat #78870). Using PCR primer sets specific to corresponding genome editing sites, DNA at each editing site is amplified by PCR reaction. PCR products are subjected to high-throughput sequencing such as by using Illumina HiSeq protocols provided by the manufacture. The frequency of site-specific mutations at each target sit is evaluated in comparison with corresponding control constructs. The efficacy of genome editing is also analyzed at the functional level. After obtaining single colony lines, each line is further grown for additional generations in non-selective glucose media to promote a homoplasmic state of the mitochondrial genome. Yeast cells are plated on glucose media such as YD medium. Single colonies are transferred to the glycerol media such as YG medium by replica plating. The efficacy of genome editing is evaluated by the output frequency of colonies incapable of growth on glycerol media, i.e. deficient in respiration due to the mutations in cob, cox1 and cox2 genes, respectively.

The next step of organellar genome editing is to create a dominant and sustainable state of the edited DNA in mitochondria, which initially contains a pool of multiple, if not hundreds of, unedited DNA. This is achieved by extending the period of enzymatic reactions of site-specific modifications in organelles. Depending on several factors such as the import efficiency of mCas9 and guide RNA into mitochondria, and the affinity between guide RNA, imported Cas9 and target sites, the length of the extended period suitable for each modification of an organelle varies. To assess the effect of extended periods, yeast lines transformed with appropriate mCas9 and guide RNA pairs are grown in selective media for corresponding constructs over a time course of hours, days and weeks. Then, each culture is subjected to evaluation at the molecular as well as functional levels as described above. The period of enzymatic states sufficient for the maintenance and phenotypic expression of edited mitochondrial genomes over generations is determined from the time course experiments.

Example 2

Targeting Cas9, Guide RNA and Donor DNA into Yeast Mitochondria

In order to edit organellar genomes precisely at the nucleotide level, donor DNA (comprising a polynucleotide modification template) is added to the site-specific endonuclease system. In one approach, donor DNA is introduced into mitochondria in combination with Cas9 and guide RNA; Cas9 and guide RNA are introduced into mitochondria as described in Example 1. In this example, the donor DNA is designed to create a specific mutation in the 15S rRNA gene in the mitochondrial genome to confer paromomycin resistance. The nucleotide substitution (C-to-G) at position 1514 can confer paromycin resistance. To create the donor DNA with the resistance allele, one primer pair is designed to carry the corresponding substitution (SEQ ID NO: 21). PCR amplification is performed by using the primer set (SEQ ID NO: 21 and 22) and yeast total DNA as substrate following standard PCR protocols. The resulted template DNA is transformed into mitochondria via DNA transformation procedures, such as biolistic methods. For transformation with donor DNA, the cells expressing Cas9 and guide RNA as described in Example 1 are used with the exception that the guide RNA is designed to cleave the vicinity of the paromomycin-resistance site of mitochondrial DNA as exemplified in SEQ ID NO: 23. The guide RNA is so designed that the cleavage site is covered by the donor DNA with overlapping sequences sufficient for homologous recombination at the both ends but the donor DNA is not recognized as the substrate for site-specific endonuclease activities. For instance, the donor DNA is modified to not include the PAM sequence that is targeted by the corresponding guide RNA. The variable targeting domain of the guide RNA is fused at the 3' end with tracrRNA sequence for association with Cas endonuclease; guide RNA expression constructs are made by using tRNA$^{Lys}$ derived methods described in Example 1.

After transformation with donor DNA, cells are pooled together and grown in galactose media to induce Cas9 protein for several generations, following the favorable amplification of the engineered DNA by adding gradually increasing amount of paromomycin in the media over additional generations. Cells are plated to make single colonies. Single colonies are replica plated on media with glycine as the sole carbon source in the presence and absence of paromomycin to identify paromomycin resistant colonies. The efficiency of genome editing by this method is shown by an increased rate of producing paromomycin resistant cells with template DNA in comparison to control cells not transformed with donor DNA. Gene editing is confirmed by sequencing of the engineered site.

A subsequent genome editing step is performed to eliminate organellar DNA that does not carry the designed modification. This is achieved by any of several approaches. One approach is to expose cells under positive selection pressure as described above. Another approach is to eliminate or reduce the replication rate of unmodified organelle DNA. This can be achieved by cleaving unmodified DNA by use of site-specific endonucleases such as zinc finger proteins, TALEN and Cas9 systems. In the Cas9 approach, expression of specific guide RNAs is used to cleave unmodified organellar DNA and thereby increase the population of modified DNA.

Example 3

Replacement of Endogenous Organellar DNA

This is an alternative method for modification of an organellar genome. In this approach, the first step is to reduce or eliminate the endogenous organellar DNA by using site-specific endonucleases such as Cas9 systems. At the same time or subsequently, a replacement organellar DNA is introduced. The replacement DNA can be fragments of organellar DNA or complete organellar DNA that convey a new genotype and corresponding trait(s) when transformed into the organelle. In the case of organellar DNA fragments, they can be integrated into the remaining organellar DNA by homologous recombination. In the case of complete organellar DNA replacement, the replacement DNA can be isolated from cultivars, lines, sub species and other species which possess DNA compositions distinct from the endogenous organellar DNA of recipient cells. One requirement of the replacement DNA can be to contain a DNA element functioning as a DNA replication origin in the recipient organelles. The replacement DNA can also be synthesized partially and/or completely. When replacement DNA is created in vitro, it can be a linear DNA with the inverted repeat sequence at the ends. The ends can facilitate homologous recombination in vitro or in vivo to create circular DNA for replication of organellar DNA in cells. The DNA created in vitro can also include exogenous DNA elements such as ones to allow selected amplification in bacterial cells.

To reduce or eliminate mitochondrial DNA, yeast cells are exposed to prolonged expression of guide RNA and Cas9 protein that are designed to be imported into mitochondria as described in Example 1 or to be synthesized directly in organelles as described in Example 4. The target sites are chosen to be unique to the endogenous mitochondrial DNA and not present in nuclear genome to reduce the chance of any damage occurring on nuclear genomes when taking the method described in Example 1. The target sites are also chosen to not be present in the replacement DNA.

Multiple cleavage sites enhance the rate of displacing endogenous organellar DNA. This can be attained by expressing multiple guide RNAs targeting different unique sequences in the endogenous mitochondrial DNA (e.g., see target sites of Example 1). After Cas9/guide RNA treatment, yeast cells that have lost mitochondrial DNA are identified by lack of respiration, inability to grow on media with glycerin as sole carbon source and the lack of mitochondrial DNA. The resulting rho$^0$ condition can also be confirmed by absence of the mitochondrial DNA band in a CsCl gradient through the method described in Example 1. Once mitochondrial DNA is deleted, cells are then transformed with replacement DNA created in vitro or in vivo; e.g., mitochondrial DNA derived from different lines or species with traits distinct from the recipient cells. In this example, mitochondrial DNA from antibiotic resistant lines (e.g. IL8-8C/R53) is isolated and transformed into recipient cells that lack the resistant trait by using the transformation methods described in Example 2. Mitochondrial DNA for use in transformation can also be created by PCR amplification of organellar DNA by use of a primer set whose 3' ends are complementary with each other, sufficient for annealing in vivo. The resulted linear DNA molecules are transformed into mitochondria. Homologous recombination activity present in the organelle creates circular organellar DNA upon transformation. Alternatively, DNA for transformation can be created synthetically in a linear as well as a circular form.

Example 4

Introduction into Yeast Mitochondria of Donor DNA and Expression Cassettes for Cas9 and Guide RNA In this example, a DNA plasmid ("Edit Plasmid") that can replicate in an organelle and encodes components of a site-specific endonuclease system such as Cas9, guide RNA and donor DNA is directly introduced into an organelle. The delivery of nucleic acids and proteins can be accomplished by utilizing methods such as bombardment ("biolistics"), electroporation and other suitable methods.

In yeast, DNA in a circular form with bacterial vector sequence (pBR322) can be transformed into mitochondria by utilizing a biolistic method. The resulted cells were crossed with a line carrying a point mutation in mitochondrial DNA. They showed that the point mutation was recovered by recombination between the plasmid DNA and mitochondrial DNA. For efficient genome editing, a plasmid DNA to be transformed into yeast mitochondria is created with expression cassettes for Cas9 and guide RNA that are customized for expression in mitochondria. The plasmid DNA also contains donor DNA to facilitate site-specific genome editing. The Cas9 gene is optimized for mitochondrial expression (SEQ ID NO: 24) and is operably linked to a COX2 promoter and a terminator (SEQ ID NO: 25 and 26, respectively). The optimization is performed by changing CTN codons to TTA, GGG/GGC to GGT, GCG/GCC to GCT, CGG/CGC to CGT, CCG/CCC to CCT, AGC to AGT, AGG to AGA, ACG/ACC to ACT, TCG/TCC to TCT and GAG to GAA as well as TGA stop codon to TAA. The polynucleotide encoding a guide RNA that contains a variable targeting domain designed for the mitochondrial 21S rRNA gene (SEQ ID NO: 27) is operably linked to a promoter and terminator for the expression of the mitochondrial 15S rRNA gene (SEQ ID NO: 28 and 29, respectively). The donor DNA fragment carries the 21S rRNA gene with the chloramphenicol resistance allele, $C^R 321$. The $C^R 321$ mutation in the mitochondrial 21S rRNA gene can confer chloramphenicol resistance in yeast. For the selection of the plasmid in mitochondria, the plasmid can also carry a positive selectable marker such as active 15S rRNA gene with the paromomycin resistance mutation described above. This plasmid is transformed into mitochondria of yeast lines such as MCC123 [rho$^0$] together with the other plasmid for nuclear transformation to select events of co-transformation of both plasmids in yeast. Transformed yeast cells are first colonized on media to allow the selection of nuclear transformants. By replica plating the colonized cells on the plates spread with a yeast line carrying the opposite mating type and wild-type mitochondrial genome, the colonies that are resistant to chloramphenicol are identified through subsequent replica-plating of mated cells on non-fermentable media such as YPGE with chloramphenicol (4 mg/ml). The increased frequency of chloramphenicol resistance colonies is confirmed by comparison with the frequency of chloramphenicol resistance colonies produced by the plasmid without Cas9 and guide RNA. Successful genome editing is further confirmed by sequencing of the edited site in mitochondrial DNA.

Example 5

Insertion of an Exogenous Gene into Mitochondrial DNA and Elimination of Unmodified Mitochondrial DNA In this example, similar to Example 4, mitochondria are transformed with an Edit Plasmid. The Edit Plasmid contains an element that allows replication in mitochondria, and additional components of a site-specific endonuclease system such as Cas9, guide RNA and donor DNA. The donor DNA is designed to be bounded by two regions homologous to the mitochondrial genome for homologous recombination, which is facilitated by site-specific DNA cleavages. Between the two homologous regions, the insertion of an expression unit is demonstrated, consisting of a COXII promoter, a polynucleotide encoding GFP fluorescence protein and a terminator. The donor DNA can have multiple expression units with or without polycistronic expression; i.e., where multiple coding regions are expressed under one promoter.

Two separate sites are targeted by Cas9-gRNA complexes in one demonstration. One Cas9 cleavage site in the COB gene is designed (variable targeting domain of: TGTCC-CATTAAGACATAAGGTACTTCTACA SEQ ID NO:30; which precedes a TGG PAM sequence), and another cleavage site in the ATP9 gene (variable targeting domain of: TGGAGCAGGTATCTCAACAATTGGTTTATTAGGAGC SEQ ID NO:31; which precedes a AGG PAM sequence). One end of the donor DNA comprising polynucleotide covers the COB cleavage site and the other end covers the ATP9 gene to facilitate homologous recombination between the donor DNA and mitochondrial DNA. The donor DNA carries mutations in the sequence near the Cas9-gRNA cleavage sites to eliminate subsequent DNA cleavage after homologous recombination events. These mutations are designed to be "silent"; i.e., the mutated sequence has the same functionality as the wild type, such as replacement of one codon with a synonymous codon encoding the same amino acid. In addition to the modification at the cleavage sites, we also design Cas9-gRNA complexes that cleave additional sites between the two primary target sites in the wild-type mitochondrial DNA but not the donor DNA and the mitochondrial DNA produced by homologous recombination of donor DNA. Additional cleavage sites facilitate the "Genome Sweep" action; i.e., elimination of wild-type mitochondrial DNA without eliminating engineered mitochondrial DNA.

In a separate demonstration, the donor DNA contains a polynucleotide encoding lactoferrin in the place of GFP.

Example 6

Genome Editing of Mammalian Mitochondrial DNA

For Cas9 import into mammalian mitochondria, Cas9 protein without nuclear localization signal element is fused with a mitochondrial targeting peptide. One such peptide is NDUFV2 MTS which has 32 amino acid residues, NH2-MFFSAALRARAAGLTAHWGRHVRNLHKTVMQN—COOH (SEQ ID NO:32). In this case, the NDUFV2 signal sequence is fused with the amino terminus of Cas9 to give a modified Cas9 (SEQ ID NO: 33). Alternatively, another signal peptide such as the one from citrate synthase (NH2-MALLTAAARLLGTKNASCLVLAARH—COOH; SEQ ID NO:34) that can function in human cells can be used to create a modified Cas9 (SEQ ID NO: 35). A polynucleotide encoding a modified Cas9 gene (with a mitochondrial target sequence) is operably linked to a promoter element such as CMV by utilizing the human transfection vector, pSF-CMV-Amp, purchased from Sigma Aldrich or is operably linked to a inducible promoter such as the TET-inducible promoter of pTRE2hyg vector, which can be purchased from Clontech.

Similar to other examples, guide RNA is fused to a mitochondrial targeting RNA; i.e., a sequence that allows import of RNA into mitochondria. In this experiment, RNAs that can be imported into human mitochondria are used. One of them is the yeast tRNA$^{Lys}$. The yeast tRNA$^{Lys}$ and its variants can be imported into human mitochondria. The other RNA used is 5S rRNA, which can be imported into human mitochondria. In the latter case, the guide RNA is cloned into Loop C that can be dispensable for mitochondrial import (SEQ ID NO: 36).

In this experiment, the guide RNA is designed to target the COX3 gene (SEQ ID NO: 37). In the guide RNA, the variable targeting domain is fused with the tracrRNA sequence as well as with a mitochondrial targeting RNA. The gRNA expression cassette consists of the polynucleotide encoding the guide RNA operably linked to a promoter and terminator that are functional in human cells. In this example, the U6 promoter for constitutive expression is used. For the 5S rRNA fusion, the promoter and terminator of the 5S rRNA gene (SEQ ID NO: 38) are also used. Guide RNA expression cassette is cloned into the plasmids carrying the Cas9 expression cassettes or cloned into distinct transfection vectors. Constructed plasmids are transfected into human cell lines such as HeLa and HEK293 as well as HeLa and HepG2 Tet-Off cells for Cas9 inducible expression from pTRE2hyg based constructs. Transfected cells undergo selection in the presence of hygromycin. Preparation of cell culture and transfection are performed for inducible expression.

Cells are harvested three days after transfection and total DNA of approximately 106 cells is extracted using a DNA extraction kit. PCR is conducted to amplify the regions encompassing the target sites and amplified DNA is deep sequenced by use of a high-throughput sequencer (e.g., MiSeq Illumina sequencer). The sequence data are analyzed to confirm modification at the target site.

Example 7

Genome Editing of Mammalian Mitochondrial DNA to Confer Resistance to Chloramphenicol In this example with mammalian cells, mitochondrial DNA is edited to confer chloramphenicol resistance by a nucleotide substitution in the 16S rRNA gene. For the purpose, three components, Cas9 protein, guide RNA and donor DNA, are targeted to mitochondria.

The chloramphenicol resistance in a mouse cell line can be mapped to a single nucleotide change (CAP$^R$) in the mitochondrial 16S rRNA gene. The guide RNA is designed to include the CAP$^R$ mutation site of the wild-type 16S rRNA gene. It is also designed in a manner that it will recognize the wild-type sequence but not the donor DNA with the CAP$^R$ mutation (SEQ ID NO: 39). The donor DNA is produced by PCR amplification of the 16S rRNA region of the mouse CAP$^R$ cells or is synthesized artificially (SEQ ID NO: 40).

Cas9 and guide RNA are targeted to mitochondria as described in Example 5. Plasmids with Cas9 and guide RNA expression cassettes are transfected into mouse cell lines such as NIH 3H3 as described above. The donor DNA is transformed into mitochondria. Transfected cells are cultured on media containing chloramphenicol (CAP). After the selection on CAP, the occurrence of resistant cells through genome editing is confirmed in comparison with controls. Finally, 16S rRNA of the CAP$^R$ cells is sequenced to confirm genome editing at the molecular level.

Example 8

Introduction into Mammalian Mitochondria of Donor DNA and Expression Cassettes for Cas9 and Guide RNA In this example, all components of genome editing including donor DNA are cloned in a plasmid DNA that is introduced into mammalian mitochondria. The plasmid DNA is introduced into mitochondria either in a circular form or in a linear form that has the ability to circularize in mitochondria. The plasmid DNA contains sequence that allows for autonomous replication in mitochondria. It can also encodes at least one selectable marker to allow for selection after transformation into mitochondria. Such a selectable marker can be the active 16S rRNA gene with CAPR mutation. The rep/ori and other elements for gene expression in mitochondria present on the plasmid DNA may be derived from species different from the target species for mitochondrial DNA editing. Additional DNA cleavage sites can be designed for the wild-type sequences that differ from the donor DNA as described in previous examples.

Example 9

Introduction of Cas Endonuclease and Guide RNA into Plastids

To edit a chloroplast genome, Cas9 is modified to have a chloroplast targeting amino acid sequence (also known as transit peptide, TP) at the N-terminus of the protein and to remove any nuclear localization signal(s). In addition, the nucleotide sequence of Cas9 is codon-optimized for the plant species for optimum expression (SEQ ID NO: 41 & 42; for nucleic acid and amino acid sequences, respectively). The transit peptides from chloroplast-targeted proteins such as ribulose bisphosphate carboxylase/oxygenase small subunit (rbcS), chlorophyll a/b binding protein (Cab) and DnaJ8 are used in the experiments. Each modified Cas9 is engineered to have a transit peptide fused translationally to the amino terminus of the Cas9 to create a TP-Cas9 (SEQ ID NO: 46). Expression of a polynucleotide encoding such a fusion protein is under control of a promoter functional in a plant, such as a CaMV 35S promoter. Cas9 without a transit peptide is used as a control (SEQ ID NO: 41 & 42).

For transport of a guide RNA into the chloroplast, RNA sequences are used that can import into the chloroplast. These plastid targeting RNAs (also referred to herein as "transit RNAs"), which can mediate import of attached heterologous RNA, include vd-5'UTR (SEQ ID NO:48) and eIF4E1 mRNA (SEQ ID NO: 49). Transcription of polynucleotides encoding these fusion transcripts is under the control of a nuclear promoter functional in a plant, such as the 35S CaMV promoter (e.g., 1.3-kb 35S promoter of pBC-Yellow) or the U6 promoter; Chromosome 8 maize U6 polymerase III promoter). Guide RNA without a plastid targeting RNA serves as a control (SEQ ID NO: 50).

As an alternative method of creating gRNAs, a sequence-specific endoribonuclease is used, such as Csy4 which is responsible for processing CRISPR transcript from Pseudomonas aeruginosa (SEQ ID NO: 51-52, for nucleic acid and amino acid sequences, respectively). The Csy4 recognition sequence is: 5'-GTT-CACTGCCGTATAGGCAG-3' (SEQ ID NO: 53). Within the primary transcript, the gRNA sequence is flanked with Csy4 recognition sequences (SEQ ID NO: 54). A polynucleotide encoding this sequence fused with a 5' plastid targeting RNA is transcribed from either a 35S CaMV promoter or a U6 promoter in the nucleus and targeted into the chloroplast. For targeting Csy4 protein into the chloroplast, one of chloroplast transit peptides listed in SEQ ID NO: 43-45 is used, as an N-terminal translational fusion to Csy4.

Example 10

Introduction into Plastids of RNA Encoding Both Cas Endonuclease and Guide RNA

Plastid targeting RNA can transport heterologous RNAs into the plastid, which then are translated by the chloroplast translation machinery. This characteristic is utilized to transport all the genome editing components as RNA molecules into the chloroplast; transported mRNA is subsequently translated and the resulting proteins participate in the editing process. In this method, an expression cassette is made comprising a promoter operably linked to a polynucleotide encoding an RNA comprising the following: plastid targeting RNA, rbs (ribosome binding site), Cas9 coding sequence, rbs, Csy4 coding sequence, Csy4 recognition sequence, gRNA, and Csy4 recognition sequence. This expression cassette is integrated into the nuclear genome by transformation. The promoter in the above recombinant DNA construct is a promoter functional in a plant, such as a CaMV 35S promoter. The resulting RNA molecule is transported into chloroplast. Once it enters chloroplast, Cas9 and Csy4 proteins are produced by the chloroplast translation machinery. A complex of Cas9 and gRNA, which is processed from the transported RNA molecule by Csy4, finds and edits the target site in the chloroplast genome.

Example 11

Guide RNA Target Site Selection

Guide RNA target sites are selected from intergenic regions as well as genic regions of the chloroplast genome. The latter examples include rpoB, psbA, rpsl15, and rp133. Deletion of the rpoB gene can show a photosynthesis-defective phenotype. Deletion of the psbA gene can yield a photosystem II deficiency. Double deletion of rps15 and rp133 can result in synthetic lethality under autotrophic conditions. Use of web-based Bioinformatics program, APE (http://biologylabs.utah.edu/jorgensen/wayned/ape/), facilitates the selection process for gRNA target sites.

To select gRNAs target sites for *N. tabacum*, the *N. tabacum* chloroplast genome sequences are used. For gRNAs target sites for *N. benthamiana*, either public sequence deposition or direct sequencing of target regions in *N. benthamiana* chloroplast genome is used, as the total chloroplast genome sequence of *N. benthamiana* is not available. In addition, *N. tabacum* chloroplast DNA sequence is also used for the design of gRNA target sites for *N. benthamiana* since closely related plant species can have highly conserved chloroplast DNA sequences. Similarly, chloroplast *Glycine max* (strain: William 82) genomic sequence from Organelle Genome Resources at NCBI is used as a reference genome for designing tentative gRNA target sites in soybean chloroplast DNA, pending sequencing of the specific line that is transformed.

For editing of the indicated genic sequence regions, the following sequences are selected for variable targeting domains. The term "Nt" corresponds to "*Nicotiana tabacum*", the term "Cp" corresponds to "Chloroplast" and the term "Glma" corresponds to "*Glycine max*". When the variable targeting domain is on the reverse complement of the genic sequence, the term "reverse" is indicated.

```
For NtCp_rpoB (RNA polymerase beta chain)       (SEQ ID NO: 55)

(SEQ ID NO: 56)
1. TTAGAGGAAGAGCCAAACAG (SEQ ID NO: 57)
2. CTTGCTATAGCCGAACGCGA

For NtCp_psbA (photosystem II protein D1)       (SEQ ID NO: 58)

(SEQ ID NO: 59)
1. GTTGATGAATGGTTATACAA (SEQ ID NO: 60)
2. GATGATCCCTACCTTATTGA

For NtCp_rps15 (ribosomal protein S15)          (SEQ ID NO: 61)

(SEQ ID NO: 62)
1. ATTTCTCAAGAAGAAAGAG (SEQ ID NO: 63)
2. TCAATTTCACCAATAAGATA

For NtCp_rpl33 (50S ribosomal protein L33)      (SEQ ID NO: 64)

(SEQ ID NO: 65)
1. GATATATTACTCAAAAGAAC (SEQ ID NO: 66)
2. AGTGTTGATAAGGTATCAAG

For GlmaCp rpoB (RNA polymerase beta chain)     (SEQ ID NO: 67)

(SEQ ID NO: 68)
1. TGTCTAAAACTACCTACAGG (SEQ ID NO: 69)
2. AGCGGAATTTCGGTCTATAC
   (reverse)

For GlmaCp psbA (photosystem II protein D1)     (SEQ ID NO: 70)

(SEQ ID NO: 71)
1. GGTGTAGCTGGTGTATTCGG (SEQ ID NO: 72)
2. TCTAGATCTAGCTGCGATCG
   (reverse)

For GlmaCp_rps15 (ribosomal protein S15)        (SEQ ID NO: 73)

(SEQ ID NO: 74)
1. ATAGAATACGAAGACTTACT
   (reverse)

(SEQ ID NO: 75)
2. TGTCAAAGAAAGATAGAATA

For GlmaCp_rpl33 (50S ribosomal protein L33)    (SEQ ID NO: 76)

(SEQ ID NO: 77)
1. CGTTGTTGCAAACATACAAT
   (reverse)

(SEQ ID NO: 78)
2. ACAGAATACGCCTAGTCGAT

For Nicotiana benthamiana rps16 (ribosomal      (SEQ ID NO: 79)
protein S16)

(SEQ ID NO: 80)
1. TTGTGGATTTGTACATCCAC
   (reverse)

(SEQ ID NO: 81)
2. TTGAACTGTTTGAAAGTTAT
   (reverse)

For Nicotiana benthamiana matK (maturase K)     (SEQ ID NO: 82)

(SEQ ID NO: 83)
1. CTTGTGCTAGAACTTTAGCT (SEQ ID NO: 84)
2. CGTTCATCTGGAAATCTTGG
   (reverse)
```

For editing of the intergenic regions, the following sequences are selected for variable targeting domains.

```
Nicotiana tabacum:
                                                (SEQ ID NO: 85)
1. AAGAACTTCCCCCTTGACAG (NtChrC; 57408 . . . 57389)

(SEQ ID NO: 86)
2. TATACAGGATGGGTAGAAAG (NtChrC; 59412 . . . 59393)

(SEQ ID NO: 87)
3. ATATAATTTTTAATAAAGGG (NtChrC; 59622 . . . 59603)

(SEQ ID NO: 88)
4. CTAGTCTTCGACACAAGAAA (NtChrC; 65704 . . . 65723)

Glycine max:
                                                (SEQ ID NO: 89)
1. ATAACAGAAGTTAAAGAAGA
   (GlmaCp_NC_007942.1_59039-59058)

(SEQ ID NO: 90)
2. ATCTGGAAACCATAGAACAG
   (GlmaCp_NC_007942.1_59100-59119)

(SEQ ID NO: 91)
3. CTATTTCGACACAAACAAGA
   (GlmaCp_NC_007942.1_62057-62038)

(SEQ ID NO: 92)
4. CTTTCTTTGACGAATTCGAG
   (GlmaCp_NC_007942.1_62361-62380)
```

Example 12

Transformation with Polynucleotides Encoding Cas Endonuclease and Guide RNAs

Gene cassettes encoding (a) Cas9 fused to a transit peptide; and (b) gRNA fused with vd-5'UTR or eIF4E1 mRNA as described above are subcloned into a binary vector, such as pPZP and introduced into plants either for transient or for stable expression. DNA encoding Csy4 fused to a transit peptide is also transformed into plants in some experiments. Any of several methods may be used to transform plants with DNA sequences. These include agroinfiltration, biolistic bombardment, and floral dip method.

Similar approaches are also applicable for other plant species including dicots such as canola and monocots such as rice, wheat and corn.

Example 13

Introduction of Donor DNA into the Plastid Via Reverse Transcriptase

A donor DNA is introduced into the plastid genome to edit the genome in at least one way selected from the group consisting of: (1) creation of a point mutation in a target gene; (2) replacement of an endogenous coding region or regulatory sequence with a heterologous DNA sequence; and (3) insertion of a heterologous DNA sequence (e.g., for expression of a heterologous protein or RNA; for regulation of an endogenous gene).

In above examples several methods are presented for delivery of Cas9 and gRNAs into a chloroplast. In the current example, a donor DNA is also delivered into a chloroplast. In one method, a donor DNA for homologous recombination in a chloroplast is generated through reverse transcription of an RNA donor molecule which is transported into a chloroplast by transit RNA-guided transport. The RNA donor molecule, which is transcribed from transformed nuclear genome, contains the following: (1) a transit RNA, (2) sequences for homologous recombination; (3) a polynucleotide modification template sequence having at least one of the following: an endogenous sequence with an intended mutation (e.g., a site-specific mutation in the 16S rRNA) and a heterologous sequence (e.g., a heterologous protein coding sequence); and (4) a sequence that serve as a priming site for reverse transcriptase. In the homologous DNA regions, additional mutations, e.g., silent point mutations, are introduced into the sequence to distinguish these regions from additional gRNA target sites on the chloroplast DNA. The additional gRNA target sites are used to cleave non-transformed copies of chloroplast DNA. Reverse transcriptase protein is targeted into the chloroplast through a translational fusion with any of plastid targeting peptides described in SEQ ID NO: 43-45. Alternatively, an mRNA molecule (with a plastid rbs) encoding a reverse transcriptase is transported into the chloroplast as a fusion molecule with any one of plastid targeting RNAs described in SEQ ID NO: 48-49 and translated in chloroplast by the endogenous translation machinery.

Example 14

Introduction of Donor DNA into the Plastid Via Co-Bombardment with Two Polynucleotides Another method to deliver donor DNA in conjunction with Cas9 and gRNAs is achieved through co-bombardment of two DNA molecules. In this approach, a first DNA molecule encoding Cas9 and gRNAs (employing chloroplast transport methods as described in previous examples) is targeted for transformation into the nuclear genome. A second DNA molecule, having a donor DNA sequence and homologous recombination sequences, is targeted for transformation into the chloroplast genome. The second DNA molecule also can contain a chloroplast origin of replication. For transformation both DNA molecules are delivered to plant cells by biolistic bombardment. Biolistic particles are prepared as follows: (1) particles are coated with both DNA molecules either simultaneously or sequentially; or (2) particles are separately coated with each DNA molecule and then combined with the same molar ratio. For selection of nuclear transformation, commonly used antibiotic markers, such as nptII and bar, and/or fluorescent protein markers can be employed. For selection of chloroplast transformation, antibiotic markers such as aadA and/or fluorescent protein markers are used. The expression cassette for the chloroplast transformation selectable marker is either part of the donor DNA carrying polynucleotide that is integrated into the plastid genome or is placed outside of the donor DNA region, but remains on the delivered DNA molecule without being integrated into the chloroplast genome.

In a variation of above example of polynucleotide modification template delivery into the chloroplast, polynucleotides encoding Cas9 and gRNA (with or without Csy4) are transformed into the nuclear genome first. Gene expression of these components are under the control of inducible promoters. With the aid of selection markers (antibiotic markers and/or fluorescent marker proteins) stably transformed plants are selected. A second transformation is performed to transform chloroplast DNA with a DNA molecule containing a polynucleotide modification template DNA, homologous recombination sequences and a selectable marker such as aadA and/or a fluorescent marker protein. Selection of transformants is performed in the presence of selection agents for both nuclear and chloroplast transgenes and under conditions where the inducible promoter on the nuclear transgenes is active to transcribe Cas9 and gRNAs, which are subsequently transported into the chloroplast via the mechanism described in the previous examples.

Example 15

Introduction of Donor DNA into the Plastid Via Agrobacterium-Mediated Transformation Donor DNA transport into the chloroplast is also performed via Agrobacterium-mediated transformation. A stable transgenic line which contains polynucleotides encoding Cas9 and gRNAs with an inducible promoter is created, as described above. This line is then transformed with a modified Agrobacterium strain, wherein the modification comprises the following: (1) addition of a chloroplast transit peptide fused to VirD2; (2) deletion of VirE2; and (3) removal of nuclear localization signals from VirD2. A binary vector is constructed having a polynucleotide modification template, homologous recombination sequences and a selection marker such as aadA and/or a fluorescent marker protein in between right and left T-DNA borders and transformed into Agrobacteria. For transformation, stable transgenic lines with polynucleotides encoding Cas9 and gRNAs are incubated with Agrobacteria. VirD2 protein which is covalently linked to single-stranded T-DNA enters into plant cells and is transported into the chloroplast via the N-terminal transit peptide. Transgenic selection is imposed by dual selection with nuclear (nptII) and chloroplast (aadA) markers and under conditions where the inducible promoter is active to transcribe polynucleotides encoding Cas9 and gRNAs, which are subsequently transported into chloroplast by the mechanism described in the previous examples.

Example 16

Introduction into Plastids of Donor DNA and Expression Cassettes for Cas9 and Guide RNA In this example, a DNA plasmid ("Edit Plasmid") that can replicate in plastids and encodes components of a site-specific endonuclease system such as Cas9, guide RNA and donor DNA, is directly introduced into the plastid. The delivery of nucleic acids and proteins can be accomplished by use of methods such as bombardment (biolistics), electroporation and other available methods. Here an example in tobacco chloroplasts is shown.

The Edit Plasmid for tobacco chloroplasts is constructed as follows. Polynucleotides encoding Cas9 and guide RNA are cloned into the vector and are operably linked to appropriate promoters and terminators to allow for expression in tobacco chloroplasts. Alternatively, these two coding regions may be linked and transcribed polycistronically under one promoter. The polycistronic RNA may be processed to give rise to separate functional RNA molecules for genome editing, one for Cas9 translation and the other for guide RNA. A polynucleotide encoding a selectable marker that enables selection of the plasmid in chloroplasts, such as the aadA gene conferring spectinomycin resistance, is also present on the plasmid DNA, operably linked with an appropriate promoter and a terminator active in chloroplasts. An expression cassette encoding a negative selectable marker gene is also present on the plasmid to allow for counter selection, i.e., selection of chloroplasts without Edit Plasmid after editing and subsequent elimination of wild-type chloroplast DNA has been achieved. The dao gene is one such negative selectable marker gene. Furthermore, an element that allows for replication of the Edit Plasmid is also present in the vector. Such an element can be derived from the chloroplast DNA of the target species or alternatively from chloroplast DNA of another species, as well as from completely synthetic sources. In addition, donor DNA is present on the vector to allow for precise DNA editing and/or the precise insertion of heterologous DNA elements at specific sites in the chloroplast DNA.

As one example, the wild-type psbA gene in tobacco chloroplast DNA is replaced with an allele carrying a single nucleotide substitution that confers resistance to the herbicide triazine. Such a mutation can be present in herbicide tolerant plants in nature. For DNA cleavage in the vicinity of the mutation site, guide RNA to target the following DNA sequence is designed.

(SEQ ID NO: 93)
ACGAGAGTTGTTGAAACTAGCATATTGGAAGATCAA

The PAM sequence (TGG) is in bold font.
The donor DNA contains the following sequence with five mutations shown in bold font.

(SEQ ID NO: 94)
ACGAGAGTTATTGAAT<u>G</u>TAGCATACTGAAAGATCAA

The atrazine resistance mutation (G) is underlined. The four additional changes that do not alter protein sequence are present to eliminate the donor DNA as being a target for the guide RNA designed for the endogenous wild-type psbA sequence. In particular, one change eliminates the PAM sequence critical for guide RNA pairing to the target polynucleic acid (e.g., target DNA) sites.

To facilitate homologous recombination, the donor DNA is bounded by longer homologous sequences upstream and downstream of the above sequence.

The Edit Plasmid is transformed into tobacco chloroplast by the biolistic approach as described in Chloroplast Biotechnology Methods and Protocols, Pal Maliga (Editor), Methods in Molecular Biology, Springer, New York (2014)(. Cells with transformed chloroplasts are selected on the media containing spectinomycin. After the cultivation of callus cells on the selective media, calli are transferred to the media containing atrazine to assess the frequency of site-specific genome editing with the donor DNA. Sequencing of callus cells resistant to the herbicide confirms the successful genome editing at the molecular level.

To increase the rate of obtaining homoplasmic chloroplasts with engineered DNA, additional target sites are designed in the wild-type sequence covered by the corresponding homologous regions adjacent to the donor DNA. To protect the donor DNA and edited DNA in the chloroplast, donor DNA harbors silent mutations that avoid cleavage by Cas9 endonuclease; e.g., replacing codons with synonymous codons coding for the same amino acids. Expression cassettes encoding the gRNA(s) corresponding to those additional target sites are cloned into the Edit Plasmid vector for expression in chloroplasts. The donor DNA with the additional gRNA target sites mutated (for protection from Cas9 endonuclease) is also present in the Edit Plasmid.

The above Edit Plasmid with increased Genome Sweep activity is transformed into tobacco chloroplast as described above. Cells with transformed chloroplasts are selected on the media containing spectinomycin. After the cultivation of callus cells on the selective media, calli are transferred to the media containing atrazine to assess the frequency of site-specific genome editing with the template DNA. Sequencing of callus cells resistant to the herbicide confirms the successful genome editing at the molecular level.

When stable inheritance of edited organellar DNA is achieved, the Edit Plasmid can be segregated out in progeny plants under non-selective conditions for the Edit Plasmid. The segregation process can be facilitated by utilizing the negative selectable marker encoded in the Edit Plasmid, e.g., D-valine selection for the dao gene.

Example 17

Regulatory Elements for Plastid Gene Expression

Expression cassettes may be constructed that have a promoter functional in a plastid operably linked to either: (a) a donor polynucleotide; or (b) a plurality of donor polynucleotide arranged as a polycistronic unit. A desired 5'-UTR can also be present in the expression cassette, operably linked to the 3'-end of the promoter.

In one expression cassette, the polynucleotide (or polynucleotides) to be transcribed can be operably linked to the following promoter::5'-UTR regulatory elements:
(a) the maize clpP promoter in combination with the maize clpP5'-UTR;
(b) the maize clpP promoter in combination with the 5' UTR from gene 10 of bacteriophage T7;

(c) the tomato psbA promoter in combination with the T7g10 5'-UTR; and (d) the tomato rrn16 promoter in combination with the accD-mod 5'-UTR.

The above regulatory elements can be obtained by PCR amplification.

Example 18

Pest Resistance Genes for Expression in Organelles

An expression cassette for use in organelle transformation is constructed using the wild-type nucleic acid sequence from *Bacillus thuringiensis* serovar *kurstaki* (U89872; SEQ ID NO:108) encoding the full-length native HD73 Cry1Ac delta-endotoxin (SEQ ID NO:109). Alternatively, a truncated native nucleic acid sequence (SEQ ID NO:110) is used, which encodes the active truncated Cry1Ac fragment. Additionally, in some cases, the nucleic acid sequence encoding the full-length or truncated Cry1Ac protein is codon-optimized for the organelle of interest.

In some cases, additional polynucleotides that encode proteins useful in conferring insect resistance to a plant are included in the above expression cassette as a polycistronic unit, or are expressed from separate expression cassettes. These polynucleotides encode the following: (a) the Cyt1Aa protein from *Bacillus thuringiensis* serovar *israelensis* (Gene ID: 5759908; SEQ ID NO:111); (b) the 20 kDa accessory protein from *Bacillus thuringiensis* serovar *israelensis* (pBt024; SEQ ID NO:112); and (c) the 19 kDa accessory protein from *Bacillus thuringiensis* serovar *israelensis*, (pBt022; SEQ ID NO:113).

Example 19

Engineered Plant with Increased Pest Resistance

In this example, a plant (e.g., soybean plant) is engineered with increased resistance to pests. Optionally, the plant also has increased resistance to herbicides.

The site-specific endonuclease system (e.g., Cas9, guide RNA, and donor DNA) of the disclosure is used to introduce one or more pesticidal proteins into the organellar (e.g., plastid) genome of a plant cell (e.g., soybean cell). The one or more pesticidal proteins or their fragments are selected from the group consisting of: Cry1Ac, Cyt1Aa (e.g, SEQ ID NO:109 or SEQ ID NO:110), Cry1Ab, Cry2Aa, Cry1I, Cry1C, Cry1D, Cry1E, Cry1Be, Cry1Fa and Vip3A.

In some cases, one or more accessory proteins are also introduced into the organellar (e.g., plastid) genome of the plant cell. The one or more accessory proteins can bind to a pesticidal protein and are selected from the group consisting of: a 20 kDa accessory protein and a 19 kDa accessory protein.

Additionally or independently, in some cases, the site-specific endonuclease system (e.g., Cas9, guide RNA, and donor DNA) is used to introduce one or more heterologous donor polynucleotides encoding a dsRNA, a siRNA, and/or a miRNA, wherein the dsRNA, the siRNA and the miRNA can suppress at least one target gene present in a plant pest, into the organellar (e.g., plastid) genome of the plant cell (e.g., the soybean cell). The dsRNA, the siRNA and the miRNA can suppress at least one target gene selected from the group consisting of: proteasome A-type subunit peptide (Pas-4), ACT, SHR, EPIC2B and PnPMAI. The RNA interference-based mechanism can be used to protect the engineered plants from pests.

Optionally, in some cases, one or more herbicide tolerance proteins is also introduced into the organellar (e.g., plastid) genome of the plant cell using the site-specific endonuclease system (e.g., Cas9, guide RNA, and donor DNA) of the disclosure. The herbicide tolerance protein can be at least one selected from the group consisting of: a 4-hydroxphenylpyruvate dioxygenase (HPPD), a sulfonylurea-tolerant acetolactate synthase (ALS), an imidazolinone-tolerant acetolactate synthase (ALS), a glyphosate-tolerant 5-enolpyruvylshikimate-3-phosphate synthase (EPSPS), a glyphosate-tolerant glyphosate oxidoreductase (GOX), a glyphosate N-acetyltransferase (GAT), a phosphinothricin acetyl transferase (PAT), a protoporphyrinogen oxidase (PROTOX), an auxin enzyme or receptor, a P450 polypeptide and an acetyl coenzyme A carboxylase (ACCase).

Example 20

Genetic Modification of Yeast Mitochondrial DNA by the Edit Plasmid Approach To show mitochondrial genome editing with our methodology in yeast, *Saccharomyces cerevisae*, various Edit Plasmid constructs were designed. The reference sequence used was a compete mitochondrial genome sequence from the *Saccharomyces* Genome Database (SGD), https://www.yeastgenome.org/. The targeted gene was the COX1 gene (also called oxi3 gene). Mutants of this gene previously have been shown to have a respiration-defective phenotype (https://www.yeastgenome.org/locus/S000007260). The following four guide RNA target sites in the COX1 gene were used (when the targeting sequence was on the reverse complement of the genic sequence, the term "reverse" is indicated):

```
                                    (SEQ ID NO: 116)
1) TTCTTTGAAGTATCAGGAGGTGG;

(SEQ ID NO: 117)
2) ATGATTATTGCAATTCCAACAGG;

(SEQ ID NO: 118)
3) GCTATTTTTAGTGGTATGGCAGG;
and (SEQ ID NO: 119)
4) ACCATGTAAATATTGTGAACCAGG
(reverse).
```

The last three nucleotides in each sequence correspond to the PAM sequence. The first target site resided in exon 5, the second in exon 4, the third one in exon 1 and the forth one at the junction of 3' end of exon 1 of the mitochondrial COX1 gene. Each Edit Plasmid contained a guide RNA expression cassette encoding guide RNA(s) directed to either one or two of the four COX1 target sites. The variable targeting domain of each guide RNA did not contain the 3-nucleotide PAM sequence listed above.

Yeast mitochondrial transformation was performed by following the protocol developed by the Fox lab (Fox et al. 1988 Proc Natl Acad Sci USA 85:7288-7292; Bonnefoy and Fox 2001 Methods Enzymol 350:97-111). It previously has been shown that plasmids derived from pBR322 were capable of replicating in yeast mitochondria (Fox et al. 1988). One of the plasmids derived from pBR322, pHD6 was used, and the plasmids had been successfully transformed into yeast mitochondria in the past (Green-Willms et al. 2001 J Biol Chem 276: 6392-6397). All cloned fragments of pHD6 by digesting with PstI and HindIII are deleted except the genomic fragment of COX3 gene to leave the pBR322 backbone for creating our constructs. The COX3 fragment (0.75 kb PacI-MboI) was used as a screenable marker for mitochondrial transformants with its capability to rescue the cox3 deletion mutant cox3-10 as described in Fox et al., 1988. The Edit Plasmid constructs contained the following elements in the pBR322 backbone: Cas9 expression cassette, guide RNA expression cassette and donor DNA in the case of DNA replacement experiments. The Cas9 expression cassette had a Cas9 coding sequence that was optimized for the expression in yeast mitochondria (SEQ ID NO: 120). As part of codon optimization, the Cas9 codons that were not used at all or were rarely used in yeast mitochondria were replaced with codons that were used frequently. Also, a number of tryptophan codons were replaced with TGA, which is a stop codon in the universal codon table but is translated into tryptophan in yeast mitochondria (Fox 1979 Proc Natl Acad Sci USA 76: 6534-6538). This was designed to prevent expression of Cas9 in the nucleus after microprojectile DNA transformation. The expression cassette with the optimized Cas9 ORF was synthesized with the minimal promoter with 5' UTR and terminator of the COX2 gene; these regulatory elements were flanked with PstI and HindIII sites, respectively (SEQ ID NO: 121 and SEQ ID NO: 122). The minimal promoter and terminator, which had the length of 71 and 119 bp, respectively (Mireau et al. 2003 Mol Gen Genomics 270:1-8), were chosen with the purpose of suppressing homologous recombination at the sites and avoiding integration into the mitochondrial genome. Several unique restriction sites (XbaI, NotI and NcoI sites) were included at the HindIII end to facilitate cloning of additional elements. One such element was the guide RNA expression cassette. Guide RNAs targeting the COX1 sequences described above were created by fusion of each targeting sequence with the tracrRNA sequence (SEQ ID NO: 123). Each guide RNA expression cassette encoded either one or two guide RNAs, which were directed to the corresponding one or two of the four COX1 target sites.

The guide RNA expression cassette contained the following elements in 5' to 3' orientation: a minimal COX3 promoter (SEQ ID NO: 124); a tRNA gene, tF(GAA) (SEQ ID NO: 125); a single guide RNA directed to a COX1 site; a second tRNA gene, tW(UCA) (SEQ ID NO: 126); and a minimal COX3 terminator element (SEQ ID NO: 127). The constructs with two guide RNAs were created by combining guide RNAs directed to COX1 sites 1 and 2, as well as to sites 3 and 4. When two guide RNA encoding sequences were present, the second one was fused directly after the tW(UCA) sequence and was flanked by a third tRNA gene, tM(CAU) (SEQ ID NO: 128) at the 3' end and before the COX3 terminator. The guide RNA expression cassettes with promoter and terminator elements were synthesized with a NotI site at the 5' end and a NcoI site at the 3' end to allow directional cloning into the pBR322 backbone that carries the Cas9 expression cassette.

For the DNA replacement experiments, the donor DNA carrying the GFP gene was synthesized and cloned into the NcoI site of constructs that encoded two guide RNAs. The nucleotide sequence (SEQ ID NO: 129) encoding GFP was codon optimized for expression in yeast mitochondria as done for Cas9 (see above). Several codons for tryptophan were changed to TGA, assuring GFP expression only in mitochondria. Also, the GFP coding region was designed to be in frame with the COX1 gene after DNA replacement. Both ends of the GFP ORF were fused with the COX1 genomic sequences at the external junction of the Cas9 cleavage sites. HR1-HR4 correspond to four short homology regions used in construction of the Edit Plasmids; they were each immediately adjacent to the corresponding guide RNA target site. The length of the homologous region at each end was chosen to be relatively short to minimize endogenous homologous recombination without Cas9 cleavages, i.e. 144 bp adjacent to the #1 guide RNA site (HR1; SEQ ID NO: 130), 115 bp adjacent to the #2 guide RNA site (HR2; SEQ ID NO: 131), 64 bp adjacent to the #3 guide RNA site (HR3; SEQ ID NO: 132) and 93 bp adjacent to the #4 guide RNA site (HR4; SEQ ID NO: 133). This design should facilitate DNA replacement induced by Cas9 activity and not by general homologous recombination. Additionally, the Edit Plasmids should remain autonomous without integrating into the genome. Furthermore, sequence variations were included at the guide RNA recognition sites within the donor DNA, so that the mitochondrial DNA after replacement would no longer be recognized by the guide RNA/Cas9 complex. This was done to prevent the deletion of the replaced DNA from the gene-edited mitochondrial genome. The variant of the first target site is listed under SEQ ID NO: 134, where 7 of the 20 nucleotides in the guide RNA recognition site have been changed. The variant of the second site was created by deleting 16 nucleotides at the 5' end of the recognition site (SEQ ID NO: 135). The third target site was modified by deleting the last five nucleotides (SEQ ID NO: 136). The fourth target site was modified by deleting 14 nucleotides at the 5' end (SEQ ID NO: 137).

The constructs made for this experiment are presented in Table 1.

TABLE 1

Components of Edit Plasmids for Yeast Mitochondria

| Construct | Expr Cassette 1* | Expr Cassette 2** | Donor DNA |
|---|---|---|---|
| HS1 | Cas9m | tF:sgRNA-3:tW | N/A |
| HS2 | Cas9m | tF:sgRNA-4:tW | N/A |
| HS3 | Cas9m | tF:sgRNA-3:tW:sgRNA-4:tM | N/A |
| HS4 | Cas9m | tF:sgRNA-3:tW:sgRNA-4:tM | HR3:GFPm:HR4 |
| HS5 | Cas9m | tF:sgRNA-3:tW:sgRNA-4:tM | HR3:GFPm:HR4*** |
| HS6 | N/A | tF:sgRNA-2:tW:sgRNA-1:tM | HR1:GFPm:HR2 |
| HS7 | N/A | tF:sgRNA-3:tW:sgRNA-4:tM | HR3:GFPm:HR4 |
| HS8 | Cas9m | tF:sgRNA-2:tW:sgRNA-1:tM | HR1:GFPm:HR2 |
| HS9 | Cas9m | tF:sgRNA-2:tW:sgRNA-1:tM | N/A |
| HS10 | Cas9m | tF:sgRNA-1:tW | N/A |
| HS11 | Cas9m | tF:sgRNA-2:tW | N/A |

*Each Expression Cassette 1 had the COX2 promoter with 5' UTR and the COX2 terminator.
**Each Expression Cassette 2 had the COX3 promoter and the COX3 terminator.
***The Donor DNA is in reverse orientation with respect to the construct HS4.

The constructs created were transformed into yeast lines that lacked mitochondrial DNA (rho°), MCC109rho0 (MATa ade2 ura3 kar1), using the biolistic microprojectile method as described in Bonnefoy and Fox, 2001. The transformation was performed together with pYES2 as a carrier plasmid with URA3 selectable marker, so that URA+ nuclear transformants could be selected first on minimal medium lacking uracil in supplements. To identify mitochondrial transformants, URA+ colonies were assayed for the ability of rescuing a cox3 deletion mutant through a cross with MCC125 (MATa lys2 rho+ cox3-10). The assay was repeated at least twice to obtain clean colonies with Edit Plasmids in the mitochondria. Isolated lines containing Edit Plasmids were then crossed with lines containing the wild-type mitochondrial genome, CUY563 (MATa ura3 ade2 leu2 ade3 rho+) and NB80 (MATa lys2 arg8 ura3 leu2 rho+), to analyze the genome editing effect by Cas9 at the target sites. In nuclear chromosomes subjected to double-strand breaks, one might expect a high frequency of mutations such as small deletions or insertions at the target sites. They are the results of Non-Homologous End-Joining (NHEJ) repair at the site of DNA cleavage triggered by the guide RNA dependent Cas9 activity. In yeast, 90% of the repair of double-strand breaks in chromosomes occurs by homologous recombination (Ricchetti et al. 1999 Nature 402:96-100). In mitochondria, where multiple copies of mitochondrial DNA are present in one organelle, the repair of dsDNA breaks through homologous recombination is expected to be significantly more frequent than in the nucleus. Under this circumstance, the frequency of indel mutations caused by re-ligation of DNA ends is expected to be extremely low in mitochondria. Due to this consideration, we focused on the detection of events caused by repair through homologous recombination, i.e., replacement with artificial donor DNA.

To assay for DNA replacement through Cas9 induced cleavages, the construct HS8 and its control construct HS6 were each transformed into a strain lacking mitochondrial DNA as described above. Each construct carried the donor DNA with GFP as well as two corresponding guide RNA genes (#1 and #2) but HS6 lacked the Cas9 expression cassette. Lines that contained each construct were identified by subsequent screening for their capability of rescuing the cox3 deletion mutant. The isolated mitochondrial transformants then were crossed with strains carrying the wild-type mitochondrial genome, CUY563 and NB80, to observe the effect of Edit Plasmids on the mitochondrial genomic DNA. The DNA replacement events at the cleavage sites then were assayed by PCR amplification of pooled cells two days after the crosses. Primer sets were used wherein one primer was from the mitochondrial genomic region in the vicinity of the cleavage sites and the other primer was from the donor DNA region, selected so that the desired PCR product could only be amplified from a correctly replaced DNA in the mitochondrial genome but not from the wild-type mitochondrial DNA nor from the Edit Plasmid. The following four primer pairs were used: primers C and 12 for the 5' end junction; and for the 3' end junction, primers D and 11, E and 11, and F and 11. Primers C, D, E and F were specific to the genomic region of the COX1 gene (SEQ ID NO: 138, 139, 140 and 141, respectively). Primers 11 and 12 were specific to the GFP gene (SEQ ID NO: 142 and 143, respectively). The PCR amplification was performed as follows: Step 1: 94° C. for 7 min, step 2: 94° C. for 30 sec, step 3: 52° C. for 30 sec, step 4: 60° C. for 1 min 30 sec, step 5: go to step 2 for 39 times, step 6: 60° C. for 10 min. The low temperature for the extension reaction was chosen to accommodate AT-rich genomic sequences. After PCR amplification, we observed the expected size of the DNA fragments from each end of the replaced DNA by using the above four distinct pairs of primers. No corresponding DNA fragments were amplified in the cell samples that were crossed with the line carrying the control construct.

The amplified DNA fragments were sequenced directly. FIG. 1 presents the sequence obtained from PCR amplification of the replaced DNA locus in transformed yeast mitochondrial DNA modified by the Edit Plasmid approach. Underlined sequences at the 5' and 3' ends indicate wild-type mitochondrial genomic sequences that are not present on the Edit Plasmid. Sequences in bold font indicate the short homologous regions present in the donor DNA and adjacent to the corresponding guide RNA target sites. Sequences that have double underlining indicate the modified guide RNA target sites present in the donor DNA; altered nucleotides are shown in bold font. The guide RNA target sites in the replaced DNA have been modified to prevent nuclease activity after integration into the mitochondrial genome. The codon-optimized GFP coding region is presented in italics. Sequences presented in lower case correspond to primers C and F that were used for amplification of the replaced DNA locus. Homologous recombination occurred as expected; i.e., there were no sequence changes either in the replaced DNA or in the surrounding wild-type mitochondrial DNA.

The sequence (SEQ ID NO: 144; FIG. 1) covering the replaced region matched with the construct completely. Also shown in FIG. 1 are sequences at the 5' and 3' ends (shown with underlining) that are wild-type mitochondrial genomic sequences not present on the Edit Plasmid, which are contiguous to the HR regions (shown in bold font) present in the Edit Plasmid. In summary, DNA replacement was observed in yeast mitochondria by use of an Edit Plasmid that encodes a Cas9 expression cassette, a multiple guide RNA expression cassette and a donor DNA template.

Furthermore, single colonies were isolated from the cross between the HS8 line carrying the Edit Plasmid and wild-type strain, NB80. GFP signal was confirmed from a fraction of colonies when viewed through a fluorescence microscope.

In order to show the autonomously replicating nature of the Edit Plasmids in mitochondria, we attempted the rescue of plasmids from the cells after the crosses described above. 1 ml of overnight cell culture after each cross was sampled and subjected to the total DNA isolation. 200 ng of total DNA obtained by use of the Quick-DNA Miniprep Plus Kit (Zymo Research) were digested with ApaI and SphI to cleave pYES2 plasmid DNA in the total DNA fraction; the HS8 plasmid should remain intact as it doesn't possess these restriction sites. After inactivating the restriction enzymes at 65° C. for 20 min, the DNA was used to transform *E. coli* cells. Multiple colonies that grew on LB medium containing carbenicillin were identified. DNA was isolated, subjected to digestion with several restriction enzymes, and the digestion products were separated by gel electrophoresis. A number of plasmids were identified from two independent crosses that showed a digestion pattern identical to the original HS8 construct, demonstrating that rescue of the original Edit Plasmid HS8 was successful. This showed that Edit Plasmids remained as autonomously replicating DNA in the presence of wild-type mitochondrial DNA, not integrated into the organelle genome.

Example 21

Genetic Modification of *Chlamydomonas reinhardtii* Chloroplast DNA by the Edit Plasmid Approach Guide RNA target sites were selected from genic regions of the *Chlamydomonas reinhardtii* chloroplast genome. The reference sequence used was a compete chloroplast genome sequence from NCBI (Accession number: NC_005353 and Version number: NC_005353.1). The targeted gene was psaA. Mutants of this gene previously have been shown to have a photosynthesis-defective phenotype (Redding et al. 1999, J Biol. Chem. 274: 10466-10473). To help design and select guide RNA target sites, a web-based Bioinformatics program was employed—CRISPOR (http://crispor.tefor-.net/, Haeussler et al. 2016 Genome Biology 17:148-159). The following sequences were selected as guide RNA targeting sites for editing of exon 3 in the psaA gene. When the targeting sequence was on the reverse complement of the genic sequence, the term "reverse" is indicated. For each 23 nucleotide target site listed below, the first 20 nucleotides are the targeting sequence present in each corresponding guide RNA and the last 3 nucleotides are the PAM sequence.

1. GGTTTAAACCCTGTTACTGGTGG (SEQ ID NO: 145)

2. CTTCACCTGTAAATGGACCACGG (SEQ ID NO: 146)
   (reverse)

3. TTTACAGGTGAAGGTCACGTTGG (SEQ ID NO: 147)

4. GTAGCTAAATAAGGGTATGGAGG (SEQ ID NO: 148)
   (reverse)

FIG. 2 presents the sequence obtained from PCR amplification of the replaced DNA locus in transformed *Chlamydomonas* plastid DNA modified by the Edit Plasmid approach. Underlined sequences at the 5' and 3' ends indicate wild-type chloroplast genomic sequence that is not present on the Edit Plasmid. Sequences in bold font indicate the short homologous regions present in the donor DNA on the Edit Plasmid. Sequences that are both in bold font and underlined indicate guide RNA target sites present in the replaced DNA. The guide RNA target sites in the donor DNA have been modified to prevent nuclease activity after integration into the plastid genome. Sequences that have double underlining indicate silent mutations at the 3' side of guide RNA sites to preclude re-cleavage by Cas9/sgRNA. The codon-optimized GFP coding region is presented in italics. Homologous recombination occurred as expected; i.e., there were no sequence changes either in the replaced DNA or in the surrounding wild-type plastid DNA.

The Edit Plasmids for *Chlamydomonas* chloroplasts were constructed as follows. Polynucleotides encoding Cas9 and guide RNA were cloned into the vector and were operably linked to appropriate promoters and terminators to allow for expression in chloroplasts. The vector was either pBR322 or pUC19, each of which contained the replication origin of pMB1 which previously was shown to replicate in chloroplasts (Boynton et al. 1988 Science 240: 1534-1538).

The nucleic acid sequence (SEQ ID NO: 149) encoding SpCas9 (SEQ ID NO: 150) was codon-optimized for *Chlamydomonas* chloroplast expression. The optimization was performed using a web-based Codon Usage Database (Nakamura et al. 2000 Nucleic Acids Res. 28: 292). The optimized gene was synthesized by GenScript (Piscataway, NJ). The promoter used for Cas9 gene expression was either the *Chlamydomonas* psaA-exon 1 promoter with its 5' UTR or the *Chlamydomonas* psbD promoter with its 5' UTR (SEQ ID NO: 151 & SEQ ID NO: 152, respectively). The terminator used for Cas9 gene expression was the rbcL 3' UTR (SEQ ID NO: 153).

For expression of sgRNA, a tRNA promoter and its corresponding 3' UTR (SEQ ID NO: 154 and SEQ ID NO: 155, respectively) were derived from the *Chlamydomonas* plastid trnW gene locus. For the proper processing of sgRNA after transcription, the endogenous chloroplast tRNA processing system was utilized as described in Xie et al. 2015 (Proc Natl Acad Sci USA 112: 3570-3575). For example, for expression of one guide RNA, a sgRNA sequence was placed between two tRNAs. The configuration was "tRNA-1-sgRNA-tRNA-2". For expression of two sgRNAs, the configuration was "tRNA-1-sgRNA-1-tRNA-2-sgRNA-2-tRNA-3". The following tRNA sequences from *Chlamydomonas* plastid DNA: trnW (SEQ ID NO: 156), trnK (SEQ ID NO: 157), and trnL (SEQ ID NO: 158) were employed.

A selectable marker expression cassette for the aadA coding region (SEQ ID NO: 159), to provide spectinomycin resistance, was also present on all the Edit Plasmid constructs. The promoter and terminator for the selectable marker expression cassette were the *Chlamydomonas* rbcL promoter with its 5' UTR (SEQ ID NO: 160) and the *Chlamydomonas* psbA 3' UTR (SEQ ID NO: 161), respectively. Plasmids that carried only a Cas9 expression cassette and selectable marker expression cassette were constructed for use as controls.

For DNA replacement experiments, donor DNA was designed which consisted of a GFP coding region surrounded by homologous recombination regions. The GFP coding sequence (SEQ ID NO: 162) was designed to be codon-optimized for *Chlamydomonas* chloroplast gene expression according to the method of Franklin et al. 2002 (Plant J 30: 733-744). For homologous recombination of the donor DNA after double-strand breaks by Cas9/double sgRNAs, we selected homologous regions of 74 or 76 bp each (HR1-HR4; SEQ ID NO: 163-SEQ ID NO: 166) from gRNA target sites in the *Chlamydomonas* chloroplast gene, psaA-Exon 3. The short length (74 or 76 bp) of each homologous sequence was chosen to minimize the occurrence of endogenous homologous recombination without double-strand breaks mediated by Cas9/guide RNA (Dauvillee et al. 2004 Photosynthesis Research 79: 219-224). The configuration of the donor DNA with its components is "$1^{st}$ HR-GFP-$2^{nd}$HR". The GFP sequence was derived from Franklin et al. 2002 (Plant J. 30:733-744). To protect the donor DNA from further cleavage by Cas9 and to facilitate the Genome Sweep process, homologous recombination sequences also contained silent mutations at the target sites that precluded cleavage by Cas9 and guide RNAs. Homologous recombination was designed to give an in-frame fusion of GFP with the psaA gene product. Components in the Edit Plasmids for DNA replacement experiments included donor DNA as well as the Cas9, double sgRNAs and selectable marker expression cassettes described in the previous section. The same vector backbone was used as in the previous section, as well. As negative controls, plasmids lacking the Cas9 expression cassette were used.

Tables 2 and 3 list the components of the constructs described in this section.

TABLE 2

Components of Edit Plasmids for *Chlamydomonas* Chloroplasts

| Construct | Expr Cassette 1* | Expr Cassette 2** | Donor DNA |
|---|---|---|---|
| YP5 | $P_{psaA}$:Cas9co | N/A | N/A |
| YP7 | $P_{psaA}$:Cas9co | 1×-sgRNA-1 | N/A |
| YP8 | $P_{psaA}$:Cas9co | 1×-sgRNA-2 | N/A |
| YP9 | $P_{psaA}$:Cas9co | 1×-sgRNA-3 | N/A |
| YP10 | $P_{psaA}$:Cas9co | 1×-sgRNA-4 | N/A |
| YP11 | $P_{psaA}$:Cas9co | 2×-sgRNA-1 | N/A |
| YP12 | $P_{psaA}$:Cas9co | 2×-sgRNA-2 | N/A |
| YP13 | $P_{psaA}$:Cas9co | 2×-sgRNA-1 | HR1:GFPco:HR2 |
| YP14 | $P_{psaA}$:Cas9co | 2×-sgRNA-2 | HR3:GFPco:HR4 |
| YP6 | $P_{psbD}$:Cas9co | N/A | N/A |
| YP15 | $P_{psbD}$:Cas9co | 1×-sgRNA-1 | N/A |
| YP16 | $P_{psbD}$:Cas9co | 1×-sgRNA-2 | N/A |
| YP17 | $P_{psbD}$:Cas9co | 1×-sgRNA-3 | N/A |
| YP18 | $P_{psbD}$:Cas9co | 1×-sgRNA-4 | N/A |
| YP19 | $P_{psbD}$:Cas9co | 2×-sgRNA-1 | N/A |
| YP20 | $P_{psbD}$:Cas9co | 2×-sgRNA-2 | N/A |
| YP21 | $P_{psbD}$:Cas9co | 2×-sgRNA-1 | HR1:GFPco:HR2 |
| YP22 | $P_{psbD}$:Cas9co | 2×-sgRNA-2 | HR3:GFPco:HR4 |
| YP23 | N/A | 2×-sgRNA-1 | HR1:GFPco:HR2 |
| YP24 | N/A | 2×-sgRNA-2 | HR3:GFPco:HR4 |
| YP25 | $P_{psaA}$:Cas9co | 2×-sgRNA-1 | HR1:GFPco:HR2 |
| YP26 | $P_{psaA}$:Cas9co | 2×-sgRNA-2 | HR3:GFPco:HR4 |
| YP27 | $P_{psbD}$:Cas9co | 2×-sgRNA-1 | HR1:GFPco:HR2 |
| YP28 | $P_{psbD}$:Cas9co | 2×-sgRNA-2 | HR3:GFPco:HR4 |
| YP29 | N/A | 2×-sgRNA-1 | HR1:GFPco:HR2 |
| YP30 | N/A | 2×-sgRNA-2 | HR3:GFPco:HR4 |
| YP31 | $P_{psaA}$:Cas9co | 2×-sgRNA-1 | N/A |
| YP32 | $P_{psaA}$:Cas9co | 2×-sgRNA-2 | N/A |

TABLE 2-continued

Components of Edit Plasmids for *Chlamydomonas* Chloroplasts

| Construct | Expr Cassette 1* | Expr Cassette 2** | Donor DNA |
|---|---|---|---|
| YP33 | $P_{psbD}$:Cas9co | 2x-sgRNA-1 | N/A |
| YP34 | $P_{psbD}$:Cas9co | 2x-sgRNA-2 | N/A |

*Each Expression Cassette 1 used the rbcL terminator.
**Each Expression Cassette 2 encoded either one (1x) or two (2x) guide RNAs.

TABLE 3

Components of Expression Cassette 2 Encoding One or Two Guide RNAs

| Name | Component Detail* |
|---|---|
| 1x-sgRNA-1 | trnW-sgRNA591-trnK |
| 1x-sgRNA-2 | trnW-sgRNA717-trnK |
| 1x-sgRNA-3 | trnW-sgRNA747-trnK |
| 1x-sgRNA-4 | trnW-sgRNA843-trnK |
| 2x-sgRNA-1 | trnW-sgRNA591-trnK-sgRNA717-trnL |
| 2x-sgRNA-2 | trnW-sgRNA747-trnK-sgRNA843-trnL |

*Each Expression Cassette 2 used both the trnW promoter and trnW terminator.

Edit Plasmids were transformed into wild-type *Chlamydomonas* (CC-125) according to the methods of Barrera et al. 2014 (Methods Mol. Biol. 1132: 391-399) and Ramesh et al. 2011 (Methods Mol. Biol. 684: 313-320). Chloroplast transformants were selected using Tris-Acetate-Phosphate (TAP) media supplemented with 100 µg/ml of Spectinomycin.

To assess DNA replacement events, we transformed Edit Plasmid YP13 containing donor DNA into CC-125 (wild-type *Chlamydomonas reinhardtii*) and randomly selected spectinomycin-resistant colonies. Control construct was YP23. Pooled transformed cell lines were used to prepare chloroplast DNAs according to Barrera et al. 2014 (Methods Mol. Biol. 1132: 391-399). Pool size for YP13 was 20 independent colonies and the pool size for YP23 was 16 independent colonies. For PCR amplification of the targeted recombination region, we used primer sets which consisted of a chloroplast genomic region-specific primer and a GFP gene-specific primer. Primer Set 1 (PS1) was designed to amplify the 5' end of GFP integration region while Primer Set 2 (PS2) was designed to amplify the 3' end.

```
1. PS1 FWD Primer
                                   (SEQ ID NO: 167)
GCTGGTTGGTTCCACTACCAC 2. PS1 REV Primer
                                   (SEQ ID NO: 168)
CACCTTCAAATTTTACTTCAGCACGTG 3. PS2 FWD Primer
                                   (SEQ ID NO: 169)
CATACGGTGTACAATGTTTCAGTCG 4. PS2 REV Primer
                                   (SEQ ID NO: 170)
GTGAGAAATAATAGCATCACGGTGAC
```

The primer sets were designed to avoid amplification of wild-type chloroplast genome or of the Edit Plasmid. Using the above primer sets, the expected size of each amplicon is the following: 852 bp for Primer Set 1 and 712 bp for Primer Set 2. After PCR amplification, we successfully obtained amplicons of the expected sizes from two independent pools of *Chlamydomonas* cell lines transformed with YP13. The corresponding DNA fragments were not amplified from YP23, the control construct without the Cas9 expression cassette.

We sequenced the amplified DNA fragments to confirm successful DNA replacement through Cas9 activity. We obtained the sequence encompassing the donor DNA locus in the transformed *Chlamydomonas* chloroplast DNA (see FIG. 2) (SEQ ID NO: 171). The genomic sequence corresponded to the expected sequence from insertion of the donor DNA at the two Cas9 cleavage sites. As seen in FIG. 2, the replaced DNA contained the two modified guide RNA target sites in the psaA gene that were encoded in the donor DNA. Additionally, the 3-nt PAM sequence is no longer present adjacent to each target sequence, corresponding to the exact sequence of the donor DNA. Also shown in FIG. 2 are sequences at the 5' and 3' ends (shown with underlining) that are wild-type chloroplast genomic sequences not present on the Edit Plasmid, which are contiguous to the HR regions (shown in bold font) present in the Edit Plasmid. In summary, DNA replacement was observed in *Chlamydomonas* chloroplasts exactly as designed by use of an Edit Plasmid that encoded a Cas9 expression cassette, a multiple guide RNA expression cassette and a donor DNA template.

Once a chloroplast DNA site is cleaved by Cas9, DNA repair should be recognizable by the presence of any of the following: nucleotide substitution, small insertion or small deletion. We analyzed spectinomycin-resistant colonies transformed with YP11 and YP31 Edit Plasmid constructs for evidence of such DNA repair. We included YP29, the construct without the Cas9 expression cassette, as a control. To enrich for edited events, we utilized the presence of the AvaII recognition sequence (GGWCC where W is either A or T) at one of the Cas9/gRNA cleavage sites (SEQ ID NO: 146, CTTCACCTGTAAATGGACCACGG). First, we extracted DNA from randomly selected *Chlamydomonas* colonies (15 colonies from YP11 transformants, 10 colonies from YP31 transformants, and five colonies from YP29 transformants). We then pooled extracted DNA for Q5® high-fidelity polymerase-based PCR amplification (New England BioLabs) of the genomic region containing the target site (one pool contained DNA from five colonies). We used the following primers: PS1 FWD Primer (SEQ ID NO: 167) and PS2 REV Primer (SEQ ID NO: 170). Amplified DNA products were purified and subjected to AvaII digestion overnight. After gel-electrophoresis, the region corresponding to 700-900 bp of each pool, containing undigested DNA of 795 bp, was cut out of an agarose gel and the DNA was extracted. Extracted DNA was then directly cloned into pMiniT2.0 vector according to a manufacturer's protocol (New England BioLabs, Ipswich, MA). We randomly selected twelve *E. coli* colonies from each pool of YP11 and YP31 transformants and eight colonies from the control YP29 pool and performed PCR amplification using the same primer pair, PS1 FWD Primer and PS2 REV Primer. Aliquots of PCR reactions were digested again with AvaII to further select candidates for DNA repair events. One each from two pools of YP11 constructs, one from one pool of YP31 transformants, four from the other pool of YP31 transformants and three from the YP29 transformants were identified and subjected to Sanger-sequencing to deduce the nucleotide composition of each candidate clone. In addition, we included PCR amplicons of 15 randomly selected colonies from the YP29 control pool for sequencing. Analysis of sequencing results showed that two transformants of YP11 and two of YP31, each from a different pool, had a single nucleotide substitution at the target sites. We observed the following two types of substitution: G to A, resulting in GAACC; and A to G, resulting in GGGCC; relative to the wild-type sequence, GGACC. Each of these two changes were detected in transformants from each construct, YP11 and YP31; however, none of the sequenced clones from the control YP29 transformants showed any change at the target site (i.e., each control transformant retained the AvaII site). In summary, we have shown that four independent nucleotide substitution events have occurred at a guide RNA target site, consistent with cleavage by Cas9 and subsequent DNA repair in the chloroplast.

That which is claimed:

1. A method for altering a genome of a mitochondrion or a plastid, the method comprising:
   (a) introducing into the mitochondrion or the plastid of a cell:
      (i) a polynucleotide encoding at least one guide ribonucleic acid (RNA), wherein the at least one guide RNA directs a polynucleotide guided polypeptide to cleave at least one target sequence present in the genome of the mitochondrion or the plastid;
      (ii) the polynucleotide guided polypeptide, wherein the polynucleotide guided polypeptide, when associated with the at least one guide RNA, cleaves the at least one target sequence; and
      (iii) a replacement deoxyribonucleic acid (DNA) comprising at least two regions of homology to the genome of the mitochondrion or the plastid, wherein each of the at least two regions of homology comprise at least 74 nucleotides; and
   (b) selecting an altered cell comprising an altered mitochondrion genome or an altered plastid genome, wherein the altered mitochondrion genome or the altered plastid genome comprises the replacement DNA.

2. The method of claim 1, wherein the replacement DNA comprises fragments of organellar DNA or a complete organellar DNA from a cultivar, line, sub-species and other species, and is distinct from the genome of the mitochondrion or the plastid.

3. The method of claim 1, wherein the at least one target sequence is not present in the replacement DNA.

4. The method of claim 1, further comprising, after (a) (ii) and prior to (a) (iii), selecting a cell wherein the genome of the mitochondrion or the plastid has been eliminated.

5. The method of claim 1, wherein a polynucleotide encoding the polynucleotide guided polypeptide is introduced into the mitochondrion or the plastid.

6. The method of claim 1, wherein the polynucleotide guided polypeptide is introduced into the mitochondrion or the plastid as a modified polynucleotide guided polypeptide, wherein the modified polynucleotide guided polypeptide comprises the polynucleotide guided polypeptide operably linked to an organelle targeting peptide.

7. The method of claim 6, wherein a polynucleotide encoding the modified polynucleotide guided polypeptide is introduced into the cell.

8. The method of claim 7, wherein the polynucleotide encoding the modified polynucleotide guided polypeptide is stably integrated into a nuclear genome of the cell.

9. The method of claim 1, wherein the polynucleotide encoding the at least one guide RNA encodes a polycistronic RNA, wherein the at least one guide RNA is present on the polycistronic RNA, and wherein the at least one guide RNA is arrayed with multiple tRNA sequences for processing from the polycistronic RNA.

10. The method of claim 1, wherein the cell is selected from the group consisting of a yeast cell, an algal cell, a plant cell, an insect cell, a non-human animal cell, and a mammalian tissue culture cell.

11. The method of claim 10, wherein the cell is the plant cell.

12. The method of claim 11, wherein the replacement DNA comprises a cytoplasmic male sterility (CMS) gene, wherein the altered cell comprises an altered mitochondrion genome, and wherein the altered mitochondrion genome comprises the replacement DNA.

13. The method of claim 11, wherein the plant cell is a rice cell, a wheat cell, or a soybean cell.

14. The method of claim 1, wherein the polynucleotide encoding the at least one guide RNA is stably integrated into the genome of the mitochondrion or the plastid.

15. The method of claim 1, wherein the polynucleotide guided polypeptide is selected from the group consisting of: a Cas9 protein, a MAD2 protein, a MAD7 protein, a CRISPR nuclease, a nuclease domain of a Cas protein, a Cpf1 protein, modified versions thereof, and any combination thereof.

16. The method of claim 1, wherein the method further comprises introducing into the mitochondrion or the plastid a polynucleotide encoding at least one selectable marker selected from the group consisting of: a positive selectable marker, a negative selectable marker, and any combination thereof.

17. The method of claim 16, wherein the polynucleotide encoding the at least one selectable marker is stably integrated into the genome of the mitochondrion or the plastid.

18. The method of claim 16, wherein the at least one selectable marker is not integrated into the genome of the mitochondrion or the plastid.

19. The method of claim 1, wherein each of the at least two regions of homology comprises less than 150 nucleotides.

* * * * *

SEQUENCE LISTING

```
Sequence total quantity: 174
SEQ ID NO: 1                moltype = DNA   length = 4163
FEATURE                     Location/Qualifiers
source                      1..4163
                            mol_type = other DNA
                            organism = synthetic construct
                            note = Synthetic Construct
SEQUENCE: 1
aaaaaagaat ggttctacca agactatata cagctacaag tcgtgctgct ctgtcgaccg   60
acaagaagta ctccattggg ctcgatatcg gcacaaacag cgtcggctgg gccgtcatta  120
cggacgagta caaggtgccg agcaaaaaat tcaaagttct gggcaatacc gatcgccaca  180
gcataaagaa gaacctcatt ggcgccctcc tgttcgactc cggggagacg gccgaagcca  240
cgcggctcaa aagaacagca cggcgcagat atacccgcag aaagaatcgg atctgctacc  300
tgcaggagat ctttagtaat gagatggcta aggtggatga ctctttcttc cataggctgg  360
aggagtcctt tttggtggag gaggataaaa agcacgagcg ccacccaatc tttggcaata  420
tcgtggacga ggtggcgtac catgaaaagt acccaaccat atatcatctg aggaagaagc  480
ttgtagacag tactgataag gctgacttgc ggttgatcta tctcgcgctg gcgcatatga  540
tcaaatttcg gggacacttc ctcatcgagg gggacctgaa cccagacaac agcgatgtcg  600
acaaactctt tatccaactg gttcagactt acaatcagct tttcgaagag aacccgatca  660
acgcatccgg agttgacgcc aaagcaatcc tgagcgctag gctgtccaaa tcccggcggc  720
tcgaaaacct catcgcacag ctccctgggg agaagaagaa cggcctgttt ggtaatctta  780
tcgccctgtc actcggctg accccaact ttaaatctaa cttcgacctg ccgaagatg  840
ccaagcttca actgagcaaa gacacctacg atgatgatct cgacaatctg ctggcccaga  900
tcggcgacca gtacgcagac cttttttgg cggcaaagaa cctgtcagac gccattctgc  960
tgagtgatat tctgcgagtg aacacggaga tcaccaaagc tccgctgagc gctagtatga 1020
tcaagcgcta tgatgagcac caccaagact tgactttgct gaaggccctt gtcagacagc 1080
aactgcctga gaagtacaag gaaattttct tcgatcagtc taaaaatggc tacgccggat 1140
acattgacgg cggagcaagc caggaggaat tttacaaatt tattaagccc atcttggaaa 1200
aaatggacgg caccgaggag ctgctggtaa agcttaacag agaagatctg ttgcgcaaac 1260
agcgcacttt cgacaatgga agcatcccc ccagattca cctgggcgaa ctgcacgcta 1320
tcctcaggcg gcaagaggat ttctacccct ttttgaaaga taacagggaa aagattgaga 1380
aaatcctcac atttcggata ccctactatg taggcccct cgccggggga aattccgat  1440
tcgcgtggat gactcgcaaa tcagaagaga ccatcactcc ctggaacttc gaggaagtcg 1500
tggataaggg ggcctctgcc cagtccttca tcgaaaggat gactaacttt gataaaaatc 1560
tgcctaacga aaaggtgctt cctaaacact ctctgctgta cgagtacttc acagtttata 1620
acgagctcac caaggtcaaa tacgtcacag aagggatgag aaagccagca ttcctgtctg 1680
gagagcagaa gaaagctatc gtggacctcc tcttcaagac gaaccggaaa gttaccgtga 1740
aacagctcaa agaagactat ttcaaaaaga ttgaatgttt cgactctgtt gaaatcagcg 1800
gagtggagga tcgcttcaac gcatccctgg gaacgtatca cgatctcctg aaaatcatta 1860
aagacagaca cttcctggac aatgaggaga acgaggacat tcttgaggac attgtcctca 1920
cccttacgtt gtttgaagat agggagatga ttgaagaacg cttgaaaact tacgctcatc 1980
tcttcgacga caaagtcatg aaacagctca agaggcgccg atatacagga tgggggcggc 2040
tgtcaagaaa actgatcaat gggatccgag acaagcagag tggaaagaca atcctggatt 2100
ttcttaagtc cgatggattt gccaaccgga acttcatgca gttgatccat gatgactctc 2160
tcacctttaa ggaggacatc cagaaagcac aagtttctgg ccaggggac agtcttcacg 2220
agcacatcgc taatcttgca ggtagcccag ctatcaaaaa gggaatactg cagaccgtta 2280
aggtcgtgga tgaactcgtc aaagtaatgg gaaggcataa gcccgagaat atcgttatcg 2340
agatggccg agagaaccaa actacccaga agggacagaa gaacagtagg gaaaggatga 2400
agaggattga agagggtata aaagaactgg ggtcccaaat ccttaaggaa caccccagttg 2460
aaaacaccca gcttcagaat gagaagctct acctgtacta cctgcagaac ggcagggaca 2520
tgtacgtgga tcaggaactg gacatcaatc ggctctccga ctacgacgtg gatcatatcg 2580
tgccccagtc tttttctcaaa gatgattcta ttgataataa agtgttgaca agatccgata 2640
aaaatagagg gaaagtcgat aacgtcccct cagaagaagt tgtcaagaaa atgaaaaatt 2700
attggcggca gctgctgaac gccaaactga tcacacaacg gaagttcgat aatctgacta 2760
aggctgaacg aggtggcctg tctgagttgg ataaagccgg cttcatcaaa aggcagcttg 2820
ttgagacacg ccagatcacc aagcacgtgg cccaaattct cgattcacgc atgaacacca 2880
agtacgatga aaatgacaaa ctgattcgaa aggtgaaagt tattactctg aagtctaagc 2940
tggtctcaga tttcagaaag gactttcagt tttataaggt gagagagatc aacaattacc 3000
accatgcgca tgatgcctac ctgaatgcag tggtaggcac tgcacttatc aaaaaatatc 3060
ccaagcttga atctgaattt gtttacgag actataaagt gtacgatgtt aggaaaatga 3120
tcgcaaagtc tgagcaggaa ataggcaagg ccaccgctaa gtacttcttt tacagcaata 3180
ttatgaattt tttcaagacc gagattacac tggccaatgg agagattcgg aagcgaccac 3240
ttatcgaaac aaacgagaa acaggagaaa tcgtgtggga caagggtagg gatttcgcga 3300
cagtccgaa ggtcctgtcc atgccgcagg tgaacatcgt taaaaagacc gaagtacaga 3360
ccggaggctt ctccaaggaa agtatcctcc cgaaaagaa cagcgacaag ctgatcgcac 3420
gcaaaaaaga ttgggacccc aagaaatacg gcgattcga ttctcctaca gtcgcttaca 3480
gtgtactggt tgtggccaaa gtggagaaag gaagtctaa aaactcaaa agcgtcaagg 3540
aactgctggg catcacaatc atggagcgat caagcttcga aaaaaacccc atcgactttc 3600
tcgaggcgaa aggatataaa gaggtcaaaa agacctcat cattaagctc cccaagtact 3660
ctctctttga gcttgaaaac ggccggaaac gaatgctcgc tagtgcgggc gagctgcaga 3720
aagtaacga gctggcactg ccctctaaat acgttaattt cttgtatctg gccagcactt 3780
atgaaaagct caaagggtct cccgaagata tgagcagaa gcagctgttc gtggaacaac 3840
acaaacacta ccttgatgag atcatcgagc aaataagcga attctccaaa agagtgatcc 3900
tcgccgacgc taacctcgat aaggtgcttt ctgcttacaa taagcacagg gataagccca 3960
tcagggagca ggcagaaaac attatcccact tgtttactct gaccaacttg ggcgcgcctg 4020
cagccttcaa gtacttcgac accaccatag acagaaagcg gtacacctct acaaaggagg 4080
tcctggacgc cacactgatt catcagtcaa ttacgggct ctatgaaaca agaatcgacc 4140
tctctcagct cggtggagac tga                                         4163
```

| SEQ ID NO: 2 | moltype = DNA length = 4145 |
|---|---|
| FEATURE | Location/Qualifiers |
| source | 1..4145 |
| | mol_type = other DNA |
| | organism = synthetic construct |
| | note = Synthetic Construct |

SEQUENCE: 2

```
gatccatgaa aagcttcatt acaaggaaca agacagccat tgacaagaag tactccattg    60
ggctcgatat cggcacaaac agcgtcggct gggccgtcat tacggacgag tacaaggtgc   120
cgagcaaaaa attcaaagtt ctgggcaata ccgatcgcca cagcataaag aagaacctca   180
ttggcgccct cctgttcgac tccggggaga cggccgaagc cacgcggctc aaaagaacag   240
cacggcgcag atatacccgc agaaagaatc ggatctgcta cctgcaggag atctttagta   300
atgagatggc taaggtggat gactcttttc tccataggct ggaggagtcc tttttggtgg   360
aggaggataa aaagcacgag cgccacccaa tctttggcaa tatcgtggac gaggtggcgt   420
accatgaaaa gtacccaacc atatatcatc tgaggaagaa gcttgtagac agtactgata   480
aggctgactt gcggttgatc tatctcgcgc tggcgcatat gatcaaattt cggggacact   540
tcctcatcga ggggacctg aacccagaca acagcgatgt cgacaaactc tttatccaac   600
tggttcagac ttacaatcag cttttcgaag agaacccgat caacgcatcc ggagttgacg   660
ccaaagcaat cctgagcgct aggctgtcca atcccggcg gctcgaaaac ctcatcgcac   720
agctccctgg ggagaagaag aacggcctgt ttggtaatct tatcgccctg tcactcgggc   780
tgaccccaa cttaaatct aacttcgacc tggccgaaga ccaaagctt caactgagca   840
aagacaccta cgatgatgat ctcgacaatc tgctggccca gatcggcgac cagtacgcag   900
accttttttt ggcggcaaag aacctgtcag acgccattct gctgagtgat attctgcgca   960
tgaacacgga gatcaccaaa gctccgctga cgctagtat gatcaagcgc tatgatgagc  1020
accaccaaga cttgactttg ctgaaggccc ttgtcagaca gcaactgcct cgagaagtaca  1080
aggaaatttt cttcgatcag tctaaaaatg gctacgccgg atacattgac ggcggagcaa  1140
gccaggagga attttacaaa tttattaagc ccatcttgga aaaaatggac ggcaccgagg  1200
agctgctggt aaagcttaac agagaagatc tgttgcgcaa acagcgcact tcgacaatg  1260
gaagcatccc ccaccagatt cacctgggcg aactgcacgc tatcctcagg cggcaagagg  1320
atttctaccc cttttttgaaa gataacaggg aaaagattga gaaatcctc acatttcgga  1380
taccctacta tgtaggcccc ctcgcccggg gaaattccag attcgcgtgg atgactcgca  1440
aatcagaaga gaccatcact ccctggaact tcgaggaagt cgtggataag ggggcctctg  1500
cccagtcctt catcgaaagg atgactaact ttgataaaa tctgcctaac gaaaaggtgc  1560
ttcctaaaca ctctctgctg tacgagtact tcacagtta taacgagctc accaaggtca  1620
aatacgtcac agaagggatg agaaagccag cattcctgtc tggagagcag aagaaagcta  1680
tcgtggacct cctcttcaag acgaaccgga agttaccgt gaaacagctc aaagaagact  1740
atttcaaaaa gattgaatgt ttcgactctg ttgaaatcag cggagtggag gatcgcttca  1800
acgcatccct gggaacgtat cacgatctcc tgaaaatcat taaagacaag gacttcctgg  1860
acaatgagga gaacgaggac attcttgagg acattgtcct cacccttacg ttgtttgaag  1920
ataggggagt gattgaagaa cgcttgaaaa cttacgctca tctcttcgac gacaaagtca  1980
tgaaacagct caagaggcgc cgatatacag gatgggggcg gctgtcaaga aaactgatca  2040
atgggatccg agacaagcag agtggaaaga caatcctgga tttttcttaag tccgatggat  2100
ttgccaaccg gaacttcatg cagttgatcc atgatgactc tctcacctttt aaggaggaca  2160
tccagaaagc acaagtttct ggccaggggg acagtcttca cgagcacatc gctaatcttg  2220
caggtagccc agctatcaaa aagggaatac tgcagaccgt taaggtcgtg gatgaactgg  2280
tcaaagtaat gggaaggcat aagcccgaga atatcgttat cgagatgcgc cgagagaacc  2340
aaactaccca gaagggacag aagaacagta gggaaaggat gaagaggatt gaagagggta  2400
taaaagaact ggggtcccaa atccttaagg aacacccagt gaaaacacc agcttcaga  2460
atgagaagct ctacctgtac tacctgcaga acggcaggga catgtacgtg gatcaggaac  2520
tggacatcaa tcggctctcc gactacgacg tggatcatat cgtgccccag tcttttttca  2580
aagatgattc tattgataat aaagtgttga caagatccga taaaaataga gggaagagtg  2640
ataacgtccc ctcagaagaa gttgtcaaga aaatgaaaaa ttattggcgg cagctgctga  2700
acgccaaact gatcacacaa cggaagttcg ataatctgac taaggctgaa cgaggtggcc  2760
tgtctgagtt ggataaagcc ggcttcatca aaaggcagct tgttgagaca cgccagatca  2820
ccaagcacgt ggcccaaatt ctcgattcac gcatgaacac caagtacgat gaaaatgaca  2880
aactgattcg agaggtgaaa gttattactc tgaagtctaa gctggtctca gatttcagaa  2940
aggactttca gttttataag gtgagagaga tcaacaatta ccaccatgcg catgatgcct  3000
acctgaatgc agtggtaggc actgcactta caaaaaata tcccaagctt gaatctgaat  3060
ttgtttacgg agactataaa gtgtacgatg ttaggaaaat gatcgcaaag tctgagcagg  3120
aaataggcaa ggccaccgct aagtacttct tttacagcaa tattatgaat ttttttcaaga  3180
ccgagattac actggccaat ggagagattc ggaagcgacc acttatcgaa acaaacggag  3240
aaacaggaga atcgtgtgg gacaagggta gggatttcgc gacagtccgg aaggtcctgt  3300
ccatgccgca ggtgaacatc gttaaaaaga ccgaggtcca gacaggaggc ttctcgaagg  3360
aaagtatcct cccgaaaagg aacagcgaca gctgatcgc acgcaaaaaa gattgggacc  3420
ccaagaaata cggcggattc gattctccta cagtcgctta cagtgtactg gttgtggcca  3480
aagtggagaa agggaagtct aaaaaactca aagcgtcaa ggaactgctg ggcatcacaa  3540
tcatggagcg atcaagcttc gaaaaaaacc ccatctcttc tcgagggcg aaaggatata  3600
agaggtcaa aaaagacctc atcattaagc ttccccaagta ctctctcttt gagcttgaaa  3660
acggccggaa acgaatgctc gctagtgcgg gcgagctgca gaaaggtaac gagctggcac  3720
tgccctctaa atacgttaat ttcttgtatc tggccagcca ctatgaaaag ctcaaaggtt  3780
ctcccgaaga taatgagcag aagcagctgt tcgtggaaca acacaaacac taccttgatg  3840
agatcatcga gcaaataagc gaattctcca aagagtgat cctcgccgac gctaacctcg  3900
ataaggtgct ttctgcttac aataagcaca gggataaggc caggaggatg ggccctcaag  3960
acattatcca cttgtttact ctgaccaact tgggcgcgcc tgcagccttc aagtacttcg  4020
acaccaccat agacagaaag cggtacacct acaaaggaa ggtcctggac gccacactga  4080
ttcatcagtc aattacgggg ctctatgaaa caagaatcga cctctctcag ctcggtggag  4140
actga                                                              4145
```

-continued

| | |
|---|---|
| SEQ ID NO: 3 | moltype = DNA   length = 342 |
| FEATURE | Location/Qualifiers |
| source | 1..342 |
| | mol_type = other DNA |
| | organism = synthetic construct |
| | note = Synthetic Construct |
| misc_difference | 1 |
| | note = misc_feature - n is a, c, g, or t |
| misc_difference | 2 |
| | note = misc_feature - n is a, c, g, or t |
| misc_difference | 3 |
| | note = misc_feature - n is a, c, g, or t |
| misc_difference | 4 |
| | note = misc_feature - n is a, c, g, or t |
| misc_difference | 5 |
| | note = misc_feature - n is a, c, g, or t |
| misc_difference | 6 |
| | note = misc_feature - n is a, c, g, or t |
| misc_difference | 7 |
| | note = misc_feature - n is a, c, g, or t |
| misc_difference | 8 |
| | note = misc_feature - n is a, c, g, or t |
| misc_difference | 9 |
| | note = misc_feature - n is a, c, g, or t |
| misc_difference | 10 |
| | note = misc_feature - n is a, c, g, or t |
| misc_difference | 11 |
| | note = misc_feature - n is a, c, g, or t |
| misc_difference | 12 |
| | note = misc_feature - n is a, c, g, or t |
| misc_difference | 13 |
| | note = misc_feature - n is a, c, g, or t |
| misc_difference | 14 |
| | note = misc_feature - n is a, c, g, or t |
| misc_difference | 15 |
| | note = misc_feature - n is a, c, g, or t |
| misc_difference | 16 |
| | note = misc_feature - n is a, c, g, or t |
| misc_difference | 17 |
| | note = misc_feature - n is a, c, g, or t |
| misc_difference | 18 |
| | note = misc_feature - n is a, c, g, or t |
| misc_difference | 19 |
| | note = misc_feature - n is a, c, g, or t |
| misc_difference | 20 |
| | note = misc_feature - n is a, c, g, or t |

```
SEQUENCE: 3
nnnnnnnnnn nnnnnnnnnn gttttagagc tagaaatagc aagttaaaat aaggctagtc    60
cgttatcaac ttgaaaaagt ggcaccgagt cggtggtgcg ccttgttggc gcaatcggta   120
gcgcgtatga ctcttaatca taaggttagg ggttcgagcc cccatcaggg ctccattctt   180
tttttttta aaacacgatg acataaattt cctttgtatg aaccgtaccc ttaataataa   240
aaggaaaaat catgctttag gtataagatt ttctgttata ttaaaattta gtatttattt   300
ttattatgct attattttt tcggtctcaa atgttactta gt                      342
```

| | |
|---|---|
| SEQ ID NO: 4 | moltype = DNA   length = 343 |
| FEATURE | Location/Qualifiers |
| source | 1..343 |
| | mol_type = other DNA |
| | organism = synthetic construct |
| | note = Synthetic Construct |
| misc_difference | 1 |
| | note = misc_feature - n is a, c, g, or t |
| misc_difference | 2 |
| | note = misc_feature - n is a, c, g, or t |
| misc_difference | 3 |
| | note = misc_feature - n is a, c, g, or t |
| misc_difference | 4 |
| | note = misc_feature - n is a, c, g, or t |
| misc_difference | 5 |
| | note = misc_feature - n is a, c, g, or t |
| misc_difference | 6 |
| | note = misc_feature - n is a, c, g, or t |
| misc_difference | 7 |
| | note = misc_feature - n is a, c, g, or t |
| misc_difference | 8 |
| | note = misc_feature - n is a, c, g, or t |
| misc_difference | 9 |
| | note = misc_feature - n is a, c, g, or t |
| misc_difference | 10 |

|                  |                                                    |
|------------------|----------------------------------------------------|
|                  | note = misc_feature - n is a, c, g, or t           |
| misc_difference  | 11                                                 |
|                  | note = misc_feature - n is a, c, g, or t           |
| misc_difference  | 12                                                 |
|                  | note = misc_feature - n is a, c, g, or t           |
| misc_difference  | 13                                                 |
|                  | note = misc_feature - n is a, c, g, or t           |
| misc_difference  | 14                                                 |
|                  | note = misc_feature - n is a, c, g, or t           |
| misc_difference  | 15                                                 |
|                  | note = misc_feature - n is a, c, g, or t           |
| misc_difference  | 16                                                 |
|                  | note = misc_feature - n is a, c, g, or t           |
| misc_difference  | 17                                                 |
|                  | note = misc_feature - n is a, c, g, or t           |
| misc_difference  | 18                                                 |
|                  | note = misc_feature - n is a, c, g, or t           |
| misc_difference  | 19                                                 |
|                  | note = misc_feature - n is a, c, g, or t           |
| misc_difference  | 20                                                 |
|                  | note = misc_feature - n is a, c, g, or t           |

```
SEQUENCE: 4
nnnnnnnnnn nnnnnnnnnn gttttagagc tagaaatagc aagttaaaat aaggctagtc   60
cgttatcaac ttgaaaaagt ggcaccgagt cggtggtgcg ccttgttagc tcagttggta  120
gagcgttcgg ctcttaaccg aaatgtcagg ggttcgagcc ccctatgagg cgccatttct  180
ttttttttt aaaacacgat gacataaatt tcctttgtat gaaccgtacc cttaataata  240
aaaggaaaaa tcatgcttta ggtataagat tttctgttat attaaaattt agtatttatt  300
tttattatgc tattatttt ttcggtctca aatgttactt agt                     343
```

|                  |                                                    |
|------------------|----------------------------------------------------|
| SEQ ID NO: 5     | moltype = DNA   length = 342                       |
| FEATURE          | Location/Qualifiers                                |
| source           | 1..342                                             |
|                  | mol_type = other DNA                               |
|                  | organism = synthetic construct                     |
|                  | note = Synthetic Construct                         |
| misc_difference  | 1                                                  |
|                  | note = misc_feature - n is a, c, g, or t           |
| misc_difference  | 2                                                  |
|                  | note = misc_feature - n is a, c, g, or t           |
| misc_difference  | 3                                                  |
|                  | note = misc_feature - n is a, c, g, or t           |
| misc_difference  | 4                                                  |
|                  | note = misc_feature - n is a, c, g, or t           |
| misc_difference  | 5                                                  |
|                  | note = misc_feature - n is a, c, g, or t           |
| misc_difference  | 6                                                  |
|                  | note = misc_feature - n is a, c, g, or t           |
| misc_difference  | 7                                                  |
|                  | note = misc_feature - n is a, c, g, or t           |
| misc_difference  | 8                                                  |
|                  | note = misc_feature - n is a, c, g, or t           |
| misc_difference  | 9                                                  |
|                  | note = misc_feature - n is a, c, g, or t           |
| misc_difference  | 10                                                 |
|                  | note = misc_feature - n is a, c, g, or t           |
| misc_difference  | 11                                                 |
|                  | note = misc_feature - n is a, c, g, or t           |
| misc_difference  | 12                                                 |
|                  | note = misc_feature - n is a, c, g, or t           |
| misc_difference  | 13                                                 |
|                  | note = misc_feature - n is a, c, g, or t           |
| misc_difference  | 14                                                 |
|                  | note = misc_feature - n is a, c, g, or t           |
| misc_difference  | 15                                                 |
|                  | note = misc_feature - n is a, c, g, or t           |
| misc_difference  | 16                                                 |
|                  | note = misc_feature - n is a, c, g, or t           |
| misc_difference  | 17                                                 |
|                  | note = misc_feature - n is a, c, g, or t           |
| misc_difference  | 18                                                 |
|                  | note = misc_feature - n is a, c, g, or t           |
| misc_difference  | 19                                                 |
|                  | note = misc_feature - n is a, c, g, or t           |
| misc_difference  | 20                                                 |
|                  | note = misc_feature - n is a, c, g, or t           |

```
SEQUENCE: 5
nnnnnnnnnn nnnnnnnnnn gttttagagc tagaaatagc aagttaaaat aaggctagtc   60
cgttatcaac ttgaaaaagt ggcaccgagt cggtggtgct ccttgttggc gcaatcggta  120
gcgcgtatga ctcttaatca taaggttagg ggttcgagcc cccatcaggg ctccattctt  180
```

```
tttttttta   aaacacgatg   acataaattt   cctttgtatg   aaccgtaccc   ttaataataa    240
aaggaaaaat  catgctttag   gtataagatt   ttctgttata   ttaaaattta   gtatttattt    300
ttattatgct  attattttt    tcggtctcaa   atgttactta   gt                        342
```

| | |
|---|---|
| SEQ ID NO: 6 | moltype = DNA   length = 343 |
| FEATURE | Location/Qualifiers |
| source | 1..343 |
| | mol_type = other DNA |
| | organism = synthetic construct |
| | note = Synthetic Construct |
| misc_difference | 1 |
| | note = misc_feature - n is a, c, g, or t |
| misc_difference | 2 |
| | note = misc_feature - n is a, c, g, or t |
| misc_difference | 3 |
| | note = misc_feature - n is a, c, g, or t |
| misc_difference | 4 |
| | note = misc_feature - n is a, c, g, or t |
| misc_difference | 5 |
| | note = misc_feature - n is a, c, g, or t |
| misc_difference | 6 |
| | note = misc_feature - n is a, c, g, or t |
| misc_difference | 7 |
| | note = misc_feature - n is a, c, g, or t |
| misc_difference | 8 |
| | note = misc_feature - n is a, c, g, or t |
| misc_difference | 9 |
| | note = misc_feature - n is a, c, g, or t |
| misc_difference | 10 |
| | note = misc_feature - n is a, c, g, or t |
| misc_difference | 11 |
| | note = misc_feature - n is a, c, g, or t |
| misc_difference | 12 |
| | note = misc_feature - n is a, c, g, or t |
| misc_difference | 13 |
| | note = misc_feature - n is a, c, g, or t |
| misc_difference | 14 |
| | note = misc_feature - n is a, c, g, or t |
| misc_difference | 15 |
| | note = misc_feature - n is a, c, g, or t |
| misc_difference | 16 |
| | note = misc_feature - n is a, c, g, or t |
| misc_difference | 17 |
| | note = misc_feature - n is a, c, g, or t |
| misc_difference | 18 |
| | note = misc_feature - n is a, c, g, or t |
| misc_difference | 19 |
| | note = misc_feature - n is a, c, g, or t |
| misc_difference | 20 |
| | note = misc_feature - n is a, c, g, or t |

```
SEQUENCE: 6
nnnnnnnnnn  nnnnnnnnnn   gttttagagc   tagaaatagc   aagttaaaat   aaggctagtc    60
cgttatcaac  ttgaaaaagt   ggcaccgagt   cggtggtgct   ccttgttagc   tcagttgta    120
gagcgttcgg  ctcttaaccg   aaatgtcagg   ggttcgagcc   ccctatgagg   cgccattcct    180
tttttttt    aaaacacgat   gacataaatt   tcctttgtta   tgaaccgtacc  cttaataata    240
aaaggaaaaa  tcatgcttta   ggtataagat   tttctgttat   attaaaattt   agtatttatt    300
tttattatgc  tattattttt   ttcggtctca   aatgttactt   agt                       343
```

| | |
|---|---|
| SEQ ID NO: 7 | moltype = DNA   length = 358 |
| FEATURE | Location/Qualifiers |
| source | 1..358 |
| | mol_type = other DNA |
| | organism = synthetic construct |
| | note = Synthetic Construct |
| misc_difference | 39 |
| | note = misc_feature - n is a, c, g, or t |
| misc_difference | 40 |
| | note = misc_feature - n is a, c, g, or t |
| misc_difference | 41 |
| | note = misc_feature - n is a, c, g, or t |
| misc_difference | 42 |
| | note = misc_feature - n is a, c, g, or t |
| misc_difference | 43 |
| | note = misc_feature - n is a, c, g, or t |
| misc_difference | 44 |
| | note = misc_feature - n is a, c, g, or t |
| misc_difference | 45 |
| | note = misc_feature - n is a, c, g, or t |
| misc_difference | 46 |

|                  |                                                      |
|------------------|------------------------------------------------------|
|                  | note = misc_feature - n is a, c, g, or t             |
| misc_difference  | 47                                                   |
|                  | note = misc_feature - n is a, c, g, or t             |
| misc_difference  | 48                                                   |
|                  | note = misc_feature - n is a, c, g, or t             |
| misc_difference  | 49                                                   |
|                  | note = misc_feature - n is a, c, g, or t             |
| misc_difference  | 50                                                   |
|                  | note = misc_feature - n is a, c, g, or t             |
| misc_difference  | 51                                                   |
|                  | note = misc_feature - n is a, c, g, or t             |
| misc_difference  | 52                                                   |
|                  | note = misc_feature - n is a, c, g, or t             |
| misc_difference  | 53                                                   |
|                  | note = misc_feature - n is a, c, g, or t             |
| misc_difference  | 54                                                   |
|                  | note = misc_feature - n is a, c, g, or t             |
| misc_difference  | 55                                                   |
|                  | note = misc_feature - n is a, c, g, or t             |
| misc_difference  | 56                                                   |
|                  | note = misc_feature - n is a, c, g, or t             |
| misc_difference  | 57                                                   |
|                  | note = misc_feature - n is a, c, g, or t             |
| misc_difference  | 58                                                   |
|                  | note = misc_feature - n is a, c, g, or t             |
| misc_difference  | 138                                                  |
|                  | note = misc_feature - n is a, c, g, or t             |
| misc_difference  | 139                                                  |
|                  | note = misc_feature - n is a, c, g, or t             |
| misc_difference  | 140                                                  |
|                  | note = misc_feature - n is a, c, g, or t             |

SEQUENCE: 7

```
gccttgttag ctcagttggt agagcgttcg gctcttaann nnnnnnnnnn nnnnnnnngt   60
tttagagcta gaaatagcaa gttaaaataa ggctagtccg ttatcaactt gaaaaagtgg  120
caccgagtcg gtggtgcnnn ttaagcaagg ataccgaaat gtcaggggtt cgagccccct  180
atgaggatcc attcttttt tttttaaaac acgatgacat aaatttcctt tgtatgaacc  240
gtacccttaa taataaaagg aaaaatcatg cttaggtat aagattttct gttatattaa  300
aatttagtat ttattttat tatgctatta tttttttcgg tctcaaatgt tacttagt    358
```

| SEQ ID NO: 8    | moltype = DNA   length = 358             |
|-----------------|------------------------------------------|
| FEATURE         | Location/Qualifiers                      |
| source          | 1..358                                   |
|                 | mol_type = other DNA                     |
|                 | organism = synthetic construct           |
|                 | note = Synthetic Construct               |
| misc_difference | 37                                       |
|                 | note = misc_feature - n is a, c, g, or t |
| misc_difference | 38                                       |
|                 | note = misc_feature - n is a, c, g, or t |
| misc_difference | 39                                       |
|                 | note = misc_feature - n is a, c, g, or t |
| misc_difference | 40                                       |
|                 | note = misc_feature - n is a, c, g, or t |
| misc_difference | 41                                       |
|                 | note = misc_feature - n is a, c, g, or t |
| misc_difference | 42                                       |
|                 | note = misc_feature - n is a, c, g, or t |
| misc_difference | 43                                       |
|                 | note = misc_feature - n is a, c, g, or t |
| misc_difference | 44                                       |
|                 | note = misc_feature - n is a, c, g, or t |
| misc_difference | 45                                       |
|                 | note = misc_feature - n is a, c, g, or t |
| misc_difference | 46                                       |
|                 | note = misc_feature - n is a, c, g, or t |
| misc_difference | 47                                       |
|                 | note = misc_feature - n is a, c, g, or t |
| misc_difference | 48                                       |
|                 | note = misc_feature - n is a, c, g, or t |
| misc_difference | 49                                       |
|                 | note = misc_feature - n is a, c, g, or t |
| misc_difference | 50                                       |
|                 | note = misc_feature - n is a, c, g, or t |
| misc_difference | 51                                       |
|                 | note = misc_feature - n is a, c, g, or t |
| misc_difference | 52                                       |
|                 | note = misc_feature - n is a, c, g, or t |
| misc_difference | 53                                       |
|                 | note = misc_feature - n is a, c, g, or t |

| | | |
|---|---|---|
| misc_difference | 54 | |
| | note = misc_feature - n is a, c, g, or t | |
| misc_difference | 55 | |
| | note = misc_feature - n is a, c, g, or t | |
| misc_difference | 56 | |
| | note = misc_feature - n is a, c, g, or t | |
| misc_difference | 136 | |
| | note = misc_feature - n is a, c, g, or t | |
| misc_difference | 137 | |
| | note = misc_feature - n is a, c, g, or t | |
| misc_difference | 138 | |
| | note = misc_feature - n is a, c, g, or t | |

SEQUENCE: 8
```
gccttgttgg cgcaatcggt agcgcgtatg actcttnnnn nnnnnnnnnn nnnnngttt    60
tagagctaga aatagcaagt taaaataagg ctagtccgtt atcaacttga aaaagtggca  120
ccgagtcggt ggtgcnnntt aagcaaggat aaatcataag gttagggtt cgagcccca   180
tcagggctcc attcttttttt tttttaaaac acgatgacat aaatttcctt tgtatgaacc  240
gtaccttaa taataaaagg aaaaatcatg ctttaggtat aagattttct gttatattaa   300
aatttagtat ttatttttat tatgctatta ttttttcgg tctcaaatgt tacttagt     358
```

| | | |
|---|---|---|
| SEQ ID NO: 9 | moltype = DNA  length = 293 | |
| FEATURE | Location/Qualifiers | |
| source | 1..293 | |
| | mol_type = other DNA | |
| | organism = synthetic construct | |
| | note = Synthetic Construct | |
| misc_difference | 1 | |
| | note = misc_feature - n is a, c, g, or t | |
| misc_difference | 2 | |
| | note = misc_feature - n is a, c, g, or t | |
| misc_difference | 3 | |
| | note = misc_feature - n is a, c, g, or t | |
| misc_difference | 4 | |
| | note = misc_feature - n is a, c, g, or t | |
| misc_difference | 5 | |
| | note = misc_feature - n is a, c, g, or t | |
| misc_difference | 6 | |
| | note = misc_feature - n is a, c, g, or t | |
| misc_difference | 7 | |
| | note = misc_feature - n is a, c, g, or t | |
| misc_difference | 8 | |
| | note = misc_feature - n is a, c, g, or t | |
| misc_difference | 9 | |
| | note = misc_feature - n is a, c, g, or t | |
| misc_difference | 10 | |
| | note = misc_feature - n is a, c, g, or t | |
| misc_difference | 11 | |
| | note = misc_feature - n is a, c, g, or t | |
| misc_difference | 12 | |
| | note = misc_feature - n is a, c, g, or t | |
| misc_difference | 13 | |
| | note = misc_feature - n is a, c, g, or t | |
| misc_difference | 14 | |
| | note = misc_feature - n is a, c, g, or t | |
| misc_difference | 15 | |
| | note = misc_feature - n is a, c, g, or t | |
| misc_difference | 16 | |
| | note = misc_feature - n is a, c, g, or t | |
| misc_difference | 17 | |
| | note = misc_feature - n is a, c, g, or t | |
| misc_difference | 18 | |
| | note = misc_feature - n is a, c, g, or t | |
| misc_difference | 19 | |
| | note = misc_feature - n is a, c, g, or t | |
| misc_difference | 20 | |
| | note = misc_feature - n is a, c, g, or t | |

SEQUENCE: 9
```
nnnnnnnnnn nnnnnnnnnn gttttagagc tagaaatagc aagttaaaat aaggctagtc    60
cgttatcaac ttgaaaaagt ggcaccgagt cggtggtgcg gggttcgagc ccccatcagg  120
gctccattct ttttttttt aaaacacgat gacataaatt tccttgtat gaaccgtacc    180
cttaataata aaggaaaaa tcatgcttta ggtataagat tttctgttat attaaaattt   240
agtatttatt tttattatgc tattattttt ttcggtctca aatgttactt agt         293
```

| | | |
|---|---|---|
| SEQ ID NO: 10 | moltype = DNA  length = 76 | |
| FEATURE | Location/Qualifiers | |
| source | 1..76 | |
| | mol_type = other DNA | |
| | organism = synthetic construct | |
| | note = Synthetic Construct | |

```
SEQUENCE: 10
gccttgttgg cgcaatcggt agcgcgtatg actcttaatc ataattcttt ttttttttaa    60
aacacgatga cataaa                                                    76

SEQ ID NO: 11           moltype = DNA  length = 136
FEATURE                 Location/Qualifiers
source                  1..136
                        mol_type = other DNA
                        organism = synthetic construct
                        note = Synthetic Construct
misc_difference         18
                        note = misc_feature - n is a, c, g, or t
misc_difference         19
                        note = misc_feature - n is a, c, g, or t
misc_difference         20
                        note = misc_feature - n is a, c, g, or t
misc_difference         21
                        note = misc_feature - n is a, c, g, or t
misc_difference         22
                        note = misc_feature - n is a, c, g, or t
misc_difference         23
                        note = misc_feature - n is a, c, g, or t
misc_difference         24
                        note = misc_feature - n is a, c, g, or t
misc_difference         25
                        note = misc_feature - n is a, c, g, or t
misc_difference         26
                        note = misc_feature - n is a, c, g, or t
misc_difference         27
                        note = misc_feature - n is a, c, g, or t
misc_difference         28
                        note = misc_feature - n is a, c, g, or t
misc_difference         29
                        note = misc_feature - n is a, c, g, or t
misc_difference         30
                        note = misc_feature - n is a, c, g, or t
misc_difference         31
                        note = misc_feature - n is a, c, g, or t
misc_difference         32
                        note = misc_feature - n is a, c, g, or t
misc_difference         33
                        note = misc_feature - n is a, c, g, or t
misc_difference         34
                        note = misc_feature - n is a, c, g, or t
misc_difference         35
                        note = misc_feature - n is a, c, g, or t
misc_difference         36
                        note = misc_feature - n is a, c, g, or t
misc_difference         37
                        note = misc_feature - n is a, c, g, or t
SEQUENCE: 11
gcgcaatcgg tagcgcannn nnnnnnnnnn nnnnnnngtt ttagagctag aaatagcaag    60
ttaaaataag gctagtccgt tatcaacttg aaaaagtggc accgagtcgg tggtgcgagc   120
ccctacagg gctctt                                                    136

SEQ ID NO: 12           moltype = DNA  length = 116
FEATURE                 Location/Qualifiers
source                  1..116
                        mol_type = other DNA
                        organism = synthetic construct
                        note = Synthetic Construct
misc_difference         18
                        note = misc_feature - n is a, c, g, or t
misc_difference         19
                        note = misc_feature - n is a, c, g, or t
misc_difference         20
                        note = misc_feature - n is a, c, g, or t
misc_difference         21
                        note = misc_feature - n is a, c, g, or t
misc_difference         22
                        note = misc_feature - n is a, c, g, or t
misc_difference         23
                        note = misc_feature - n is a, c, g, or t
misc_difference         24
                        note = misc_feature - n is a, c, g, or t
misc_difference         25
                        note = misc_feature - n is a, c, g, or t
misc_difference         26
                        note = misc_feature - n is a, c, g, or t
```

| | |
|---|---|
| misc_difference | 27 |
| | note = misc_feature - n is a, c, g, or t |
| misc_difference | 28 |
| | note = misc_feature - n is a, c, g, or t |
| misc_difference | 29 |
| | note = misc_feature - n is a, c, g, or t |
| misc_difference | 30 |
| | note = misc_feature - n is a, c, g, or t |
| misc_difference | 31 |
| | note = misc_feature - n is a, c, g, or t |
| misc_difference | 32 |
| | note = misc_feature - n is a, c, g, or t |
| misc_difference | 33 |
| | note = misc_feature - n is a, c, g, or t |
| misc_difference | 34 |
| | note = misc_feature - n is a, c, g, or t |
| misc_difference | 35 |
| | note = misc_feature - n is a, c, g, or t |
| misc_difference | 36 |
| | note = misc_feature - n is a, c, g, or t |
| misc_difference | 37 |
| | note = misc_feature - n is a, c, g, or t |

SEQUENCE: 12
gcgcaatcgg tagcgcannn nnnnnnnnnn nnnnnnngtt ttagagctag aaatagcaag 60
ttaaataag gctagtccgt tatcaacttg aaaaagtggc accgagtcgg tggtgc 116

| | |
|---|---|
| SEQ ID NO: 13 | moltype = DNA length = 118 |
| FEATURE | Location/Qualifiers |
| source | 1..118 |
| | mol_type = other DNA |
| | organism = synthetic construct |
| | note = Synthetic Construct |
| misc_difference | 1 |
| | note = misc_feature - n is a, c, g, or t |
| misc_difference | 2 |
| | note = misc_feature - n is a, c, g, or t |
| misc_difference | 3 |
| | note = misc_feature - n is a, c, g, or t |
| misc_difference | 4 |
| | note = misc_feature - n is a, c, g, or t |
| misc_difference | 5 |
| | note = misc_feature - n is a, c, g, or t |
| misc_difference | 6 |
| | note = misc_feature - n is a, c, g, or t |
| misc_difference | 7 |
| | note = misc_feature - n is a, c, g, or t |
| misc_difference | 8 |
| | note = misc_feature - n is a, c, g, or t |
| misc_difference | 9 |
| | note = misc_feature - n is a, c, g, or t |
| misc_difference | 10 |
| | note = misc_feature - n is a, c, g, or t |
| misc_difference | 11 |
| | note = misc_feature - n is a, c, g, or t |
| misc_difference | 12 |
| | note = misc_feature - n is a, c, g, or t |
| misc_difference | 13 |
| | note = misc_feature - n is a, c, g, or t |
| misc_difference | 14 |
| | note = misc_feature - n is a, c, g, or t |
| misc_difference | 15 |
| | note = misc_feature - n is a, c, g, or t |
| misc_difference | 16 |
| | note = misc_feature - n is a, c, g, or t |
| misc_difference | 17 |
| | note = misc_feature - n is a, c, g, or t |
| misc_difference | 18 |
| | note = misc_feature - n is a, c, g, or t |
| misc_difference | 19 |
| | note = misc_feature - n is a, c, g, or t |
| misc_difference | 20 |
| | note = misc_feature - n is a, c, g, or t |

SEQUENCE: 13
nnnnnnnnnn nnnnnnnnnn gttttagagc tagaaatagc aagttaaaat aaggctagtc 60
cgttatcaac ttgaaaaagt ggcaccgagt cggtggtgcg agccccctac agggctct 118

| | |
|---|---|
| SEQ ID NO: 14 | moltype = DNA length = 20 |
| FEATURE | Location/Qualifiers |
| source | 1..20 |

```
                        mol_type = unassigned DNA
                        organism = Saccharomyces cerevisiae
SEQUENCE: 14
actgatagaa gtgtagtaag                                                  20

SEQ ID NO: 15           moltype = DNA  length = 20
FEATURE                 Location/Qualifiers
source                  1..20
                        mol_type = unassigned DNA
                        organism = Saccharomyces cerevisiae
SEQUENCE: 15
atgattattg caattccaac                                                  20

SEQ ID NO: 16           moltype = DNA  length = 20
FEATURE                 Location/Qualifiers
source                  1..20
                        mol_type = unassigned DNA
                        organism = Saccharomyces cerevisiae
SEQUENCE: 16
attccacgat acttactacg                                                  20

SEQ ID NO: 17           moltype = DNA  length = 20
FEATURE                 Location/Qualifiers
source                  1..20
                        mol_type = unassigned DNA
                        organism = Saccharomyces cerevisiae
SEQUENCE: 17
tcagcaacac caaatcaaga                                                  20

SEQ ID NO: 18           moltype = DNA  length = 79
FEATURE                 Location/Qualifiers
source                  1..79
                        mol_type = other DNA
                        organism = synthetic construct
                        note = Synthetic Construct
SEQUENCE: 18
gttttagagc tagaaatagc aagttaaaat aaggctagtc cgttatcaac ttgaaaaagt      60
ggcaccgagt cggtggtgc                                                   79

SEQ ID NO: 19           moltype = DNA  length = 269
FEATURE                 Location/Qualifiers
source                  1..269
                        mol_type = unassigned DNA
                        organism = Saccharomyces cerevisiae
SEQUENCE: 19
tctttgaaaa gataatgtat gattatgctt tcactcatat ttatacagaa acttgatgtt      60
ttctttcgag tatatacaag gtgattacat gtacgtttga agtacaactc tagattttgt     120
agtgccctct tgggctagcg gtaaaggtgc gcatttttc acaccctaca atgttctgtt      180
caaaagattt tggtcaaacg ctgtagaagt gaaagttggt gcgcatgttt cggcgttcga     240
aacttctccg cagtgaaaga taaatgatc                                       269

SEQ ID NO: 20           moltype = DNA  length = 20
FEATURE                 Location/Qualifiers
source                  1..20
                        mol_type = unassigned DNA
                        organism = Saccharomyces cerevisiae
SEQUENCE: 20
tttttttgtt ttttatgtct                                                  20

SEQ ID NO: 21           moltype = DNA  length = 23
FEATURE                 Location/Qualifiers
source                  1..23
                        mol_type = unassigned DNA
                        organism = Saccharomyces cerevisiae
SEQUENCE: 21
actaatcact catcaggcgt tga                                              23

SEQ ID NO: 22           moltype = DNA  length = 21
FEATURE                 Location/Qualifiers
source                  1..21
                        mol_type = unassigned DNA
                        organism = Saccharomyces cerevisiae
SEQUENCE: 22
caatggcatc cccttggacg c                                                21

SEQ ID NO: 23           moltype = DNA  length = 20
FEATURE                 Location/Qualifiers
source                  1..20
                        mol_type = unassigned DNA
```

|                    | organism = Saccharomyces cerevisiae |      |
|--------------------|--------------------------------------|------|
| SEQUENCE: 23       |                                      |      |
| agttaccgta ggggaacctg |                                   | 20   |

| SEQ ID NO: 24 | moltype = DNA  length = 4107 |
|---------------|------------------------------|
| FEATURE       | Location/Qualifiers          |
| source        | 1..4107                      |
|               | mol_type = other DNA         |
|               | organism = synthetic construct |
|               | note = Synthetic Construct   |

SEQUENCE: 24

```
atggacaaga agtactctat tggtttagat atcggtacaa acagtgtcgg ttgggctgtc     60
attactgacg aatacaaggt gcctagtaaa aaattcaaag ttttaggtaa tactgatcgt    120
cacagtataa agaagaactt aattggtgct ttattattcg actctggtga aactgctgaa    180
gctactcgtt taaaaagaac agcacgtcgt agatatactc gtagaaagaa tcgtatctgc    240
tacttacagg aaatctttag taatgaaatg gctaaggtgg atgactcttt cttccataga    300
ttagaagaat cttttttggt ggaagaagat aaaaagcacg aacgtcaccc aatctttggt    360
aatatcgtgg acgaagtggc ttaccatgaa aagtacccaa ctatatatca tttaagaaag    420
aagttagtag acagtactga taaggctgac ttgcgtttga tctatttagc tttagctcat    480
atgatcaaat ttcgtggaca cttcttaatc gaaggtgact taaacccaga caacagtgat    540
gtcgacaaat tatttatcca attagttcag acttacaatc agttattcga agaaaaccct    600
atcaacgcat ctggagttga cgctaaagca atcttaagtg ctagattatc taaatctcgt    660
cgtttagaaa acttaatcgc acagttacct ggtgaaaaga gaacggtttt atttggtaat    720
ttaatcgctt tatcattagg tttaactcct aactttaaat ctaacttcga cttagctgaa    780
gatgctaagt acaattaag taaagacact tacgatgatg atttagacaa tttattagct    840
cagatcggtg accagtacgc agacttattt ttggctgcaa agaacttatc agacgctatt    900
ttattaagtg atattttacg agtgaacact gaaatcacta aagctccttt aagtgctagt    960
atgatcaagc gttatgatga acaccaccaa gacttgactt tgttaaaggc tttagtcaga   1020
cagcaattac ctgaaaagta caggaaatt ttcttcgatc agtctaaaaa tggttacgct   1080
ggatacattg acggtggagc aagtcaggaa gaattttaca aattattaa gcctatcttg   1140
gaaaaaatgg acgtactga agaattatta gtaaagttaa acagagaaga tttattgcgt   1200
aaacagcgta ctttcgacaa tggaagtatc cctcaccaga ttcacttagg tgaattacac   1260
gctatcttaa gacgtcaaga agatttctac ctttttttga aagataacag agaaaagatt   1320
gaaaaaatct taacatttcg tataccttac tatgtaggtc ctttagctcg tggaaattct   1380
agattcgctt ggatgactcg taaatcagaa gaaactatca ctccttggaa cttcgaagaa   1440
gtcgtggata agggtgcttc tgctcagtct ttcatcgaaa gaatgactaa ctttgataaa   1500
aatttaccta acgaaaaggt gttacctaaa cactctttat tatacgaata cttcacagtt   1560
tataacgaat taactaaggt caaatacgtc acagaaggta tgagaaagcc agcattctta   1620
tctggagaac agaagaaagc tatcgtggac ttattattca agactaaccg taaagttact   1680
gtgaaacagt taaagaagaa ctatttcaaa aagattgaat gtttcgactc tgttgaaatc   1740
agtggagtgg aagatcgttt caacgcatct ttaggaactt atcacgattt attaaaaatc   1800
attaaagaca aggacttctt agacaatgaa gaaaacgaag acatttttaga agacattgtc   1860
ttaactttaa ctttgtttga agatagagaa atgattgaag aacgtttgaa aacttacgct   1920
catttattcg acgacaaagt catgaaacag ttaaagagac gtcgatatac aggatgggt   1980
cgtttatcaa gaaaattaat caatggtatc cgagacaagc agagtggaaa gacaatctta   2040
gatttttaa agtctgatgg atttgctaac cgtaacttca tgcagttgat ccatgatgac   2100
tctttaactt ttaaggaaga catccagaaa gcacaagttc ctggtcaggg tgacagttta   2160
cacgaacaca tcgctaattt agcaggtagt ccagctatca aaagggaat attacagact   2220
gttaaggtcg tggatgaatt agtcaaagta atgggaagac ataagcctga aaatatcgtt   2280
atcgaaatgg ctcgagaaaa ccaaactact cagaagggac agaagaacag tagagaaaga   2340
atgaagaaa ttgaagaagg tataaagaa ttaggttctc aaatcttaaa ggaacaccca   2400
gttgaaaaca ctcagttaca gaatgaaaag ttatacttat actacttaca gaacggtaga   2460
gacatgtacg tggatcagga attagacatc aatcgtttat ctgactacga cgtggatcat   2520
atcgtgcctc agtctttttt aaaagatgat tctattgata taaagtgtt gacaagatct   2580
gataaaaata gaggtaagag tgataacgtc ccttcagaag aagttgtcaa gaaaatgaaa   2640
aattattggc gtcagttatt aaacgctaaa ttaatcacac aacgtaagtt cgataattta   2700
actaaggctg aacgaggtgg tttatctgaa ttggataaag ctggttctat caaaagacag   2760
ttagttgaaa cacgtcagat cactaagcac gtggctcaaa ttttagattc acgtatgaac   2820
actaagtacg atgaaatga caaattaatt cgagaagtga aagttattac tttaaagtct   2880
aagttagtct cagatttcag aaaggacttt cagttttata aggtgagaga atcaacaat   2940
taccaccatg ctcatgatgc ttacttaaat gcagtggtag gtactgcatt aatcaaaaaa   3000
tatcctaagt tagaatctga atttgtttac ggagactata agtgtacga tgttagaaaa   3060
atgatcgcaa agtctgaaca ggaaatagg aaggctactg ctaagtactt cttttacagt   3120
aatattatga attttttcaa gactgaaatt acattagcta ttggagaaat tcgtaagcga   3180
ccattaatcg aaacaaacgg agaaacagga gaaatcgtgt gggacaaggg tagagatttc   3240
gctacagtcc gtaaggtctt atctatgcct caggtgaaca tcgttaaaaa gactgaagta   3300
cagactggag gtttctctaa ggaaagtatc ttacctaaaa gaaacagtga caagttaatc   3360
gcacgtaaaa aagattggga cctaagaaa tacggtggat tcgattctcc tacgctcgct   3420
tacagtgtat tagttgtggc taaagtggaa aaggtaaget ctaaaaatt aaaaagtgtc   3480
aaggaattat taggtatcac aatcatgaa cgatcaagtt tcgaaaaaaa ccctatcgac   3540
tttttagaag ctaaaggata taagaagtc aaaaaagact taatcattaa gttacctaag   3600
tactctttat ttgaattaga aacggtcgt aacgaatgt tagctagtgc tggtaattta   3660
cagaaaggta cgaattagc attccttct aaatacgtta atttcttgta tttagctagt   3720
cactatgaaa agttaaaagg ttcctgaa gataatgaac agagcagtt attcgtgcga   3780
caacacaaac actacttaga tgaaatcatc gaacaaataa gtgaattctc taaaagagtg   3840
atcttagctg acgctaactt agataagtg ttatctgctt acaataagca cagagataag   3900
cctatcagag aacaggcaga aaacattatc cacttgttta ctttaactaa cttgggtgct   3960
cctgcagctt tcaagtactt cgacactact atagacagaa agcgttacac ttctacaaag   4020
gaagtcttag acgctacatt aattcatcag tcaattactg gtttatatga aacaagaatc   4080
```

```
gacttatctc agttaggtgg agactaa                                            4107

SEQ ID NO: 25           moltype = DNA   length = 1037
FEATURE                 Location/Qualifiers
source                  1..1037
                        mol_type = unassigned DNA
                        organism = Saccharomyces cerevisiae
SEQUENCE: 25
tttatatata ttaaaataat attaataaat aattactcct cctagcagga ttcacatctc          60
cttcggccgg actccttcgg ggtccgcccc gcggggcgg gccggactat tttattatta          120
ttaaatagat gttcattaaa taattataaa tataatttat cttttaaata tatatatata         180
atataatatt taaatatata ttaaaataa ataaataaat aattaattaa taaaaacata          240
taatgtatat ttatctataa aaaattaa ttaaattaat atattattac agttccgggg           300
gccggccacg ggagccggaa ccccgaagga gataaataa taaataaata taaataattc          360
ttcttcttta aaattaaata aaataaaata aaaaggggg cggactcctt cggggtcccg          420
cccccctccg cggggcggac tattttattt ttaaatatat attatattaa taatataaat         480
ataagtcccc gccccggcgg ggaccccgaa ggagtataaa taaaaattaa taatatatta         540
tatatatatt attaataa taataataat aataataata ataaataata actccttgct           600
tcatacccttt ataaataagg taatcactaa tatattataa taataaaaat tatatatatt        660
atatataatc taaatattat atattttaat aaatattaat atatatgata tgaatatat           720
tagtttttgg gaagcgggaa tcccgtaagg agtgagggac ccctccctaa cgggaggagg          780
accgaaggag ttttagtatt tttttttttt taataaaata tgattaataa                    840
tattatatat attatttata aaaataatat ataatttaa ttattttaa taaaaaaagg            900
tggggttgat aataataat aatattttt attttaattt ataatatata ataataaatt           960
ataaataaat tttaattaaa agtagtatta acatatatta aatagacaaa agagtctaaa        1020
ggttaagatt tattaaa                                                       1037

SEQ ID NO: 26           moltype = DNA   length = 619
FEATURE                 Location/Qualifiers
source                  1..619
                        mol_type = unassigned DNA
                        organism = Saccharomyces cerevisiae
SEQUENCE: 26
ttaatattta cttattatta atatttttaa ttattaaaaa taataataat aataataatt          60
ataaataatat tcttaaatat aataaagata tagatttata ttctattcaa tcaccttata         120
ttaaaaatat aaatattatt aaaagaggtt atcatacttc tttaaataat aaattaatta         180
ttgttcaaaa agataataaa aataataata agaataattt agaaatagat aattttata          240
aatgattagt aggatttaca gatggagatg gtagttttta tattaaatta aatgataaaa         300
aatatttaag atttttttat ggttttagaa tacatattga tgataagca tgtttagaaa          360
agattagaaa tatattaaat ataccttcta atttttgaaga actacttaaa acaattatat        420
tagtaaattc acaaaagaaa tggttatatt ctaatattgt aactattttt gataagtatc         480
cttgtttaac aattaaaat tatagttatt ataatgaaa aatagctata attaataatt           540
taaatggtat atcttatat aataaagatt tattaaatat taaaaataca attaataatt          600
atgaagtata atatccata                                                      619

SEQ ID NO: 27           moltype = DNA   length = 23
FEATURE                 Location/Qualifiers
source                  1..23
                        mol_type = unassigned DNA
                        organism = Saccharomyces cerevisiae
SEQUENCE: 27
gaggaaatgt tgagtcgaca tcg                                                 23

SEQ ID NO: 28           moltype = DNA   length = 1000
FEATURE                 Location/Qualifiers
source                  1..1000
                        mol_type = unassigned DNA
                        organism = Saccharomyces cerevisiae
SEQUENCE: 28
taataaatat ttataaaaag aataatttat atttataata tataatttat atattttatt          60
tttattatac aattaatata aaatataaaa tattaaatat taaatattaa atattaaata         120
ttaaatatta atttttatag gggttatata ataattatat ttataattat ataatattaa         180
aaagggtatt tttataatta ttcatttttt attttattta taaaaatatt aatttttaata        240
agtattgaat acttatata atataaatat taattacata attaataatt aaataatt            300
taataatatt attaaattt attttata attattatt tataaaattc tattttttatt           360
attattattt ttattttatt ttaaagatt aatataataa ttattaatat attaaaaatc         420
ttttattata ttaatattta taaaaagta tttataaaaa aagatgtata aatttataaa          480
ttatataata ttattaattt aataataat aatattattc ctttgtgatt gtcaatttag         540
ttaatcattg ttattaataa aggaagata taaaaatat tctccttctt aaaaaggggt          600
tcggttcccc cccgtaaggg gggggtcct cactccttg gtcggactcc ttcggtcc              660
gccccgcggg ggcgggccgg actaatttaa ctttttaat taatattaat attattata           720
tttttaatat ataaaataa ataatttat ttttattaat agtatatatt taaaacaata          780
aaatagtatt aattatataa aattatataa aatatatat aattttatta tatatatata          840
tattataata tttaataagt tttttatata aattttattta ttatttatat aatagattaa        900
taatttattt tattattaat aagtaataaa taatagtttt ttataataat aatagttaa          960
atatatatat attattatat tagttatata ataaggaaaa                              1000

SEQ ID NO: 29           moltype = DNA   length = 531
FEATURE                 Location/Qualifiers
```

```
source                     1..531
                           mol_type = unassigned DNA
                           organism = Saccharomyces cerevisiae
SEQUENCE: 29
taaatattaa tctaaatatt aatataaata ttaatattaa tagttccggg gcccggccac    60
gggagccgga accccgaaag gagaaatatt aatataaata taaatattaa tataaatata   120
aatataaata taaatatatt ttaatataat ataatataat atataatata ttatataaat   180
ataatatata aataatataa taaaatattt taatatatat ataatataat ataattatta   240
ttataatttta atataaatta ttattataat ttaataaata aaataaataa ataattataa   300
ttataattat aattataatc tcaatatata aatgataaat tattataaat acaaaggaaa   360
taattgattt ttaaaatata tttaataaaa tatataatat aaattatact ttttttgtta   420
ttatataata attatattaa tatatttaat agaattaaac tccttcggcc ggactattat   480
tcattttata tattaatgat aaatcattaa ttattattaa taaatttatt t            531

SEQ ID NO: 30             moltype = DNA  length = 30
FEATURE                   Location/Qualifiers
source                    1..30
                          mol_type = unassigned DNA
                          organism = Saccharomyces cerevisiae
SEQUENCE: 30
tgtcccatta agacataagg tacttctaca                                     30

SEQ ID NO: 31             moltype = DNA  length = 36
FEATURE                   Location/Qualifiers
source                    1..36
                          mol_type = unassigned DNA
                          organism = Saccharomyces cerevisiae
SEQUENCE: 31
tggagcaggt atctcaacaa ttggtttatt aggagc                              36

SEQ ID NO: 32             moltype = AA  length = 32
FEATURE                   Location/Qualifiers
source                    1..32
                          mol_type = protein
                          organism = Homo sapiens
SITE                      1
                          note = Amine methionine
SITE                      32
                          note = Carboxyl asparagine
SEQUENCE: 32
MFFSAALRAR AAGLTAHWGR HVRNLHKTVM QN                                  32

SEQ ID NO: 33             moltype = DNA  length = 4200
FEATURE                   Location/Qualifiers
source                    1..4200
                          mol_type = other DNA
                          organism = synthetic construct
                          note = Synthetic Construct
SEQUENCE: 33
atgttcttct ccgcggcgct ccgggcccgg gcggctggcc tcaccgccca ctggggaaga    60
catgtaagga atttgcataa gacagttatg caaaatgaca agaagtactc cattgggctc   120
gatatcggca caaacagcgt cggctgggcc gtcattacgg acgagtacaa ggtgccgagc   180
aaaaaaattca aagttctggg caataccgat cgccacagca taaagaagaa cctcattggc   240
gccctcctgt tcgactccgg ggagacggcc gaagccacgc ggctcaaaag aacagcacgg   300
cgcagatata cccgcagaaa gaatcggatc tgctacctgc aggagatctt tagtaatgag   360
atggctaagg tggatgactc tttcttccat aggctggagg agtccttttt ggtggaggag   420
gataaaaagc acgagcgcca cccaatcttt ggcaatatcg tggacgaggt ggcgtaccat   480
gaaaagtacc caaccatata tcatctgagg aagaagcttg tagacagtac tgataaggct   540
gacttgcggt tgatctatct cgcgctggcg catatgatca aatttcgggg acacttcctc   600
atcgaggggg acctgaaccc agacaacagc gatgtcgaca aactcttttat ccaactggtt   660
cagacttaca atcagctttt cgaagagaac ccgatcaacg catccggagt tgacgccaaa   720
gcaatcctga gcgctaggct gtccaaatcc cggcggctcg aaaacctcat cgcacagctc   780
cctggggaga gaagaacgg cctgtttggt aatcttatcg ccctgtcact cgggctgacc   840
cccaacttta aatctaactt cgacctggcc gaagatgcca agcttcaact gagcaaagac   900
acctacgatg atgatctcga caatctgctg gcccagatcg cgaccagta cgcagacctt   960
ttttggcgg caaagaacct gtcagacgcc attctgctga gtgatattct gcgagtgaac  1020
acggagatca ccaaagctcc gctgagcgct agtatgatca agcgctatga tgagcaccac  1080
caagacttga ctttgctgaa ggcccttgtc agacagcaac ttcctgagaa gtacaaggaa  1140
atttttcttcg atcagtctaa aaatggctac gccagtatac ttgacggcgg agcaagccag  1200
gaggaatttt acaaatttat taagcccatc ttgaaaaaaa tggacggcac cgaggagctg  1260
ctggtaaagc ttaacagaga agatctgttg cgcaaacagc gcactttcga caatggaagc  1320
atccccacc agattcacct gggcgaactg cacgctatcc tcaggcggca gaggatttc  1380
tacccctttt tgaaagataa cagggaaaag attgagaatt ccctcacatt tcggataccc  1440
tactatgtag gccccctcgc ccggggaaat tccagattcg cgtggatgac tcgcaaatca  1500
gaagagacca tcactccctg gaacttcgag gaagtcgtgg ataaggggc tctgcccag  1560
tccttcatcg aaaggatgac taactttgat aaaaatctgc taacgaaaaa ggtgcttcct  1620
aaacactctc tgctgtacga gtacttcaca gtttataacg agctcaccaa ggtcaaatac  1680
gtcacagaag ggatgagaaa gccagcattc ctgtctggag agcagaagaa agctatcgtg  1740
gacctcctct tcaagacgaa ccggaaagtt accgtgaaac agctcaaaga agactatttc  1800
```

-continued

```
aaaaagattg aatgtttcga ctctgttgaa atcagcggag tggaggatcg cttcaacgca  1860
tccctgggaa cgtatcacga tctcctgaaa atcattaaag acaaggactt cctggacaat  1920
gaggagaacg aggacattct tgaggacatt gtcctcaccc ttacgttgtt tgaagatagg  1980
gagatgattg aagaacgctt gaaaacttac gctcatctct tcgacgacaa agtcatgaaa  2040
cagctcaaga ggcgccgata tacaggatgg gggcggctgt caagaaaact gatcaatggg  2100
atccgagaca agcagagtgg aaagacaatc ctggattttc ttaagtccga tggatttgcc  2160
aaccggaact tcatgcagtt gatccatgat gactctctca cctttaagga ggacatccag  2220
aaagcacaag tttctggcca gggggacagt cttcacgagc acatcgctaa tcttgcaggt  2280
agcccagcta tcaaaaaggg aatactgcag accgttaagg tcgtggatga actcgtcaaa  2340
gtaatgggaa ggcataagcc cgagaatatc gttatcgaga tggcccgaga gaaccaaact  2400
acccagaagg gacagaagaa cagtagggaa aggatgaaga ggattgaaga gggtataaaa  2460
gaactggggt cccaaatcct taaggaacac ccagttgaaa acacccagct tcagaatgag  2520
aagctctacc tgtactacct gcagaacggc agggacatgt acgtggatca ggaactggac  2580
atcaatcggc tctccgacta cgacgtggat catatcgtga cccagtcttt tctcaaagat  2640
gattctattg ataataaagt gttgacaaga tccgataaaa atagagggaa gagtgataac  2700
gtccctcag aagaagttgt caagaaaatg aaaaattatt ggcggcagct gctgaacgcc  2760
aaactgatca cacaacggaa gttcgataat ctgactaagg ctgaacgagg tggcctgtct  2820
gagttggata aagccggctt catcaaaagg cagcttgttg agacacgcca gatcaccaag  2880
cacgtggccc aaattctcga ttcacgcatg aacaccaagt acgatgaaaa tgacaaactg  2940
attcgagagg tgaaagttat tactctgaag tctaagctgg tctcagattt cagaaaggac  3000
tttcagtttt ataaggtgag agagatcaac aattaccacc atgcgcatga tgcctacctg  3060
aatgcagttg taggcactgc acttatcaaa aaatatccca acttgaatc tgaatttgtt  3120
tacgagact ataaagtgta cgatgttagg aaaatgatcg caaagtctga gcaggaaata  3180
ggcaaggcca ccgctaagta cttcttttac agcaatatta tgaatttttt caagaccgag  3240
attacactgg ccaatggaga gattcggaag cgaccactta tcgaaacaaa cggagaaaca  3300
ggagaaatcg tgtgggacaa gggtagggat ttcgcgacga tccggaaggt cctgtccgta  3360
ccgcaggtga acatcgttaa aaagaccgaa gtacagaccg gaggcttctc caaggaaagt  3420
atcctcccga aaaggaacag cgacaagctg atcgcacgca aaaaagattg ggaccccaag  3480
aaatacggcg gattcgattc tcctacagtc gcttacagtg tactggttgt ggccaaagtg  3540
gagaaaggga agtctaaaaa actcaaaagc gtcaaggaac tgctgggcat cacaatcatg  3600
gagcgatcaa gcttcgaaaa aaacccatcc gactttctcg aggcgaaagg atataaagag  3660
gtcaaaaaag acctcatcat taagcttccc aagtactctc tctttgagct tgaaaacggc  3720
cggaaacgaa tgctcgctag tgcgggcgag ctgcagaaag gtaacgagct ggcactgccc  3780
tctaaatacg ttaatttctt gtatctggcc agccactatg aaaagctcaa agggtctcaa  3840
gaagataatg agcagaagca gctgttcgtg gaacaacaa aacactacct tgatgagatc  3900
atcgagcaaa taagcgaatt ctccaaaaga gtgatcctcg ccgacgctaa cctcgataag  3960
gtgctttctg cttacaataa gcacagggat aagcccatca gggagcaggc agaaaacatt  4020
atccacttgt ttactctgac caacttgggc gcgcctgcag ccttcaagta cttcgacacc  4080
accatagaca gaaagcggta cacctctaca aaggaggtcc tggacgccac actgattcat  4140
cagtcaatta cggggctcta tgaaacaaga atcgacctct ctcagctcgg tggagactga  4200

SEQ ID NO: 34          moltype = AA   length = 25
FEATURE                Location/Qualifiers
source                 1..25
                       mol_type = protein
                       organism = Homo sapiens
SITE                   1
                       note = Amine methionine
SITE                   25
                       note = Carboxyl histidine
SEQUENCE: 34
MALLTAAARL LGTKNASCLV LAARH                                        25

SEQ ID NO: 35          moltype = DNA   length = 4227
FEATURE                Location/Qualifiers
source                 1..4227
                       mol_type = other DNA
                       organism = synthetic construct
                       note = Synthetic Construct
SEQUENCE: 35
atggctttac ttactgcggc cgcccggctc ttgggaacca agaatgcatc ttgtcttgtt    60
cttgcagccc ggcatatggc tttacttact gcggccgccc ggctcttggg aaccaagaat   120
gcagacaaga agtactccat tgggctcgat atcggcacaa acagcgtcgg ctgggccgtc   180
attacggacg agtacaaggt gccgagcaaa aaattcaaag ttctgggtaa taccgatcgc   240
cacagcataa agaagaacct cattggcgcc ctcctgttcg actccgggga cggccgaa     300
gccacgcggc tcaaaagaac agcacggcgc agatataccc gcagaaagaa tcggatctgc   360
tacctgcagg agatctttag taatgagatg gctaaggtgg atgactcttt cttccatagg   420
ctggaggagt ccttttttgg tggaggaggat aaaaagcacg agcgccaccc aatctttggc   480
aatatcgtgg acgaggtggc gtaccatgaa agtacccaa ccatatatca tctgaggaag   540
aagcttgtag acagtactga taaggctgac ttgcggttga tctatctcgc gctggcgcat   600
atgatcaaat tcggggaca cttcctcatc gaggggacc tgaacccaga caacagcgat   660
gtcgacaaac tctttatcca actggttcag acttacaatc agcttttcga agagaacccg   720
atcaacgcat ccggagttga cgccaaagca atcctgagcg ctaggctgtc caaatcccgg   780
cggctcgaaa acctcatcgc acagttccct gggagagaaa gaaacggcct gtttggtaat   840
cttatcgccc tgtcactcgg gctgaccccc aactttaaaat ctaacttcga cctggccgaa   900
gatgccaagc ttcaactgag caaagacacc tacgatgatg atctcgacaa tctgctggcc   960
cagatcggcg accagtacgc agaccttttt tggcggcaa agaaccgtc agacgccatt  1020
ctgctgagtg atattctgcg agtgaacacg gagatcacca agctccgct gagcgctagt  1080
atgatcaagc gctatgatga gcaccaccaa gacttgactt tgctgaaggc ccttgtcaga  1140
```

```
cagcaactgc ctgagaagta caaggaaatt ttcttcgatc agtctaaaaa tggctacgcc   1200
ggatacattg acggcggagc aagccaggag gaattttaca aatttattaa gcccatcttg   1260
gaaaaaatgg acggcaccga ggagctgctg gtaaagctta acagagaaga tctgttgcgc   1320
aaacagcgca ctttcgacaa tggaagcatc cccaccaga ttcacctggg cgaactgcac   1380
gctatcctca ggcggcaaga ggattctac ccctttttga aagataacag ggaaaagatt   1440
gagaaaatcc tcacatttcg gatacctac tatgtaggcc ccctcgcccg gggaaattcc   1500
agattcgcgt ggatgactcg caaatcagaa gagaccatca ctcctggaa cttcgaggaa   1560
gtcgtggata aggggcctc tgcccagtcc ttcatcgaaa ggatgactaa cttgataaa   1620
aatctgccta acgaaaaggt gcttcctaaa cactctctgc tgtacgagta cttcacagtt   1680
tataacgagc tcaccaaggt caaatacgtc acagaaggga tgagaaagcc agcattcctg   1740
tctggagagc agaagaaagc tatcgtggac ctcctcttca agacgaaccg gaaagttacc   1800
gtgaaacagc tcaaagaaga ctatttcaaa aagattgaat gtttcgactc tgttgaaatc   1860
agcggagtgg aggatcgctt caacgcatcc ctgggaacgt atcacgatct cctgaaaatc   1920
attaaagaca aggacttcct ggacaatgag gagaacgagg acattcttga ggacattgtc   1980
ctcaccctta cgttgtttga agataggag atgattgaag aacgcttgaa aacttacgct   2040
catctcttcg acgacaaagt catgaaacag ctcaagaggc gccgatatac aggatggggg   2100
cggctgtcaa gaaaactgat caatgggatc cgagacaagc agagtggaaa gacaatcctg   2160
gattttctta gtccgatggg attgccaac cggaacttca tgcagttgat ccatgatgac   2220
tctctcacct taaggagga catccagaaa gcacaagttt ctggccaggg ggacagtctt   2280
cacgagcaca tcgctaatct tgcaggtagc ccagctatca aaagggaat actgcagacc   2340
gttaaggtcg tggatgaact cgtcaaagta atgggaaggc ataagcccga gaatatcgtt   2400
atcgagatgg cccgagagaa ccaaactacc cagaagggac agaagaacag tagggaaagg   2460
atgaagagga ttgaagaggg tataaaagaa ctggggtccc aaatccttaa ggaacaccca   2520
gttgaaaaca cccagcttca gaatgagaag ctctacctgt actacctgca gaacggcagg   2580
gacatgtacg tggatcagga actggacatc aatcggctct ccgactacga cgtggatcat   2640
atcgtgcccc agtcttttct caaagatgat tctattgata ataaagtgtt gacaagatcc   2700
gataaaaata gagggaagag tgataacgtc ccctcagaag aagttgtcaa gaaaatgaaa   2760
aattattggc ggcagctgct gaacgccaaa ctgatcacac aacggaagtt cgataatctg   2820
actaaggctg aacgaggtgg cctgtctgag ttggataaag ccggcttcat caaaaggcag   2880
cttgttgaga cacgccagat caccaagcac gtggcccaaa ttctcgattc acgcatgaac   2940
accaagtacg atgaaaatga caaactgatt cgagaggtga agttattac tctgaagtcc   3000
aagctggtct cagatttcag aaaggacttt cagtttata aggtgagaga gatcaacaat   3060
taccaccatg cgcatgatgc ctacctgaat gcagtggtag gcactgcact tatcaaaaaa   3120
tatcccaagc ttgaatctga atttgtttac ggagactata aagtgtacga tgttaggaaa   3180
atgatcgcaa agtctgagca ggaaatagcc aaggcaccg ctaagtactt cttttacagg   3240
aatattatga atttttcaa gaccgagatt acactggcca atggagagat tcggaagcga   3300
ccacttatcg aaacaacgg agaaacagga gaaatcgtgt gggacaaggg tagggatttc   3360
gcgacagtcc ggaaggtcct gtccatgccg caggtgaaca tcgttaaaaa gaccgaagta   3420
cagaccggag gcttctccaa ggaaagtatc ctcccgaaca acagcga caagctgatc   3480
gcacgcaaaa aagattggga ccccaagaaa tacggcggat tcgattctcc tacagtcgct   3540
tacagtgtac tggtttgtgc caaagtggag aaagggaagt ctaaaaaact caaaagcgtc   3600
aaggaactgc tgggcatcac aatcatggag cgatcaagct tcgaaaaaaa ccccatcgac   3660
tttctcgagg cgaaaggata taagaggtc aaaaaagacc tcatcattaa gcttcccaag   3720
tactctctct ttgagcttga aaacggccgg aaacgaatgc tcgctagtgc gggcgagctg   3780
cagaaaggta acgagctggc actgcccctct aaatacgtta atttcttgta tctgccagc   3840
cactatgaaa agctcaaagg gtctcccgaa gataatgagc agaagcagct gttcgtggaa   3900
caacacaaac actaccttga tgagatcatc gagcaaataa ccgaattctc caaagagtg   3960
atcctcgccg acgctaacct cgataaggtg ctttctgctt acaataagca cagggataag   4020
cccatcaggg agcaggcaga aaacattatc cacttgttta ctctgaccaa cttgggcgcg   4080
cctgcagcct tcaagtactt cgacaccacc atagacagaa agcggtacac ctctacaaag   4140
gaggtcctgg acgccacact gattcatcag tcaattacgg ggctctatga aacaagaatc   4200
gacctctctc agctcggtgg agactga                                      4227

SEQ ID NO: 36          moltype = DNA   length = 120
FEATURE                Location/Qualifiers
source                 1..120
                       mol_type = unassigned DNA
                       organism = Homo sapiens
SEQUENCE: 36
gcctacggcc ataccaccct gaacgcgccc gatctcgtct gatctcggaa gctaagcagg   60
gtcgggcctg gttagtactt ggatgggaga ccacctggga ataccgggtg ctgtaggctt   120

SEQ ID NO: 37          moltype = DNA   length = 22
FEATURE                Location/Qualifiers
source                 1..22
                       mol_type = unassigned DNA
                       organism = Homo sapiens
SEQUENCE: 37
gtctggtgag tagtgcatgg ct                                            22

SEQ ID NO: 38          moltype = DNA   length = 460
FEATURE                Location/Qualifiers
source                 1..460
                       mol_type = unassigned DNA
                       organism = Homo sapiens
SEQUENCE: 38
agccccgcgg ccccgggctg gcggtgtcgg ctgcaatccg gcgggcacgg ccgggccggg   60
ctgggctctg gggcagcca ggcgcctcct tcagcgccta cggccatacc accctgaacg   120
cgcccgatct cgtctgatct cggaagctaa gcagggtcgg gcctggttag tacttggatg   180
```

-continued

```
ggagaccacc tgggaatacc gggtgctgta ggcttttct ttggcttttt gctgtttctt      240
tcctttcttt ccagacggag tctcgccctc tcgcccaggc tggagtgcgg tggcgccatc    300
tcggctcact gcaagctccg cctcccgggt ccacgccatt cccggcctc agcctcccga     360
gtagctgggc ctacaggcgc ccgccaccac gcccggccac tttgttctat ttttcctaga    420
gacgggcttt caccctgtta gccgggatgg tctggagctc                          460

SEQ ID NO: 39            moltype = DNA   length = 20
FEATURE                  Location/Qualifiers
source                   1..20
                         mol_type = unassigned DNA
                         organism = Mus musculus
SEQUENCE: 39
gatgtcctga tccaacatcg                                                 20

SEQ ID NO: 40            moltype = DNA   length = 432
FEATURE                  Location/Qualifiers
source                   1..432
                         mol_type = unassigned DNA
                         organism = Mus musculus
SEQUENCE: 40
tttcggttgg ggtgacctcg gagaataaaa aatcctccga atgattataa cctagactta     60
caagtcaaag taaaatcaac atatcttatt gacccagata tattttgatc aacggaccaa    120
gttaccctag ggataacagc gcaatcctat ttaagagttc atatcgacaa ttagggttta    180
cgacctcgac gttggatcag gacatcccaa tggtgtagaa gctattaatg gttcgtttgt    240
tcaacgatta aagtcctacg tgatctgagt tcagaccgga gcaatccagg tcggtttcta    300
tctatttacg atttctccca gtacgaaagg acaagagaaa tagagccacc ttacaaataa    360
gcgctctcaa cttaatttat gaataaaatc taaataaaat atatacgtac accctctaac    420
ctagagaagg tt                                                        432

SEQ ID NO: 41            moltype = DNA   length = 4296
FEATURE                  Location/Qualifiers
source                   1..4296
                         mol_type = other DNA
                         organism = synthetic construct
                         note = Synthetic Construct
SEQUENCE: 41
atggataaga agtactctat cggacttgac atcggaacca actctgttgg atgggctgtt     60
atcaccgatg agtacaaggt tccatctaag aagttcaagg ttcttggaaa caccgataga   120
cactctatca agaagaacct tatcggtgct cttcttttcg attctggaga gaccgctgag   180
gctaccagat tgaagagaac cgctagaaga agatacacca gaagaaagaa cagaatctgc   240
taccttcagg aaatcttctc taacgagatg gctaaggttg atgattcttt cttccacaga   300
cttgaggagt cttttccttgt tgaggaggat aagaagcacg agagacaccc aatcttcgga   360
aacatcgttg atgaggttgc ttaccacgag aagtacccaa ccatctacca ccttagaaag   420
aagttggttg attctaccga taaggctgat cttagactta tctaccttgc tcttgctcac   480
atgatcaagt tcagaggaca cttccttatc gagggagacc ttaacccaga taactctgat   540
gttgataagt tgttcatcca gcttgttcag acctacaacc agcttttcga ggagaaccca   600
atcaacgctt ctggagttga tgctaaggct atccttttcg ctagacttaa gtctcgt       660
agacttgaga accttatcgc tcagcttcca ggagagaaga gaacggact tttcggaaac   720
cttatcgctc tttctcttgg acttacccca aacttcaagt ctaacttcga tcttgctgag   780
gatgctaagt tgcagctttc taaggatacc tacgatgatg atcttgataa ccttcttgct   840
cagatcggag atcagtacgc tgatctttttc cttgctgcta agaaccttct tgatgctatc   900
cttctttctg acatccttag agttaacacc gagatcacca aggctccact ttctgcttct   960
atgatcaaga gatacgatga gcaccaccag gatcttaccc ttttgaaggc tcttgttaga 1020
cagcagcttc cagagaagta caaggaaatc ttcttcgatc agtctaagaa cggatacgct 1080
ggatacatcg atggaggagc ttctcaggag gagttctaca agttcatcaa gccaatcctt 1140
gagaagatgg atggaaccga ggagcttctt gttaagttga acagagagga tcttcttaga 1200
aagcagagaa ccttcgataa cggatctatc ccacaccaga tccaccttgg agagcttcac 1260
gctatccttc gtagacagga ggatttctac ccattcttga aggataacag agagaagatc 1320
gagaagatcc ttacccttcag aatcccatac tacgttggac cacttgctag aggaaactct 1380
cgtttcgctt ggatgaccga aaagtctgag gagaccatca ccccttggaa cttcgaggag 1440
gtaagtttct gcttctaccct tgatatata tataataatt atcattaatt agtagtaata 1500
taatatttca aatattttt tcaaaataaa agaatgtagt atatagcaat tgcttttctg 1560
tagtttataa gtgtgtatat tttaatttat aacttttcta atatatgacc aaaatttgtt 1620
gatgtgcagg ttgttgataa gggagcttct gctcagtctt tcatcgagag aatgaccaac 1680
ttcgataaga accttccaaa cgagaaggtt cttccaaagc actctcttct ttacgagtac 1740
ttcaccgttt acaacgagct taccaaggtt aagtacgtta ccgagggaat gagaaagcca 1800
gctttccttt ctgagagcca gaagaaggct atcgttgatc ttcttttcaa gaccaacaga 1860
aaggttaccg ttaagcagtt gaaggaggat tacttcaaga agatcgagtg cttcgattct 1920
gttgaaatct ctggagttga ggatagattc aacgcttctc ttggaaccta ccacgatctt 1980
ttgaagatca tcaaggataa ggatttcctt gataacgagg agaacgagga catccttgag 2040
gacatcgttc ttacccttac ccttttcgag gatagagaga tgatcgagga gagactcaag 2100
acctacgctc acctttttcga tgataaggtt atgaagcagt tgaagagaag aagatacacc 2160
ggatggggta ctttctctcg taagttgatc aacggaatca gagataagca gtctggaaag 2220
accatctaca tttcttgaa gtctgatgga ttcgctaaca gaaacttcat gcagcttatc 2280
cacgatgatt ctcttaccctt caaggaggac atccagaagg ctcaggtttc tggacaggga 2340
gattctcttc acgagcacat cgctaacctt gctggatctc cagctatcaa gaagggaatc 2400
cttcagaccg ttaaggttgt tgatgagctt gttaaggtta gggtagaca agccagag    2460
aacatcgtta tcgagatggc tagagagaac cagaccaccc agaagggaca gaagaactct 2520
cgtgagagaa tgaagagaat cgaggaggga atcaaggagc ttggatctca aatcttgaag 2580
```

```
gagcacccag ttgagaacac ccagcttcag aacgagaagt tgtaccttta ctaccttcag   2640
aacggaagag atatgtacgt tgatcaggag cttgacatca acagactttc tgattacgat   2700
gttgatcaca tcgttccaca gtctttcttg aaggatgatt ctatcgataa caaggttctt   2760
acccgttctg ataagaacag aggaaagtct gataacgttc catctgagga ggttgttaag   2820
aagatgaaga actactggag acagcttctt aacgctaagt tgatcaccca gagaaagttc   2880
gataacctta ccaaggctga gagaggagga cttttctgagc ttgataaggc tggattcatc   2940
aagagacagc ttgttgagac cagacagatc accaagcacg ttgctcagat ccttgattct   3000
cgtatgaaca ccaagtacga tgagaacgat aagttgatca gagaggttaa ggttataccc   3060
ttgaagtcta agttggtttc tgatttcaga aaggatttcc agttctacaa ggttagagag   3120
atcaacaact accaccacgc tcacgatgct taccttaacg ctgttgttgg aaccgctctt   3180
atcaagaagt acccaaagtt ggagtctgag ttcgtttacg gagattacaa ggtttacgat   3240
gttagaaaga tgatcgctaa gtctgagcag gagatcggaa aggctaccgc taagtacttc   3300
ttctactcta acatcatgaa cttcttcaag accgagatca cccctgctaa cggagagatc   3360
agaaagagac cacttatcga gaccaacgga gaccggagg agatcgtttg ggataaggga   3420
agagatttcg ctaccgttag aaaggttctt tctatgccac aggttaacat cgttaagaaa   3480
accgaggttc agaccggagg attctctaag gagtctatcc ttccaaagag aaactctgat   3540
aagttgatcg ctagaaagaa ggattgggac ccaaagaagt acggaggatt cgattctcca   3600
accgttgctt actctgttct tgttgttgct aaggttgaga agggaagctc taagaagttg   3660
aagtctgtta aggagcttct tggaatcacc atcatggagc gttcttcttt cgagaagaac   3720
ccaatcgatt tccttgaggc taagggatac aaggaggtta agaaggatct tatcatcaag   3780
ttgccaaagt actctctttt cgagcttgag aacgaagaa agaagaatgct tgcttctgct   3840
ggagagcttc agaagggaaa cgagcttgct ctttccatcta agtacgttaa cttcctttac   3900
cttgcttctc actacgagaa gttgaaggga tctccagagg ataacgagca gaagcagctt   3960
ttcgttgagc agcacaagca ctaccttgat gagatcatcg agcaaatctc tgagttctct   4020
aagagagtta tccttgctga tgctaaccct gataagttcc tttctgctta caacaagcac   4080
agagataagc caatcagaga gcaggctgag aacatcaac accttttcac ccttaccaac   4140
cttggtgctc cagctgcttt caagtacttc gataccacca tcgatagaaa aagataccacc   4200
tctaccaagg aggttcttga tgctacccctt atccaccagt ctatcaccgg actttacgag   4260
accagaatcg atctttctca gcttggagga gattga                              4296

SEQ ID NO: 42                  moltype = AA   length = 1368
FEATURE                        Location/Qualifiers
source                         1..1368
                               mol_type = protein
                               organism = synthetic construct
                               note = Synthetic Construct
SEQUENCE: 42
MDKKYSIGLD IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD                1368

SEQ ID NO: 43                  moltype = AA   length = 80
FEATURE                        Location/Qualifiers
source                         1..80
                               mol_type = protein
                               organism = Arabidopsis thaliana
SEQUENCE: 43
MASSMLSSAT MVASPAQATM VAPFNGLKSS AAFPATRKAN NDITSITSNG GRVNCMQVWP    60
PIGKKKFETL SYLPDLTDSE                                                80

SEQ ID NO: 44                  moltype = AA   length = 80
FEATURE                        Location/Qualifiers
source                         1..80
                               mol_type = protein
                               organism = Arabidopsis thaliana
SEQUENCE: 44
MASNSLMSCG IAAVYPSLLS SSKSKFVSAG VPLPNAGNVG RIRMAAHWMP GEPRPAYLDG    60
SAPGDFGFDP LGLGEVPANL                                                80
```

```
SEQ ID NO: 45             moltype = AA   length = 80
FEATURE                   Location/Qualifiers
source                    1..80
                          mol_type = protein
                          organism = Arabidopsis thaliana
SEQUENCE: 45
MTIALTIGGN GFSGLPGSSF SSSSSSFRLK NSRRKNTKML NRSKVVCSSS SSVMDPYKTL   60
KIRPDSSEYE VKKAFRQLAK                                              80

SEQ ID NO: 46             moltype = DNA   length = 4467
FEATURE                   Location/Qualifiers
source                    1..4467
                          mol_type = other DNA
                          organism = synthetic construct
                          note = Synthetic Construct
SEQUENCE: 46
atggcttcct ctatgctctc ttccgctact atggttgcct ctccggctca ggccactatg   60
gtcgctcctt tcaacggact taagtcctcc gctgccttcc cagccacccg caaggctaac  120
aacgacatta cttccatcac aagcaacggc ggaagagtta actgcatgca ggtggataag  180
aagtactcta tcggacttga catcggaacc aactctgttg gatgggctgt tatcaccgat  240
gagtacaagg ttccatctaa gaagttcaag gttcttggaa acaccgatag acactctatc  300
aagaagaacc ttatcggtgc tctttctttc gattctggaa agccgctaga ggctaccaga  360
ttgaagagaa ccgctagaag aagatacacc agaagaaaga acagaatctg ctaccttcag  420
gaaatcttct ctaacgagat ggctaaggtt gatgattctt cttccacag acttgaggag  480
tctttccttg tgaggagga taagaagcac gagagacacc caatcttcgg aaacatcgtt  540
gatgaggttg cttaccacga gaagtaccca accatctcac accttagaaa gaagttggtt  600
gattctaccg ataaggctga tcttagactt atctaccttg ctcttgctca catgatcaag  660
ttcagaggac acttccttat cgagggagac cttaacccag ataactctga tgttgataag  720
ttgttcatcc agcttgttca gacctacaac cagctttttcg aggagaaccc aatcaacgct  780
tctgagttg atgctaaggc tatccttttct gctagacttt ctaagtctcg tagacttgag  840
aaccttatcg ctcagcttcc aggagagaag aagaacggac tttttcggaaa ccttatcgct  900
ctttctcttg gacttacccc aaacttcaag tctaacttcg atcttgctga ggatgctaag  960
ttgcagcttt ctaaggatac ctacgatgat gatcttgata ccttcttgc tcagatcgga 1020
gatcagtacg ctgatcttttt ccttgctgct aagaacctttt ctgatgctact ccttctttct 1080
gacatcctta gagttaacac cgagataacc aaggctccac ttttctgcttc tatgatcaag 1140
agatacgatg agcaccacca ggatcttacc cttttgaagg ctcttgttag acagcagctt 1200
ccagagaagt acaaggaaat cttcttcgat cagtctaaga acggatacgc tggatacatc 1260
gatggaggag cttctcagga ggagttctac aagttcatca agccaatcct tgagaagatg 1320
gatgaaccg aggagcttct tgttaagttg aacagagagg atctttcttag aaagcagaga 1380
accttcgata acggatctat cccacaccag atccaccttg agagcttca cgctatcctt 1440
cgtagacagg aggatttcta cccattcttg aaggataaca gagagaagat cgagaagatc 1500
cttaccttca gaatcccata ctacgttgga ccacttgcta gaggaaactc tcgtttcgct 1560
tggatgacca gaaagtctga ggagaccatc accccttga acttcgagga ggtaagttc 1620
tgcttctacc tttgatatat ataataat atcattaat tagtagtaat ataatatttc 1680
aaatattttt ttcaaaataa aagaatgtag tatatagcaa ttgcttttct gtagtttata 1740
agtgtgtata ttttaattta taacttttct aatatatgac caaaatttgt tgatgtgcag 1800
gttgttgata agggagcttc tgctcagtct ttcatcgaga aatgaccaa cttcgataag 1860
aaccttccaa acgagaaggt tcttccaaag cactctcttc tttacgagta cttcaccgtt 1920
tacaacgagc ttaccaaggt taagtacgtt accgagggaa tgagaaagcc agcttttcctt 1980
tctggagagc agaagaaggc tatcgttgat cttcttttca agaccaacag aaaggttacc 2040
gttaagcagt tgaaggagga ttacttcaag aagatcgagt gcttcgattc tgttgaaatc 2100
tctggagttg aggatagatt caacgcttct cttggaacct accacgatct tttgaagatc 2160
atcaaggata aggatttcct tgataacgag gagaacgagg acatccttga ggacatcgtt 2220
cttacccttta cccttttcga gatagagag atgatcgagg agagactcaa gacctacgct 2280
caccttttcg atgataaggt tatgaagcag ttgaagagaa gaagatacac cggatgggt 2340
agactttctc gtaagttgat caacggaatc agagataagc agtctggaaa gaccatcctt 2400
gatttcttga gtctgatgg attcgctaac agaaacttca tgcagcttat ccacgatgat 2460
tctcttacct tcaaggagga catccagaag gctcaggttt ctggacaggg agattctctt 2520
cacgagcaca tcgctaaacct tgctggatct ccagctatca agaagggaat ccttcagacc 2580
gttaaggttg ttgatgagct tgttaaggtt atgggtagac acaagccaga gaacatcgtt 2640
atcgagatgg ctagagagaa ccagaccacc cagaagggac agaagaactc tcgtgagaga 2700
atgaagagaa tcgaggaggg aatcaaggag cttggatctc aaatcttgaa ggagcaccca 2760
gttgagaaca cccagcttca gaacgagaag ttgtaccttt actacttca gaacggaaga 2820
gatatgtacg ttgatcagga gcttgacatc aacagactt ctgattacga tgttgatcac 2880
atcgttccac agtctttctt gaaggatgat tctatcgata caaggttct tacccgttct 2940
gataagaaca gaggaaagtc tgataacgtt ccatctgagg aggttgttaa gaagatgaag 3000
aactactgga gacagcttct taacgctaag ttgatcaccc agaaaagtt cgataacctt 3060
accaaggctg agagaggagg acttcttgag cttgataagg ctggattcat caagagacag 3120
cttgttgaga ccagacagat caccaagcac gttgctcaga tccttgattc tcgtatgaac 3180
accaagtacg atgagaacga taagttgatc agagagggtta aggttatcac cttgaagtct 3240
aagttggttt ctgatttcag aaaggatttc cagttctaca aggttagaga gatcaacaac 3300
taccaccacg ctcacgatgc ttaccttaac gctgttgttg aaccgctct tatcaagaag 3360
tacccaaagt tggagtctga gttcgtttac ggagattaca aggtttacga tgttagaaag 3420
atgatcgcta agtctgagca ggagatcgga aaggctaccg ctaagtactt cttctactct 3480
aacatcatga acttcttcaa gaccgagatc acccttgcta cggagagat cagaaagaga 3540
ccacttatcg agaccaacgg agaagccgga gagatcgttt gggataaggg aagagatttc 3600
gctaccgtta gaaaggttct ttctatgcca caggttaaca tcgttaagaa accgaggtt 3660
cagaccggag gattctctaa ggagtctatc cttccaaaga gaaactctga taagttgatc 3720
gctagaaaga aggattggga cccaaagaag tacggaggat tcgattctcc aaccgttgct 3780
```

```
tactctgttc ttgttgttgc taaggttgag aagggaaagt ctaagaagtt gaagtctgtt  3840
aaggagcttc ttggaatcac catcatggag cgttcttctt tcgagaagaa cccaatcgat  3900
ttccttgagg ctaagggata caaggaggtt aagaaggatc ttatcatcaa gttgccaaag  3960
tactctcttt tcgagcttga aacggaaga aagagaatgc ttgcttctgc tggagagctt  4020
cagaagggaa acgagcttgc tcttccatct aagtacgtta acttcctta ccttgcttct  4080
cactacgaga agttgaaggg atctccagag gataacgagc agaagcagct tttcgttgag  4140
cagcacaagc actaccttga tgagatcatc gagcaaatct ctgagttctc taagagagtt  4200
atccttgcta tgctaaccct tgataaggtt ctttctgctt acaacaagca cagagataag  4260
ccaatcagag agcaggctga gaacatcatc caccttttca cccttaccaa ccttggtgct  4320
ccagctgctt tcaagtactt cgataccacc atcgatagaa aaagatacac ctctaccaag  4380
gaggttcttg atgctaccct tatccaccag tctatcaccg gactttacga gaccagaatc  4440
gatctttctc agcttggagg agattga                                      4467

SEQ ID NO: 47           moltype = AA   length = 1424
FEATURE                 Location/Qualifiers
source                  1..1424
                        mol_type = protein
                        organism = synthetic construct
                        note = Synthetic Construct
SEQUENCE: 47
MASSMLSSAT MVASPAQATM VAPFNGLKSS AAFPATRKAN NDITSITSNG GRVCMQVDKK    60
YSIGLDIGTN SVGWAVITDE YKVPSKKFKV LGNTDRHSIK KNLIGALLFD SGETAEATRL   120
KRTARRRYTR RKNRICYLQE IFSNEMAKVD DSFFHRLEES FLVEEDKKHE RHPIFGNIVD   180
EVAYHEKYPT IYHLRKKLVD STDKADLRLI YLALAHMIKF RGHFLIEGDL NPDNSDVDKL   240
FIQLVQTYNQ LFEENPINAS GVDAKAILSA RLSKSRRLEN LIAQLPGEKK NGLFGNLIAL   300
SLGLTPNFKS NFDLAEDAKL QLSKDTYDDD LDNLLAQIGD QYADLFLAAK NLSDAILLSD   360
ILRVNTEITK APLSASMIKR YDEHHQDLTL LKALVRQQLP EKYKEIFFDQ SKNGYAGYID   420
GGASQEEFYK FIKPILEKMD GTEELLVKLN REDLLRKQRT FDNGSIPHQI HLGELHAILR   480
RQEDFYPFLK DNREKIEKIL TFRIPYYVGP LARGNSRFAW MTRKSEETIT PWNFEEVVDK   540
GASAQSFIER MTNFDKNLPN EKVLPKHSLL YEYFTVYNEL TKVKYVTEGM RKPAFLSGEQ   600
KKAIVDLLFK TNRKVTVKQL KEDYFKKIEC FDSVEISGVE DRFNASLGTY HDLLKIIKDK   660
DPLDNEENED ILEDIVLTLT LFEDREMIEE RLKTYAHLFD DKVMKQLKRR RYTGWGRLSR   720
KLINGIRDKQ SGKTILDFLK SDGFANRNFM QLIHDDSLTF KEDIQKAQVS GQGDSLHEHI   780
ANLAGSPAIK KGILQTVKVV DELVKVMGRH KPENIVIEMA RENQTTQKGQ KNSRERMKRI   840
EEGIKELGSQ ILKEHPVENT QLQNEKLYLY YLQNGRDMYV DQELDINRLS DYDVDHIVPQ   900
SFLKDDSIDN KVLTRSDKNR GKSDNVPSEE VVKKMKNYWR QLLNAKLITQ RKFDNLTKAE   960
RGGLSELDKA GFIKRQLVET RQITKHVAQI LDSRMNTKYD ENDKLIREVK VITLKSKLVS  1020
DFRKDFQFYK VREINNYHHA HDAYLNAVVG TALIKKYPKL ESEFVYGDYK VYDVRKMIAK  1080
SEQEIGKATA KYFFYSNIMN FFKTEITLAN GEIRKRPLIE TNGETGEIVW DKGRDFATVR  1140
KVLSMPQVNI VKKTEVQTGG FSKESILPKR NSDKLIARKK DWDPKKYGGF DSPTVAYSVL  1200
VVAKVEKGKS KKLKSVKELL GITIMERSSF EKNPIDFLEA KGYKEVKKDL IIKLPKYSLF  1260
ELENGRKRML ASAGELQKGN ELALPSKYVN FLYLASHYEK LKGSPEDNEQ KQLFVEQHKH  1320
YLDEIIEQIS EFSKRVILAD ANLDKVLSAY NKHRDKPIRE QAENIIHLFT LTNLGAPAAF  1380
KYFDTTIDRK RYTSTKEVLD ATLIHQSITG LYETRIDLSQ LGGD                   1424

SEQ ID NO: 48           moltype = DNA   length = 330
FEATURE                 Location/Qualifiers
source                  1..330
                        mol_type = other DNA
                        organism = synthetic construct
                        note = Synthetic Construct
SEQUENCE: 48
ttggcgaaac cccatttcga cctttcggtc tcatcagggg tggcacacac caccctatgg    60
ggagaggtcg tcctctatct ctcctggaag gccggagcaa tccaaaagag gtacacccac   120
ccatgggtcg ggactttaaa ttcggaggat tcgtccttta aacgttcctc caagagtccc   180
ttccccaaac ccttactttg taagtgtggt tcggcgaatg taccgtttcg tcctttcgga   240
ctcatcaggg aaagtacaca cttttcgacg gtgggttcgt cgacacctct ccccctccca   300
ggtactatcc cctttccagg atttgttccc                                    330

SEQ ID NO: 49           moltype = DNA   length = 942
FEATURE                 Location/Qualifiers
source                  1..942
                        mol_type = unassigned DNA
                        organism = Arabidopsis thaliana
SEQUENCE: 49
acgagaggaa gtacattagt ttggagaaga gtaatagaca gagagataga gagaaagaga    60
agcagttcga agaaacaatg gcggtagaag acactcccaa atctgttgta acggaagaag   120
ctaagcctaa ttcaatagag aatccgattg atcgatacca tgaggaaggt gatgatgccg   180
aagaaggaga gatcgccgga ggagaaggag acggaaacgt tgacgaatcg agcaaatccg   240
gtgttcctga atcgcatcct ctggaacatt catggacttt ctggttcgat aatcctgctg   300
tgaaatcgaa acaaacctct tggggaagtt ccttgcgacc cgtgtttacg tttccaactg   360
ttgaggaatt tggagtttg tacaacaaca tgaagcatcc gagcaagtta gctcacggag   420
ctgacttcta ctgtttcaaa cacatcattg aacctaagtg gaggatcct atttgtgcta   480
atggaggaaa atggactatg acttttccca aggagaagtg tgataagagc tggctctaca   540
ctttgcttgc attgattgga gagcagtttg atcatggaga tgaaatatgt ggagcagttg   600
tcaacattag aggaaagcaa gaaggatat ctatttggac taaaaatgct tcaaacgaag   660
ctgctcaggt gagcattgga aaacaatgga aggagtttct cgattacaac aacagcatag   720
gtttcatcat ccatgaggat gcgaagaagc tcgacaggaa tgcaaagaac gcttacaccg   780
cttgaaacct ctcaaatctt tgcattgttt caattacagt tttgtatgtg agagatctct   840
```

```
atttatctaa acatgacttg acagtctgtc tttgctagtg ttgattgttc acgaagctct    900
aacatttcat ttagtaatat attagtatgg ttcttcataa ta                       942

SEQ ID NO: 50              moltype = DNA   length = 96
FEATURE                    Location/Qualifiers
source                     1..96
                           mol_type = other DNA
                           organism = synthetic construct
                           note = Synthetic Construct
misc_difference            1
                           note = misc_feature - n is a, c, g, or t
misc_difference            2
                           note = misc_feature - n is a, c, g, or t
misc_difference            3
                           note = misc_feature - n is a, c, g, or t
misc_difference            4
                           note = misc_feature - n is a, c, g, or t
misc_difference            5
                           note = misc_feature - n is a, c, g, or t
misc_difference            6
                           note = misc_feature - n is a, c, g, or t
misc_difference            7
                           note = misc_feature - n is a, c, g, or t
misc_difference            8
                           note = misc_feature - n is a, c, g, or t
misc_difference            9
                           note = misc_feature - n is a, c, g, or t
misc_difference            10
                           note = misc_feature - n is a, c, g, or t
misc_difference            11
                           note = misc_feature - n is a, c, g, or t
misc_difference            12
                           note = misc_feature - n is a, c, g, or t
misc_difference            13
                           note = misc_feature - n is a, c, g, or t
misc_difference            14
                           note = misc_feature - n is a, c, g, or t
misc_difference            15
                           note = misc_feature - n is a, c, g, or t
misc_difference            16
                           note = misc_feature - n is a, c, g, or t
misc_difference            17
                           note = misc_feature - n is a, c, g, or t
misc_difference            18
                           note = misc_feature - n is a, c, g, or t
misc_difference            19
                           note = misc_feature - n is a, c, g, or t
misc_difference            20
                           note = misc_feature - n is a, c, g, or t
SEQUENCE: 50
nnnnnnnnnn nnnnnnnnnn gttttagagc tagaaatagc aagttaaaat aaggctagtc     60
cgttatcaac ttgaaaaagt ggcaccgagt cggtgc                               96

SEQ ID NO: 51              moltype = DNA   length = 567
FEATURE                    Location/Qualifiers
source                     1..567
                           mol_type = unassigned DNA
                           organism = Pseudomonas aeruginosa
SEQUENCE: 51
atgggtgatc attatctgga tattcggctg aggcctgatc cagagttccc acctgcgcag     60
ctgatgtctg tcctttttgg caaacttcat caggccctgg ttgcccaggg cggagatcgg    120
ataggggtaa gctttccaga cctcgacgaa agccggagcc gcctgggaga acgcctgcgg    180
atccacgctt ctgccgacga tctgagagcc ttgctggcaa ggccatggct tgaggggctc    240
cgggatcacc tgcagtttgg cgaacccgcc gttgttcccc acccaacccc ttatcggcag    300
gtgtctagag tgcaggccaa atctaatcca gaacggctgc gacggcgact catgcggcga    360
catgatctta gcgaggaaga ggcccgaaaa agaatccctg ataccgtggc ccgcgcccct    420
gacttgcctt ttgtcacact gcggtccaag agtacgggc agcatttcag acttttcatt    480
cgacacgggc cactgcaagt taccgccgaa gaaggaggct tacttgtta tggactctcc    540
aagggaggtt tcgtgccctg gttttga                                        567

SEQ ID NO: 52              moltype = AA   length = 188
FEATURE                    Location/Qualifiers
source                     1..188
                           mol_type = protein
                           organism = Pseudomonas aeruginosa
SEQUENCE: 52
MGDHYLDIRL RPDPEFPPAQ LMSVLFGKLH QALVAQGGDR IGVSFPDLDE SRSRLGERLR     60
IHASADDLRA LLARPWLEGL RDHLQFGEPA VVPHPTPYRQ VSRVQAKSNP ERLRRRLMRR    120
HDLSEEEARK RIPDTVARAL DLPFVTLRSQ STGQHFRLFI RHGPLQVTAE EGGFTCYGLS    180
```

KGGFVPWF                                                                188

SEQ ID NO: 53            moltype = DNA   length = 20
FEATURE                  Location/Qualifiers
source                   1..20
                         mol_type = unassigned DNA
                         organism = Pseudomonas aeruginosa SEQUENCE: 53
gttcactgcc gtataggcag                                                    20

SEQ ID NO: 54            moltype = DNA   length = 272
FEATURE                  Location/Qualifiers
source                   1..272
                         mol_type = other DNA
                         organism = synthetic construct
                         note = Synthetic Construct
misc_difference          21
                         note = misc_feature - n is a, c, g, or t
misc_difference          22
                         note = misc_feature - n is a, c, g, or t
misc_difference          23
                         note = misc_feature - n is a, c, g, or t
misc_difference          24
                         note = misc_feature - n is a, c, g, or t
misc_difference          25
                         note = misc_feature - n is a, c, g, or t
misc_difference          26
                         note = misc_feature - n is a, c, g, or t
misc_difference          27
                         note = misc_feature - n is a, c, g, or t
misc_difference          28
                         note = misc_feature - n is a, c, g, or t
misc_difference          29
                         note = misc_feature - n is a, c, g, or t
misc_difference          30
                         note = misc_feature - n is a, c, g, or t
misc_difference          31
                         note = misc_feature - n is a, c, g, or t
misc_difference          32
                         note = misc_feature - n is a, c, g, or t
misc_difference          33
                         note = misc_feature - n is a, c, g, or t
misc_difference          34
                         note = misc_feature - n is a, c, g, or t
misc_difference          35
                         note = misc_feature - n is a, c, g, or t
misc_difference          36
                         note = misc_feature - n is a, c, g, or t
misc_difference          37
                         note = misc_feature - n is a, c, g, or t
misc_difference          38
                         note = misc_feature - n is a, c, g, or t
misc_difference          39
                         note = misc_feature - n is a, c, g, or t
misc_difference          40
                         note = misc_feature - n is a, c, g, or t
misc_difference          137
                         note = misc_feature - n is a, c, g, or t
misc_difference          138
                         note = misc_feature - n is a, c, g, or t
misc_difference          139
                         note = misc_feature - n is a, c, g, or t
misc_difference          140
                         note = misc_feature - n is a, c, g, or t
misc_difference          141
                         note = misc_feature - n is a, c, g, or t
misc_difference          142
                         note = misc_feature - n is a, c, g, or t
misc_difference          143
                         note = misc_feature - n is a, c, g, or t
misc_difference          144
                         note = misc_feature - n is a, c, g, or t
misc_difference          145
                         note = misc_feature - n is a, c, g, or t
misc_difference          146
                         note = misc_feature - n is a, c, g, or t
misc_difference          147
                         note = misc_feature - n is a, c, g, or t
misc_difference          148

| | | note = misc_feature - n is a, c, g, or t |
|---|---|---|
| misc_difference | 149 | |
| | | note = misc_feature - n is a, c, g, or t |
| misc_difference | 150 | |
| | | note = misc_feature - n is a, c, g, or t |
| misc_difference | 151 | |
| | | note = misc_feature - n is a, c, g, or t |
| misc_difference | 152 | |
| | | note = misc_feature - n is a, c, g, or t |
| misc_difference | 153 | |
| | | note = misc_feature - n is a, c, g, or t |
| misc_difference | 154 | |
| | | note = misc_feature - n is a, c, g, or t |
| misc_difference | 155 | |
| | | note = misc_feature - n is a, c, g, or t |
| misc_difference | 156 | |
| | | note = misc_feature - n is a, c, g, or t |

SEQUENCE: 54

```
gttcactgcc gtataggcag nnnnnnnnnn nnnnnnnnnn gttttagagc tagaaatagc    60
aagttaaaat aaggctagtc cgttatcaac ttgaaaaagt ggcaccgagt cggtgcgttc   120
actgccgtat aggcagnnnn nnnnnnnnnn nnnnngttt tagagctaga aatagcaagt   180
taaaataagg ctagtccgtt atcaacttga aaaagtggca ccgagtcggt gcgttcactg   240
ccgtataggc aggttcactg ccgtataggc ag                                272
```

| SEQ ID NO: 55 | moltype = DNA   length = 3213 |
|---|---|
| FEATURE | Location/Qualifiers |
| source | 1..3213 |
| | mol_type = unassigned DNA |
| | organism = Nicotiana tabacum |

SEQUENCE: 55

```
atgctcgggg atggaaatga gggaatatct acaatacctg gatttaatca gatacaattt    60
gaaggatttt gtaggttcat tgatcaaggt ttgacggaag aactttataa gtttccaaaa   120
attgaagata cagatcaaga aattgaattt caattatttg tggaaacata tcaattggtc   180
gaaccctga taaaggaaag agatgctgtg tatgaatcac tcacatattc ttctgaatta   240
tatgtatccg cgggattaat ttggaaaaac agtaggata tgcaagaaca acaattttt   300
atcggaaaca ttcctctaat gaattccctg gaacttcta tagtcaatgg aatatataga   360
attgtgatca atcaaatatt gcaaagtccc ggtatttatt accgatcaga attggaccat   420
aacggaattt cggtctatac cggcaccata atatcgatt ggggaggaag atcagaatta   480
gaaattgata gaaaagcaag gatatgggct cgtgtaagta ggaaacaaaa aatatctatt   540
ctagttctat catcagctat gggtttgaat ctaagagaaa ttctagagaa tgtttgctat   600
cctgaaattt ttttgtcttt tctgagtgat aaggagagaa aaaaattgg gtcaaaagaa   660
aatgccattt tggagtttta tcaacaattt gcttgtgtag gtggcgatcc ggtattttct   720
gaatccttat gtaaggaatt acaaaagaaa ttctttcaac aaagatgtga attaggaagg   780
attggtcgac gaaatatgaa ccgaagactg aaccttgata taccccagaa caatacatt   840
ttgttaccac gagatatatt ggcagccgcc gatcatttga ttgggctgaa atttggaatg   900
ggtgcacttg acgatatgaa tcatttgaaa ataaacgta ttcgttctgt agcagatctt   960
ttacaagatc aattcggatt ggctctggtt cgtttagaaa atgtggttcg ggggactata  1020
tgtgagcaa ttcggcataa attgataccg acacctcaga atttggtaac ctcaactcca  1080
ttaacaacta cttatgaatc cttttcggt ttacacccat tatctcaagt tttggatcga  1140
actaatccat tgacacaaat agttcatggg agaaaattaa gttatttggg ccctggagga  1200
ctgacagggc gcactgctag ttttcggata cgagatatcc atcctagtca ctatggacgt  1260
atttgcccaa ttgacacatc tgaaggaatc aatgttggac ttattggatc cttagcaatt  1320
catgcgagga ttggtcattg gggatctcta gaaagccctt tttatgaaat ttctgagagg  1380
tcaaccgggg tacggatgct ttatttatca ccaggtagag atgaatacta tatggtagcg  1440
gcaggaaatt ctttagcctt aaatcaggat attcaggaag aacaggttgt tccagctcga  1500
taccgtcaag aattcttgac tattgcatgg gaacaggttc atcttcgaag tatttttcct  1560
tttcaatatt tttctattgg agcttccctc attccttta tcgaacataa tgatgcgaat  1620
cgagcttta tgagttctaa tatgcaacgt caagcagttc ctctttctcg ctccgagaaa  1680
tgcattgttg gaactgggtt ggaacgacaa gcagctctag attcgggggc tcttgctata  1740
gccgaacgcg agggaaggt cgtttatacc aatactgaca agattctttt agcaggtaat  1800
ggagatattc taagcattcc attagttata tatcaacgtt ccaataaaaa tacttgtatg  1860
catcaaaaac tccaggttcc tcggggtaaa tgcattaaaa agggacaaat tttagcggat  1920
ggtgctgcta cggttggtgg cgaacttgct ttggggaaaa acgtattagt agcttatatg  1980
ccgtgggagc gttacaattc tgaagatgca gtacttatta gcgagcgttt ggtatattga  2040
gatatttata cttcttttca catacgaaa atgaaattc agactcatgt gacaagccaa  2100
ggccctgaaa agtaactaa tgaaataccg catttagaag cccatttact ccgcaattta  2160
gataaaaatg gaattgtgat gctgggatct tgggtagaga caggtgatat tttagtaggt  2220
aaattaacac cccaggtcgt gaaagaatcg tcgtatgccc cggaagatag attgttacga  2280
gctatacttg gtattcaggt atctacttca aaagaaactt gtctaaaact acctatggt  2340
ggcaggggtc gggttattga tgtgaggtgg atccagaaga ggggtggttc tagttataat  2400
cccgaaacga ttcgtgtata tattttacag aaacgtgaaa tcaaagtagg cgataaagta  2460
gctggaagac acgaaataa aggtatcatt tccaaaattt tgcctagaca agatatgcct  2520
tatttacaag atggaagatc cgttgatatg gtctttaacc cattaggagt accttcacga  2580
atgaatgtag gacagatatt tgaatgttca ctagggttag cagggagtct gctagacaga  2640
cattatcgaa tagcacccttt tgatgagaga tatgaacaag aagcttcgag aaaacttgtg  2700
ttttctgaat tatatgaagc cagtaagcaa acagcgaatc catgggtatt tgaacccgaa  2760
tatccaggaa aaagcagaat atttgatgga aggacgggga tcctttttga caacccgtt  2820
ataataggaa agccttatat cttgaaatta attcatcaag ttgatgataa aatccatggg  2880
cgctccagtg gacattatgc gcttgttaca caacaacccc ttagagaag agccaaacag  2940
```

```
ggggggacagc gggtaggaga aatggaggtt tgggctctag aagggtttgg ggttgctcat   3000
attttacaag agatgcttac ttataaatcg gatcatatta gagctcgcca ggaagtactt   3060
ggtactacga tcattggggg aacaatacct aatcccgaag atgctccaga atcttttcga   3120
ttgctcgttc gagaactacg atctttagct ctggaactga atcatttcct tgtatctgag   3180
aagaacttcc agattaatag gaaggaagct taa                                3213

SEQ ID NO: 56          moltype = DNA   length = 20
FEATURE                Location/Qualifiers
source                 1..20
                       mol_type = unassigned DNA
                       organism = Nicotiana tabacum
SEQUENCE: 56
ttagaggaag agccaaacag                                                 20

SEQ ID NO: 57          moltype = DNA   length = 20
FEATURE                Location/Qualifiers
source                 1..20
                       mol_type = unassigned DNA
                       organism = Nicotiana tabacum
SEQUENCE: 57
cttgctatag ccgaacgcga                                                 20

SEQ ID NO: 58          moltype = DNA   length = 1062
FEATURE                Location/Qualifiers
source                 1..1062
                       mol_type = unassigned DNA
                       organism = Nicotiana tabacum
SEQUENCE: 58
atgactgcaa ttttagagag acgcgaaagc gaaagcctat ggggtcgctt ctgtaactgg     60
ataactagca ctgaaaaccg tctttacatt ggatggtttg gtgttttgat gatccctacc    120
ttattgacgg caacttctgt atttattatt gccttcattg ctgctcctcc agtagacatt    180
gatggtattc gtgaacctgt ttcagggtct ctacttacg gaaacaatat tatttccggt     240
gccattattc ctacttctgc agctataggt ttacattttt acccaatctg ggaagcggca    300
tccgttgatg aatggttata caacggtggt ccttatgaac taattgttct acacttctta    360
cttggcgtag cttgttacat gggtcgtgag tgggagctta gtttccgtct gggtatgcga    420
ccttggattg ctgttgcata ttcagctcct gttgcagctg ctaccgcagt tttcttgatc    480
tacccaattg gtcaaggaag ttttttctga tggtatgcctc taggaatctc tggtactttc    540
aatttcatga ttgtattcca ggctgagcac aacatcctta tgcacccatt tcacatgtta    600
ggcgtagctg gtgtattcgg cggctcccta ttcagtgcta tgcatggttc cttggtaact    660
tctagtttga tcagggaaac cacagaaaat gaatctgcta atgaaggtta cagattcggt    720
caagaggaag aaacttataa catcgtagcc gctcatggtt atttggccg attgatcttc     780
caatatgcta gtttcaacaa ctctcgttcg ttacacttct tcctagctgc ttggcctgta    840
gtaggtatct ggtttaccgc tttaggtatc agcactatgg ctttcaacct aaatggtttc    900
aatttcaacc aatctgtagt tgacagtcaa ggccgtgtaa ttaatacttg ggctgatatc    960
attaaccgtg ctaaccttgg tatggaagtt atgcatgaac gtaatgctca caacttccct   1020
ctagacctag ctgctatcga agctccatct acaaatggat aa                      1062

SEQ ID NO: 59          moltype = DNA   length = 20
FEATURE                Location/Qualifiers
source                 1..20
                       mol_type = unassigned DNA
                       organism = Nicotiana tabacum
SEQUENCE: 59
gttgatgaat ggttatacaa                                                 20

SEQ ID NO: 60          moltype = DNA   length = 20
FEATURE                Location/Qualifiers
source                 1..20
                       mol_type = unassigned DNA
                       organism = Nicotiana tabacum
SEQUENCE: 60
gatgatccct accttattga                                                 20

SEQ ID NO: 61          moltype = DNA   length = 264
FEATURE                Location/Qualifiers
source                 1..264
                       mol_type = unassigned DNA
                       organism = Nicotiana tabacum
SEQUENCE: 61
atggtaaaaa attctgtcat ttcagttatt tctcaagaag aaaagagagg atctgttgaa     60
tttcaagtat tcaatttcac caataagata cggagactta cttcacattt agaattgcac    120
aaaaagact atttatctca gagaggtttg aagaaaattt gggaaaacg tcaacgactc      180
ctagcttatt tgtcaaaaaa aaatagagta cgttataaag aattaattaa tcagttggac    240
attcgagaga caaaaactcg ttaa                                            264

SEQ ID NO: 62          moltype = DNA   length = 20
FEATURE                Location/Qualifiers
source                 1..20
                       mol_type = unassigned DNA
```

```
                                organism = Nicotiana tabacum
SEQUENCE: 62
atttctcaag aagaaaagag                                                      20

SEQ ID NO: 63           moltype = DNA  length = 20
FEATURE                 Location/Qualifiers
source                  1..20
                        mol_type = unassigned DNA
                        organism = Nicotiana tabacum
SEQUENCE: 63
tcaatttcac caataagata                                                      20

SEQ ID NO: 64           moltype = DNA  length = 201
FEATURE                 Location/Qualifiers
source                  1..201
                        mol_type = unassigned DNA
                        organism = Nicotiana tabacum
SEQUENCE: 64
atggccaagg ggaaagatgt ccgagtaacg gtgattttgg aatgtactag ttgtgtccga          60
aacagtgttg ataaggtatc aagaggtatt tccagatata ttactcaaaa gaaccggcac         120
aatacgccta atcgattaga attgaaaaaa ttctgtccct attgttacaa acatacgatt         180
catggggaga taaagaaata g                                                   201

SEQ ID NO: 65           moltype = DNA  length = 20
FEATURE                 Location/Qualifiers
source                  1..20
                        mol_type = unassigned DNA
                        organism = Nicotiana tabacum
SEQUENCE: 65
gatatattac tcaaaagaac                                                      20

SEQ ID NO: 66           moltype = DNA  length = 20
FEATURE                 Location/Qualifiers
source                  1..20
                        mol_type = unassigned DNA
                        organism = Nicotiana tabacum
SEQUENCE: 66
agtgttgata aggtatcaag                                                      20

SEQ ID NO: 67           moltype = DNA  length = 3213
FEATURE                 Location/Qualifiers
source                  1..3213
                        mol_type = unassigned DNA
                        organism = Glycine max
SEQUENCE: 67
atgcttgggg atggaaatga aggaatgtct acactacctg gattgaatca gatacaattt          60
gaagggtttt gtaggttcat tgatcggggc ttaccagaag ggcttttta gtttccaaaa         120
attgaggata cagatcaaga aattgaattt caattatttg tagaaacata tcaattatta         180
gaacccttga taaacgaaaa agatgctgta tatgaatcgc ttacatattc tgctgaatta         240
tatgtatctg cgggattaat ttggaaaagt agtagggaca tacaagaaca aactattttt         300
gttggaaaca ttcctttaat gaattctctg ggaacttcta tagtaaatgg aatatacaga         360
attgtaatca atcaaatatt gcaaagccct ggtatttatt accgttcaga attggaccct         420
agcggaattt cggtctatac tggcaccata atatcgagact gggggggtag attagaatta         480
gagattgata gaaaagcaag gatatgggct cgtgtgagta ggaaacgaaa aatatctatt         540
ctagttttat catcagctat gggttcgaat ttaagcgaaa ttctagagaa tgtttggttat         600
cctgaaattt tcgtttcttt cctaaatgat aaggataaaa aaaaaatagg gtcaaaagaa         660
aatgccattt tggagtttta tcgacaattt gcttgtgttg gtggagatcc agtattttct         720
gaatctttat gtaaagaatt acaaaaaaaa tttttttcaac aaagatgtga attaggaagg         780
attggtcgac gaaatatgaa ccaaaagctt aatcttgata tacctcagaa caatacattt         840
ttgttaccac gagatatatt gacagctgcg gatcatttga ttggaatgaa atttggaatg         900
ggtacacttg acgatataaa tcatttgaaa aataaacgta ttcgttcggt agcagatcta         960
ttacaagatc aatttggatt ggccctggtt cgtttagaaa atatggttag aggaactata        1020
tgtggagcaa ttagacataa attgataccg actcctcaga atttggtgac ttcaactcca        1080
ttaacaacta cttatgaatc ttttttttgga ttacatccat tatctcaagt tttggatcaa        1140
actaatccat tgacccaaat agttcatggg agaaaaattga gttatttggg ccctggagga        1200
ttgacgggggc gaactgctag ttttcggata cgagatatcc accctagtca ctatggacgc        1260
atttgtccaa ttgacacgtc ggaaggaatc aatgttggac ttattggatc tctagcaatt        1320
catgcgagga ttggtagttg ggggtccata gaaagtccat tttatgaaat atctgagaga        1380
tcaaaaagaa tacgcatgct ttatttatca ccaagtagga atgaatacta tatggtagca        1440
acaggaaatt ctttggcact taatcgagat attcaggagg aacagactgt tccagcccga        1500
taccgtcaag aatttcttac gattgcatgg aacaggttc atcttcgaag tatttttccc         1560
ttccaatatt tttctattgg agcttctctg attccttttta ttgaacataa tgatgccaat        1620
cgagctttaa tgagttctaa tatgcaacgt caagcagttc cgctttctca gtccgaaaaa        1680
tgcattgttg gaactggatt ggaacgccaa gtagcttag attcaggggt ttccgctata        1740
gccgaacacg agggaaacat catttatacc aatactgaca ggatatttt atttggtaat        1800
ggagatactc taagcattcc attaactata tatcaacgtt ccaacaaaaa tacttgtatg        1860
catcaaaaac cccaggttcg ccgaggtaaa tgtataaaaa agggacaaat tttagcggat        1920
ggtgctgcta cagttgacgg cgaactcgct ttggaaaaaa acgtcttagt agcttatatg        1980
ccatgggaag gttacaattc tgaagatgct gtactcatta atgagcgtct ggtctatgaa        2040
```

```
gatatttata cttcttttca catacgaaa tatgaaattc agactcatat gacaagctat    2100
ggttctgaaa gaatcactaa taaaattcca catctagaag cccatttact cagaaattta    2160
gacaaaaatg gaattgtgat cctcgggtcg tgggtagaaa cgggtgatat tttagtgggt    2220
aaattaacac ctcaaatggc aaaagaatcc tcgtattccc ccgaagatag attattacga    2280
gctatacttg gcattcaggt atccacctca aaggaaactt gtctaaaact acctacaggc    2340
ggtaggggta gagttattga tgtgagatgg atccaaaaaa aggggggttc cagttataat    2400
ccagaaacga ttcgtatata tattttacag aaacgtgaaa ttaaagtagg agataaagtg    2460
gctgggagac atggaaataa aggtatcgtt tcaaaaattt tgtctagaca ggatatgcct    2520
tatttgcaag atggaagacc cgttgatatg gtcttcaatc cactaggggt accttcacga    2580
atgaatgtag gacaaatatt tgaatgctcg ctcgggttag caggaggtat gctagaaaga    2640
cattatcgaa taacacctt tgatgagaga tatgaacaag aagcttcgag aaaactagtg    2700
ttttctgaat tatatgaagc cagtaaacaa acatctaatc catggatatt tgaacccgag    2760
tatccaggaa aaagcaaaat ctttgatgga agaacaggga attcttttaa acagcctgct    2820
ataatgggaa aaccttatat tttgaaatta attcatcaag ttgatgataa aatacatgga    2880
cgttccagtg gacattatgc acttgttaca caacaaccac ttagaggaag ggccaagcag    2940
ggaggacaac gggtaggcga aatggaggtt tgggccttgg aaggatttgg tgttgctcat    3000
attttacaag agatgcttac ttataaatct gatcatatta aaactcgcca agaagtactc    3060
gggactacga tcattggagg aacaatacct aaacctacag atgctccaga atcttttaga    3120
ttgctagttc gagaattacg atctttagct atggaactga atcattccct tgtatccgag    3180
aagaacttcc ggattcatag gaaggaagct taa                                3213

SEQ ID NO: 68           moltype = DNA   length = 20
FEATURE                 Location/Qualifiers
source                  1..20
                        mol_type = unassigned DNA
                        organism = Glycine max
SEQUENCE: 68
tgtctaaaac tacctacagg                                                20

SEQ ID NO: 69           moltype = DNA   length = 20
FEATURE                 Location/Qualifiers
source                  1..20
                        mol_type = unassigned DNA
                        organism = Glycine max
SEQUENCE: 69
agcggaattt cggtctatac                                                20

SEQ ID NO: 70           moltype = DNA   length = 1062
FEATURE                 Location/Qualifiers
source                  1..1062
                        mol_type = unassigned DNA
                        organism = Glycine max
SEQUENCE: 70
atgactgcaa ttttagagag acgcgagagc gaaagcctat ggggtcgctt ctgtaactgg      60
ataaccagca ccgaaaatcg tcttttacatt ggatggtttg gtgttttgat gattcctact     120
ttattgaccg caacttctgt atttattatc gcttttattg ctgcccctcc agtagatatt     180
gatggtattc gtgagcctgt ttctggatct ctacttttgg gaaacaatat catttctgtt     240
gccattattc ctacttctgc ggctataggt ttgcactttt atcctatttg ggaagcggca     300
tctgttgatg aatggttata caacggcggt ccttatgaac taattgttct acacttctta     360
cttggtgtag cttgctacat ggggcgtgag tgggaactta gttttcgttt gggtatgcgt     420
ccttgattg ctgttgcata ttcagctcct gttgcagccg ctactgctgt tttcttgatg     480
tatcctattg gtcagggaag cttttcagat ggtatgcctc taggaatttc aggtactttc     540
aattttatga ttgtatttca ggctgagcat aaatattctta tgcatccatt tcacatgtta     600
ggtgtagctg gtgtattcgg cggctcccta ttcagtgcta tgcatggttc cttggtaact     660
tctagtttga tcaggggaaac cacagaaaat gaatctgtca atgaaggtta cagatttggt     720
caagaggaag aaacctataa tattgtagct gctcatggtt attttggccg attgatcttc     780
caatatgcaa gttcaacaa ttctcgttct ttacattttct tcttagctgc ttggcctgta     840
gtaggtattt ggtttaccgc tttaggtatc agcactatgg ctttcaactt aaatggtttc     900
aatttcaacc aatccgtagt tgatagtcaa ggtcgtgtaa ttaatacctg ggctgatatt     960
attaaccgag ctaaccttgg tatgaagta atgcatgaac gtaatgctca taatttccct    1020
ctagatcgag ctgcgatcga cgctccatct attaatggat aa                       1062

SEQ ID NO: 71           moltype = DNA   length = 20
FEATURE                 Location/Qualifiers
source                  1..20
                        mol_type = unassigned DNA
                        organism = Glycine max
SEQUENCE: 71
ggtgtagctg gtgtattcgg                                                20

SEQ ID NO: 72           moltype = DNA   length = 20
FEATURE                 Location/Qualifiers
source                  1..20
                        mol_type = unassigned DNA
                        organism = Glycine max
SEQUENCE: 72
tctagatcta gctgcgatcg                                                20

SEQ ID NO: 73           moltype = DNA   length = 273
```

| FEATURE | Location/Qualifiers |
|---|---|
| source | 1..273<br>mol_type = unassigned DNA<br>organism = Glycine max |

SEQUENCE: 73

```
atggtaaaaa attcaattat acctgttatt tcacaagaaa aaaagaaaa aaacccagga    60
tcggttgaat ttcaaatatt caaatttacc gatagaatac gaagacttac ttcacatttt   120
gaattgcacc gaaaagacta tttatctcaa agaggtttac gtaaaatttt gggaaaacga   180
caaagattgc tgtcttattt gtcaaagaaa gatagaatac ggtataaaaa attaataaat   240
cagtttgata ttcgagagtc acaaattcgt taa                                273
```

| SEQ ID NO: 74 | moltype = DNA  length = 20 |
|---|---|
| FEATURE | Location/Qualifiers |
| source | 1..20<br>mol_type = unassigned DNA<br>organism = Glycine max |

SEQUENCE: 74

```
atagaatacg aagacttact                                                20
```

| SEQ ID NO: 75 | moltype = DNA  length = 20 |
|---|---|
| FEATURE | Location/Qualifiers |
| source | 1..20<br>mol_type = unassigned DNA<br>organism = Glycine max |

SEQUENCE: 75

```
tgtcaaagaa agatagaata                                                20
```

| SEQ ID NO: 76 | moltype = DNA  length = 201 |
|---|---|
| FEATURE | Location/Qualifiers |
| source | 1..201<br>mol_type = unassigned DNA<br>organism = Glycine max |

SEQUENCE: 76

```
atggccaaag gtaaagatat ccgagtaatt gttattttgg aatgtaccgg ttgtgataaa    60
aagagtgtta ataaggaatc aacgggtatt tctagatata taactaaaag gaatcgacag   120
aatacgccta gtcgattgga attgagaaaa ttttgtcccc gttgttgcaa acatacaatt   180
cacgcagaaa taaagaaata g                                             201
```

| SEQ ID NO: 77 | moltype = DNA  length = 20 |
|---|---|
| FEATURE | Location/Qualifiers |
| source | 1..20<br>mol_type = unassigned DNA<br>organism = Glycine max |

SEQUENCE: 77

```
cgttgttgca acatacaat                                                 20
```

| SEQ ID NO: 78 | moltype = DNA  length = 20 |
|---|---|
| FEATURE | Location/Qualifiers |
| source | 1..20<br>mol_type = unassigned DNA<br>organism = Glycine max |

SEQUENCE: 78

```
acagaatacg cctagtcgat                                                20
```

| SEQ ID NO: 79 | moltype = DNA  length = 864 |
|---|---|
| FEATURE | Location/Qualifiers |
| source | 1..864<br>mol_type = unassigned DNA<br>organism = unidentified<br>note = Nicotiana benthamiana |

SEQUENCE: 79

```
gtgcgacttg aaggacagga tccgttgtgg atttgtacat ccaccatttt atgtaggaat    60
gaaggtgctc ttggctcgac atcattggtt ctgtttcatt agattagaac ccctcttttt   120
tgttgtcttg gaatgtaaat agtccatgat ggagctcgag tagaaagtat taatttattt   180
ctcggggcaa gagtctaggg ttaatgccaa tcaataaaaa aattggaaca acttcgtaaa   240
tgtattttcg gtatggaaat cgaaagaatc caattcgagc aagtttccaa ttcaaaaatt   300
tcttggaatt gatcaaactt tttcgatcca agtgtttca cgcgggaatc catcgtctgt    360
aggattcttt catagaaatc gcaaaagggg tatgttgctg ccattttgaa aggattaaaa   420
agcaccgaag taatgtctaa acccaatgat ttaaaataaa acaaagataa aggatcccag   480
aacaaggaaa cacctttttt attgtcttaa taactggatc gaactgaaga atccaaatcc   540
attttaaacg agacaaacat aaaaggagga agaccgctc aataaatgaa attgccgaaa    600
gattttcctt tgaactgttt gaaagttatc caacttgagt tatgagagta cgaatggttt   660
cttttcatt ttcaggaaga aagaagaaaa aaaagactta catctttaat tgatttgatc    720
attttatgga cccagttgtc atttcttaga tagaattcca tacagagata aaacctcgaa   780
tcaatcattt ttctcgagcc gtacgaggag aaagcttcct atacgtttct aggggggtg    840
ttgttcatct acatctatcc caat                                          864
```

| SEQ ID NO: 80 | moltype = DNA  length = 20 |
|---|---|
| FEATURE | Location/Qualifiers |

```
source                    1..20
                          mol_type = unassigned DNA
                          organism = unidentified
                          note = Nicotiana benthamiana
SEQUENCE: 80
ttgtggattt gtacatccac                                                     20

SEQ ID NO: 81             moltype = DNA   length = 20
FEATURE                   Location/Qualifiers
source                    1..20
                          mol_type = unassigned DNA
                          organism = unidentified
                          note = Nicotiana benthamiana
SEQUENCE: 81
ttgaactgtt tgaaagttat                                                     20

SEQ ID NO: 82             moltype = DNA   length = 1578
FEATURE                   Location/Qualifiers
source                    1..1578
                          mol_type = unassigned DNA
                          organism = unidentified
                          note = Nicotiana benthamiana
SEQUENCE: 82
tttcaaatgg aagaaatcca aagatattta cagccagata gatcgcaaca acacaacttc         60
ctatatccac ttatctttca ggagtatatt tatgcacttg ctcatgatca tggtttaaat        120
agaaacaagt cgattttgtt ggaaaatcca ggttataaca ataaatttag tttcctaatt        180
gtgaaacgtt taattacccg aatgtatcaa cagaatcatt ttcttatttc tactaatgat        240
tctaacaaaa attcattttt ggggtgcaac aagagtttgt attctcaaat gatatcagag        300
ggatttgcgt ttattgtgga aattccgttt tctctacgat taatatcttc tttatcttct        360
ttcgaaggca aaaaggtttt taaatctcat aatttacgat caattcattc aacatttcct        420
tttttagagg acaattttc acatctaaat tatgtattag atatactaat accctacccc         480
gttcatctgg aaatcttggt tcaaactctt cgctattggg taaaagatgc ctcttcttta        540
catttattac gattctttct ccatgaatat tggaatttga atagtcttat tacttcaaag        600
aagcccggtt actcctttc aaaaaaaat caaagattct tcttcttctt atataattct          660
tatgtatatg aatgcgaatc cactttcgtc tttctacgga accaatcttc tcatttacga        720
tcaacatctt ttggagcct tcttgaacga atatatttct atggaaaaat agaacgtctt         780
gtagaagtct tgctaagga ttttcaggtt acctatggt tattcaagga tcttttcatg         840
cattatgtta ggtatcaagg aaaatccatt ctggcttcaa aagggacgtt tcttttgatg        900
aataaatgga aattttaccct tgtcaattt tggcaatgtc attttctct gtgctttcac        960
acaggaagga tccatataaa ccaattatcc aatcatccc gtaactttat gggctatctt       1020
tcaagtgtgc gactaaatcc ttcaatggta cgtagtcaaa tgttagaaaa tcatttcta        1080
atcaataatg caattaagaa gttcgatacc cttgttccaa ttattccttt gattggatca       1140
ttagctaaag caaacttttg taccgtatta gggcatccca ttagtaaacc ggtttggtcc       1200
gatttatcag attctgatat tattgaccga tttgggcgta tatgcagaaa tcttttttcat      1260
tattatagcg gatcttccaa aaaaaagact ttatatcgaa taaagtatat acttcgactt       1320
tcttgtgcta gaacttagc tcggaaacac aaaagtactg tacgcacttt tttgaaaaga       1380
tcgggctcgg aattattgga agaattttta acgtcggaag aacaagttct ttctttgacc       1440
ttcccacgag cttcttctag tttgtgggga gtatataagaa gtcggatttg gtatttggat     1500
attttttgta tcaatgatct ggcgaattat caatgattca ttcttagatt ttctaaatat       1560
aaatttgttt ctaaatga                                                    1578

SEQ ID NO: 83             moltype = DNA   length = 20
FEATURE                   Location/Qualifiers
source                    1..20
                          mol_type = unassigned DNA
                          organism = unidentified
                          note = Nicotiana benthamiana
SEQUENCE: 83
cttgtgctag aactttagct                                                     20

SEQ ID NO: 84             moltype = DNA   length = 20
FEATURE                   Location/Qualifiers
source                    1..20
                          mol_type = unassigned DNA
                          organism = unidentified
                          note = Nicotiana benthamiana
SEQUENCE: 84
cgttcatctg gaaatcttgg                                                     20

SEQ ID NO: 85             moltype = DNA   length = 20
FEATURE                   Location/Qualifiers
source                    1..20
                          mol_type = unassigned DNA
                          organism = Nicotiana tabacum
SEQUENCE: 85
aagaacttcc cccttgacag                                                     20

SEQ ID NO: 86             moltype = DNA   length = 20
FEATURE                   Location/Qualifiers
```

```
source                  1..20
                        mol_type = unassigned DNA
                        organism = Nicotiana tabacum
SEQUENCE: 86
tatacaggat gggtagaaag                                                       20

SEQ ID NO: 87           moltype = DNA  length = 20
FEATURE                 Location/Qualifiers
source                  1..20
                        mol_type = unassigned DNA
                        organism = Nicotiana tabacum
SEQUENCE: 87
atataatttt taataaaggg                                                       20

SEQ ID NO: 88           moltype = DNA  length = 20
FEATURE                 Location/Qualifiers
source                  1..20
                        mol_type = unassigned DNA
                        organism = Nicotiana tabacum
SEQUENCE: 88
ctagtcttcg acacaagaaa                                                       20

SEQ ID NO: 89           moltype = DNA  length = 20
FEATURE                 Location/Qualifiers
source                  1..20
                        mol_type = unassigned DNA
                        organism = Glycine max
SEQUENCE: 89
ataacagaag ttaaagaaga                                                       20

SEQ ID NO: 90           moltype = DNA  length = 20
FEATURE                 Location/Qualifiers
source                  1..20
                        mol_type = unassigned DNA
                        organism = Glycine max
SEQUENCE: 90
atctggaaac catagaacag                                                       20

SEQ ID NO: 91           moltype = DNA  length = 20
FEATURE                 Location/Qualifiers
source                  1..20
                        mol_type = unassigned DNA
                        organism = Glycine max
SEQUENCE: 91
ctatttcgac acaacaaga                                                        20

SEQ ID NO: 92           moltype = DNA  length = 20
FEATURE                 Location/Qualifiers
source                  1..20
                        mol_type = unassigned DNA
                        organism = Glycine max
SEQUENCE: 92
ctttctttga cgaattcgag                                                       20

SEQ ID NO: 93           moltype = DNA  length = 36
FEATURE                 Location/Qualifiers
source                  1..36
                        mol_type = unassigned DNA
                        organism = Nicotiana tabacum
SEQUENCE: 93
acgagagttg ttgaaactag catattggaa gatcaa                                     36

SEQ ID NO: 94           moltype = DNA  length = 36
FEATURE                 Location/Qualifiers
source                  1..36
                        mol_type = other DNA
                        organism = synthetic construct
                        note = Synthetic Construct
SEQUENCE: 94
acgagagtta ttgaatgtag catactgaaa gatcaa                                     36

SEQ ID NO: 95           moltype = AA  length = 14
FEATURE                 Location/Qualifiers
source                  1..14
                        mol_type = protein
                        organism = Saccharomyces cerevisiae
SEQUENCE: 95
MVLPRLYTAT SRAA                                                             14
```

```
SEQ ID NO: 96              moltype = AA  length = 1384
FEATURE                    Location/Qualifiers
source                     1..1384
                           mol_type = protein
                           organism = synthetic construct
                           note = Synthetic Construct
SEQUENCE: 96
MVLPRLYTAT SRAALSTDKK YSIGLDIGTN SVGWAVITDE YKVPSKKFKV LGNTDRHSIK    60
KNLIGALLFD SGETAEATRL KRTARRRYTR RKNRICYLQE IFSNEMAKVD DSFFHRLEES   120
FLVEEDKKHE RHPIFGNIVD EVAYHEKYPT IYHLRKKLVD STDKADLRLI YLALAHMIKF   180
RGHFLIEGDL NPDNSDVDKL FIQLVQTYNQ LFEENPINAS GVDAKAILSA RLSKSRRLEN   240
LIAQLPGEKK NGLFGNLIAL SLGLTPNFKS NFDLAEDAKL QLSKDTYDDD LDNLLAQIGD   300
QYADLFLAAK NLSDAILLSD ILRVNTEITK APLSASMIKR YDEHHQDLTL LKALVRQQLP   360
EKYKEIFFDQ SKNGYAGYID GGASQEEFYK FIKPILEKMD GTEELLVKLN REDLLRKQRT   420
FDNGSIPHQI HLGELHAILR RQEDFYPFLK DNREKIEKIL TFRIPYYVGP LARGNSRFAW   480
MTRKSEETIT PWNFEEVVDK GASAQSFIER MTNFDKNLPN EKVLPKHSLL YEYFTVYNEL   540
TKVKYVTEGM RKPAFLSGEQ KKAIVDLLFK TNRKVTVKQL KEDYFKKIEC FDSVEISGVE   600
DRFNASLGTY HDLLKIIKDK DFLDNEENED ILEDIVLTLT LFEDREMIEE RLKTYAHLFD   660
DKVMKQLKRR RYTGWGRLSR KLINGIRDKQ SGKTILDFLK SDGFANRNFM QLIHDDSLTF   720
KEDIQKAQVS GQGDSLHEHI ANLAGSPAIK KGILQTVKVV DELVKVMGRH KPENIVIEMA   780
RENQTTQKGQ KNSRERMKRI EEGIKELGSQ ILKEHPVENT QLQNEKLYLY YLQNGRDMYV   840
DQELDINRLS DYDVDHIVPQ SFLKDDSIDN KVLTRSDKNR GKSDNVPSEE VVKKMKNYWR   900
QLLNAKLITQ RKFDNLTKAE RGGLSELDKA GFIKRQLVET RQITKHVAQI LDSRMNTKYD   960
ENDKLIREVK VITLKSKLVS DFRKDFQFYK VREINNYHHA HDAYLNAVVG TALIKKYPKL  1020
ESEFVYGDYK VYDVRKMIAK SEQEIGKATA KYFFYSNIMN FFKTEITLAN GEIRKRPLIE  1080
TNGETGEIVW DKGRDFATVR KVLSMPQVNI VKKTEVQTGG FSKESILPKR NSDKLIARKK  1140
DWDPKKYGGF DSPTVAYSVL VVAKVEKGKS KKLKSVKELL GITIMERSSF EKNPIDFLEA  1200
KGYKEVKKDL IIKLPKYSLF ELENGRKRML ASAGELQKGN ELALPSKYVN FLYLASHYEK  1260
LKGSPEDNEQ KQLFVEQHKH YLDEIIEQIS EFSKRVILAD ANLDKVLSAY NKHRDKPIRE  1320
QAENIIHLFT LTNLGAPAAF KYFDTTIDRK RYTSTKEVLD ATLIHQSITG LYETRIDLSQ  1380
LGGD                                                              1384

SEQ ID NO: 97              moltype = AA  length = 12
FEATURE                    Location/Qualifiers
source                     1..12
                           mol_type = protein
                           organism = Saccharomyces cerevisiae
SEQUENCE: 97
MKSFITRNKT AI                                                      12

SEQ ID NO: 98              moltype = AA  length = 1379
FEATURE                    Location/Qualifiers
source                     1..1379
                           mol_type = protein
                           organism = synthetic construct
                           note = Synthetic Construct
SEQUENCE: 98
MKSFITRNKT AIDKKYSIGL DIGTNSVGWA VITDEYKVPS KKFKVLGNTD RHSIKKNLIG    60
ALLFDSGETA EATRLKRTAR RRYTRRKNRI CYLQEIFSNE MAKVDDSFFH RLEESFLVEE   120
DKKHERHPIF GNIVDEVAYH EKYPTIYHLR KKLVDSTDKA DLRLIYLALA HMIKFRGHFL   180
IEGDLNPDNS DVDKLFIQLV QTYNQLFEEN PINASGVDAK AILSARLSKS RRLENLIAQL   240
PGEKKNGLFG NLIALSLGLT PNFKSNFDLA EDAKLQLSKD TYDDDLDNLL AQIGDQYADL   300
FLAAKNLSDA ILLSDILRVN TEITKAPLSA SMIKRYDEHH QDLTLLKALV RQQLPEKYKE   360
IFFDQSKNGY AGYIDGGASQ EEFYKFIKPI LEKMDGTEEL LVKLNREDLL RKQRTFDNGS   420
IPHQIHLGEL HAILRRQEDF YPFLKDNREK IEKILTFRIP YYVGPLARGN SRFAWMTRKS   480
EETITPWNFE EVVDKGASAQ SFIERMTNFD KNLPNEKVLP KHSLLYEYFT VYNELTKVKY   540
VTEGMRKPAF LSGEQKKAIV DLLFKTNRKV TVKQLKEDYF KKIECFDSVE ISGVEDRFNA   600
SLGTYHDLLK IIKDKDFLDN EENEDILEDI VLTLTLFEDR EMIEERLKTY AHLFDDKVMK   660
QLKRRRYTGW GRLSRKLING IRDKQSGKTI LDFLKSDGFA NRNFMQLIHD DSLTFKEDIQ   720
KAQVSGQGDS LHEHIANLAG SPAIKKGILQ TVKVVDELVK VMGRHKPENI VIEMARENQT   780
TQKGQKNSRE RMKRIEEGIK ELGSQILKEH PVENTQLQNE KLYLYYLQNG RDMYVDQELD   840
INRLSDYDVD HIVPQSFLKD DSIDNKVLTR SDKNRGKSDN VPSEEVVKKM KNYWRQLLNA   900
KLITQRKFDN LTKAERGGLS ELDKAGFIKR QLVETRQITK HVAQILDSRM NTKYDENDKL   960
IREVKVITLK SKLVSDFRKD FQFYKVREIN NYHHAHDAYL NAVVGTALIK KYPKLESEFV  1020
YGDYKVYDVR KMIAKSEQEI GKATAKYFFY SNIMNFFKTE ITLANGEIRK RPLIETNGET  1080
GEIVWDKGRD FATVRKVLSM PQVNIVKKTE VQTGGFSKES ILPKRNSDKL IARKKDWDPK  1140
KYGGFDSPTV AYSVLVVAKV EKGKSKKLKS VKELLGITIM ERSSFEKNPI DFLEAKGYKE  1200
VKKDLIIKLP KYSLFELENG RKRMLASAGE LQKGNELALP SKYVNFLYLA SHYEKLKGSP  1260
EDNEQKQLFV EQHKHYLDEI IEQISEFSKR VILADANLDK VLSAYNKHRD KPIREQAENI  1320
IHLFTLTNLG APAAFKYFDT TIDRKRYTST KEVLDATLIH QSITGLYETR IDLSQLGGD   1379

SEQ ID NO: 99              moltype = DNA  length = 39
FEATURE                    Location/Qualifiers
source                     1..39
                           mol_type = other DNA
                           organism = synthetic construct
                           note = Synthetic Construct
SEQUENCE: 99
aaagagctcg gatcctctat gtattaatag aatctatag                          39
```

```
SEQ ID NO: 100          moltype = DNA  length = 33
FEATURE                 Location/Qualifiers
source                  1..33
                        mol_type = other DNA
                        organism = synthetic construct
                        note = Synthetic Construct
SEQUENCE: 100
aaaccatggt agattaatat tattaaattt aag                                33

SEQ ID NO: 101          moltype = DNA  length = 48
FEATURE                 Location/Qualifiers
source                  1..48
                        mol_type = other DNA
                        organism = synthetic construct
                        note = Synthetic Construct
SEQUENCE: 101
aaaccatggg tatatctcct tctttaaatt taagtaaaaa aactacac                48

SEQ ID NO: 102          moltype = DNA  length = 80
FEATURE                 Location/Qualifiers
source                  1..80
                        mol_type = other DNA
                        organism = synthetic construct
                        note = Synthetic Construct
SEQUENCE: 102
aaaagagctc acatatacct tggttgacac gagtatataa gtcatgttat actgttgaat   60
gggagaccac aacggtttcc                                               80

SEQ ID NO: 103          moltype = DNA  length = 37
FEATURE                 Location/Qualifiers
source                  1..37
                        mol_type = other DNA
                        organism = synthetic construct
                        note = Synthetic Construct
SEQUENCE: 103
ttttatgcat atgtatatct ccttcttaaa gttaaac                            37

SEQ ID NO: 104          moltype = DNA  length = 27
FEATURE                 Location/Qualifiers
source                  1..27
                        mol_type = other DNA
                        organism = synthetic construct
                        note = Synthetic Construct
SEQUENCE: 104
aaaagagctc gctcccccgc cgtcgtt                                       27

SEQ ID NO: 105          moltype = DNA  length = 43
FEATURE                 Location/Qualifiers
source                  1..43
                        mol_type = other DNA
                        organism = synthetic construct
                        note = Synthetic Construct
SEQUENCE: 105
ctgaatctgg gggaacactt tcccagaaat atagtcatcc ctg                     43

SEQ ID NO: 106          moltype = DNA  length = 42
FEATURE                 Location/Qualifiers
source                  1..42
                        mol_type = other DNA
                        organism = synthetic construct
                        note = Synthetic Construct
SEQUENCE: 106
gggatgacta tatttctggg aaagtgttcc cccagattca ga                      42

SEQ ID NO: 107          moltype = DNA  length = 33
FEATURE                 Location/Qualifiers
source                  1..33
                        mol_type = other DNA
                        organism = synthetic construct
                        note = Synthetic Construct
SEQUENCE: 107
ttttatgcat agagttttct tgcccccctat ttg                               33

SEQ ID NO: 108          moltype = DNA  length = 3537
FEATURE                 Location/Qualifiers
source                  1..3537
                        mol_type = unassigned DNA
                        organism = Bacillus thuringiensis
```

```
SEQUENCE: 108
atggataaca atccgaacat caatgaatgc attccttata attgtttaag taaccctgaa    60
gtagaagtat taggtggaga aagaatagaa actggttaca ccccaatcga tatttccttg   120
tcgctaacgc aatttctttt gagtgaattt gttcccggtg ctggatttgt gttaggacta   180
gttgatataa tatgggggat ttttggtccc tctcaatgag acgcatttct tgtacaaatt   240
gaacagttaa ttaaccaaag aatagaagaa ttcgctagga accaagccat ttctagatta   300
gaaggactaa gcaatcttta tcaaatttac gcagaatctt ttagagagtg ggaagcagat   360
cctactaatc cagcattaag agaagagatg cgtattcaat tcaatgacat gaacagtgcc   420
cttacaaccg ctattcctct ttttgcagtt caaaattatc aagttcctct tttatcagta   480
tatgttcaag ctgcaaattt acatttatca gttttgagag atgtttcagt gtttggacaa   540
aggtggggat ttgatgccgc gactatcaat agtcgttata atgatttaac taggcttatt   600
ggcaactata cagattatgc tgtacgctgg tacaatacgg gattagaacg tgtatgggga   660
ccggattcta gagattgggt aaggtataat caatttagaa gagaattaac actaactgta   720
ttagatatcg ttgctctgtt cccgaattat gatagtagaa gatatccaat tcgaacagtt   780
tcccaattaa caagagaaat ttatacaaac ccagtattag aaaatttga tggtagtttt   840
cgaggctcgg ctcagggcat agaaagaagt attaggagtc cacatttgat ggatatactt   900
aacagtataa ccatctatac ggatgctcat aggggttatt attattggtc agggcatcaa   960
ataatggctt ctcctgtcgg ttttttcggg ccagaattca cgttccgct atatgaacc  1020
atgggaaatg cagctccaca acaacgtatt gttgctcaac taggtcaggg cgtgtataga  1080
acattatcgt ccactttata tagaagacct tttaatatag ggataaataa tcaacaacta  1140
tctgttcttg acgggacaga atttgcttat ggaacctcct caaatttgcc atccgctgta  1200
tacagaaaaa gcgaaccggt agattcgctg atgaaatac cgccacagaa taacaacgtg  1260
ccacctaggc aaggatttag tcatcgatta agccatgttt caatgtttcg ttcaggcttt  1320
agtaatagta gtgtaagtat aataaagagc cctatgttct cttggataca tcgtagtgct  1380
gaatttaata atataattgc atcggatagt attactcaaa tccctgcagt gaagggaaac  1440
tttcttttta atggttctgt aatttcagga ccaggttctg ctggtgggga cttagttaga  1500
ttaaatagta gtgaaataa cattcagaat agagggtata ttgaagttcc aattcacttc  1560
ccatcgacat ctaccagata tcgagttcgt gtacggtatg cttctgtaac cccgattcac  1620
ctcaacgtta attggggtaa ttcatccatt tttttccaata cagtaccagc tacagctacg  1680
tcattagata atctacaatc aagtgatttt ggttattttg aaagtgccaa tgcttttaca  1740
tcttcattag gtaatatagt aggtgttaga aatttagtg ggactgcagg agtgataata  1800
gacagatttg aatttattcc agttactgca cactcgagg ctgaatataa tctgaaaaga  1860
gcgcagaagg cggtgaatgc gctgtttacg tctacaaacc aactagggct aaaaacaaat  1920
gtaacgatt atcatattga tcaagtgtcc aatttagtta cgtatttatc ggatgaattt  1980
tgtctggatg aaaagcgaga attgtccgga aaagtcaaac atgcgaagcg actcagtgat  2040
gaacgcaatt tactccaaga ttcaaatttc aaagacatta ataggcaacc agaacgtggg  2100
tggggcggaa gtacagggat taccatccaa ggaggggatg acgtatttaa agaaaattac  2160
gtcacactat caggtacctt tgatgagtgc tatccaacat atttgtatca aaaaatcgat  2220
gaatcaaaat taaaagcctt taccgttat caattaagag gtgtatcga agatagtcaa  2280
gacttagaaa tctatttaat tcgctacaat gcaaaacatg aaacagtaaa tgtgccaggt  2340
acgggttcct tatggccgct ttcagcccaa agtccaatcg aaagtgtgg agagccgaat  2400
cgatgcgcgc cacaccttga atggaatcct gacttagatt gttcgtgtag ggatggagaa  2460
aagtgtgccc atcattcgca tcatttctcc ttagacattg atgtaggatg tacagactta  2520
aatgaggacc taggtgtatg ggtgatcttt aagattaaga cgcaagatgg gcacgcaaga  2580
ctagggaatc tagagtttct cgaagagaaa ccattagtag gagaagcgct agctcgtgtg  2640
aaaagagcgg agaaaaaatg gagagacaaa cgtgaaaaat tggaatggga aacaaatatc  2700
gtttataaag aggcaaaaga atctgtagat gcttttattg taaactctca atatgatcaa  2760
ttacaagcgg atacgaatat tgccatgatt catgcggcag ataaacgtgt tcatagcatt  2820
cgagaagctt atctgcctga gctgtctgtg attccgggtg tcaatgcggc tattttgaa  2880
gaattagaag ggcgtatttt cactgcattc tccctatatg atgcgagaaa tgtcattaaa  2940
aatggtgatt ttaataatgg cttatcctgc tggaacgtga aagggcatgt agatgtagaa  3000
gaacaaaaca accaacgttc ggtccttgtt gttccggaat gggaagcaga agtgtcacaa  3060
gaagttcgtg tctgtccggg tcgtggctat atccttcgtg tcacagcgta caggaggga  3120
tatggagaag gttgcgtaac cattcatgag atcgagaaca atacagacga actgaagttt  3180
agcaactgcg tagaagagga aatctatcca aataacacg taacgtgaa tgattatact  3240
gtaaatcaag aagaatacgg aggtgcgtac acttctcgta atcgaggata taacgaagct  3300
ccttccgtac cagctgatta tgcgtcagtc tatgaagaaa atcgtatac agatggacga  3360
agagagaatc cttgtgaatt taacagaggg tatagggatt acacgccact accagttggt  3420
tatgtgacaa agaattaga atacttccca gaaccgata aggtatggat tgagattgga  3480
gaaacggaag gaacatttat cgtggacagc gtggaattac tccttatgga ggaatag    3537

SEQ ID NO: 109           moltype = AA  length = 1178
FEATURE                  Location/Qualifiers
source                   1..1178
                         mol_type = protein
                         organism = Bacillus thuringiensis
SEQUENCE: 109
MDNNPNINEC IPYNCLSNPE VEVLGGERIE TGYTPIDISL SLTQFLLSEF VPGAFVLGL    60
VDIIWGIFGP SQWDAFLVQI EQLINQRIEE FARNQAISRL EGLSNLYQIY AESFREWEAD   120
PTNPALREEM RIQFNDMNSA LTTAIPLFAV QNYQVPLLSV YVQAANLHLS VLRDVSFGQ   180
RWGFDAATIN SRYNDLTRLI GNYTDYAVRW YNTGLERVWG PDSRDWVRYN QFRRELTLTV   240
LDIVALFPNY DSRRYPIRTV SQLTREIYTN PVLENFDGSF RGSAQGIERS IRSPHLMDIL   300
NSITIYTDAH RGYYYWSGHQ IMASPVGFSG PEFTFPLYGT MGNAAPQQRI VAQLGQGVYR   360
TLSSTLYRRP FNIGINNQQL SVLDGTEFAY GTSSNLPSAV YRKSGTVDSL DEIPPQNNNV   420
PPRQGFSHRL SHVSMFRSGF SNSSVSIIRA PMFSWIHRSA EFNNIIASDS ITQIPAVKGN   480
FLFNGSVISG PGFTGDDLVR LNSSGNNIQN RGYIEVPIHF PSTSTRYRVR VRYASVTPIH   540
LNVNWGNSSI FSNTVPATAT SLDNLQSSDF GYFESANAFT SSLGNIVGVR NFSGTAGVII   600
DRFEFIPVTA TLEAEYNLER AQKAVNALFT STNQLGLKTN VTDYHIDQVS NLVTYLSDEF   660
CLDEKRELSE KVKHAKRLSD ERNLLQDSNF KDINRQPERG WGGSTGITIQ GGDDVFKENY   720
```

```
VTLSGTFDEC YPTYLYQKID ESKLKAFTRY QLRGYIEDSQ DLEIYLIRYN AKHETVNVPG    780
TGSLWPLSAQ SPIGKCGEPN RCAPHLEWNP DLDCSCRDGE KCAHHSHHFS LDIDVGCTDL    840
NEDLGVWVIF KIKTQDGHAR LGNLEFLEEK PLVGEALARV KRAEKKWRDK REKLEWETNI    900
VYKEAKESVD ALFVNSQYDQ LQADTNIAMI HAADKRVHSI REAYLPELSV IPGVNAAIFE    960
ELEGRIFTAF SLYDARNVIK NGDFNNGLSC WNVKGHVDVE EQNNQRSVLV VPEWEAEVSQ    1020
EVRVCPGRGY ILRVTAYKEG YGEGCVTIHE IENNTDELKF SNCVEEEIYP NNTVTCNDYT    1080
VNQEEYGGAY TSRNRGYNEA PSVPADYASV YEEKSYTDGR RENPCEFNRG YRDYTPLPVG    1140
YVTKELEYFP ETDKVWIEIG ETEGTFIVDS VELLLMEE                            1178

SEQ ID NO: 110            moltype = DNA  length = 1848
FEATURE                   Location/Qualifiers
source                    1..1848
                          mol_type = unassigned DNA
                          organism = Bacillus thuringiensis
SEQUENCE: 110
atggataaca atccgaacat caatgaatgc attccttata attgtttaag taaccctgaa    60
gtagaagtat taggtggaga aagaatagaa actggttaca ccccaatcga tatttccttg    120
tcgctaacgc aatttctttt gagtgaattt gttcccggtg ctggatttgt gttaggacta    180
gttgatataa tatggggaat ttttggtccc tctcaatggg acgcatttct tgtacaaatt    240
gaacagttaa ttaaccaaag aatagaagaa ttcgctagga accaagccat ttctagatta    300
gaaggactaa gcaatcttta tcaaatttac gcagaatctt ttagagagtg ggaagcagat    360
cctactaatc cagcattaag agaagagatg cgtattcaat taatgacat gaacagtgcc    420
cttacaaccg ctattcctct ttttgcagtt caaaattatc aagttcctct tttatcagta    480
tatgttcaag ctgcaaattt acatttatca gttttgagag atgtttcagt gtttggacaa    540
aggtggggat tgatgccgc gactatcaat agtcgttata atgatttaac taggcttat    600
ggcaactata cagattatgc tgtacgctgg tacaatacgg gattagaacg tgtatgggga    660
ccggattcta gagattgggt aaggtataat caatttagaa gagaattaac actaactgta    720
ttagatatcg ttgctctgtt cccgaattat gatagtagaa gatatccaat cgaacagtta    780
tcccaattaa caagagaaat ttatacaaac ccagtattag aaaattttga tggtagtttt    840
cgaggctcgg ctcagggcat agaaagaagt attaggagtc cacatttgat ggatatactt    900
aacagtataa ccatctatac ggatgctcat agggggttatt attattggtc agggcataca    960
ataatggctt ctcctgtcgg ttttcgggg ccagaattca cgtttccgct atatggaacc    1020
atgggaaatg cagctccaca caacgtatt gttgctcaac taggtcaggg cgtgtataga    1080
acattatcgt ccactttata tagaagacct tttaatatag ggataaataa tcaacaacta    1140
tctgttcttg acgggacaga atttgcttat ggaacctcct caaatttgcc atccgctgta    1200
tacagaaaaa gcggaacggt agattcgctg atgaaatac cgccacagaa taacaacgtg    1260
ccacctaggc aaggatttag tcatcgatta agccatgttt caatgtttcg ttcaggcttt    1320
agtaatagta gtgtaagtat aataagagct cctatgttct cttggataca tcgtagtgct    1380
gaatttaata atataattgc atcggatagt attactcaaa tccctgcagt gaagggaaac    1440
tttcttttta atggttctgt aatttcagga ccaggattta ctggtgggga cttagttaga    1500
ttaaatagta gtggaaataa cattcagaat agagggtata ttgaagttcc aattcacttc    1560
ccatcgacat ctaccagata tcgagttcgt gtacggtatg cttctgtaac cccgattcac    1620
ctcaacgtta attgggggtaa ttcatccatt ttttccaata cagtaccagc tacagctacg    1680
tcattagata atctacaatc aagtgatttt ggttatttg aaagtgccaa tgcttttaca    1740
tcttcattag gtaatatagt aggtgttaga aattttagtg ggactgcagg agtgataata    1800
gacagatttg aatttattcc agttactgca acactcgagg ctgaatag                1848

SEQ ID NO: 111            moltype = DNA  length = 750
FEATURE                   Location/Qualifiers
source                    1..750
                          mol_type = unassigned DNA
                          organism = Bacillus thuringiensis
SEQUENCE: 111
atggaaaatt taatcattg tccattagaa gatataaagg taaatccatg gaaaacccct    60
caatcaacag caagggttat tacattacgt gttgaggctc aaatgaaat caataatctt    120
ctttctatta acgaaattga taatccgaat tatatattgc aagcaattat gttagcaaat    180
gcatttcaaa atgcattagt tcccacttct acagatttg gtgatgccct acgctttagt    240
atgccaaaag gtttagaaat cgcaaacaca attcaccga tggtgctgt agtgagttat    300
gttgatcaaa atgtaactca aacgaataac caagtaagtg ttatgattaa taagtctta    360
gaagtgttaa aaactgtatt aggagttgca ttaagtggat ctgtaataga tcaattaact    420
gcagcagtta caaatacgtt tacaaattta aatactcaaa aaaatgaagc atggattttc    480
tggggcaagg aaactgctaa tcaaacaaat tacacataca atgtcctgtt tgcaatccaa    540
aatgcccaaa ctggtggcgt tatgtattgt gtaccagttg ttttgaaat taaagtatca    600
gcagtaaagg aacaagtttt attttcaca attcaagatt ctgcgagcta caatgttaac    660
atccaatctt tgaaatttgc acaaccatta gttagctcaa gtcagtatcc aattgcagat    720
cttactagcg ctattaatgg aaccctctaa                                    750

SEQ ID NO: 112            moltype = DNA  length = 549
FEATURE                   Location/Qualifiers
source                    1..549
                          mol_type = unassigned DNA
                          organism = Bacillus thuringiensis
SEQUENCE: 112
atgacagaaa atggagtgtt ttataaaata ttcacaacag aaaataataa ttttgtata    60
aatcctactt tgttagaaag ggttttttaaa aataatttag atgaatttga tttttcgcta    120
gtaaaaaaaa acttagaaca tgagaagaat tgtgtgatta cttctacaat gaatcaaaca    180
atttctttcg agaatatgaa tagtacgaaa tggggcata agacatattc tttttttaaat    240
caaacagtat taaataataa ggggaattct tctttagagg aacaagtctc taatattttt    300
tatagatgtg tatatatgga agttggaaaa tcaagttcat atattaaacc tcttgagcag    360
```

-continued

```
gattctaata aaataaggta tgtttgtagt ttgctcttta tagtgcccta taagaataac  420
ataacatcaa ttattccagt aaatttacaa ctaacattat tatcgaaaaa tgtaaaacaa  480
tcctcttcta caaatatatt ttcaggagat atacatttta atatggtaac aatgacttat  540
ttaactta                                                           549

SEQ ID NO: 113          moltype = DNA  length = 540
FEATURE                 Location/Qualifiers
source                  1..540
                        mol_type = unassigned DNA
                        organism = Bacillus thuringiensis
SEQUENCE: 113
atgaatatga attttgattt cgaggatcat gaaaataaga atttatctgt gcaggaggaa  60
catcaccatt gtagtgaagg aggggaacat aaaatagcat tttgttgtgt agtctcaatt  120
ccaaaaggtt ttaaatatgt tgcccattgt gatccgaaat ttgtatataa ccttgattgt  180
ctatccgttt caaaagaaaa atgccgtaag gttgttccta tagaaggatg tggatgtgca  240
gaggtagatt tacatgtatt aaaggtaaag ggatgcatct catttgtatc gaatatagaa  300
atagaaccta ttcatgaatg catgacctgc tcagcaaatc cacataaaga aaacattgct  360
gtgagttgcc aagatactgt ctgcgtagat caagttttgt attgcagtgt agattgtttg  420
ccagattgtg atattaattg tgataatgta aaaatttgcg atgtgagcat tgaaccaatt  480
ggagattgtg attgtcacgc ggtgaaaatt aaagggaaat tttcacttca ctataaataa  540

SEQ ID NO: 114          moltype = DNA  length = 2155
FEATURE                 Location/Qualifiers
source                  1..2155
                        mol_type = unassigned DNA
                        organism = Heterodera glycines
SEQUENCE: 114
tattcttggg tctgcaacta acaaatccca aagaattttt ccggtagaaa catgttttgg  60
acacgttgga gaggaatcaa aatatgttgc tgtgatccaa ataagaaaac aaatttatat  120
caaacattta gatccaaatt caatcatttt ctaaacaaca gctgacaaat aattgaattc  180
atcaagaagt ttccatcggt ttctgttgtt cgataggccc aatttgactc aacagcgctc  240
caatcgcttc gacatttaaa atttgctgct cacaataccc aggctgaata gttacaacag  300
ttctgttagt atttattagc tttctaaaaa tgaacttgcc tccccattgg tgccatccac  360
ccatttgagc accttaaaaa tgaattgcta gtaaattaac gtgtattttt gtattcaccg  420
caatttcgat attctgcgcc cccgattgga ccactggggc taaagacttg agcatcagtt  480
taagcgtaga ctcctcatca gctgtgttgt cgttgccgta ttctttctcc agatactcct  540
tcacaatctt ttcatttcgc cctattgaac cggccaacaa ttcgtagtaa actccggacg  600
gttccgtctt gaaaagatga ggggtcccat cagaatcgaa gcctccgaca agcattgaaa  660
ttccaaaagg ccgacggcca gtggtttgag tgtatctcta aacaaacaaa aagttactca  720
gatgttgtaa gtcaattgac ctgttttata tcagctatga tgcgagagat atgcatgaca  780
gatacgcggt cctcaagcgt caatttgtaa ttttcgcatt caactcgagc acggtcgata  840
aggacgcgtg catcggcgct gagtccggcg aatgcgacca taacatgcta aacataggcg  900
tgcattgaag aggaataagg aatttaccga atccaatgca tgtattttac gaatggtacg  960
ttcgtcttgc agagtcggga tagatttctg caaaataaaa gttcaccaga acagtttaag  1020
caatttttat gtctgtgaat acactagcta aaaataattt actttttcga ctccaattac  1080
aacacaattt tttcctttca cggcaaccta aagcaatgca cattaatatt tttaaaaagc  1140
aataaaacgc accgctgttg agcccttctt cactgcttct tgcgcatagt caacttgaaa  1200
aagtctgcca tccggagaaa aaatcgtaat tgcacgatca taacgctcca tagtttattt  1260
gctaaaatca agcttacaaa aagcggttag gcatttaaaa tttaagctcc gtaaaaattc  1320
aattaaaaat catcacattt atttttttaa tttttcaatt tttaaatttt tcttttttgg  1380
cgaactgtct acccttgtaa cttctaaaaa aggagttgag actgaaatcc cgcgccagat  1440
cccgtcccga cctgtctctg ttttccatag tgaacaaata attattgttg tatttttact  1500
ctttcgctgc tccacacaca tctctttcat gaactttaga caaaaagtat tttaatgcgt  1560
cttgagaagt gttggttttg ttcatcaaca atttatccgg gccacggaat tcaattcgta  1620
cgtaacgacg caacggtgaa aacaatttat tgttatagta cataataaat taaaattttt  1680
gtttaggttt tcaagttttg taggtcaaaa tgcaacaaat tatttaaaaa gaagaagaac  1740
ccgcgcaaat tgaaatggac gaaggcatcg cggcgaattc ggggaaaagt tagtgtttga  1800
tttttgtttt tactctttta catttattgt aaatttaaat ttcttttact ctttaggaat  1860
tggtcaacga tgttactcaa gcgatggaaa ttcgcagaaa cgaaccgaca aaatatgata  1920
gaaacctttg ggaaactgca ggtaaatcgt ccatatatac caacaaaccg taacgacgaa  1980
aaaaagtacc ggaagggaga atccgcaaaa tctttgctct cggacactta aacatttttc  2040
ctgttttaaa tttttcatgg acgaaaaaac atatacagcg gttttcgcca aaaaaaaaat  2100
aaccaatttg ggtagacaag tatgtctaat aaatcttcca tttgaatttt gattt       2155

SEQ ID NO: 115          moltype = DNA  length = 148
FEATURE                 Location/Qualifiers
source                  1..148
                        mol_type = unassigned DNA
                        organism = Heterodera glycines
SEQUENCE: 115
tcatttcgcc ctattgaacc ggccaacaat tcgtagtaaa ctccggacgg ttccgtcttg  60
aaaagatgag ggtcccatc agaatcgaag cctccgacaa gcattgaaat tccaaaaggc  120
cgacggccag tggtttgagt gtatctct                                     148

SEQ ID NO: 116          moltype = DNA  length = 23
FEATURE                 Location/Qualifiers
source                  1..23
                        mol_type = unassigned DNA
                        organism = Saccharomyces cerevisiae
```

```
SEQUENCE: 116
ttctttgaag tatcaggagg tgg                                                 23

SEQ ID NO: 117              moltype = DNA   length = 23
FEATURE                     Location/Qualifiers
source                      1..23
                            mol_type = unassigned DNA
                            organism = Saccharomyces cerevisiae
SEQUENCE: 117
atgattattg caattccaac agg                                                 23

SEQ ID NO: 118              moltype = DNA   length = 23
FEATURE                     Location/Qualifiers
source                      1..23
                            mol_type = unassigned DNA
                            organism = Saccharomyces cerevisiae
SEQUENCE: 118
gctattttta gtggtatggc agg                                                 23

SEQ ID NO: 119              moltype = DNA   length = 24
FEATURE                     Location/Qualifiers
source                      1..24
                            mol_type = unassigned DNA
                            organism = Saccharomyces cerevisiae
SEQUENCE: 119
accatgtaaa tattgtgaac cagg                                                24

SEQ ID NO: 120              moltype = DNA   length = 4107
FEATURE                     Location/Qualifiers
source                      1..4107
                            mol_type = other DNA
                            organism = synthetic construct
                            note = Synthetic Construct
SEQUENCE: 120
atggataaaa aatattcaat cggtttagat atcggtacaa attcagtagg ttgagctgta         60
atcacagatg aatataaagt accttcaaaa aaatttaaag tattaggtaa tacagataga        120
cattcaatca aaaaaaattt aatcggtgct ttattatttg attcaggtga aacagctgaa        180
gctacaagat taaaaagaac agctagaaga agatatacaa gaagaaaaaa tagaatctgt        240
tatttacaag aaatctttc aaatgaaatg gctaaagtag atgattcatt tttccataga         300
ttagaagaat cattttagt tgaagaagat aaaaaacatg aaagcatcc tatctttggt          360
aatatcgtag atgaagtagc ttatcatgaa aaatatccta caatctatca tttaagaaaa        420
aaattagtag attcaactga taaagctgat ttaagattaa tctatttagc tttagctcat        480
atgatcaaat ttagaggtca tttcttaatc gaaggtgatt taaatcctga taattcagat        540
gtagataaat tattcatcca attagtacaa acatataatc aattatttga agaaaatcct        600
atcaatgctt caggtgtaga tgctaaagca atcttatcag ctagattatc aaaatcaaga        660
agattagaaa atttaatcgc tcaattacct ggagaaaaaa aaaatggttt atttggtaat        720
ttaatcgcat tatcattagg tttaactcct aatttcaaat caaatttcga tttagctgaa        780
gatgcaaaat tacaattatc taaagataca tatgatgatg atttagataa tttattagct        840
caaatcggtg atcaatatgc tgatttattc ttagctgcta aaaatttatc agatgctatc        900
ttattatcag atatcttaag agtaaataca gaaatcacaa agcacccttt atcagcttca        960
atgatcaaaa gatatgatga acatcatcaa gatttaacat tattaaaagc tttagtaaga       1020
caacaattac cagaaaaata taaagaaatc ttctttgatc aatcaaaaaa tggttatgct       1080
ggttatatcg atggtggtgc ttctcaagaa gaattctata aattcatcaa acctatctta       1140
gaaaaaatgg atggtacaga agaattatta gtaaaattaa atagaagaga tttattaaga       1200
aaacaaagaa catttgataa tggttcaatc cctcatcaaa tccatttagg tgaattacat       1260
gcaatcttaa gaagacaaga agattttat cctttcttaa agataatag agaaaaaatc         1320
gaaaaaatct taacatttag aatcccttat tatgtaggtc ctttagctag aggtaattca       1380
agatttgctt gaatgacaag aaaatcagaa gaaacaatca caccttggaa ttttgaagaa       1440
gtagtagata aaggagcttc agcacaatca tttatcgaaa gaatgacaaa ttttgataaa       1500
aatttaccta atgaaaaagt tttacctaaa cattcattat tatatgaata tttcacagta       1560
tataatgaat taacaaaagt aaaatatgta acagaaggta tgagaaaacc tgcttttttta       1620
tcaggtgaac aaaaaaaagc aatcgtagat ttattattta aaacaaatag aaaagtaaca       1680
gtaaaacaat taaagaagaa ttatttcaaa aaatcgaat gttttgattc agtagaaatc        1740
tctggtgtag aagatagatt taatgcttct taggtacat atcatgattt attaaaaatc        1800
atcaaagata aagatttctt agataatgaa gaaatgaag atatcttaga agatatcgta        1860
ttaacattaa cttattcga agatagaaa atgatcgaag aagatttaaa acatatgct          1920
catttatttg atgataaagt aatgaaacaa ttaaaagaa gaagatatac tggttgaggt        1980
agattatcaa gaaaattaat caatggtatc agagatcaaa atctggtaa aacaatctta        2040
gatttcttaa aatcagatgg ttttgctaat agaaatttca tgcaattaat ccatgatgat       2100
agttaacctt ttaagaagaa tatccaaaaa gctcaagtat caggtcaagg tgattcatta       2160
catgaacata tcgctaattt agctggttct cctgctatca aaaaggtat cttacaaact       2220
gtaaagttg tagatgaat tagtaaagtt atgggtagac ataaacctga aatatcgta         2280
atcgaaatgg caagagaaaa tcaaacaaca caaaaaggac aaaaaaattc aagagaaaga       2340
atgaaaagaa tcgaagaagg tatcaaagaa ttaggttcac aaatcttaaa agaacatcct       2400
gtagaaaata cacaattaca aaatgaaaaa ttatatttat attatttaca aaatggtaga       2460
gatatgtatg tagatcaaga attagatatc aatagattat ctgattatga tgtagatcat       2520
atcgtacctc aatcattctt aaaagatgat tcaatcgata taaagtatt aacaagatca       2580
gataaaaaata gaggtaaaag tgataatgta ccttctgaag aagttgtaaa aaaaatgaaa      2640
aattattgaa gacaattatt aaatgctaaa ttaatcacac aaagaaaatt cgataattta      2700
```

-continued

```
acaaaagctg aaagaggtgg tttatcagaa ttagataaag ctggtttcat caaaagacaa   2760
ttagttgaaa caagacaaat cactaaacat gttgctcaaa tcttagatag tagaatgaat   2820
acaaaatatg atgaaaatga taaattaatc agagaagtaa aagtaatcac attaaaatct   2880
aaattagtat cagatttttag aaaagatttt caattctata aagtaagaga aatcaataat   2940
tatcatcatg ctcatgatgc ttatttaaat gctgtagtag gtacagcttt aatcaaaaaa   3000
tatccaaaat tagaatcaga atttgtatat ggagattata aagtatatga tgttagaaaa   3060
atgatcgcta aatcagaaca agaaatcggt aaagctactg ctaaatattt cttttattca   3120
aatatcatga attttttcaa aactgaaatc actttagcta atggtgaaat cagaaaaaga   3180
cctttaatcg aaacaaatgg tgaaactggt gaaatcgtat gagataaagg tagagatttt   3240
gctacagtaa gaaaagtatt atcaatgcct caagtaaaata tcgttaaaaa aactgaagta   3300
caaactggtg gttttctaa agaatcaatc ttaccaaaaa gaaattcaga taaattaatc    3360
gctagaaaaa aagattgaga tccaaaaaaa tatggtggtt tcgattcacc tacagtagca   3420
tattcagtat tagtagtagc aaaagtagaa aaagtaact ctaaaaaatt aaaatcagta    3480
aaagaattat taggtatcac aatcatggaa agatcatcat tcgaaaaaaa tccaatcgat   3540
tttttagaag ctaaaggtta taagaagtt aaaaaagatt taatcatcaa attacctaaa   3600
tatagtttat ttgaattaga aaatggaaga aaaagaatgt tagcatcagc tggtgaatta   3660
caaaaaggta atgaattagc attaccatct aaatatgtta atttcttata tttagcatca   3720
cattatgaaa aattaaaagg ttctcctgaa gataatgaac aaaacaatt atttgtaaa    3780
caacataaac attatttaga tgaaatcatc gaacaaatct cagaattttc aaaaagagta   3840
atcttagcag atgcaaattt agataaagtt ttatctgctt ataataaaca tagagataaa   3900
cctatcagag aacaagcaga aaatatcatc catttattca cattaacaaa tttaggtgct   3960
cctgctgctt tcaaatattt cgatacaaca atcgataaa aagatatac ttcaacaaaa    4020
gaagtattag atgcaacatt aatccatcaa tcaatcacag gtttatatga aactagaatc   4080
gatttatctc aattaggtgg tgattaa                                       4107

SEQ ID NO: 121           moltype = DNA   length = 88
FEATURE                  Location/Qualifiers
source                   1..88
                         mol_type = unassigned DNA
                         organism = Saccharomyces cerevisiae
SEQUENCE: 121
ctgcaggact agtaaataaa ttttaattaa aagtagtatt aacatattat aaatagacaa   60
aagagtctaa aggttaagat ttattaaa                                      88

SEQ ID NO: 122           moltype = DNA   length = 148
FEATURE                  Location/Qualifiers
source                   1..148
                         mol_type = unassigned DNA
                         organism = Saccharomyces cerevisiae
SEQUENCE: 122
ttaatattta cttattatta atattttaa ttattaaaaa taataataat aataataatt    60
ataataatat tcttaaatat aataaagata tagatttata ttctattcaa tcaccttatt   120
ctagaagcgg ccgcaccatg gaaagctt                                      148

SEQ ID NO: 123           moltype = DNA   length = 97
FEATURE                  Location/Qualifiers
source                   1..97
                         mol_type = unassigned DNA
                         organism = Saccharomyces cerevisiae
SEQUENCE: 123
ttctttgaag tatcaggagg gttttagagc tagaaatagc aagttaaaat aaggctagtc   60
cgttatcaac ttgaaaaagt ggcaccgagt cggtgct                            97

SEQ ID NO: 124           moltype = DNA   length = 75
FEATURE                  Location/Qualifiers
source                   1..75
                         mol_type = unassigned DNA
                         organism = Saccharomyces cerevisiae
SEQUENCE: 124
tatatattat gtattattat ataaatatat atatatatta tattataagt aataataagt   60
attatattat atata                                                    75

SEQ ID NO: 125           moltype = DNA   length = 75
FEATURE                  Location/Qualifiers
source                   1..75
                         mol_type = unassigned DNA
                         organism = Saccharomyces cerevisiae
SEQUENCE: 125
gcttttatag cttagtggta aagcgataaa ttgaagattt atttacatgt agttcgattc   60
tcattaaggg caata                                                    75

SEQ ID NO: 126           moltype = DNA   length = 76
FEATURE                  Location/Qualifiers
source                   1..76
                         mol_type = unassigned DNA
                         organism = Saccharomyces cerevisiae
SEQUENCE: 126
aggagattag cttaattggt atagcattcg ttttacacac gaaagattat aggttcgaac   60
cctatatttc ctaaat                                                   76
```

```
SEQ ID NO: 127          moltype = DNA  length = 118
FEATURE                 Location/Qualifiers
source                  1..118
                        mol_type = unassigned DNA
                        organism = Saccharomyces cerevisiae
SEQUENCE: 127
ttattaataa ttaacaataa ttaatatatt ataatttata tatatatatt ttatattatt     60
ataataatat tcttacaaat ataattatta tatattattc cttcaaaact cctaacgg      118

SEQ ID NO: 128          moltype = DNA  length = 76
FEATURE                 Location/Qualifiers
source                  1..76
                        mol_type = unassigned DNA
                        organism = Saccharomyces cerevisiae
SEQUENCE: 128
gagcttgtat agtttaattg gttaaaacat ttgtctcata aataaataat gtaaggttca     60
attccttcta caagta                                                    76

SEQ ID NO: 129          moltype = DNA  length = 744
FEATURE                 Location/Qualifiers
source                  1..744
                        mol_type = other DNA
                        organism = synthetic construct
                        note = Synthetic Construct
SEQUENCE: 129
atgacacatt tagaaagaag tagacaaatg tcaaaaggtg aagaattatt cactggagta     60
gtacctatct tagtagaatt agatggtgat gtaaatggtc ataaattctc agtatcaggt    120
gaaggtgaag gtgatgctac atatggtaaa ttaacattaa aattcatctg tacaacaggt    180
aaattacctg taccttgacc tacattagta acaacattcg gatatggagt acaatgtttc    240
gcaagatatc ctgatcatat gaaacaactac gatttcttca aatcagcaat gcctgaaggt    300
tacgtacaag aaagaacaat cttcttcaaa gatgatggta attataaaac aagagctgaa    360
gtaaaattcg aaggtgatac attagtaaat agaatcgagt taaaaggtat cgatttcaaa    420
gaagatggta atatcttagg tcataaatta gaatataatt ataattcaca taatgtatat    480
atcatggctg ataaacaaaa aaatggtatc aaagtaaatt tcaaaatcag acataataatc    540
gaagacggtt cagtacaatt agcagatcat tatcaacaaa atacacctat cggtgatggt    600
cctgtattat tacctgataa tcattactta agtacacaat cagctttatc aaaagatcct    660
aatgaaaaaa gagatcatat ggtattatta gaatttgtaa cagctgctgg tatcacacat    720
ggtatggatg aattatataa ataa                                           744

SEQ ID NO: 130          moltype = DNA  length = 144
FEATURE                 Location/Qualifiers
source                  1..144
                        mol_type = unassigned DNA
                        organism = Saccharomyces cerevisiae
SEQUENCE: 130
atgagaacaa atggtatgac aatgcataaa ttaccattat ttgtatgatc aattttcatt     60
acagcgttct tattattatt atcattacct gtattatctg ctggtattac aatgttatta    120
ttagatagaa acttcaatac ttca                                           144

SEQ ID NO: 131          moltype = DNA  length = 115
FEATURE                 Location/Qualifiers
source                  1..115
                        mol_type = unassigned DNA
                        organism = Saccharomyces cerevisiae
SEQUENCE: 131
aattaaaatt ttctcatgat taataaatcc ctttagcaag gataaaaata aaataaaaa      60
taaaagttg atcagaaatt atcaaaaaat aaataataat aatataataa aaaca         115

SEQ ID NO: 132          moltype = DNA  length = 64
FEATURE                 Location/Qualifiers
source                  1..64
                        mol_type = unassigned DNA
                        organism = Saccharomyces cerevisiae
SEQUENCE: 132
aatggtacaa agatgattat attcaacaaa tgcaaaagat attgcagtat tatattttat     60
gtta                                                                 64

SEQ ID NO: 133          moltype = DNA  length = 93
FEATURE                 Location/Qualifiers
source                  1..93
                        mol_type = unassigned DNA
                        organism = Saccharomyces cerevisiae
SEQUENCE: 133
aattcacaat tatttaatgg tgcgcctctc agtgcgtata tttcgttgat gcgtctagca     60
ttagtattat gaatcatcaa tagatactta aaa                                 93

SEQ ID NO: 134          moltype = DNA  length = 23
FEATURE                 Location/Qualifiers
```

|  |  |  |
|---|---|---|
| source | 1..23<br>mol_type = other DNA<br>organism = synthetic construct<br>note = Synthetic Construct | |
| SEQUENCE: 134<br>tttttcggag tttctggtgg agg | | 23 |
| SEQ ID NO: 135<br>SEQUENCE: 135<br>000 | moltype =   length = | |
| SEQ ID NO: 136<br>FEATURE<br>source | moltype = DNA   length = 23<br>Location/Qualifiers<br>1..23<br>mol_type = other DNA<br>organism = synthetic construct<br>note = Synthetic Construct | |
| misc_difference | 19<br>note = misc_feature - n is a, c, g, or t | |
| misc_difference | 20<br>note = misc_feature - n is a, c, g, or t | |
| misc_difference | 21<br>note = misc_feature - n is a, c, g, or t | |
| misc_difference | 22<br>note = misc_feature - n is a, c, g, or t | |
| misc_difference | 23<br>note = misc_feature - n is a, c, g, or t | |
| SEQUENCE: 136<br>gctattttta gtggtatgnn nnn | | 23 |
| SEQ ID NO: 137<br>SEQUENCE: 137<br>000 | moltype =   length = | |
| SEQ ID NO: 138<br>FEATURE<br>source | moltype = DNA   length = 22<br>Location/Qualifiers<br>1..22<br>mol_type = unassigned DNA<br>organism = Saccharomyces cerevisiae | |
| SEQUENCE: 138<br>ctattcaggc acattcagga cc | | 22 |
| SEQ ID NO: 139<br>FEATURE<br>source | moltype = DNA   length = 20<br>Location/Qualifiers<br>1..20<br>mol_type = unassigned DNA<br>organism = Saccharomyces cerevisiae | |
| SEQUENCE: 139<br>ttttatcctt gctaaaggga | | 20 |
| SEQ ID NO: 140<br>FEATURE<br>source | moltype = DNA   length = 20<br>Location/Qualifiers<br>1..20<br>mol_type = unassigned DNA<br>organism = Saccharomyces cerevisiae | |
| SEQUENCE: 140<br>tttgataatt tctgatcaac | | 20 |
| SEQ ID NO: 141<br>FEATURE<br>source | moltype = DNA   length = 23<br>Location/Qualifiers<br>1..23<br>mol_type = unassigned DNA<br>organism = Saccharomyces cerevisiae | |
| SEQUENCE: 141<br>agaggtatac caacacaaga ttc | | 23 |
| SEQ ID NO: 142<br>FEATURE<br>source | moltype = DNA   length = 22<br>Location/Qualifiers<br>1..22<br>mol_type = other DNA<br>organism = synthetic construct<br>note = Synthetic Construct | |
| SEQUENCE: 142<br>caggtgaagg tgaaggtgat gc | | 22 |
| SEQ ID NO: 143<br>FEATURE<br>source | moltype = DNA   length = 23<br>Location/Qualifiers<br>1..23<br>mol_type = other DNA | |

```
                           organism = synthetic construct
                           note = Synthetic Construct
SEQUENCE: 143
gatctgctaa ttgtactgaa ccg                                            23

SEQ ID NO: 144         moltype = DNA   length = 1308
FEATURE                Location/Qualifiers
source                 1..1308
                       mol_type = other DNA
                       organism = synthetic construct
                       note = Synthetic Construct
SEQUENCE: 144
ctattcaggc acattcagga cctagtgtag atttagcaat ttttgcatta catttaacat    60
caatttcatc attattaggt gctattaatt tcattgtaac aacattaaat atgagaacaa   120
atggtatgac aatgcataaa ttaccattat ttgtatgatc aatttcatt acagcgttct    180
tattattatt atcattacct gtattatctg ctggtattac aatgttatta ttagatagaa   240
acttcaatac ttcattttc ggagtttctg gtggaggtgg tggaatgaca catttagaaa    300
gaagtagaca aatgtcaaaa ggtgaagaat tattcactgg atagtacct atcttagtag    360
aattagatgg tgatgtaaat ggtcataaat tctcagtatc aggtgaaggt gaaggtgatg   420
ctacatatgg taaattaaca ttaaaattca tctgtacaac aggtaaatta cctgtacctt   480
gacctacatt agtaacaaca ttcggatatg gagtacaatg tttcgcaaga tatcctgatc   540
atatgaaaca acatgatttc ttcaaatcag caatgcctga aggttacgta caagaaagaa   600
caatcttctt caaagatgat ggtaattata aacaagagc tgaagtaaaa ttcgaaggtg    660
atacattagt aaatagaatc gagttaaaag gtatcgattt caagaagat ggtaatatct    720
taggtcataa attagaatat aattataatt cacataatgt atatatcatg gctgataaac   780
aaaaaaatgg tatcaaagta aatttcaaaa tcagactata tcgaagac ggttcagtac    840
aattagcaga tcattatcaa caaaatacac ctatcggtga tggtcctgta ttattacctg   900
ataatcatta cttaagtaca caatcagctt atcaaaaga tcctaatgaa aaagagatc    960
atatggtatt attagaattt gtaacagctg ctggtatcac acatggtatg gatgaattat  1020
ataaataaca acaggaatta aaattttctc atgattaata aatccctta gcaaggataa  1080
aaataaaaat aaaaataaaa agttgatcag aaattatcaa aaaataaata ataataat    1140
aataaaaaca tatttaaata ataataatat aattataata aatatataata aaggtaattt  1200
atatgatatt tatccaagat caaatagaaa ttatattcaa ccaaataata ttaataaaga  1260
attagtagta tatggttata atttagaatc ttgtgttggt atacctct             1308

SEQ ID NO: 145         moltype = DNA   length = 23
FEATURE                Location/Qualifiers
source                 1..23
                       mol_type = unassigned DNA
                       organism = Chlamydomonas reinhardtii
SEQUENCE: 145
ggtttaaacc ctgttactgg tgg                                            23

SEQ ID NO: 146         moltype = DNA   length = 23
FEATURE                Location/Qualifiers
source                 1..23
                       mol_type = unassigned DNA
                       organism = Chlamydomonas reinhardtii
SEQUENCE: 146
cttcacctgt aaatggacca cgg                                            23

SEQ ID NO: 147         moltype = DNA   length = 23
FEATURE                Location/Qualifiers
source                 1..23
                       mol_type = unassigned DNA
                       organism = Chlamydomonas reinhardtii
SEQUENCE: 147
tttacaggtg aaggtcacgt tgg                                            23

SEQ ID NO: 148         moltype = DNA   length = 23
FEATURE                Location/Qualifiers
source                 1..23
                       mol_type = unassigned DNA
                       organism = Chlamydomonas reinhardtii
SEQUENCE: 148
gtagctaaat aagggtatgg agg                                            23

SEQ ID NO: 149         moltype = DNA   length = 4107
FEATURE                Location/Qualifiers
source                 1..4107
                       mol_type = other DNA
                       organism = synthetic construct
                       note = Synthetic Construct
SEQUENCE: 149
atggacaaaa aatactcaat tggtttagat attggtacaa attcagttgg ttgggctgtt    60
attacagatg aatataaagt tccaagtaaa aaatttaaag ttttaggtaa tacagatcgt   120
cactcaatta agaaaaactt aattggtgct ttattatttg attcaggtga acagctgaa    180
gctacacgtt taaacgtac agctcgtcgt cgttatacac gtcgtaaaaa tcgtatttgt   240
tatttacaag aaattttctc aaatgaaatg gctaaagttt atgattcatt ttttcaccgt   300
```

-continued

```
ttagaagaat catttttagt tgaagaagat aaaaaacacg aacgtcaccc aattttggt    360
aatattgttg atgaagttgc ttatcacgaa aaatatccaa caattatca cttacgtaaa   420
aaattagttg attcaactga taaagctgat ttacgtttaa tttatttagc tttagctcac   480
atgattaaat tccgtggtca cttcttaatt gaaggtgatt taaacccaga taattcgat    540
gttgacaaat tattcattca attagttcaa acatataatc aatttattga agaaaatcca   600
attaatgctt caggtgttga tgctaaagca attttatcag ctcgtttatc aaaatcacgt   660
cgtttagaaa acttaattgc tcaattacca ggtgaaaaga aaaatggttt attcggtaac   720
ttaattgcat tatcattagg tttaacacca aatttcaaat caaacttcga tttagctgaa   780
gatgctaaat tacaattatc aaaagataca tacgatggta atttagataa attattagca   840
caaattggtg atcaatatgc tgatttattc ttagctgcta aaaacttatc agatgctatt   900
ttattatcag atattttacg tgttaataca gaaattacaa aagctccatt atcagcttca   960
atgattaaac gttatgatga acaccaccaa gatttaacat tattaaaagc tttagttcgt  1020
caacaattac ctgaaaaata caagaaatt ttcttcgatc aatctaaaaa tggttatgct   1080
ggttatattg atggtggtgc ttcacaagaa gaattctata aattcattaa acctattta   1140
gaaaaaatgg atggtacaga agaattatta gttaaattaa atcgtgaaga tttattacgt  1200
aaacaacgta catttgataa tggttcaatt cctcaccaaa ttcatttagg tgaattacac  1260
gcaattttac gtcgtcaaga agattttat ccattcttaa aagataatcg tgaaaaaatt   1320
gaaaaaattt taacatttcg tattccatat tatgtaggtc cattagctcg tggtaattca  1380
cgtttcgctt ggatgacacg taaatctgaa gaaacaatta caccttggaa ttttgaagaa  1440
gttgttgata aaggtgctag tgctcaatca tttattgaac gtatgacaaa tttcgacaaa  1500
aacttaccaa atgaaaagt tttaccaaaa cactcattat tatatgaata tttcacagtt   1560
tataatgaat taacaaaagt taaatatgtt acagaaggta tgcgtaaacc tgcatttta   1620
agtggtgaac aaaagaaagc tattgttgac ttattattca aaacaaatcg taaagttaca  1680
gttaaacaat aaaagaaga ttactttaag aaaattgaat gttttgattc agtagaaatt   1740
tcaggtgtag aagatcgttt caatgcttca ttaggtacat accacgattt attaaaaatt  1800
attaaagaca aagactttt agataatgaa gaaaatgaaa atattttaga agatattgtt   1860
ttaacattaa cattattcga agatcgtgaa atgattaag aacgtttaaa aacatatgct   1920
cacttatttg atgataaagt tatgaaacaa ttaaaacgtc gtcgttacac aggttgggt   1980
cgtttatctc gtaaattaat taacggtatt cgtgacaaac aatcaggtaa aacaatttta  2040
gatttcttaa aatcagatgg ttttgctaat cgtaacttta tgcaattaat tcacgatgat  2100
tctttaacat tcaaagaaga tattcaaaaa gctcaagttt caggtcaagg tgattcatta  2160
cacgaacaca ttgctaactt agctggttct ccagctatta aaaaaggtat tttacaaaca  2220
gttaaagttg tagatgaatt agtaaaagta atgggtcgtc acaaaccaga aacattgtt   2280
attgaaatgg cacgtgaaaa tcaaacaaca caaaaggtc aaaagaactc acgtgaacgt   2340
atgaaacgta ttgaagaagg tattaaagaa ttaggttcac aaatttaaa agaacaccca   2400
gttgaaaata cacaattaca aaacgaaaaa ttatatttat actatttaca aaatggtcgt  2460
gatatgtatg tagatcaaga attagatatt aaccgtttat cagattatga tgttgatcac  2520
attgttccac aatctttctt aaaagacgat tcaattgata acaaagttt aacacgttca   2580
gataaaaacc gtggtaaatc agatagtgta ccatcagaag aagtagttaa gaaatgaaa  2640
aactattggc gtcaattatt aaatgcaaaa ttaattacaa aacgtaaatt cgataactta  2700
acaaaagctg aacgtggtgg tttatcagaa ttagacaaag ctggtttcat taaacgtcaa  2760
ttagtagaaa cacgtcaaat tactaaacac gttgctcaaa ttttagactc tcgtatgaat  2820
acaaaatatg atgaaaatga taattaatt cgtgaagtta aagttattac attaaaatca  2880
aaattagtat cagatttccg taaagatttc caattctaca aagttcgtga aattaacaac  2940
tatcaccacg ctcacgatgc ttacttaaat gctgttgttg gtactgcatt aattaaaaaa  3000
tacccaaaat tagaatctga attcgtttat ggtgactata agtttatga tgtacgtaaa   3060
atgattgcta aatcagaaca agaaattggt aaagctactt ctaaatactt tttctattca  3120
aacattatga atttctttaa aactgaaatt acattagcta acggtgaaat tcgtaaacgt  3180
ccattaattc aaactaatgg tgaaactggt gaaattgtat gggataaag tcgtgattc   3240
gctacagttc gtaaagtatt atcaatgcca caagttaata ttgttaaaaa aactgaagtt  3300
caaacaggtg gtttttcaaa agaatctatt ttacctaaac gtaactcaga caaattaatt  3360
gctcgtaaaa aagattggga tcctaaaaaa tatggtggtt tcgattcacc aacagtagct  3420
tattcagtat tagttgtagc taaagtagaa aaagtaaat ctaaaaaatt aaaatcagta   3480
aaagaattat taggttattac aattatgaa cgttcatcat tcgagaaaaa cccaattgat  3540
ttcttagaag ctaaaggtta taaagaagtt aaaaaagatt taattattaa attaccaaaa  3600
tactctttat ttgaattaga aaacggtcgt aaacgtatgt tagcttctgc tggtgaatta  3660
caaaaaggta atgaattagc attaccatca aaatatgtaa atttcttata cttagcttca  3720
cactacgaaa aattaaaagg ttcaccagaa gataacgaac aaaaacaatt attcgttgaa  3780
caacataaac actatttaga tgaaattatt gaacaaattt acaatttc aaaacgtaaa   3840
attttagctg atgctaattt agataaagtt ttatctgctt ataacaaaca ccgtgataaa  3900
cctattcgtg aacaagctga aaacattatt cacttattta cattaacaaa tttaggtgct  3960
ccagctgctt tcaaatattt cgatacaaca attgaccgta aacgttacac atcaacaaaa  4020
gaagttttag acgctacatt aattcatcaa tcaattcag gtttatatga aacacgtatt   4080
gatttaagtc aattaggtgg tgattaa                                      4107
```

SEQ ID NO: 150         moltype = AA  length = 1368
FEATURE               Location/Qualifiers
source                1..1368
                         mol_type = protein
                         organism = Streptococcus pyogenes SEQUENCE: 150
```
MDKKYSIGLD IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
```

```
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGD               1368

SEQ ID NO: 151           moltype = DNA   length = 279
FEATURE                  Location/Qualifiers
source                   1..279
                         mol_type = unassigned DNA
                         organism = Chlamydomonas reinhardtii
SEQUENCE: 151
tcttaattca acatttttaa gtaaatactg ttttaatgtta tacttttacg aatacacata    60
tggtaaaaaa taaaacaata tctttaaaat aagtaaaaat aatttgtaaa ccaataaaaa   120
atatatttat ggtataatat aacatatgat gtaaaaaaaa ctatttgtct aatttaataa   180
ccatgcattt tttatgaaca cataataatt aaaagcgttg ctaatggtgt aaataatgta   240
tttattaaat taaataattg ttattataag gagaaatcc                          279

SEQ ID NO: 152           moltype = DNA   length = 414
FEATURE                  Location/Qualifiers
source                   1..414
                         mol_type = unassigned DNA
                         organism = Chlamydomonas reinhardtii
SEQUENCE: 152
aaatggatat ttggtacatt taattccaca aaaatgtcca atacttaaaa tacaaaatta    60
aaagtattag ttgtaaactt gactaacatt ttaaatttta aattttttcc taattatata   120
ttttacttgc aaaatttata aaaatttat gcattttat atcataatta taaaaccttt   180
attcatggtt tataatataa taattgtgat gactatgcac aaagcagttc tagtcccata   240
tataatacta tatataaccc gtttaaagat ttatttaaaa atatgtgtgt aaaaaatgct   300
tatttttaat tttatttat ataagttata atattaaata cacaatgatt aaaattaaat   360
aataataaat ttaacgtaac gatgagttgt tttttttattt tggagataca cgca        414

SEQ ID NO: 153           moltype = DNA   length = 258
FEATURE                  Location/Qualifiers
source                   1..258
                         mol_type = unassigned DNA
                         organism = Chlamydomonas reinhardtii
SEQUENCE: 153
tttttatttt tcatgatgtt tatgtgaata gcataaacat cgttttatt tttatggtgt    60
ttaggttaaa tacctaaaca tcattttaca tttttaaaat taagttctaa agttatcttt   120
tgtttaaatt tgcctgtctt tataaattac gatgtgccag aaaaataaaa tcttagcttt   180
ttattataga atttatcttt atgtattata ttttataagt tataataaaa gaaatagtaa   240
catactaaag cggatgta                                                 258

SEQ ID NO: 154           moltype = DNA   length = 102
FEATURE                  Location/Qualifiers
source                   1..102
                         mol_type = unassigned DNA
                         organism = Chlamydomonas reinhardtii
SEQUENCE: 154
ttaacccatg attaacaact atatcaataa aatcaatttg tagtgaaata ctctgattga    60
cattaaaata ataccatgat aaaaattata ataacaaatt tt                      102

SEQ ID NO: 155           moltype = DNA   length = 101
FEATURE                  Location/Qualifiers
source                   1..101
                         mol_type = unassigned DNA
                         organism = Chlamydomonas reinhardtii
SEQUENCE: 155
tttttcctaa tgtactttgt tgtaaaagtg gctggtttaa ccttttttagg tttcggattg    60
aacaataatg gcagttaaga gtcactaaag ctgctgtata g                       101

SEQ ID NO: 156           moltype = DNA   length = 73
FEATURE                  Location/Qualifiers
source                   1..73
                         mol_type = unassigned DNA
                         organism = Chlamydomonas reinhardtii
SEQUENCE: 156
acgtcctag ttcagtcggt agaacgcagg tttccaaaac ctgatgtcgt gggttcaatt    60
```
cctacagggc gtg                                                              73

SEQ ID NO: 157          moltype = DNA   length = 72
FEATURE                 Location/Qualifiers
source                  1..72
                        mol_type = unassigned DNA
                        organism = Chlamydomonas reinhardtii
SEQUENCE: 157
gggttgctaa ctcaatggta gagtactcgg ctcttaaccg ataagttctg ggttcgagtc           60
ccaggtaacc ca                                                              72

SEQ ID NO: 158          moltype = DNA   length = 82
FEATURE                 Location/Qualifiers
source                  1..82
                        mol_type = unassigned DNA
                        organism = Chlamydomonas reinhardtii
SEQUENCE: 158
gccttcgtga tggaactggt agacatcctg gttttaggaa ccagtgctga aaggcgtgcc           60
ggttcaaatc cggccgaagg ca                                                   82

SEQ ID NO: 159          moltype = DNA   length = 795
FEATURE                 Location/Qualifiers
source                  1..795
                        mol_type = other DNA
                        organism = synthetic construct
                        note = Synthetic Construct
SEQUENCE: 159
atggctcgtg aagcggttat cgccgaagta tcaactcaac tatcagaggt agttggcgtc           60
atcgagcgcc atctcgaacc gacgttgctg ccgtacatt tgtacggctc cgcagtggat          120
ggcggcctga agccacacag tgatattgat ttgctggtta cggtgaccgt aaggcttgtg          180
gaaacaacgc ggcgagcttt gatcaacgac cttttggaaa cttcggcttc ccctggagag          240
agcgagattc tccgcgctgt agaagtcacc attgttgtgc acgacgacat cattccgtgg          300
cgttatccta ctaagcgcga actgcaattt ggagaatggc agcgcaatga cattcttgca          360
ggtatctccg agccagccac gatcgacatt gatctggcta tcttgctgac aaaagcaaga          420
gaacatagcg ttgccttggt aggtccagcg gcggagaac tctttgatcc ggttcctgaa          480
caggatctat ttgaggcgct aaatgaaacc ttaacgctat ggaactcgcc gcccgactgg          540
gctggcgatg agcgaaatgt agtgcttacg ttgtcccgca tttggtacag cgcagtaacc          600
ggcaaaatcg cgccgaagga tgtcgctgcc gactgggcaa tggagcgcct gccggcccag          660
tatcagcccg tcatacttga agctagacag gcttatcttg acaagaaga gatcgcttg           720
gcctcgcgcg cagatcagtt ggaagaattt gtccactacg tgaaaggcga gatcactaag          780
gtagttggca aataa                                                          795

SEQ ID NO: 160          moltype = DNA   length = 189
FEATURE                 Location/Qualifiers
source                  1..189
                        mol_type = unassigned DNA
                        organism = Chlamydomonas reinhardtii
SEQUENCE: 160
catataccta aaggcccttt ctatgctcga ctgataagac aagtacataa atttgctagt           60
ttacattatt ttttatttct aaatatataa tatatttaaa tgtatttaaa attttttcaac         120
aattttttaaa ttatatttcc ggacagatta ttttaggatc gtcaaaagaa gttacattta         180
tttatataa                                                                 189

SEQ ID NO: 161          moltype = DNA   length = 400
FEATURE                 Location/Qualifiers
source                  1..400
                        mol_type = unassigned DNA
                        organism = Chlamydomonas reinhardtii
SEQUENCE: 161
ttttttttta aactaaaata aatctggtta accatacctg gtttatttta gtttatacac           60
acttttcata tatatatact taatagctac cataggcagt tggcaggacg tcccctttacg         120
ggacaaatgt atttattgtt gcctgccaac tgcctaatat aaatattagt ggacgtcccc          180
ttccccttac gggcaagtaa acttagggat tttaatgctc cgttaggagg caaataaatt          240
ttagtggcag ttgcctcgcc tatcggctaa caagttcctt gcagtgtatat aaatatcctg         300
ccaactgccg atatttatat actaggcagt ggcggtacca ctcgactaat atttatattc         360
cgtaagacgt cctccttcgg agtatgtaaa catgctaagt                                400

SEQ ID NO: 162          moltype = DNA   length = 717
FEATURE                 Location/Qualifiers
source                  1..717
                        mol_type = other DNA
                        organism = synthetic construct
                        note = Synthetic Construct
SEQUENCE: 162
atggctaaag gtgaagaatt attcacaggt gttgtaccta ttttagtaga attagacggt           60
gatgtaaacg gtcacaaatt ttcagttct ggtgaaggtg aaggtgacgc aacttatggt          120
aaattaacac ttaaattcat ttgtactaca ggtaaattac cagtaccttg gccatcatta          180
gttacaactt ttacatacgg tgtacaatgt ttcagtcgtt accctgatca catgaaacaa          240
catgactttt tcaaatctgc tatgccagaa ggttatgttc aagaacgtac tatttttttc          300

-continued

```
aaagatgacg gtaattataa aacacgtgct gaagtaaaat ttgaaggtga tactttagtt   360
aaccgtattg aattaaaagg tattgacttc aaagaagatg gtaatatttt aggtcacaaa   420
cttgaatata actacaattc acataacgta tatattatgg cagacaaaca aaaaaatggt   480
attaaagtaa actttaaaat tcgtcataat atcgaggatg gttctgtaca attagctgac   540
cactatcaac aaaacacacc aattggtgat ggtcctgttt tacttccaga caatcattat   600
ttaagtactc aatctgcttt atcaaaagat cctaacgaaa aacgtgacca catggtatta   660
cttgaatttg ttacagcagc tggtattact cacggtatgg atgaattata caaataa    717
```

| | | |
|---|---|---|
| SEQ ID NO: 163 | moltype = DNA length = 74 | |
| FEATURE | Location/Qualifiers | |
| source | 1..74 | |
| | mol_type = unassigned DNA | |
| | organism = Chlamydomonas reinhardtii | |

SEQUENCE: 163
```
gctcctttct ttactttaaa ctggagtgaa tacagtgatt tcttaacatt taaaggtggt    60
ttaaaccctg ttac                                                      74
```

| | | |
|---|---|---|
| SEQ ID NO: 164 | moltype = DNA length = 76 | |
| FEATURE | Location/Qualifiers | |
| source | 1..76 | |
| | mol_type = unassigned DNA | |
| | organism = Chlamydomonas reinhardtii | |

SEQUENCE: 164
```
tccatttaca ggtgaaggtc acgttggttt atatgaaatt ttaacaactt cttggcatgc    60
acaattagct attaac                                                    76
```

| | | |
|---|---|---|
| SEQ ID NO: 165 | moltype = DNA length = 76 | |
| FEATURE | Location/Qualifiers | |
| source | 1..76 | |
| | mol_type = unassigned DNA | |
| | organism = Chlamydomonas reinhardtii | |

SEQUENCE: 165
```
gtactaactg gggtattggt cacagtatga agaaatttt agaagctcac cgtggtccat     60
ttacaggtga aggtca                                                    76
```

| | | |
|---|---|---|
| SEQ ID NO: 166 | moltype = DNA length = 76 | |
| FEATURE | Location/Qualifiers | |
| source | 1..76 | |
| | mol_type = unassigned DNA | |
| | organism = Chlamydomonas reinhardtii | |

SEQUENCE: 166
```
tacccttatt tagctactga ttacggtaca caattatcat tatttacaca ccacacatgg    60
attggtggtt tctgta                                                    76
```

| | | |
|---|---|---|
| SEQ ID NO: 167 | moltype = DNA length = 21 | |
| FEATURE | Location/Qualifiers | |
| source | 1..21 | |
| | mol_type = unassigned DNA | |
| | organism = Chlamydomonas reinhardtii | |

SEQUENCE: 167
```
gctggttggt tccactacca c                                              21
```

| | | |
|---|---|---|
| SEQ ID NO: 168 | moltype = DNA length = 27 | |
| FEATURE | Location/Qualifiers | |
| source | 1..27 | |
| | mol_type = other DNA | |
| | organism = synthetic construct | |
| | note = Synthetic Construct | |

SEQUENCE: 168
```
caccttcaaa ttttacttca gcacgtg                                        27
```

| | | |
|---|---|---|
| SEQ ID NO: 169 | moltype = DNA length = 25 | |
| FEATURE | Location/Qualifiers | |
| source | 1..25 | |
| | mol_type = other DNA | |
| | organism = synthetic construct | |
| | note = Synthetic Construct | |

SEQUENCE: 169
```
catacggtgt acaatgtttc agtcg                                          25
```

| | | |
|---|---|---|
| SEQ ID NO: 170 | moltype = DNA length = 26 | |
| FEATURE | Location/Qualifiers | |
| source | 1..26 | |
| | mol_type = unassigned DNA | |
| | organism = Chlamydomonas reinhardtii | |

SEQUENCE: 170
```
gtgagaaata atagcatcac ggtgac                                         26
```

| | | |
|---|---|---|
| SEQ ID NO: 171 | moltype = DNA length = 1408 | |

```
FEATURE          Location/Qualifiers
source           1..1408
                 mol_type = other DNA
                 organism = synthetic construct
                 note = Synthetic Construct
SEQUENCE: 171
gctggttggt tccactacca caaagctgct ccaaaactag aatggttcca aaacgttgaa    60
tcaatgttaa accaccactt aggtggtctt cttggtttag gtagtttagc ttgggctggt   120
caccaaattc acgtttcttt accagtaaac aaattattag atgctggtgt agatccaaaa   180
gaaattccac ttcctcatga tttattatta aatcgtgcta ttatggctga cttatacca    240
agttttgcta aaggtattgc tcctttcttt actttaaact ggagtgaata cagtgatttc   300
ttaacattta aaggtggttt aaaccctgtt acattatcag gttctgctgg ttcagcagct   360
ggtatggcta aaggtgaaga attattcaca ggtgttgtac ctattttagt agaattagac   420
ggtgatgtaa acggtcacaa attttcagtt tctggtgaag gtgaaggtga cgcaacttat   480
ggtaaattaa cacttaaatt catttgtact acaggtaaat taccagtacc ttggccatca   540
ttagttacaa cttttacata cggtgtacaa tgtttcagtc gttaccctga tcacatgaaa   600
caacatgact ttttcaaatc tgctatgcca gaaggttatg ttcaagaacg tactattttt   660
ttcaaagatg acggtaatta taaaacgt gctgaagtaa aatttgaagg tgatacttta   720
gttaaccgta ttgaattaaa aggtattgac ttcaaagaag atggtaatat tttaggtcac   780
aaacttgaat ataactacaa ttcacataac gtatatatta tggcagacaa acaaaaaaat   840
ggtattaaag taaactttaa aattcgtcat aatatcgagg atggttctgt acaattagct   900
gaccactatc aacaaaacac accaattggt gatggtcctg ttttacttcc agacaatcat   960
tatttaagta ctcaatctgc tttatcaaaa gatcctaacg aaaaacgtga ccacatggta  1020
ttacttgaat ttgttacagc agctggtatt actcacggta tggatgaatt atacaaataa  1080
tccatttaca ggtgaaggtc acgttggttt atatgaaatt ttaacaactt cttggcatgc  1140
acaattagct attaacttag cttttatttgg ttcgttatca attattgtag ctcaccacat  1200
gtacgcaatg cctccatacc cttatttagc tactgattac ggtacacaat tatcattatt  1260
tacacaccac acatggattg gtggtttctg tattgttggt gctggtgctc acgcagctat  1320
tttcatggtt cgtgactacg atcctactaa taactacaac aacttattag accgtgtaat  1380
tcgtcaccgt gatgctatta tttctcac                                     1408

SEQ ID NO: 172       moltype = AA length = 16
FEATURE              Location/Qualifiers
source               1..16
                     mol_type = protein
                     organism = Drosophila melanogaster
SEQUENCE: 172
RQIKIWFQNR RMKWKK                                                      16

SEQ ID NO: 173       moltype = AA length = 9
FEATURE              Location/Qualifiers
source               1..9
                     mol_type = protein
                     organism = unidentified
SEQUENCE: 173
LAGLIDADG                                                               9

SEQ ID NO: 174       moltype = AA length = 10
FEATURE              Location/Qualifiers
source               1..10
                     mol_type = protein
                     organism = synthetic construct
VARIANT              1..10
                     note = This sequence may encompass 1-10 residues
SEQUENCE: 174
GGGGGGGGGG                                                             10
```